(12) United States Patent
Bauman et al.

(10) Patent No.: US 10,683,514 B2
(45) Date of Patent: Jun. 16, 2020

(54) MICROORGANISMS ENGINEERED FOR INCREASED PRODUCTIVITY

(71) Applicant: Synthetic Genomics, Inc., La Jolla, CA (US)

(72) Inventors: Nicholas Bauman, San Diego, CA (US); Imad Ajjawi, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 16/509,095

(22) Filed: Jul. 11, 2019

(65) Prior Publication Data

US 2019/0323023 A1    Oct. 24, 2019

Related U.S. Application Data

(62) Division of application No. 15/256,460, filed on Sep. 2, 2016, now Pat. No. 10,351,869.

(60) Provisional application No. 62/214,780, filed on Sep. 4, 2015.

(51) Int. Cl.
| | | |
|---|---|---|
| *C12N 15/82* | (2006.01) | |
| *C07K 14/405* | (2006.01) | |
| *C12P 7/64* | (2006.01) | |

(52) U.S. Cl.
CPC ........ *C12N 15/8247* (2013.01); *C07K 14/405* (2013.01); *C12N 15/8261* (2013.01); *C12P 7/6409* (2013.01); *C12P 7/6436* (2013.01); *C12P 7/6463* (2013.01)

(58) Field of Classification Search
None
See application file for complete search history.

(56) References Cited

U.S. PATENT DOCUMENTS

| 2009/0070897 A1 | 3/2009 | Goldman et al. |
| 2009/0183270 A1 | 7/2009 | Adams et al. |
| 2014/0212941 A1 | 7/2014 | Lee |
| 2014/0304848 A1 | 10/2014 | Abad et al. |

FOREIGN PATENT DOCUMENTS

| CN | 101 210 251 A | 7/2008 |
| JP | 2002 095481 A | 4/2002 |
| WO | WO 2000/008160 A2 | 2/2000 |
| WO | WO 2001/055301 A2 | 8/2001 |

OTHER PUBLICATIONS

Corteggiani et al. (GenBank Sequence Accesion No. AZIL01000516; pp. 1-35; Published Feb. 14, 2014).*
Bork et al.: "Go hunting in sequence databases but watch for the traps"; TIG, 12:425-427, 1996.
Database WPI, Thomson Scientific, AN 2008-N03327, week 200877, XP002790915.
Database WPI, Thomson Scientific, AN 2002-439990, week 200247, XP002790914.
Doerks et al.: "Protein annotation: detective work for function prediction"; TIG, 14:248-250, 1998.
Guo, Haiwei H. et al.: "Protein tolerance to random amino acid change"; PNAS, 101: 9205-9210, 2004.
Hussain, Muzammal et al.: "Skp1 Implications in cancer and SCF-oriented anti-cancer drug discovery"; Pharmacological Research 111:34-42, 2016.
International Search Report dated Feb. 7, 2017, regarding PCT/US2016/050285.
Keskin, Ozlem et al.: "A new, structurally non redundant, diverse data set of protein—protein interfaces and its implications"; Protein Science, 13:1043-1055, 2004.
McConnell, Jane R. et al.: "Role of PHABULOSA and PHAVOLUTA in determining redial patterning in shoots"; Nature, 411:709-713, 2001.
Ngo, Thomas et al.: "Computational Complexity, Protein Structure Prediction, and the Levinthal Paradox"; The Protein Folding Problem and Tertiary Structure Prediction, K. Merz., and S. Le Grand (eds.) pp. 492-495, 1994.
Rao, Venkateswara et al.: "Arabidopsis SKP1-like protein 13 positively regulates seed germination and seedling growth under abiotic stress"; Journal of Experimental Biology, 69:3899-3915; 2018.
Smith and Zhang: "The challenges of genome sequence annotation of 'The devil in in the details'"; Nature Biotechnology, 15:1222-1223, 1997.
Supplementary European Search Report dated Aug. 2, 2019, regarding EP 16 84 3151.
Supplementary Partial European Search Report dated May 10, 2019, regarding EP 16 84 3151.
Thornton et al.: "From structure to function: Approached and limitations"; Nature structural Biology, structural genomics supplement, Nov. 2000.
Wells, James A.: "Additivity of Mutational Effects in Proteins"; Biochemistry 29:8509-8517, 1990.

* cited by examiner

*Primary Examiner* — Vinod Kumar
(74) *Attorney, Agent, or Firm* — DLA Piper LLP (US)

(57) ABSTRACT

The application provides recombinant microorganisms with increased productivity with respect to control or wildtype microorganisms. The recombinant microorganisms can include a non-native gene encoding a SKP1 polypeptide or a CHORD-derived polypeptide. Increased productivity can be increased biomass or lipid productivity. These recombinant microorganisms can be used to produce products of interest.

3 Claims, 12 Drawing Sheets
Specification includes a Sequence Listing.

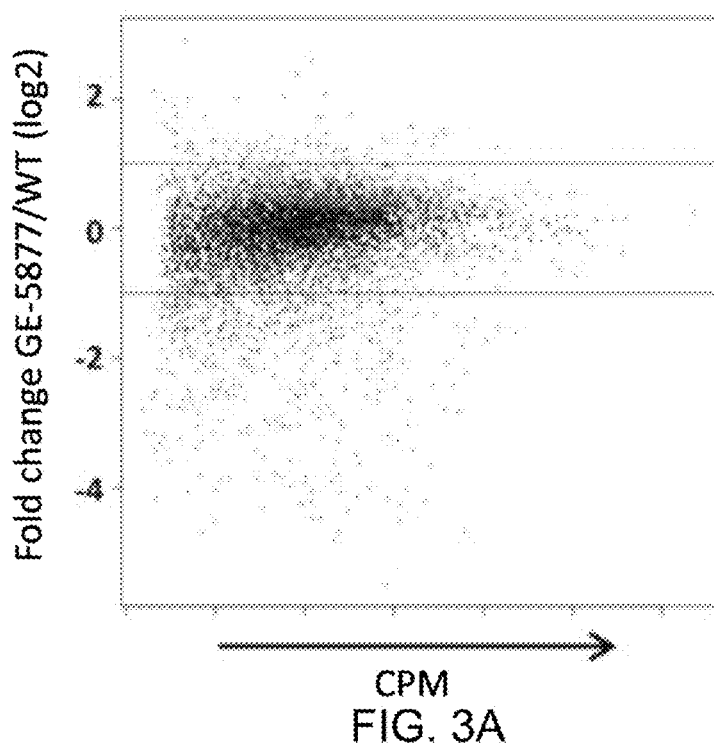

FIG. 3A

| Pathway ID | Pathway Name | # Genes | Trend |
|---|---|---|---|
| GO:0000082 | BP: G1/S transition of mitotic cell cycle | 9 | Up |
| GO:0000216 | BP: M/G1 transition of mitotic cell cycle | 5 | Up |
| GO:0000278 | BP: Mitotic cell cycle | 14 | Up |
| GO:0000502 | CC: Proteasome complex | 29 | Up |
| GO:0000722 | BP: Telomere maintenance via recombination | 5 | Up |
| GO:0000775 | CC: Chromosome, centromeric region | 8 | Up |
| GO:0000776 | CC: Kinetochore | 8 | Up |
| GO:0001501 | BP: Skeletal system development | 4 | Up |
| GO:0001649 | BP: Osteoblast differentiation | 4 | Up |
| GO:0003690 | MF: Double-stranded DNA binding | 7 | Up |

FIG. 3B

MICROORGANISMS ENGINEERED FOR INCREASED PRODUCTIVITY

CROSS-REFERENCE TO RELATED APPLICATIONS

This application is a divisional application of U.S. application Ser. No. 15/256,460 filed Sep. 2, 2016, now issued as U.S. Pat. No. 10,351,869; which claims the benefit under 35 USC § 119(e) to U.S. Application Ser. No. 62/214,780 filed Sep. 4, 2015. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, named SGII1960-2_ST25.txt was created on Jul. 10, 2019 and is 246 KB. The file can be accessed using Microsoft Word on a computer that uses Windows OS.

BACKGROUND OF THE INVENTION

Field of the Invention

The present application relates generally to the field of molecular biology and genetics. Specifically, this application relates to methods and materials involved in modulating biomass productivity in microorganisms such as, for example, microalgae. This application further provides recombinant microorganisms such as microalgae having increased productivity.

Background of the Invention

Microalgae have recently attracted considerable interest owing to numerous consumer products and applications that can be produced from these organisms. The microalgae-based product portfolio stretches from biomass production for food and animal feed to valuable products extracted from microalgal biomass, including triglycerides which can be converted into biodiesel. With the development of advanced culture and screening techniques, microalgal biotechnology can help meet the high demands of food, pharmaceutical, and energy industries. Low biomass yields contribute to the relatively high cost of algal biofuels and other products. As a result, scientists are continually striving to improve algal biomass productivity.

Progression through the cell cycle in eukaryotes is regulated through synthesis/degradation and phosphorylation/dephosphorylation of cell cycle-regulating proteins. The Skp, Cullin, F-box containing complex (SCF complex) is a ubiquitin ligase complex that controls the transition between G1/S and G2/M phases by marking key proteins for proteasomal degradation (Cordozo and Pagano (2004) Nature Rev Mol Cell Biol 5:739-751; Vodermaier (2014) Curr Biol 14: R787-R796; Wei et al. (2004) Nature 428:194-198). In addition to ubiquitinating cell cycle proteins, the SCF complex marks various other cellular proteins for degradation. SCF complex contains three core subunits and a number of less critical components. The core components include SKP1, Cullin (CUL1), and F-box protein (SKP2, Cdc4). SKP1 serves as a bridging protein forming a connection between the Cullin and F-box proteins (Schulman et al. (2000) Nature 408:381-386).

SUMMARY OF THE INVENTION

The present application describes the discovery that particular genes associated with the SCF complex and associated pathways, which when overexpressed in microorganisms such as algae or heterokont microorganisms, confer increased productivity on the microorganisms. The genes encode growth regulators such as SKP1 polypeptides or polypeptides derived from a CHORD polypeptide.

In one aspect the present invention provides a recombinant microorganism comprising a non-native nucleic acid molecule that includes a nucleic acid sequence encoding a SKP1 polypeptide. The non-native nucleic acid molecule can include one or more nucleic acid sequences juxtaposed with the nucleic acid sequence encoding a SKP1 polypeptide that is not juxtaposed with an SKP1 gene in nature. In some embodiments, a non-native nucleic acid molecule includes a nucleic acid sequence encoding a SKP1 polypeptide operably linked to a regulatory sequence, such as a promoter, that is not operably linked to the SKP1-encoding sequence in nature. Alternatively or in addition, the non-native nucleic acid molecule can include sequences for mediating integration of nucleic acid sequences into a host genome, one or more selectable marker genes, and/or one or more detectable marker genes. The recombinant microorganism that includes a non-native nucleic acid molecule as provided herein can have increased productivity, for example increased biomass productivity, such as AFDW or TOC productivity, and/or increased lipid productivity, such as increased FAME productivity, with respect to a control microorganism that does not include the non-native nucleic acid molecule.

In various embodiments the non-native nucleic acid molecule can include a nucleic acid sequence encoding a SKP1 polypeptide having at least 65%, at least 70%, at least 75%, at least 80%, at least 85%, at least 90%, at least 95% identity, or between 95% and 100% identity (sequence homology) to a naturally-occurring SKP1 polypeptide. The encoded SKP1 polypeptide can include one or both of a SKP family tetramerization domain of Pfam PF03931 and a SKP family dimerization domain of Pfam PF01466. In some examples, the amino acid sequence comprises at least one Pfam03931 domain and at least one Pfam01466 domain. In some examples, a non-native nucleic acid molecule comprises a polypeptide having a SKP1 family domain having at least 65%, at least 70%, at least 75%, at least 80%, at least 85%, at least 90%, at least 95% identity, or between 95% and 100% identity (sequence homology) to SEQ ID NO:101 and/or a SKP1 family domain having at least 65%, at least 70%, at least 75%, at least 80%, at least 85%, at least 90%, at least 95% identity, or between 95% and 100% identity (sequence homology) to SEQ ID NO:102.

In some embodiments, the nucleic acid sequence that encodes a SKP1 polypeptide is a cDNA and/or lacks one or more introns of the native gene from which the SKP1-encoding sequence is derived. Alternatively or in addition, the nucleic acid sequence that encodes a SKP1 polypeptide can include one or more introns that are not present in the native gene from which the SKP1-encoding sequence is derived. For example, one or more introns included in the SKP1 transgene may be a naturally-occurring intron of the SKP1 gene from which the transgene is derived, or can be an intron derived from a different naturally-occurring gene, and/or one or more introns may be entirely or partially engineered sequences. In various embodiments, alternatively or in addition to any of the above, a nucleic acid sequence encoding a SKP1 polypeptide can be codon-optimized for a host microorganism and/or can encode a SKP1 polypeptide that includes one or more amino acid changes, additions, or deletions with respect to a naturally-occurring SKP1 gene from which it is derived. In various embodiments, a recombinant microorganism as provided herein can be genetically engineered to include a non-native nucleic acid molecule that includes a sequence encoding a SKP1 polypeptide that has at least 65%, at least 70%, at least 75%, at least 80%, at least 85%, at least 90%, at least 95%, or between 95% and 100% identity to a naturally-occurring SKP1 polypeptide, including but not limited to a SKP1 polypeptide derived from the same species or the same genus as the recombinant host microorganism. In various examples a recombinant microorganism as provided herein includes a non-native nucleic acid molecule that includes a nucleic acid sequence encoding a SKP1 polypeptide having has at least 65%, at least 70%, at least 75%, at least 80%, at least 85%, at least 90%, at least 95%, or between 95% and 100% identity to a SKP1 polypeptide selected from the group consisting of SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90.

In some examples, a recombinant microorganism as provided herein includes a non-native nucleic acid molecule that includes a nucleic acid molecule encoding a SKP1 polypeptide having at least 65%, at least 70%, at least 75%, at least 80%, at least 85%, at least 90%, at least 95%, or between 95% and 100% identity to a SKP1 polypeptide that is endogenous to the host microorganism. The non-native nucleic acid molecule in various embodiments can further comprise a promoter operably linked to the SKP1-encoding sequence, where the promoter can be a promoter the SKP1-encoding sequence is not operably linked to in nature. A promoter operably linked to a SKP1 encoding nucleic acid sequence may be derived from the same species as the host microorganism or may be from a different species. In exemplary embodiments a recombinant microorganism according to the present invention includes a non-native nucleic acid molecule that includes a nucleic acid sequence that encodes a SKP1 polypeptide, where SKP1 polypeptide has an amino acid sequence that is at least 65%, at least 70%, at least 75%, at least 80%, at least 85%, at least 90%, at least 95%, or between 95% and 100% identical to the amino acid sequence of a naturally-occurring SKP1 polypeptide derived from the host organism, and the nucleic acid sequence that encodes the SKP1 polypeptide is operably linked to a promoter that is not operably linked to the SKP1-encoding sequence in nature. The non-native nucleic acid molecule is expressed in the microorganism to result in a higher level of a SKP1 transcript being present in the recombinant microorganism than occurs in a control microorganism that is not transformed with the non-native nucleic acid molecule, and exhibits higher productivity, for example, higher biomass or lipid productivity, than a control microorganism that does not include the non-native nucleic acid molecule encoding a SKP1 polypeptide.

In alternative embodiments, the non-native nucleic acid molecule that is transformed into the host microorganism does not include a promoter operably linked to the nucleic acid sequence encoding a SKP1 polypeptide. In some such embodiments, the nucleic acid sequence encoding the SKP1 polypeptide can, following transformation of the non-native nucleic acid molecule into the host cell, become integrated into the host genome such that it becomes operably linked to a regulatory sequence such as a promoter of the host genome that directs expression of the SKP1-encoding sequence. The non-native nucleic acid molecule can include, in various examples, a selectable marker gene or a detectable marker gene, such as, for example, a gene encoding a fluorescent protein.

In some embodiments, a recombinant microorganism as provided herein can be a heterokont such as a labyrinthulomycete species, and can include a non-native gene encoding a SKP1 polypeptide having at least 65%, at least 70%, at least 75%, at least 80%, at least 85%, at least 90%, at least 95%, or between 95% and 100% identity (sequence homology) to a SKP1 polypeptide of a heterokont species, such as, but not limited to, a labyrinthulomycete SKP1 polypeptide such as but not limited to SEQ ID NO:73 or SEQ ID NO:74.

In further embodiments, a recombinant microorganism as provided herein can be a heterokont alga such as a diatom species, and can include a non-native gene encoding a SKP1 polypeptide having at least 65%, at least 70%, at least 75%, at least 80%, at least 85%, at least 90%, at least 95%, or between 95% and 100% identity (sequence homology) to a SKP1 polypeptide of a diatom species, such as, but not limited to any of SEQ ID NO:65, SEQ ID NO:70, SEQ ID NO:71, SEQ ID NO:72, SEQ ID NO:75, SEQ ID NO:76, SEQ ID NO:77, SEQ ID NO:78, SEQ ID NO:79, SEQ ID NO:80, and SEQ ID NO:81. As nonlimiting examples, the recombinant host microorganism can be a species of *Amphora, Chaetoceros, Cyclotella, Fragilaropsis, Navicula, Nitzschia, Phceodactylum, Thalassiosira*, or *Hantzschia*.

In additional embodiments, a recombinant microorganism as provided herein can in some examples be a heterokont alga such as a eustigmatophyte species, and can include a non-native gene encoding a SKP1 polypeptide having at least 65%, at least 70%, at least 75%, at least 80%, at least 85%, at least 90%, at least 95%, or between 95% and 100% identity (sequence homology) to a SKP1 polypeptide of a eustigmatophyte species, such as, but not limited to any of SEQ ID NO:28, SEQ ID NO:68, and SEQ ID NO:69. For example, the recombinant host microorganism can be a species of *Eustigmatos, Monodus, Pseudostaurastrum, Vischeria*, or *Nannochloropsis*.

In yet further embodiments, a recombinant microorganism as provided herein can be a green alga such as a chlorophyte species, and can include a non-native gene encoding a SKP1 polypeptide having at least 65%, at least 70%, at least 75%, at least 80%, at least 85%, at least 90%, at least 95%, or between 95% and 100% identity (sequence homology) to a SKP1 polypeptide of a chlorophyte species such as, but not limited to any of SEQ ID NO:66, SEQ ID NO:67, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90. As nonlimiting examples, the recombinant host microorganism can be a species of *Carteria, Chlamydomonas, Chlorella, Parachlorella, Pseudochlorella, Tetrachlorella, Desmodesmus, Scenedesmus, Dunaliella, Haematococcus, Nannochloris, Neochloris, Ostreococcus, Picochlorum, Tetraselmis*, and *Volvox*.

The foregoing sequences are exemplary only. In various examples the recombinant microorganism can be a heterokont or algal microorganism, such as, for example, a labyrinthulomycete, a diatom (e.g., Bacillariophyte), a Eustigmatophyte, or a green alga (e.g., a member of the division Chlorophyta, for example, such as but not limited to a member of the classes Chlorophyceae, Chlorodendrophyceae, or Trebouxiophyceae) and the non-native nucleic acid molecule can include a nucleic acid sequence encoding a SKP1 polypeptide having at least 65%, at least 70%, at least 75%, at least 80%, at least 85%, at least 90%, at least 95% identity, or between 95% and 100% identity (sequence homology) to a SKP1 polypeptide of the host microorganism. SKP1 encoding nucleic acid sequence can be operably linked to a promoter on the nucleic acid molecule that is transformed into the genetically engineered microorganism, or the SKP1-encoding nucleic acid sequence can be introduced into the host microorganism and directed to insert into a site in the genome whereby it becomes operably linked to a promoter endogenous to the host microorganism that is not naturally operably linked to a SKP1 gene.

In another aspect of the present invention, a recombinant microorganism is provided that has increased productivity, such as biomass productivity, such as AFDW or TOC productivity, and/or lipid productivity, such as FAME productivity, with respect to a control microorganism in which the recombinant microorganism comprises a non-native nucleic acid molecule encoding a polypeptide comprising at least 60% of a CHORD domain. For example, a recombinant microorganism can include a non-native nucleic acid molecule comprising a nucleic acid sequence encoding a CHORD-derived polypeptide that includes at least 60% of an amino acid sequence of a CHORD domain of a naturally-occurring CHORD polypeptide, or an amino acid sequence having at least 80% identity thereto. In various embodiments, a recombinant microorganism can include a non-native nucleic acid molecule encoding a CHORD-derived polypeptide that includes a single CHORD domain or a portion thereof. The single CHORD domain or portion thereof may be derived from the sequence of a CHORD polypeptide of the host microorganism, and may be part of a chimeric protein in which the CHORD domain sequences are fused to amino acid sequences of a non-CHORD polypeptide.

In various embodiments, a recombinant microorganism as provided herein can include a non-native nucleic acid molecule that includes a sequence encoding a CHORD-derived polypeptide that comprises a single CHORD domain or a portion thereof of a CHORD polypeptide having at least 65%, at least 70%, at least 75%, at least 80%, at least 85%, at least 90%, at least 95%, or between 95% and 100% identity (sequence homology) to any of SEQ ID NO:22, SEQ ID NO:91, SEQ ID NO:92, SEQ ID NO:93, SEQ ID NO:94, SEQ ID NO:95, and SEQ ID NO:96. The CHORD polypeptide from which the sequences are derived may be any CHORD polypeptide, and may optionally be derived from a CHORD polypeptide of the same species as the recombinant microorganism or may not be derived from a CHORD polypeptide of the same species as the recombinant microorganism. The non-native nucleic acid molecule that is introduced into the engineered microorganism can include a promoter operably linked to the CHORD polypeptide. The promoter that is operably linked to the nucleic acid sequence encoding the CHORD-derived polypeptide can be a promoter not naturally operably linked to a CHORD gene, and can optionally be derived from the host microorganism.

In alternative embodiments, the non-native nucleic acid molecule that is transformed into the host microorganism does not include a promoter operably linked to the nucleic acid sequence encoding a SKP1 polypeptide. In some such embodiments, the nucleic acid sequence encoding the SKP1 polypeptide can, following transformation of the non-native nucleic acid molecule into the host cell, become integrated into the host genome such that it becomes operably linked to a regulatory sequence such as a promoter of the host genome that directs expression of the SKP1-encoding sequence. The non-native nucleic acid molecule can include, in various examples, a selectable marker gene or a detectable marker gene, such as, for example, a gene encoding a fluorescent protein.

In some examples, the CHORD domain of a CHORD-derived polypeptide encoded by a nucleic acid sequence of a non-native nucleic acid molecule introduced into a microorganism can have at least 65%, at least 70%, at least 75%, at least 80%, at least 85%, at least 90%, at least 95% identity, or between 95% and 100% identity to SEQ ID NO:4. In further examples, the polypeptide comprises an amino acid sequence having at least 65%, at least 70%, at least 75%, at least 80%, at least 85%, at least 90%, at least 95% identity, or between 95% and 100% identity to SEQ ID NO:99 or at least 60% contiguous amino acids thereof. In additional examples, the CHORD-derived polypeptide can have at least 65%, at least 70%, at least 75%, at least 80%, at least 85%, at least 90%, at least 95%, or between 95% and 100% identity to SEQ ID NO:100.

A recombinant microorganism according to any of the above examples, e.g., a recombinant microorganism comprising a non-native gene encoding a CHORD-derived polypeptide or a SKP1 polypeptide as described herein, can have enhanced productivity with respect to a control microorganism. Increased productivity of any of the described recombinant microorganisms can be increased biomass, such as AFDW or TOC, productivity. The biomass productivity can be at least 5% increased with respect to a control cell. For example, the biomass productivity can be increased between about 5% and about 500%, or between about 10% and about 300%, or between about 10% and about 200%, or between about 10% and about 100%, with respect to a control cell. In some examples, the biomass, such as AFDW or TOC, productivity can be between about 5% and about 500%, between about 5% and about 300%, between about 10% and about 200%, between about 15% and about 200%, between about 20% and about 200%, between about 25% and about 200%, between about 30% and about 200%, between about 40% and about 200%, between about 50% and about 200%, between about 5% and about 100%, between about 10% and about 100%, between about 15% and about 100%, between about 20% and about 100%, between about 25% and about 100%, between about 30% and about 100%, between about 40% and about 100%, or between about 50% and about 100%, with respect to a control cell. In various examples, the biomass productivity increase can be determined after 1, 2, 3, 4, 5, 6, 7, 8, 9, 10, 11, 12, 13, 14 or more days of semi-continuous growth. Alternatively, the biomass productivity increase can be demonstrated after at least 1, 2, 3, 4, 5, 6, or 7 days of batch growth.

A further aspect of the present invention is a recombinant microorganism according to any of the previous examples, e.g., a recombinant microorganism comprising a non-native gene encoding a CHORD-derived polypeptide or a SKP1 polypeptide as described herein, wherein the recombinant microorganism demonstrates increased lipid productivity, for example, increased FAME productivity. The FAME productivity can be at least 5% increased with respect to a control microorganism, such as, for example, increased between about 5% and about 500%, or between 10% and about 300%, or about 10% and about 200%, or about 10% and about 100%, or about 15% and about 90%, a with respect to a control microorganism. In some examples, the lipid, such as FAME, productivity can be between about 5% and about 500%, between about 5% and about 300%, between about 10% and about 200%, between about 15% and about 200%, between about 20% and about 200%, between about 25% and about 200%, between about 30% and about 200%, between about 40% and about 200%, between about 50% and about 200%, between about 5% and about 100%, between about 10% and about 100%, between about 15% and about 100%, between about 20% and about 100%, between about 25% and about 100%, between about 30% and about 100%, between about 40% and about 100%, or between about 50% and about 100%, with respect to a control cell. In some examples, the increased FAME productivity increase can be demonstrated after 1, 2, 3, 4, 5, 6, 7, 8, 9, 10, 11, 12, 13, 14 or more days of semi-continuous growth. Alternatively or in addition, the FAME productivity increase can be demonstrated after at least 1, 2, 3, 4, 5, 6, or 7 days of batch growth.

Suitable host microorganisms to be modified using materials and methods according to the present invention include, but are not limited to, algal cells, heterokont cells, or fungal cells. Heterokont species considered for use in this invention include, but are not limited to, Bacillariophytes, Eustigmatophytes, and Labyrinthulomycetes. Labyrinthulomycetes include, for example, species of *Labryinthula, Labryinthuloides, Thraustochytrium, Schizochytrium, Aplanochytrium, Aurantiochytrium, Oblongichytrium, Japonochytrium, Diplophrys,* and *Ulkenia.*

Algal species suitable for the method of the present invention include microalgae such as, for example, species of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Ehpsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phceodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox.* Non-limiting examples of exemplary species include, for instance, diatoms such as, for example, a species of any of the genera *Amphora, Chaetoceros, Cyclotella, Fragilaropsis, Navicula, Nitzschia, Phceodactylum,* or *Thalassiosira,* or Eustigmatophytes such as species of any of the genera *Eustigmatos, Monodus, Nannochloropsis, Pseudostaurastrum,* or *Vischeria.*

In various aspects of the present invention, a microorganism that includes a non-native gene as provided herein can have improved productivity when compared with a control microorganism that does not include the non-native gene. Higher productivity can be demonstrated, for example, by measuring growth rates or total organic carbon (TOC) or ash free dry weight accumulation, or by quantitating any of various biomolecules produced by the recombinant microorganism (such as for example, one or more lipids, polymers, proteins, pigments, carbohydrates, etc.).

Also provided herein are methods of producing biomass or at least one bioproduct by culturing recombinant microorganisms having increased productivity, such as any of the recombinant microorganisms disclosed herein. The methods include culturing a recombinant microorganism as disclosed herein that includes a non-native nucleic acid encoding a CHORD-derived polypeptide or a SKP1 polypeptide as disclosed herein in a suitable medium to provide a microorganism culture and recovering biomass or at least one bioproduct from the culture. The method can optionally include inducing expression of the non-native gene. The microorganism can be a heterokont species, such as such as a labyrinthuylomycete of any of the genera *Labryinthula, Labryinthuloides, Thraustochytrium, Schizochytrium, Aplanochytrium, Aurantiochytrium, Oblongichytrium, Japonochytrium, Diplophrys,* and *Ulkenia.* The microorganism in some examples can be a microalga, such as but not limited to a species of any of the genera disclosed herein. The algal culture can in some examples be a photoautotrophic culture. Nonlimiting examples of products that can be made using the methods include biomass, lipids, polyketides, terpenoids, pigments, antioxidants, vitamins, nucleotides, nucleic acids, amino acids, carbohydrates, alcohols, hormones, cytokines, peptides, proteins, or polymers. The bioproduct can be further defined as a food, feed, biofuel, bio-chemical, pharmaceutical, or medicinal product.

For example, the method of producing biomass or at least one bioproduct can include culturing a recombinant algal microorganism as disclosed herein that includes a non-native nucleic acid molecule encoding a CHORD-derived polypeptide or a SKP1 polypeptide, wherein said algal microorganism belongs to a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phceodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox,* to produce biomass or at least one bioproduct. The method can optionally further include recovering biomass or at least one bioproduct from the culture, for example, from the culture medium, whole culture, or cells. The algal cell can, for example, belong to a genus selected from the group consisting of *Chlorella, Cyclotella, Eustigmatos, Monodus, Nannochloropsis, Parachlorella, Phceodactylum, Pseudochlorella, Pseudostaurastrum, Vischeria,* and *Tetraselmis.* In some instances, the culturing is performed under photoautotrophic conditions. Nonlimiting examples of products that can be made using the methods include biomass, lipids, polyketides, terpenoids, pigments, antioxidants, vitamins, nucleotides, nucleic acids, amino acids, carbohydrates, alcohols, hormones, cytokines, peptides, proteins, or polymers. The bioproduct can be further defined as a food, feed, biofuel, bio-chemical, pharmaceutical, or medicinal product.

In a further aspect the present invention provides isolated or recombinant nucleic acid molecules comprising a nucleic acid sequence encoding a polypeptide that includes an amino acid sequence having at least 60%, at least 65%, at least 70%, at least 75%, at least 80%, at least 85%, at least 90%, at least 95%, or about 100% identity to a polypeptide sequence selected from the group consisting of: SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90.

In some examples, an isolated or recombinant nucleic acid molecule as provided herein can encode a polypeptide that includes an amino acid sequence that encodes at least a portion of a CHORD domain, and in some examples can include a single CHORD domain or a portion of a CHORD domain, which can be, for example, a CHORD domain having at least 80% identity to SEQ ID NO:4 or at least 60% of SEQ ID NO:4, e.g., at least 36, 37, 38, 39, or 40 contiguous amino acids of SEQ ID NO:4. For example, the isolated or recombinant nucleic acid molecule can encode a polypeptide having at least 60%, 65%, 70%, 75%, 80%, 85%, 90%, 95%, or 99% identity to SEQ ID NO:22, SEQ ID NO:99, or SEQ ID NO:100.

In another aspect of the present invention, an isolated or recombinant nucleic acid molecule is provides that encodes a polypeptide that includes an amino acid sequence that encodes at least one SKP1 family protein domain selected from the group consisting of at least one Pfam3931 domain having at least 80% identity to SEQ ID NO:101 and at least one Pfam1466 domain having at least 80% identity to SEQ ID NO:102.

The isolated or recombinant nucleic acid molecule can encode a polypeptide that is a SKP1 protein or has at least 80% identity to a SKP1 polypeptide of a plant or microbial species. Alternatively or in addition, the polypeptide can have at least 50%, at least 55%, at least 60%, at least 65%, at least 70%, at least 75%, at least 80%, at least 85%, at least 90%, at least 95%, or about 100% identity to a SKP1 polypeptide of a microalga or heterokont species.

For example, an isolated or recombinant nucleic acid molecule can encode a polypeptide that includes an amino acid sequence having at least 65%, at least 70%, at least 75%, at least 80%, and least 85%, at least 90%, at least 95%, or about 100% identity to a polypeptide sequence selected from the group consisting of SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90.

In various examples the recombinant nucleic acid sequence encoding the polypeptide has at least one mutation with respect to a naturally-occurring gene or lacks at least one intron that is present in the naturally-occurring gene. Alternatively or in addition, the disclosed recombinant nucleic acid sequence comprises cDNA. Further alternatively or in addition, the nucleic acid sequence encoding the polypeptide can be operably linked to a heterologous promoter and/or may be a vector.

In another example, the nucleic acid molecule encodes a guide RNA of a CRISPR/Cas9 system, wherein the guide RNA targets at least a portion of a naturally occurring microorganism gene encoding a polypeptide having an amino acid sequence with at least 55%, at least 60%, at least 65%, at least 70%, at least 75%, at least 80%, at least 85%, at least 90%, at least 95%, or about 100% identity to SEQ ID NO:22 or SEQ ID NO:92.

In some examples, expression of a recombinant nucleic acid molecule as disclosed above in a microorganism results in increased productivity of the microorganism, such as enhanced proliferation, biomass accumulation, or production of a biomolecule.

BRIEF DESCRIPTION OF THE DRAWINGS

FIG. 2A) Cartoon depicting the site of vector integration into the intron between the third and fourth exons of CHORD gene 3266 in strain GE-5877 as determined by MiSeq analysis. Location of primers used for PCR verification of insertion are depicted as thin black arrows flanking the vector integration site. FIG. 2B) Picture of gel after separating PCR products of the CHORD genomic region in insertion mutant GE-5877 compared to wildtype WE-3730: 1 and 4: molecular weight markers, 2: WE3730 (wild type) DNA, 3: GE-5877 (CHORD insertion) DNA. Expected sizes for the wild type and GE-5877 are 386 base pairs and 4505 base pairs respectively. FIG. 2C) Bar graph showing transcript levels as determined by qRT-PCR of two distinct regions of the CHORD-3266 transcript. Sequence specific primers sets for Exon 2 and Exon 4 were used to amplify the specified regions from wild type and GE-5877 samples. Exon 2 is upstream of the vector integration site, while Exon 4 is downstream of the vector integration site. qRT-PCR was performed on RNA samples isolated on Day 4 of the growth assay depicted in panel C. FIG. 2D) Line graphs showing optical density and FIG. 2E) cell counts for wild type and GE-5877 over six days of batch growth. FIG. 2F) Bar graphs depicting FAME and FIG. 2G) total organic carbon (TOC) productivities on Day 4 and Day 6 of the growth assay depicted in panel C.

FIGS. 3A-3B provide transcriptomic data. FIG. 3A) Scatter plot depicting global gene expression analysis of the CHORD mutant GE-5877 transcriptome against wild type WE-3730. Light colored dots represent statistically significant fold changes across the biological replicates while the horizontal bars indicate a 1.5 fold cut-off. FIG. 3B) Gene Ontology (GO) analysis for GO categories enriched for genes with altered expression in CHORD mutant strain GE-5877. The top 10 categories with statistical significance are shown. Abbreviations: CPM, counts per million reads; BP, Biological process; CC, cellular component; MF, molecular function.

FIG. 4A) Diagram of wild type and mutant CHORD-3266 gene locus. Exons are labeled and intervening thin lines are introns. CHORD domain 1 and CHORD domain 2 are depicted by white boxes flanking Exon 2 and 3 and Exon 3 and 4 respectively. Transcripts detected by MiSeq analysis are represented by thin black arrows below the gene diagram. Wildtype strain WE-3730 only contained the native CHORD-3266 transcript while strain GE-5877 expressed two non-native fusion transcripts, labeled 5' fusion transcript and 3' fusion transcript respectively. FIG. 4B) Diagram of approaches taken to recapitulate the phenotype of GE-5877. Unsuccessful approaches included knocking out Exon 1, knocking out Exon 4, and overexpressing exons 1-3 and the productivity results are represented by white downward facing arrow or equal sign. Overexpressing the 3' fusion transcript comprising the end of the integrated vector, intron 3 and Exon 4 resulted in increase productivity compared to wild type, which is depicted by the solid upward facing arrow. FIG. 4C) Line graph depicting absorbance of strain GE899 expressing the 3' fusion transcript compared to original CHORD mutant GE-5877 and wild type strain WE-3730 over the course of 5 days of batch growth.

FIG. 8A) FAME and FIG. 8B) TOC produced by the cultures in Assay 1. FIG. 8C) FAME and FIG. 8D) TOC produced by the cultures in Assay 2. For each semicontinuous assay, each strain was run in triplicate. Data points represent the average of three replicates and error bars depict standard deviation.

DETAILED DESCRIPTION OF THE INVENTION

Figure 1:
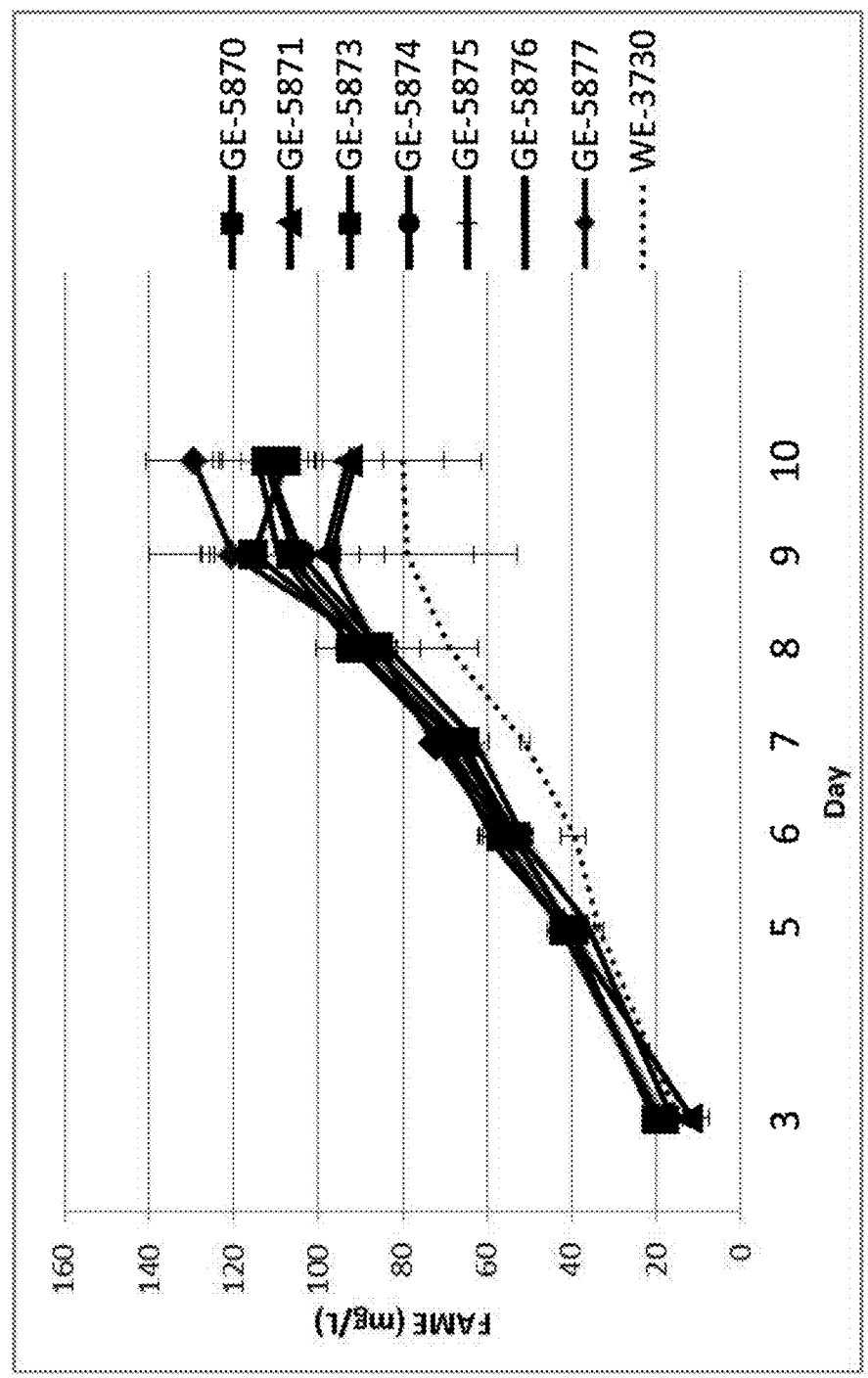
FIG. 1 provides a graph depicting fatty acid methyl ester (FAME) values over 10 days of batch growth for eight different *Nannochloropsis gaditana* strains. All random integrant mutant strains (GE-5870, GE-5871, GE-5873, GE-5874, GE-5875, GE-5876, and GE-5877) outperform wildtype strain WE-3730.

The present application relates to compositions, methods, and related materials for modifying characteristics of microorganisms, particularly those associated with improved productivity. In various aspects, the application discloses recombinant microorganisms, such as microalgae and heterokonts that express a non-native gene that affects productivity, such as, for example, biomass or lipid productivity.

Throughout this disclosure, various information sources are referred to and/or incorporated by reference. The information sources include, for example, scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. It should also be noted that the reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

Some Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof "A and/or B" is used herein to include all of the following alternatives: "A", "B", and "A and B".

"About" can mean plus or minus 10% of the provided value. Where ranges are provided, they are inclusive of the boundary values. "About" can additionally or alternately mean either within 10% of the stated value, or within 5% of the stated value, or in some cases within 2.5% of the stated value, or, "about" can mean rounded to the nearest significant digit.

Reference to properties that are "substantially the same" or "substantially identical" without further explanation of the intended meaning, is intended to mean the properties are within 10%, and preferably within 5%, and may be within 2.5%, of the reference value. Where the intended meaning of "substantially" in a particular context is not set forth, the term is used to include minor or irrelevant deviations that are not believed to be material to the characteristics considered important in the context of the invention.

As used herein, "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, y-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that function in a manner similar to a naturally-occurring amino acid.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation) that does not encode a complete functional open reading frame or that has decreased expression due to alteration or disruption of gene regulatory sequences. An attenuated gene may also be a gene targeted by a construct that reduces expression of the gene, such as, for example, an antisense RNA, microRNA, RNAi molecule, or ribozyme. Attenuated gene expression can be gene expression that is eliminated, for example, reduced to an amount that is insignificant or undetectable. Attenuated gene expression can also be gene expression that results in an RNA or protein that is not fully functional or nonfunctional, for example, attenuated gene expression can be gene expression that results in a truncated RNA and/or polypeptide.

"Biofuels", as used herein, refer to renewable energy sources from living organisms, such as higher plants, fungi, algae, or microorganisms. As such, biofuels can be solid, liquid or gaseous fuels derived from algal, fungal, microbial or plant materials, biomass, sugars or starches, such as ethanol or biodiesel derived from vegetable oils or algal oil, and the like. A biofuel is a fuel in its own right, but may be blended with petroleum-based fuels to generate a finished fuel. A biofuel may be used as a replacement for petrochemically-derived gasoline, diesel fuel, or jet fuel.

A "cDNA" is a DNA molecule that comprises at least a portion of the nucleotide sequence of an mRNA molecule, with the exception that the DNA molecule substitutes the nucleobase thymine, or T, in place of uridine, or U, occurring in the mRNA sequence. A cDNA can be single-stranded or double-stranded, and can be the complement of the mRNA sequence. In preferred examples, a cDNA does not include one or more intron sequences that occur in the naturally-occurring gene (in the genome of an organism) that the cDNA corresponds to. For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene, but are separated by an intron). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences and/or compiled from the sequences of multiple partial cDNAs.

A "control microorganism", "control organism", or "control cell" as used in the present invention provides a reference point for measuring changes in phenotype of the subject microorganism, organism, or cell. A control microorganism, organism, or cell may comprise, for example, (a) a wild-type microorganism, organism, or cell, i.e., of the same genotype as the starting material for the genetic alteration which resulted in the subject microorganism, organism, or cell; (b) a microorganism, organism or cell of the same genotype as the starting material but which has been transformed with a null construct (i.e., a construct which has no known effect on the trait of interest, such as a construct lacking a gene encoding the polypeptide of interest, e.g., lacking a gene encoding a CHORD, CHORD-derived, CHORD-like, SKP1, or SKP1-like polypeptide); (c) a microorganism, organism, or cell which is a non-transformed segregant among progeny of a subject microorganism, organism, or cell; or (d) the subject microorganism, organism, or cell itself, under conditions in which the gene of interest is not expressed. In some instances, "control microorganism" may in some cases refer to a microorganism that does not contain the exogenous nucleic acid present in the transgenic microorganism of interest, but otherwise has the same or similar genetic background as such a transgenic ("engineered" or "recombinant") microorganism.

"Domains" are groups of substantially contiguous amino acids in a polypeptide that can be used to characterize protein families and/or parts of proteins. Such domains may have a "fingerprint", "motif", or "signature" that can comprise conserved primary sequence, secondary structure, and/or three-dimensional conformation. Generally, domains are correlated with specific in vitro and/or in vivo activities. A domain can be of any size, by way of example, a domain may have a length of from 4 amino acids to about 400 amino acids, e.g., from 4 to about 200 amino acids, or 8 to about 150 amino acids, or 4 to about 10 amino acids, or about 10 to about 100 amino acids, or about 15 to about 65 amino acids, or about 20 to about 100 amino acids, or about 25 to 120 amino acids, or about 100 to about 200 amino acids, or about 300 to about 500 amino acids.

"Down-regulation" refers to regulation that decreases production of expression products (mRNA, polypeptide, biological activity, or combinations of any thereof) relative to basal or native states.

The term "endogenous," within the context of the present disclosure refers to any polynucleotide, polypeptide or protein sequence which is a natural part of a cell.

"Exogenous" with respect to a nucleic acid or gene indicates that the nucleic or gene has been introduced ("transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. An exogenous nucleic acid can also be a sequence that is homologous to an organism (i.e., the nucleic acid sequence occurs naturally in that species or encodes a polypeptide that occurs naturally in the host species) that has been reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. An nucleic acid is considered exogenous if it has been introduced into a progenitor of the cell, organism, or strain under consideration.

"Fragment", with respect to a polynucleotide, refers to a clone or any part of a polynucleotide molecule, particularly a part of a polynucleotide that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, for example at least about 30 nucleotides or at least about 50 nucleotides of any of the sequences provided herein. Exemplary polynucleotide fragments are the first sixty consecutive nucleotides of the polynucleotides listed in the Sequence Listing. Exemplary fragments can additionally or alternatively include fragments that comprise, consist essentially of, or consist of a region that encodes a conserved CHORD or SKP1 family domain of a polypeptide. Exemplary fragments can additionally or alternatively include fragments that comprise a conserved domain of a polypeptide.

Fragments may additionally or alternatively include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, for example at least about 20 amino acid residues in length, for example at least about 30 amino acid residues in length. Preferentially a fragment is a functional fragment that has at least one property or activity of the polypeptide from which it is derived, such as, for example, the fragment can include a functional domain or conserved domain of a polypeptide. A domain can be characterized, for example, by a Pfam or Conserved Domain Database (CDD) designation.

As used herein, the term "CHORD-derived polypeptide" refers to polypeptides comprising at least 60% of a CHORD domain or comprising an amino acid sequence having at least 80% identity to at least 60% of a CHORD domain of a naturally occurring polypeptide, for example, comprises an amino acid sequence having at least 80% identity to at least 35, at least 36, at least 37, at least 38, at least 39, or at least 40 contiguous amino acids of a naturally-occurring CHORD domain. In specific examples, the CHORD domain has at least 80% identity to at least 36 contiguous amino acids of SEQ ID NO:4 or at least 80% identity to at least 36 contiguous amino acids of a CHORD domain (amino acids 273-338) of SEQ ID NO:92. In further examples, the polypeptide comprises an amino acid sequence having at least 80% identity to the amino acid sequence of SEQ ID NO:99 or at least 35, 40, 45, 50, or 100 contiguous amino acids thereof. For example, the polypeptide can have at least 65%, at least 70%, at least 75%, at least 80%, at least 85%, at least 90%, at least 95%, or between 95% and 100% identity to SEQ ID NO:100.

The term "functional homolog" as used herein describes those molecules that have sequence similarity and also share at least one functional characteristic such as a biochemical activity. Functional homologs will typically give rise to the same characteristics to a similar, but not necessarily the same, degree. Functionally homologous proteins give the same characteristics where the quantitative measurement produced by one homolog is at least 10% of the other; more typically, at least 20%, between about 30% and about 40%; for example, between about 50% and about 60%; between about 70% and about 80%; or between about 90% and about 95%; between about 98% and about 100%, or greater than 100% of that produced by the original molecule. Thus, where the molecule has enzymatic activity the functional homolog will have the above-recited percent enzymatic activities compared to the original enzyme. Where the molecule is a DNA-binding molecule (e.g., a polypeptide) the homolog will have the above-recited percentage of binding affinity as measured by weight of bound molecule compared to the original molecule.

A functional homolog and the reference polypeptide may be naturally occurring polypeptides, and the sequence similarity may be due to convergent or divergent evolutionary events. Functional homologs are sometimes referred to as orthologs, where "ortholog", refers to a homologous gene or protein that is the functional equivalent of the referenced gene or protein in another species.

Variants of a naturally-occurring functional homolog, such as polypeptides encoded by mutants or a wild-type coding sequence, may themselves be functional homologs. As used herein, functional homologs can also be created via site-directed mutagenesis of the coding sequence for a productivity-modulating polypeptide, for example a CHORD, CHORD-derived, or SKP1 polypeptide, or by combining domains from the coding sequences for different naturally-occurring CHORD, CHORD-derived, or SKP1 polypeptides. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of biomass-modulating polypeptides. Sequence analysis can involve BLAST, Reciprocal BLAST, or PSI-BLAST analysis of non-redundant databases using amino acid sequence of a biomass-modulating polypeptide as the reference sequence. Amino acid sequence is, in some instances, deduced from the nucleotide sequence. Typically, those polypeptides in the database that have greater than 40% sequence identity are candidates for further evaluation for suitability as a biomass-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in productivity-modulating polypeptides, e.g., conserved functional domains.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

When used in reference to a polynucleotide, a gene, a nucleic acid, a polypeptide, or an enzyme, the term "heterologous" refers to a polynucleotide, gene, a nucleic acid, polypeptide, or an enzyme not derived from the host species, e.g., is from a different species with respect to the host cell. For example, a transgenic *Nannochloropsis* microorganism transformed with the coding sequence for a fatty acid desaturase from a *Tetraselmis* microorganism or from a plant is transformed with a heterologous desaturase gene. When referring to nucleic acid sequences operably linked or otherwise joined to one another in a nucleic acid construct or molecule, "heterologous sequences", as used herein, are those that are not operably linked or are not contiguous to each other in nature. For example, a promoter from *Tetraselmis* sp. is considered heterologous to a *Nannochloropsis* coding region sequence. Also, a promoter from a gene encoding a CHORD, CHORD-derived, CHORD-like, SKP1, or SKP1-like gene from Nannochloropsis is considered heterologous to a sequence encoding a *Nannochloropsis* fatty acid desaturase. Similarly, when referring to a gene regulatory sequence or to an auxiliary nucleic acid sequence used for maintaining or manipulating a gene sequence (e.g., a promoter, enhancer, 5' untranslated region, 3' untranslated region, Kozak sequence, poly A addition sequence, intron sequence, splice site, ribosome binding site, internal ribosome entry sequence, genome homology region, recombination site, etc.), "heterologous" means that the regulatory sequence or auxiliary sequence is from a different source (e.g., different gene, whether from the same or different species as the host organisms) than the gene with which the regulatory or auxiliary nucleic acid sequence is juxtaposed in a construct, genome, chromosome, or episome. When referring to a protein functional domain, such as a localization sequence or a receptor binding site, "heterologous" can also mean that the protein functional domain is from a different source (e.g., protein) than the rest of the protein region with which it is juxtaposed in an engineered protein. Similarly, when referring to a promoter sequence of an engineered gene, "heterologous" means that the promoter is derived from a different gene than that to which it is linked by genetic engineering.

Furthermore, the term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g., a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter," even though the promoter may be derived from the same species (or, in some cases, the same organism) as the gene to which it is linked.

When used in reference to a polynucleotide, a gene, a nucleic acid, a polypeptide, or an enzyme, the term "homologous" refers to a polynucleotide, gene, a nucleic acid, polypeptide, or an enzyme derived from the host species, e.g., is from the same species with respect to the host cell, regardless of whether the homologous polynucleotide, gene, nucleic acid, polypeptide, or enzyme has been introduced into the host cell (exogenous) or is endogenous with respect to the host cell.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable. In some circumstances "substantially free" may mean that the nucleic acid molecule or nucleotide sequence is free of at least 95% (w/w) of cellular material and components.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell such that it differs in sequence or location in the genome with respect to its position in a non-manipulated organism (i.e., is juxtaposed with or operably linked to sequences it is not juxtaposed with or operably linked to in a non-transformed organism) is considered "non-native". Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid molecule that comprises a gene or a portion thereof can be a coding (sense) strand or a non-coding (antisense) strand.

A nucleic acid molecule or sequence may be "derived from" an indicated source, which includes the isolation (in whole or in part) of a nucleic acid segment from an indicated source. A nucleic acid molecule or sequence may also be derived from an indicated source by, for example, direct cloning, PCR amplification, or artificial synthesis from the indicated polynucleotide source or based on a sequence associated with the indicated polynucleotide source, which may be, for example, a species of organism. Genes or nucleic acid molecules or sequences (such as, for example promoters) derived from a particular source or species also include genes or nucleic acid molecules or sequences having sequence modifications with respect to the source nucleic acid molecules. For example, a gene or nucleic acid molecule or sequence derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. In some examples the sequence may be truncated or internally deleted with respect to the nucleic acid sequence from which it is derived, as for example, a promoter that may be shortened or internally deleted with respect to a naturally-occurring promoter from which it is derived. A gene or nucleic acid molecule or sequence that is derived from a referenced gene or nucleic acid molecule or sequence that encodes a functional RNA or polypeptide can encode a functional RNA or polypeptide having at least 65%, at least 70%, at least 75%, at least 80%, at least 85%, at least 90%, or at least 95%, sequence identity with the referenced or source functional RNA or polypeptide, or to a functional fragment thereof. For example, a gene or nucleic acid molecule or sequence that is derived from a referenced gene or nucleic acid molecule or sequence that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be substantially free of chemicals beyond buffer or solvent, for example. "Substantially free" is not intended to mean that other components beyond the novel nucleic acid molecules are undetectable.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest.

"Percentage of sequence identity" or "percent (%) [sequence] identity", as used herein, is determined by comparing two optimally locally aligned sequences over a comparison window defined by the length of the local alignment between the two sequences. (This may also be considered percentage of homology or "percent (%) homology".) The amino acid sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g., BLAST). The percentage identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (*Add. APL. Math.* 2:482, 1981), by the global homology alignment algorithm of Needleman and Wunsch (*J. Mol. Biol.* 48:443, 1970), by the search for similarity method of Pearson and Lipman (*Proc. Natl. Acad. Sci. USA* 85: 2444, 1988), by heuristic implementations of these algorithms (NCBI BLAST, WU-BLAST, BLAT, SIM, BLASTZ), or by inspection. GAP and BESTFIT, for example, can be employed to determine their optimal alignment of two sequences that have been identified for comparison. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, for example, at least 70%, at least 80%, at least 85%, at least 90%, at least 95%, or at least 96%, 97%, 98% or 99% sequence identity compared to a reference sequence using the programs. In addition, pairwise sequence homology or sequence similarity, as used refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Query nucleic acid and amino acid sequences were searched against subject nucleic acid or amino acid sequences residing in public or proprietary databases. Such searches were done using the National Center for Biotechnology Information Basic Local Alignment Search Tool (NCBI BLAST v 2.18) program. The NCBI BLAST program is available on the interne from the National Center for Biotechnology Information (blast.ncbi.nlm.nih.gov/Blast.cgi). Typically the following parameters for NCBI BLAST were used: Filter options were set to "default", the Comparison Matrix was set to "BLOSUM62", the Gap Costs were set to "Existence: 11, Extension: 1", the Word Size was set to 3, the Expect (E threshold) was set to 1e-3, and the minimum length of the local alignment was set to 50% of the query sequence length. Sequence identity and similarity may also be determined using GENOMEQUEST™ software (Gene-IT, Worcester, Mass. USA).

A "promoter" refers to a transcription control sequence that is capable of initiating transcription in a host cell and can drive or facilitate transcription of a nucleotide sequence or fragment thereof of the instant invention. Such promoters need not be of naturally-occurring sequences. In addition, it will be understood that such promoters need not be derived from the target host cell or host organism. The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within 1 kb, 2 kb, 3 kb, 4 kb, 5 kb or more of the transcriptional start site of a gene, where the additional sequences can influence the rate of transcription of the downstream gene and optionally the responsiveness of the promoter to developmental, environmental, or biochemical (e.g., metabolic) conditions.

"Polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or, in the case of peptidomimetics, other bonds such as, for example, ester or ether bonds. Full-length polypeptides, truncated polypeptides, point mutants, insertion mutants, splice variants, chimeric proteins, and fragments thereof are encompassed by this definition. As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

As used herein, the expression "substantially conserved amino acid sequences" refers to regions of amino acid homology between polypeptides of the same type or family from different sources. In the present invention, examples of substantially conserved amino acid sequences include those specified as CHORD domains in FIG. 4 and FIG. 5, as well as SKP1 family tetramerization and dimerization domains as are highlighted in FIG. 6. One skilled in the art could align the amino acid sequences of CHORD-like or SKP1-like polypeptides, from different sources to CHORD and SKP1 polypeptide sequences described herein to identify the segments therein which are the substantially conserved amino acid sequences defined herein. The skilled person could then determine whether the identified segments have the characteristics disclosed and claimed in the present invention.

As used herein "progeny" means a descendant, offspring, or derivative of an organism. For example, daughter cells from a transgenic alga are progeny of the transgenic alga. Because certain modifications may occur in succeeding generations due to either mutations or environmental influences, such progeny, descendant, or derivatives may not, in fact, be identical to the parent cell, but are still included within the scope of the term as used herein.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering, for example, by expression of a genetically engineered nucleic acid molecule in a cell. The term "recombinant protein" as used herein refers to a protein produced by genetic engineering regardless of whether the amino acid varies from that of a wild-type protein.

The term "regulatory region" "regulatory sequence", "regulatory element", or "regulatory element sequence", as used in the present invention, refer to a nucleotide sequence that influences transcription or translation initiation or rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

As used herein, "transgenic organism" refers to an organism which comprises a heterologous polynucleotide, that is, a polynucleotide that has been introduced into the organism by non-natural means (human intervention). When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. Generally, the heterologous polynucleotide is stably integrated within the genome such that the polynucleotide is passed on to successive generations, although it can also be present on an episome, and may be present on a synthetic chromosome of the transgenic organism. The non-native polynucleotide may be integrated into the genome alone or as part of a recombinant expression cassette. In additional examples, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases, zinc finger nucleases, TALENs, or Crisper nucleases. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

For nucleic acids and polypeptides, the term "variant" is used herein to denote a polypeptide, protein, or polynucleotide molecule with some differences, generated synthetically or naturally, in their base or amino acid sequences as compared to a reference polypeptide or polynucleotide, respectively, such that the variant has at least 70% sequence identity to the reference polypeptide or polynucleotide. In other embodiments the variant can have at least 80%, at least 95%, at least 90% or at least 95%, at least 97%, at least 98%, or at least 99% sequence identity to the reference polypeptide or polynucleotide. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation, phosphorylation, etc.).

As used herein, "vector" refers to a nucleic acid molecule that includes at least one of a selectable marker gene or an origin of replication or autonomous replication sequence (ARS) that allows the vector to be replicated in a host cell, and in some examples includes both a selectable marker gene and at least one origin of replication or ARS. A vector in various examples includes one or more expression sequences and/or can include at least one sequence for mediating recombination.

Gene and protein Accession numbers, commonly provided in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 100, less than about 80, less than about 50, less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free -OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" [of a gene product] includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination to knockout a particular gene of interest. In still other embodiments, RNAi or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TALENs, and/or CRISPR technologies, and the like. A mutant is therefore not a naturally-occurring organism. A mutant organism of interest will typically have a phenotype different than that of the corresponding wild type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; can be a gene that has one or more point mutations leading to a change in the amino acid of the encoded protein or results in aberrant splicing of the gene transcript, etc.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 28.0 (May 2015) based on the UniProt protein database release 2012_06. Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) Nucleic Acids Research 26, 263-266; Bateman (2004) *Nucleic Acids Research* 32, Database Issue, D138-D141; Finn (2006) *Nucleic Acids Research* Database Issue 34, D247-251; Finn (2010) *Nucleic Acids Research* Database Issue 38, D211-222). By accessing the Pfam database, for example, using any of the above-reference websites, protein sequences can be queried against the HMMs using HMMER homology search software (e.g., HMMER2, HMMER3, or a higher version, hmmerj anelia.org/). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

"The same conditions" or "the same culture conditions", as used herein, means substantially the same conditions, that is, any differences between the referenced conditions are minor and not relevant to the function or properties of the microorganism that are material to the invention, e.g., do not affect lipid production or biomass production.

"Nitrogen replete" conditions, with respect to a particular cell type, are conditions under which the cell does not experience growth deficient due to insufficient nitrogen.

As used herein "lipid" or "lipids" refers to fats, waxes, fatty acids, fatty acid derivatives such as fatty alcohols, wax esters, alkanes, and alkenes, sterols, monoglycerides, diglycerides, triglycerides, phospholipids, sphingolipids, saccharolipids, and glycerolipids. "FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. Lipid productivity can be assessed as FAME productivity in milligrams per liter (mg/L) and for algae, may be reported as grams per meter$^2$ per day (g/m$^2$/day). In the semi-continuous assays provided herein, mg/L values are converted to g/m2/day by taking into account the area of incident irradiance (the SCPA flask rack aperture of 1½"× 3⅜", or 0.003145 m$^2$) and the volume of the culture (550 ml). To obtain productivity values in g/m2/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise.

"Biomass" refers to cellular mass, whether of living or dead cells, and can be assessed, for example, as aspirated pellet weight, but is more preferably dry weight (e.g., lyophilate of a culture sample or pelleted cells), ash-free dry weight (AFDW), or total organic carbon (TOC), using methods known in the art. Biomass increases during the growth of a culture under growth permissive conditions and may be referred to as "biomass accumulation" in batch cultures, for example. In continuous or semi-continuous cultures that undergo steady or regular dilution, biomass that is produced that would otherwise accumulate in the culture is removed during culture dilution. Thus, daily biomass productivity (increases in biomass) by these cultures can also be referred to as "biomass accumulation". Biomass productivity can be assessed as TOC productivity in milligrams per liter (mg/L) and for algae, may be reported as grams per meter$^2$ per day (g/m$^2$/day). In the semi-continuous assays provided herein, mg/L values are converted to g/m2/day by taking into account the area of incident irradiance (the SCPA flask rack aperture of 1½"×3⅜", or 0.003145 m$^2$) and the volume of the culture (550 ml). To obtain productivity values in g/m2/day, mg/L values are multiplied by the daily dilution rate (30%) and a conversion factor of 0.175. Where biomass is expressed as a percentage, the percentage is a weight percent unless indicated otherwise.

In the context of the invention, a "nitrogen source" is a source of nitrogen that can be taken up and metabolized by the subject microorganism and incorporated into biomolecules for growth. For example, compounds including nitrogen that cannot be taken up and/or metabolized by the microorganism for growth (e.g., nitrogen-containing biological buffers such as Hepes, Tris, etc.) are not considered nitrogen sources in the context of the invention.

Disclosed herein are methods for manipulating, assaying, culturing, and analyzing microorganisms. The invention set forth herein also makes use of standard methods, techniques, and reagents for cell culture, transformation of microorganisms, genetic engineering, and biochemical analysis that are known in the art.

All headings are for the convenience of the reader and do not limit the invention in any way.

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein; this reference does not constitute an admission that any of these documents forms part of the common general knowledge in the art.

The discussion of the general methods given herein is intended for illustrative purposes only and are not intended to be limiting. Other alternative methods and embodiments will be apparent to those of skill in the art upon review of this disclosure.

Mutant Microorganisms Having Increased Productivity

The invention provides mutant microorganisms having at least 5% increased biomass productivity, such as AFDW or TOC, compared to a control microorganism and/or at least 5% increased lipid productivity, such as FAME, (e.g., higher productivity per day, preferably averaged over the culture period) with respect to the control microorganism when both the mutant microorganism and control microorganism are cultured under identical conditions. Biomass productivity can be assessed, for example, as ash-free dry weight (AFDW) production or productivity (e.g., amount produced per day) or total organic carbon (TOC) production or productivity using methods well-known in the art. A mutant microorganism as provided herein can demonstrate a biomass productivity increase of at least 5% with respect to a control microorganism. For example, the biomass productivity, such as AFDW or TOC, can be increased between about 5% and about 500%, or between about 10% and about 300%, or between about 10% and about 200%, or between about 10% and about 100%, with respect to a control microorganism. In various examples, the biomass, such as AFDW or TOC, productivity increase can be determined after 1, 2, 3, 4, 5, 6, 7, 8, 9, 10, 11, 12, 13, 14 or more days of semi-continuous or continuous growth. Alternatively or in addition, the biomass, such as AFDW or TOC, productivity increase can be demonstrated after at least 1, 2, 3, 4, 5, 6, or 7 days of batch growth. Alternatively or in addition to, productivity or biomass productivity or bioproduct productivity is herein determined over a period of time that can be up to, for example, 1 year, 180 days, 90 days, 30 days, 14 days, 7 days, or 5 days.

In some examples, a mutant microorganism as provided herein produces higher amounts of lipid with respect to a control microorganism, for example, under culture conditions in which both the mutant and control microorganism are producing biomass. The lipid or FAME productivity can be at least 5% increased with respect to a control microorganism, such as, for example, increased between about 5% and about 500%, or between 10% and about 300%, or about 10% and about 200%, or about 10% and about 100%, or about 15% and about 90%, a with respect to a control microorganism. In some examples, the increased FAME productivity increase can be demonstrated after 1, 2, 3, 4, 5, 6, 7, 8, 9, 10, 11, 12, 13, 14 or more days of semi-continuous or continuous growth. Alternatively or in addition, the FAME productivity increase can be demonstrated after at least 1, 2, 3, 4, 5, 6, or 7 days of batch growth. In some examples, a mutant microorganism as provided herein produces higher amounts of lipid with respect to a control microorganism under culture conditions in which both the mutant and control microorganism are producing biomass and actively dividing.

Methods of measuring the amount of lipid produced by microorganisms are well-known in the art and provided in the examples herein. Total extractable lipid can be determined according to Folch et al. (1957) *J. Biol. Chem.* 226: 497-509; Bligh & Dyer (1959) *Can. J. Biochem. Physiol.* 37: 911-917; or Matyash et al. (2008) *J. Lipid Res.* 49:1137-1146, for example, and the percentage of biomass present as lipid can also be assessed using Fourier transform infrared spectroscopy (FT-IR) (Pistorius et al. (2008) *Biotechnol & Bioengin.* 103:123-129). Additional references for gravimetric analysis of FAME and TAGs are provided in U.S. Pat. No. 8,207,363 and WO 2011127118 for example, each incorporated herein by reference in its entirety.

Biomass can be assessed by measuring total organic carbon (TOC) or by other methods, such as measuring ash-free dry weight (AFDW). Methods for measuring TOC are known in the art (e.g., U.S. Pat. No. 8,835,149) and are provided herein. Methods of measuring AFDW are also well-known and can be found, for example, in U.S. Pat. No. 8,940,508, incorporated herein by reference in its entirety.

The properties of a recombinant microorganism as provided herein having increased lipid production or biomass production are compared to the same properties of a control microorganism that may be a wild type organism of the same species as the mutant, and is preferably the progenitor strain of the lipid-overproducing mutant. Alternatively, a control microorganism can be a microorganism that is substantially identical to the genetically engineered microorganism with the exception that the control microorganism does not include a non-native nucleic acid molecule as disclosed herein whose expression in the recombinant host leads to higher biomass or lipid productivity. For example, a control microorganism can be a genetically engineered microorganism or classically mutated organism that has been further engineered to generate a recombinant microorganism as disclosed herein that includes a SKP1 or CHORD-derived polypeptide having increased biomass, such as TOC, productivity and/or increased lipid productivity as disclosed herein.

In some examples, a control microorganism can be a microorganism that is substantially identical to recombinant microorganism that includes a non-native gene encoding a SKP1 or CHORD-derived polypeptide, with the exception that the control microorganism does not comprise a non-native nucleic acid molecule as disclosed herein, that leads to an enhanced growth phenotype (i.e., the gene or gene fragment whose expression results in increased biomass, such as AFDW or TOC, productivity or increased lipid, such as FAME, productivity, compared to a control microorganism). The properties of an enhanced productivity mutant comprising a nonnative nucleic acid molecule as disclosed herein (resulting in increased lipid, such as FAME, or biomass, such as AFDW or TOC, productivity) are also be compared with the same properties of a control microorganism that does not comprise said nonnative nucleic acid molecule (regardless of whether the cell or microorganism is "wild-type"). For example, a control microorganism may be a recombinant microorganism not comprising said nonnative nucleic acid molecule as disclosed herein, whose effects are being assessed, etc.

Polynucleotides and Polypeptides of the Invention

In one aspect of the present invention, the disclosure provides isolated or recombinant nucleic acid molecules, nucleic acid molecules that interfere with these nucleic acid molecules, and nucleic acid molecules that hybridize to these nucleic acid molecules. Additional aspects of the present application include the polypeptides encoded by the isolated or recombinant nucleic acid molecules of the present invention.

CHORD Proteins and CHORD-Derived Polypeptides

A CHORD protein can be identified by the sequence characteristics of the CHORD domain. CHORD domains are modules approximately 60 amino acids in length that bind two zinc ions and are usually arranged in tandem, that is, typical CHORD proteins include at least two CHORD domains. Six cysteine and two histidine residues are invariant within the CHORD domain. Three other residues are also invariant and some positions are confined to positive, negative, or aromatic amino acids. In some instances, the CHORD domain has the consensus sequence C-x(4)-C-x(12-13)-C-x(2)-H-x(14)-CC-x(15-16)-C-x(4)-H, where "C" represents cysteine, "H" represents histidine, and "x(n)" represents a string of "n" number of amino acid residues, where the amino acid residue "x" is any amino acid residue. CHORD polypeptides can be identified by methods known in the art such as in silico homology searching (e.g., BLAST searches), genome sequencing and bioinformatic analysis, by PCR (for example, using degenerate primers homologous to conserved sequences such as a CHORD domain) by hybridization, etc. A large number of genome sequences are available in public online databases, including NCBI (National Center for Biotechnology Information) that may be searched for SKP1 and CHORD genes.

An isolated or recombinant nucleic acid molecule as provided herein has a sequence that encodes a polypeptide having an amino acid sequence with at least 65%, at least 70%, at least 75%, at least 80%, at least 85%, at least 90%, at least 95%, at least 96%, at least 97%, at least 98%, or at least 99% identity to a cysteine and histidine rich domain (CHORD) protein selected from the group consisting of SEQ ID NO:22, SEQ ID NO:91, SEQ ID NO:92, SEQ ID NO:93, SEQ ID NO:94, SEQ ID NO:95, SEQ ID NO:96, and fragments thereof. In various examples, an isolated or recombinant nucleic acid molecule as provided herein encodes a "CHORD-derived polypeptide" that includes at least a portion of a CHORD domain of a naturally-occurring CHORD protein or an amino acid sequence having at least 80%, at least 85%, at least 90%, at least 95%, at least 96%, at least 97%, at least 98%, or at least 99% identity thereto. For example, a CHORD-derived polypeptide can have an incomplete CHORD domain, for example, at least 60% but not 100% of a CHORD domain, and can have, for example, at least 35, at least 36, at least 37, at least 38, at least 39, or at least 40 contiguous amino acids of a naturally-occurring CHORD domain or an amino acid sequence at least 80% at least 85%, at least 90%, at least 95%, at least 96%, at least 97%, at least 98%, or at least 99% identity thereto. The CHORD-derived polypeptide can include additional amino acid sequence derived from a naturally-occurring CHORD protein and/or can include amino acid sequence not derived from a naturally-occurring CHORD protein. For example, a CHORD-derived polypeptide can include a portion of a CHORD protein fused to amino acid sequences of a non-CHORD protein, such that the CHORD-derived polypeptide includes amino acid sequence derived from a naturally-occurring CHORD protein (that can include at least a portion of a CHORD domain) and additional amino acid sequences not derived from a CHORD protein. The CHORD protein fragment in some examples can comprise the amino acid sequence of SEQ ID NO:4, SEQ ID NO:99, or SEQ ID NO:100.

An isolated or recombinant nucleic acid molecule as provided herein or a non-native nucleic acid molecule of a recombinant microorganism as disclosed herein can encode a CHORD-derived polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to at least a portion of a CHORD polypeptide of a plant or microbial species, such as, for example, a CHORD polypeptide of a plant, microalgal, or heterokont species. In various examples, the nucleic acid molecules disclosed herein comprise a nucleic acid sequence that encodes a CHORD-derived polypeptide having at least 65% sequence identity to at least a portion of a naturally-occurring polypeptide of an algal or heterokont species, for example, at least 85% sequence identity to a CHORD domain of a naturally-occurring polypeptide of an algal or heterokont species. Alternatively or in addition, the nucleic acid sequence can encode a CHORD-derived polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to a CHORD domain of SEQ ID NO:22, SEQ ID NO:91, SEQ ID NO:92, SEQ ID NO:93, SEQ ID NO:94, SEQ ID NO:95, or SEQ ID NO:96. The CHORD-derived polypeptide in some examples can comprise the amino acid sequence of SEQ ID NO:4, SEQ ID NO:99, or SEQ ID NO:100 or an amino acid sequence having at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4, SEQ ID NO:99, or SEQ ID NO:100.

SKP1 Polypeptides

An isolated or recombinant nucleic acid molecule as provided herein has a sequence that encodes a polypeptide having an amino acid sequence with at least 65%, at least 70%, at least 75%, at least 80%, at least 85%, at least 90%, at least 95%, at least 96%, at least 97%, at least 98%, or at least 99% identity to a S-phase kinase-associated protein 1 (SKP1) protein, e.g., a naturally occurring SKP1 protein such as a SKP1 protein of the engineered host microorganism.

For example, a non-native nucleic acid molecule as provided herein can include a nucleic acid sequence encoding a SKP1 polypeptide having at least 65%, at least 70%, at least 75%, at least 80%, at least 85%, at least 90%, at least 95%, at least 96%, at least 97%, at least 98%, or at least 99% identity to a SKP1 polypeptide selected from the group consisting of SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90.

SKP1 is a member of the SCF complex, binds to F-box containing proteins, and is involved in the ubiquitin protein degradation pathway. A SKP1 protein can be identified by the sequence characteristics of the SKP1 family tetramerization and dimerization domains, as provided herein. A polypeptide comprising a SKP1 family tetramerization domain can recruit to pfam PF03931, e.g., with a bit score greater than the gathering cutoff (21.9), and an E value of less than 1.00E-2 or less than 1.00E-10, when queried against the Pfam database. A polypeptide comprising a SKP1 family dimerization domain can recruit to pfam PF01466, e.g., with a bit score greater than the gathering cutoff (21.2), and an E value of less than 1.00E-2 or less than 1.00E-10., when queried against the Pfam database. Exemplary SKP1 polypeptides comprise both a SKP1 family tetramerization domain (pfam PF03931) and a SKP1 family dimerization domain (pfam PF01466). SKP1 polypeptides can be identified by methods known in the art such as in silico homology searching (e.g., BLAST searches), genome sequencing and bioinformatic analysis, by PCR (for example, using degenerate primers homologous to conserved sequences such as a SKP1 family dimerization domain or SKP1 family tetramerization domain) by hybridization, etc.

An isolated or recombinant nucleic acid molecule as provided herein can encode a polypeptide at least 50%, at least 55%, at least 60%, at least 65%, at least 70%, at least 75%, at least 80%, at least 85%, at least 90%, at least 95%, at least 96%, at least 97%, at least 98%, or at least 99% identity to a SKP1 polypeptide of a plant or microbial species, such as, for example, a SKP1 polypeptide of a plant, microalgal, or heterokont species. In various examples, the nucleic acid molecules disclosed herein comprise a nucleic acid sequence that encodes a SKP1 polypeptide having at least 65% sequence identity to a naturally-occurring polypeptide of an algal or heterokont species, for example, at least 85% sequence identity to a naturally-occurring polypeptide of an algal or heterokont species. Alternatively or in addition, the nucleic acid sequence can encode a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to of SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90, and fragments thereof.

An isolated or recombinant nucleic acid molecule as provided herein, or a non-native nucleic acid molecule of a recombinant microorganism as disclosed herein can in some examples have a nucleotide sequence that is different from (i.e., not 100% identical to) a nucleotide sequence of a naturally-occurring gene and/or the isolated or recombinant nucleic acid molecule can be a cDNA. For example, an isolated or recombinant nucleic acid molecule as provided herein can include a protein-encoding region that lacks one or more intervening non-coding sequences (introns) that are found in the genome of the organism that includes the gene, and can include two or more protein-encoding sequences of the gene that are continuous, where the two or more sequences are separated by introns in the unaltered genome of an organism. For example, the nucleic acid molecule can comprise a cDNA, in which the cDNA comprises a different sequence than is found in the genome of a naturally-occurring organism. Alternatively or in addition, the nucleic acid molecule can comprise a protein-encoding gene that includes a 5' untranslated region that is not contiguous with the protein-encoding portion of the nucleic acid molecule in the genome of a non-genetically modified organism. Alternatively or in addition to any of the above, the nucleic acid molecule can have a sequence that has one or more nucleobase changes with respect to the sequence of a naturally-occurring gene in the genome of an organism. For example, the nucleic acid molecule can have a sequence that has one or more nucleobase substitutions, deletions, or additions with respect to the sequence of a naturally-occurring gene in the genome of an organism.

Additionally, an isolated or recombinant nucleic acid molecule as provided herein (e.g., a non-native nucleic acid molecule as disclosed herein), when expressed in a microbial host cell, can confer higher productivity, especially lipid, such as FAME, and biomass, such as AFDW or TOC, on the microbial host cell. In some examples, expression of a nucleic acid molecule as disclosed herein in a microalgal or heterokont cell can result in the microalgal or heterokont cell having higher productivity, especially lipid, such as FAME, and biomass, such as AFDW or TOC, when compared with a control cell that does not express the nucleic acid molecule, for example, the microbial host cell can demonstrate a higher growth rate, greater biomass productivity, or higher rate or level of production of a biomolecule such as, for example, a lipid, protein, pigment, or carbohydrate, including an alcohol. For example, the host cell can exhibit higher productivity, especially lipid, such as FAME, and biomass, such as AFDW or TOC, with respect to a control cell of one or more products the host cell is engineered to synthesize.

An isolated nucleic acid molecule of the present invention can be produced using recombinant DNA technology (e.g., any or a combination of any of reverse transcription, restriction, ligation, polymerase reactions, including polymerase chain reaction (PCR) amplification, cloning, in vitro or in vivo recombination, etc.) or chemical synthesis. Isolated nucleic acid molecules include natural nucleic acid molecules and homologs thereof, including, but not limited to, natural allelic variants and modified nucleic acid molecules in which nucleotides have been inserted, deleted, and/or substituted, in such a manner that such modifications provide the desired effect on the biological activity of polypeptides as described herein.

A nucleic acid molecule variant can be produced using a number of methods known to those skilled in the art (see, for example, Sambrook et al. Molecular Cloning: A Laboratory Manual. 2nd ed. N.Y., Cold Spring Harbor Laboratory, Cold Spring Harbor Laboratory Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules, and combinations thereof. Nucleic acid molecule homologs can be selected from a mixture of modified nucleic acids by screening for the function of the protein encoded by the nucleic acid and/or by hybridization with a wild-type gene.

According to some embodiments of the present application, nucleic acid molecules of the present invention will include those nucleic acid molecules that specifically hybridize, or hybridize under high stringency conditions, to nucleic acid molecules encoding a polypeptide with at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4, SEQ ID NO:99, SEQ ID NO:100, SEQ ID NO:22, SEQ ID NO:91, SEQ ID NO:92, SEQ ID NO:93, SEQ ID NO:94, SEQ ID NO:95, SEQ ID NO:96, or to SEQ ID NO:101, SEQ ID NO:102, SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90, and fragments thereof and complements thereof and their fragments, under moderate or high stringency conditions.

As used herein, two nucleic acid molecules are said to be capable of specifically hybridizing to one another if the two molecules are capable of forming an anti-parallel, double-stranded nucleic acid structure. Two molecules are said to be minimally complementary if they can hybridize to one another with sufficient stability to permit them to remain annealed to one another under at least conventional low-stringency conditions. Similarly, the molecules are said to be complementary if they can hybridize to one another with sufficient stability to permit them to remain annealed to one another under conventional high-stringency conditions. A nucleic acid molecule is said to be the complement of another nucleic acid molecule if they exhibit complete complementarity. As used herein, molecules are said to exhibit complete complementarity when every nucleotide of one of the molecules is complementary to a nucleotide of the other. Departures from complete complementarity are permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations employed.

Conventional stringency conditions are described by Sambrook et al., supra, and by Haymes et al. In: Nucleic Acid Hybridization, A Practical Approach, IRL Press, Washington, D.C. (1985). For example, appropriate stringency conditions which promote DNA hybridization include, for example, 6.0× sodium chloride/sodium citrate (SSC) at about 45° C., followed by a wash of 2.0×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These and other conditions are known to those skilled in the art, or can be found in Current Protocols in Molecular Biology, John Wiley & Sons, N.Y. (1989), 6.3.1-6.3.6. Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5× Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70×C for several hours to overnight. High stringency conditions are preferably provided by 6×SSC, 5× Denhardt's solution, 100 mg/mL fish sperm DNA, and 0.1% (w/v) SDS, with incubation at 55° C. for several hours. Hybridization is generally followed by several wash steps. The wash compositions generally comprise 0.5× to about 10×SSC, and 0.01% (w/v) to about 0.5% (w/v) SDS with a 15 min incubation at about 20° C. to about 70° C. Preferably, the nucleic acid segments remain hybridized after washing at least one time in 0.1×SSC at 65° C.

A subset of the nucleic acid molecules of this invention includes fragments of the disclosed polynucleotides consisting of oligonucleotides of at least 12, at least 15, for example at least 16 or 17, or for example at least 18 or 19, such as at least 20 or more, consecutive nucleotides. Such oligonucleotides are fragments of the larger molecules having a sequence selected from the polynucleotide sequences in the Sequence Listing, and find use, for example, as interfering molecules, probes and primers for detection of the polynucleotides of the present invention.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule useful in the present invention, or of a size sufficient to encode an amino acid sequence having a biological activity of at least one domain of a polypeptide according to the present invention, e.g., CHORD, CHORD-derived, SKP1, and other CHORD-like, and other SKP1-like polypeptides disclosed herein. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to encode a biologically active fragment of a domain of a CHORD, CHORD-derived, or SKP1 polypeptide, an entire CHORD, CHORD-derived, or SKP1 polypeptide, or several domains within an open reading frame encoding a CHORD, CHORD-derived, or SKP1 polypeptide.

The present invention provides, in various examples, nucleotide sequences comprising regions that encode polypeptides that may be the complete protein encoded by the gene represented by the polynucleotide, or may be fragments of the encoded protein. For example, polynucleotides provided herein can encode polypeptides constituting a substantial portion of the complete protein or one of its domains, for example, constituting a sufficient portion of the complete protein to provide the relevant biological activity, e.g., the activity of a CHORD domain or portion thereof. Of particular interest are polynucleotides of the present invention that encode at least 35 contiguous amino acids of a CHORD domain that may be optionally provided in a fusion protein with other non-CHORD sequences. Such polynucleotides may be expressed in transgenic cells or transgenic organisms to produce cells and organisms having higher productivity, for example, higher biomass, such as AFDW or TOC, or lipid, such as FAME, productivity.

Further, a nucleic acid molecule as provided herein, including a nucleic acid molecule that includes sequences that encode a CHORD, CHORD-derived, or SKP1 polypeptide, or fragments thereof, can be expressed in a recombinant host cell and the effects of expression of the nucleic acid molecule on the organism's productivity, especially lipid, such as FAME, and biomass, such as AFDW or TOC, can be assayed. Productivity can be measured, for example, by growth assays (e.g., monitoring propagation by cell counts or optical density), by determining total organic carbon (TOC) of ash-free dry weight accumulated over time, or by assessing the amount of any product of interest, for example, proteins, carbohydrates, lipids, pigments, etc. using methods used in the art, including without limitation, gas chromatography (GC), HPLC, immunological detection, biochemical and/or enzymatic detection, etc.

Also of interest in the present invention are variants of the polynucleotides provided herein. Such variants may be naturally-occurring, including homologous polynucleotides from the same or a different species, or may be non-natural variants, for example polynucleotides synthesized using chemical synthesis methods, or generated using recombinant DNA techniques. With respect to nucleotide sequences, degeneracy of the genetic code provides the possibility to substitute at least one base of the protein encoding sequence of a gene with a different base without causing the amino acid sequence of the polypeptide produced from the gene to be changed. Hence, the DNA of the present invention may also have any base sequence that has been changed from any polynucleotide sequence in the Sequence Listing by substitution in accordance with degeneracy of the genetic code. References describing codon usage are readily available.

In addition, the skilled artisan will further appreciate that changes can be introduced by mutation of the nucleotide sequences of the invention, thereby leading to changes in the amino acid sequence of the encoded CHORD, CHORD-derived, or SKP1 proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted nonessential amino acid residues. A "nonessential" amino acid residue, as used herein, is a residue that can be altered from the wild-type sequence of a presently disclosed CHORD, CHORD-derived, CHORD-like, SKP1, or SKP1-like protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Figure 6:
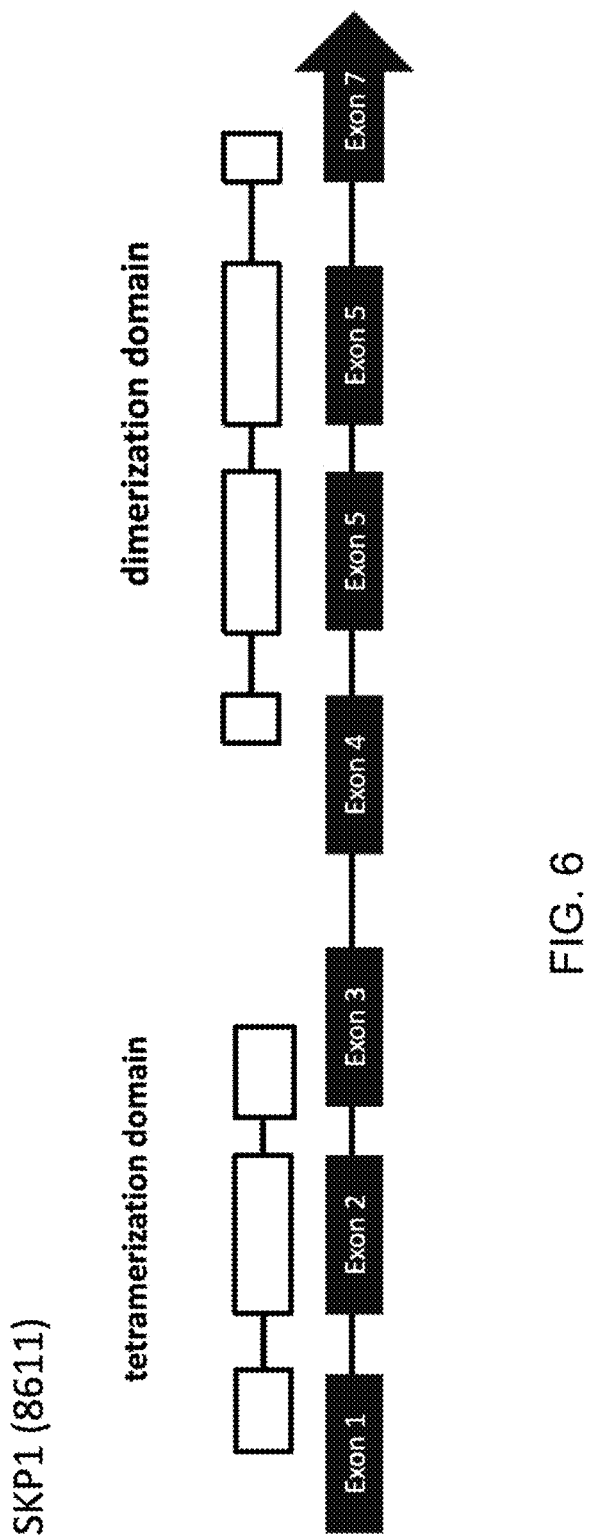
FIG. 6 depicts a gene diagram of SKP1-8611. Exons are labeled and the intervening spaces are introns. Sequence encoding SKP1 family tetramerization and dimerization domains are labeled and depicted by white boxes spanning Exons 1-3 and Exons 4-7 respectively.

In a particular non-limiting exemplification, conserved residues, domains and motifs of a disclosed CHORD protein are indicated in FIG. 4 and can be recognized in the sequences of the Sequence Listing. In a particular nonlimiting exemplification, conserved residues, domains and motifs of a disclosed SKP1 protein are indicated in FIG. 6 and can be recognized in the sequences of the Sequence Listing. As discussed above, it will be appreciated by one skilled in the art that amino acid substitutions may be made in non-conserved regions that retain the function of the polypeptide. In general, such substitutions would not be made for conserved amino acid residues, or for amino acid residues residing within a conserved motif, where such residues may be essential for protein activity. Examples of residues that are conserved and that may be essential for protein activity include, for example, residues that are identical between all proteins contained in an alignment of the amino acid sequences of the present invention and known CHORD, CHORD-derived, or SKP1 protein sequences. Examples of residues that are conserved but that may allow conservative amino acid substitutions and still retain activity include, for example, residues that have only conservative substitutions between all proteins contained in an alignment of the amino acid sequences of the present invention and known CHORD, CHORD-derived, or SKP1 sequences. However, one of skill in the art would understand that functional variants may have minor conserved or non-conserved alterations in the conserved residues.

CHORD variants include proteins having an amino acid sequence that differs from any one of the polypeptides in the group consisting of SEQ ID NO:4, SEQ ID NO:99, SEQ ID NO:22, SEQ ID NO:91, SEQ ID NO:92, SEQ ID NO:93, SEQ ID NO:94, SEQ ID NO:95, and SEQ ID NO:96, by at least one amino acid deletion, insertion, or substitution at one or more of the positions corresponding to the conserved amino acid residues described herein, and combinations of any thereof. In some preferred embodiments, such CHORD variants include proteins having an amino acid sequence that differs from any one of the polypeptides in the Sequence Listing, by an amino acid deletion, insertion, or substitution at one or more of the positions corresponding to the conserved amino acid residues as identified in previously, and combinations of any thereof.

SKP1 variants include proteins having an amino acid sequence that differs from any one of the polypeptides in the group consisting of SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90, by at least one amino acid deletion, insertion, or substitution at one or more of the positions corresponding to the conserved amino acid residues described herein, and combinations of any thereof. In some preferred embodiments, such SKP1 variants include proteins having an amino acid sequence that differs from any one of the polypeptides in the Sequence Listing, by an amino acid deletion, insertion, or substitution at one or more of the positions corresponding to the conserved amino acid residues as identified in previously, and combinations of any thereof.

Alternatively or in addition, variant nucleotide sequences can be made by introducing mutations randomly along all or part of the coding sequence, such as by saturation mutagenesis, and the resultant mutants can subsequently be screened for ability to confer activity of CHORD-derived, CHORD-like, or SKP1-like protein in order to identify mutants that retain CHORD or SKP1 protein activity, respectively. For example, following mutagenesis, the encoded protein can be expressed recombinantly, and the activity of the protein can be determined using standard assay techniques as disclosed hereinabove.

Methods for such manipulations are known in the art. For example, amino acid sequence variants of a CHORD or SKP1 protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired CHORD, CHORD-derived, CHORD-like, SKP1, or SKP1-like activity. However, it is understood that the ability of a CHORD, CHORD-derived, CHORD-like, SKP1, or SKP1-like to confer an increase in productivity, especially lipid, such as FAME, and biomass, such as AFDW or TOC, may be improved by the use of such techniques upon the compositions of this invention. For example, one may express a CHORD, CHORD-derived, CHORD-like, SKP1, or SKP1-like polypeptide in host cells that exhibit high rates of base-misincorporation during DNA replication, such as Stratagene XL-1 Red cell (Fischer Scientific). After propagation in such strains or cells, one can isolate the CHORD, CHORD-derived, CHORD-like, SKP1, or SKP1-like protein or CHORD, CHORD-derived, CHORD-like, SKP1, or SKP1-like encoding DNA (for example by preparing plasmid DNA, or by amplifying by PCR and cloning the resulting PCR fragment into a vector), followed by culture the mutated CHORD, CHORD-derived, CHORD-like, SKP1, or SKP1-like protein or CHORD, CHORD-derived, CHORD-like, SKP1, or SKP1-like genes in a non-mutagenic strain or cell, and identify mutated CHORD, CHORD-derived, CHORD-like, SKP1, or SKP1-like protein or CHORD, CHORD-derived, CHORD-like, SKP1, or SKP1-like genes with an ability to increase host cell productivity, especially lipid, such as FAME, and biomass, such as AFDW or TOC, for example by performing an assay to test for CHORD, CHORD-derived, CHORD-like, SKP1, or SKP1-like activity in vivo and in vitro.

Alternatively or in addition, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Domain swapping or shuffling is another mechanism for generating altered CHORD, CHORD-derived, CHORD-like, SKP1, or SKP1-like proteins. Conversed domains may be swapped between CHORD, CHORD-derived, CHORD-like, SKP1, or SKP1-like proteins, resulting in hybrid or chimeric CHORD, CHORD-derived, CHORD-like, SKP1, or SKP1-like polypeptides with improved biomass, such as AFDW or TOC, productivity. Methods for generating recombinant proteins and testing them for improved biomass, such as AFDW or TOC, productivity are known in the art. Accordingly, the molecules of the present invention also include fusions between two or more CHORD, CHORD-derived, CHORD-like, SKP1, or SKP1-like genes or polypeptides. Different domains of different genes or polypeptides can be fused. CHORD, CHORD-derived, CHORD-like, SKP1, or SKP1-like gene fusions can be linked directly or can be attached by additional amino acids that link the two of more fusion partners.

Gene fusions can be generated by basic recombinant DNA techniques, examples of which are described below herein. Selection of gene fusions will depend on the desired phenotype caused by the gene fusion. For instance, if phenotypes associated with the A domain of one CHORD, CHORD-derived, CHORD-like, SKP1, or SKP1-like protein are desired with phenotypes associated with the B domain of a second CHORD, CHORD-derived, CHORD-like, SKP1, or SKP1-like protein, a fusion of the first CHORD, CHORD-derived, CHORD-like, SKP1, or SKP1-like protein's A domain to the second CHORD, CHORD-derived, CHORD-like, SKP1, or SKP1-like protein's B domain would be created. The fusion can subsequently be tested in vitro or in vivo for the desired phenotypes.

CHORD, CHORD-derived, CHORD-like, SKP1, or SKP1-like polypeptides are also encompassed within the present invention. In an embodiment of this aspect, by "CHORD, CHORD-derived, CHORD-like, SKP1, or SKP1-like polypeptide" is intended a polypeptide having an amino acid sequence comprising any one of the amino acid sequences in the Sequence Listing (e.g., SEQ ID NO:4, SEQ ID NO:99, or SEQ ID NO:100, SEQ ID NO:22, SEQ ID NO:91, SEQ ID NO:92, SEQ ID NO:93, SEQ ID NO:94, SEQ ID NO:95, SEQ ID NO:96, SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90), or fragments or variants thereof. Fragments, biologically active portions, and variants thereof are also provided, and may be used to practice the methods of the present invention.

Altered or improved variants: It is contemplated that DNA sequences of a CHORD, CHORD-derived, CHORD-like, SKP1, or SKP1-like and respective homologs may be altered by various methods, and that these alterations may result in DNA sequences encoding proteins with amino acid sequences different than that encoded by a CHORD, CHORD-derived, CHORD-like, SKP1, or SKP1-like gene of the present invention. The CHORD, CHORD-derived, CHORD-like, SKP1, or SKP1-like protein may be altered in various ways including amino acid substitutions, deletions, truncations, and insertions of one or more amino acids of the polypeptide sequences set forth in the Sequence Listing, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Also considered are polypeptides having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4, SEQ ID NO:99, or SEQ ID NO:100, SEQ ID NO:22, SEQ ID NO:91, SEQ ID NO:92, SEQ ID NO:93, SEQ ID NO:94, SEQ ID NO:95, SEQ ID NO:96, SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90, or to a fragment or conserved domain thereof, such as a CHORD domain, a SKP1 family tetramerization domain, or a SKP1 family dimerization domain. The polypeptides will preferably be biologically active with respect to either a structural attribute, such as the capacity of a polypeptide to be bound by an antibody or to bind to a target nucleotide sequence (or to compete with another molecule for such binding). Alternatively or in addition, such an attribute may be catalytic and thus involve the capacity of the molecule to mediate a chemical reaction (for an enzymatic protein), or transcriptional regulation response (for a transcription factor), or structural (for a protein subunit of a larger complex). The polypeptides and polypeptides of the present invention may also be recombinant.

In general, the biological activity or biological action of a protein or domain refers to any function(s) exhibited or performed by the protein or domain that is ascribed to the naturally-occurring form of the protein as measured or observed in vivo (i.e., in the natural physiological environment of the protein) or in vitro (i.e., under laboratory conditions). As used herein, a functional domain of a CHORD, CHORD-derived, or SKP1 polypeptide is a domain that is capable of performing a biological function of a CHORD, CHORD-derived, or SKP1 polypeptide. For example, a biological activity of a CHORD, CHORD-derived, or SKP1 polypeptide and the individual domains that make up a CHORD, CHORD-derived, or SKP1 polypeptide includes the CHORD domain, or the SKP1 family tetramerization domain, or SKP1 family dimerization domain, respectively, as discussed herein. Also considered is a CHORD, CHORD-derived, or CHORD-like polypeptide fragment that functions as a dominant-negative polypeptide that block the function of the native full-length CHORD or CHORD-like polypeptide.

Any of a variety of methods well known in the art may be used to make or to obtain one or more of the above-described polypeptides. The polypeptides of the invention can be chemically synthesized or polypeptides can be made using standard recombinant techniques in heterologous expression systems such as E. coli, yeast, insects, etc. Antibodies to the polypeptides of the present invention, or to variants or fragments thereof, are also encompassed. A variety of techniques and methods for producing antibodies are well known in the art (see, for example, Harlow and Lane (1988) Antibodies: A Laboratory Manual, Cold Spring Harbor Laboratory, Cold Spring Harbor, N.Y.; U.S. Pat. No. 4,196,265), and can be used to make an antibody according to the invention disclosed herein.

Nucleic Acid Constructs

Another aspect of the present invention relates to recombinant nucleic acid molecules comprising a nucleic acid sequence encoding an amino acid sequence having a biological activity of at least one domain of a CHORD, CHORD-derived, CHORD-like, SKP1, or SKP1-like polypeptide as described herein. Typically, such a recombinant nucleic acid molecule includes at least one nucleic acid molecule of the present invention operably linked to one or more transcription control sequences. As used herein, the phrase "recombinant molecule" or "recombinant nucleic acid molecule" primarily refers to a nucleic acid molecule or nucleic acid sequence operably linked to a transcription control sequence, but can be used interchangeably with the phrase "nucleic acid molecule", when such nucleic acid molecule is a recombinant molecule as discussed herein.

The invention provides nucleic acid constructs comprising a nucleic acid sequence as provided herein operably linked to one or more sequences that can regulate or mediate transcription, translation, or integration of nucleotide sequences into a host genome. For example, the invention provides expression constructs that comprise one or more "expression control elements" or sequences that regulate expression transcription of an operably linked gene, or translation of the transcribed RNA. For example, an expression control element can be a promoter that can be operably linked to a gene of interest or antisense sequence in an expression construct or "expression cassette". Various algal promoters are known and can be used, including those disclosed in U.S. Patent Appl. Pub. No. US 2013/0023035; U.S. patent application Ser. No. 13/486,930, filed Jun. 1, 2012; U.S. patent application Ser. No. 13/693,585, filed Dec. 4, 2012; and U.S. patent application Ser. No. 13/915,522, filed Jun. 11, 2013. A promoter used in a construct may in some instances be regulatable, e.g., inducible.

An inducible promoter can be responsive to, e.g., light intensity or high or low temperature, and/or can be responsive to specific compounds. The inducible promoter may be, for example, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof An inducible promoter can also be responsive to light or dark (e.g., U.S. Pat. Nos. 8,318,482; 5,750,385; 5,639,952), metals (*Eukaryotic Cell* 2:995-1002 (2003)) or temperature (U.S. Pat. No. 5,447,858; Abe et al. Plant Cell Physiol. 49: 625-632 (2008); Shroda et al. *Plant J.* 21: 121-131 (2000). The foregoing examples are not limiting as to the types of promoters or specific promoters that may be used. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g., to confer inducibility on a promoter that operates in the host species.

In aspects where the nucleic acid construct does not contain a promoter in operable linkage with the nucleic acid sequence encoding the gene of interest (e.g., a CHORD-derived or SKP1 gene) the nucleic acid sequence can be transformed into the cells such that it becomes operably linked to an endogenous promoter by, e.g., homologous recombination, site specific integration, and/or vector integration. In some instances, genomic host sequences included in a nucleic acid construct for mediating homologous recombination into the host genome may include gene regulatory sequences, for example, a promoter sequence, that can regulate expression of a gene or antisense or RNAi sequence of the nucleic acid construct. In such examples, the transgene(s) of the construct can become operably linked to a promoter that is endogenous to the host microorganism. The endogenous promoter(s) may be regulatable, e.g., inducible.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell. Yet in other embodiments, a recombinant molecule of the present invention comprises an organelle targeting signal to enable an expressed protein to be transported and delivered to the target cellular organelle. It will be appreciated by one skilled in the art that a variety of organelle targeting signals can be used including, but not limited to, nuclear localization signal (NLS), chloroplast targeting signal, and mitochondria-targeting sequence.

A nucleic acid molecule as described herein can be cloned into suitable vector and can be used to transform or transfect any suitable host. The selection of vectors and methods to construct them are commonly known to the art and are described in general technical references (see, e.g., Sambrook and Russell, Molecular Cloning, A Laboratory Manual, Cold Spring Harbor Laboratory Press, 2001). Thus, in some embodiments of the invention, the recombinant nucleic acid molecule is a recombinant vector. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences. The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain one or more selectable genetic markers.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell or microorganism (i.e., used for targeted gene disruption, modification, or knock-out technology). Such a vector may also be known in the art as a "knock-out" vector. In one aspect of this embodiment, a portion of the vector, which is typically the nucleic acid molecule inserted into the vector (i.e., the insert), has a nucleic acid sequence that is homologous to a nucleic acid sequence of a target gene in the host cell (i.e., a gene which is targeted to be modified, deleted, or inactivated). The nucleic acid sequence of the vector insert is designed to bind to the target gene such that the target gene and the insert undergo homologous recombination, whereby the endogenous target gene is modified, deleted, inactivated or attenuated (i.e., by at least a portion of the endogenous target gene being mutated or deleted).

Constructs for homologous recombination into an algal or heterokont genome (e.g., for disruption or gene replacement of a regulator gene) can include a nucleotide sequence of a CHORD, CHORD-derived, CHORD-like, SKP1, or SKP1-like gene or ortholog, such as for example any provided herein, or sequences from the algal or heterokont genome that are adjacent to the CHORD, CHORD-derived, CHORD-like, SKP1, or SKP1-like gene in the host organism. For example, a construct for homologous recombination can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of a gene targeted for knock-out or gene replacement such as a CHORD, CHORD-derived, CHORD-like, SKP1, or SKP1-like gene or ortholog, such as any disclosed herein, and/or genomic DNA adjacent thereto. For example, the sequences for mediating homologous recombination in a construct can include one or more nucleotide sequences from or adjacent to a naturally-occurring algal or heterokont gene encoding a CHORD, CHORD-derived, CHORD-like, SKP1, or SKP1-like polypeptide, wherein the CHORD, CHORD-derived, CHORD-like, SKP1, or SKP1-like polypeptide comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to any one of the amino acid sequences in the Sequence Listing. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of any one of the nucleic acid sequences in the Sequence Listing, and/or an adjacent region of the corresponding genome.

For example, the sequences for mediating homologous recombination in a construct can include one or more nucleotide sequences from or adjacent to a naturally-occurring algal or heterokont gene encoding a CHORD, CHORD-derived, CHORD-like, SKP1, or SKP1-like polypeptide, wherein the CHORD, CHORD-derived, CHORD-like, SKP1, or SKP1-like polypeptide comprises an amino acid sequence having at least 80%, for example, at least 85%, at least 90%, at least 95% identity, or at least 99% to any one of SEQ ID NO:4, SEQ ID NO:99, or SEQ ID NO:100, SEQ ID NO:22, SEQ ID NO:91, SEQ ID NO:92, SEQ ID NO:93, SEQ ID NO:94, SEQ ID NO:95, SEQ ID NO:96, SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90. For example, a construct for homologous recombination can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of a regulator gene that encodes a CHORD, CHORD-derived, CHORD-like, SKP1, or SKP1-like polypeptide, such as any disclosed herein, and/or genomic DNA adjacent thereto. For example, the sequences for mediating homologous recombination in a construct can include one or more nucleotide sequences from or adjacent to a naturally-occurring algal or heterokont gene encoding a CHORD, CHORD-derived, CHORD-like, SKP1, or SKP1-like protein, wherein the CHORD, CHORD-derived, CHORD-like, SKP1, or SKP1-like protein comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to any one of SEQ ID NO:4, SEQ ID NO:99, or SEQ ID NO:100, SEQ ID NO:22, SEQ ID NO:91, SEQ ID NO:92, SEQ ID NO:93, SEQ ID NO:94, SEQ ID NO:95, SEQ ID NO:96, SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of any one of the nucleic acid sequences encoding a CHORD, CHORD-derived, CHORD-like, SKP1, or SKP1-like indicated in the Sequence Listing and/or an adjacent region of the corresponding genome.

General discussion above with regard to recombinant nucleic acid molecules and transformation of host cells is intended to be applied to any recombinant nucleic acid molecule discussed herein, including those encoding any amino acid sequence having a biological activity of at least one domain from a CHORD, CHORD-derived, CHORD-like, SKP1, or SKP1-like polypeptide, those encoding amino acid sequences from other CHORD, CHORD-derived, CHORD-like, SKP1, or SKP1-like polypeptides, and those encoding other proteins or domains.

Information in the Sequence Listing

The amino acid sequences provided in the Sequence Listing are annotated to indicate one or several known homologs of the respective sequences. Some sequences contain "Pfam" domains which are indicative of particular functions and/or applications. The specific Pfam domains are described in more detail by various sources, such as "sanger.ac.uk" or "pfam.janelia.org". Thus, various practical applications of the amino acid sequences in the sequence listing are immediately apparent to those of skill in the art based on their similarity to known sequences.

The amino acid sequences provided in the Sequence Listing are also annotated to indicate one or several known homologs of the respective sequences. Some amino acid sequences contain conserved domains, such as CHORD domain, which recruits to pfam PF04968. The conserved domains indicative of SKP1-family members that Applicants have identified in the polypeptides described herein include the SKP1 family tetramerization domain, which recruits to pfam PF03931, and the SKP1 family dimerization domain, which recruits to Pfam PF01466.

Additional information of sequence applications comes from similarity to sequences in public databases. Entries in the "miscellaneous features" sections of the Sequence Listing labeled "NCBI GI:" and "NCBI Desc:" provide additional information regarding the respective homologous sequences. In some cases, the corresponding public records, which may be retrieved from www.ncbi.nlm.nih.gov, cite publications with data indicative of uses of the annotated sequences. The sequence descriptions and the Sequence Listing attached hereto comply with the rules governing nucleotide and/or amino acid sequences disclosures in patent application as set forth in 37 C.F.R. § 1.182-1.185.

From the disclosure of the Sequence Listing, it can be seen that the nucleotides and polypeptides of the inventions are useful, depending upon the respective individual sequence, to make transgenic organisms having one or more altered growth and phenotype characteristics such as, for example, increased productivity, for example, increased biomass, such as AFDW or TOC productivity or increase lipid, such as FAME, productivity. The present invention further encompasses nucleotides that encode the above described polypeptides, such as those included in the Sequence Listing, as well as the complements and/or fragments thereof, and include alternatives thereof based upon the degeneracy of the genetic code.

Recombinant Microorganism

The invention also provides a recombinant microorganism that includes a non-native nucleic acid molecule that includes a nucleic acid sequence that encodes a CHORD, CHORD-derived, or SKP1 protein, in which the recombinant microorganism has higher productivity, for example, higher biomass productivity, such as AFDW or TOC productivity, and/or lipid productivity, such as FAME productivity, than does a control microorganism substantially identical to the recombinant microorganism except that the control microorganism does not include a non-native nucleic acid molecule comprising a nucleic acid sequence that encodes a CHORD, CHORD-derived, or SKP1 protein. A CHORD, CHORD-derived, or SKP1 protein can be any CHORD, CHORD-derived, or SKP1 protein, such as, for example, one whose sequence is available from gene, protein, or genome databases or scientific literature, or a variant thereof. A recombinant microorganism as provided herein can in some examples include a non-native nucleic acid molecule that encodes a SKP1 protein as provided herein, for example, can include a nucleic acid sequence that encodes a polypeptide having at least 95% identity to an endogenous SKP1 polypeptide of the recombinant microorganism. A recombinant microorganism as provided herein can in some examples include a non-native nucleic acid molecule that encodes a CHORD-derived protein as provided herein, for example, can include a nucleic acid sequence that encodes a polypeptide that includes an amino acid sequence having at least 95% identity to a CHORD domain or at least 60% of a CHORD domain of an endogenous CHORD polypeptide of the recombinant microorganism.

In various examples, a recombinant microorganism as provided herein includes a non-native gene that encodes a polypeptide having an amino acid sequence with at least 65%, at least 70%, at least 75%, at least 80%, at least 85%, at least 90%, at least 95%, at least 96%, at least 97%, at least 98%, or at least 99% identity to a CHORD, CHORD-derived, or SKP1 polypeptide selected from the group consisting of: SEQ ID NO:4, SEQ ID NO:99, SEQ ID NO:100, SEQ ID NO:22, SEQ ID NO:91, SEQ ID NO:92, SEQ ID NO:93, SEQ ID NO:94, SEQ ID NO:95, SEQ ID NO:96, SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90. In some examples, the non-native gene encodes a polypeptide having a CHORD, CHORD-derived, or SKP1 polypeptide or functional domain thereof in which the polypeptide has at least 50%, at least 55%, at least 60%, at least 65%, at least 70%, at least 75%, at least 80%, at least 85%, at least 90%, at least 95%, at least 96%, at least 97%, at least 98%, or at least 99% identity to a CHORD, CHORD-derived, or SKP1 polypeptide of a microalgal or heterokont species. The recombinant microorganism can exhibit higher productivity, such as higher biomass productivity, such as AFDW or TOC productivity, and can also exhibit higher lipid productivity, e.g., higher FAME productivity, than is exhibited by a control microorganism substantially identical to the recombinant microorganism that includes the non-native gene encoding a polypeptide having a CHORD, CHORD-derived, or SKP1 polypeptide, with the exception that the control microorganism does not include a non-native gene encoding a polypeptide having a CHORD, CHORD-derived, or SKP1 polypeptide or fragment thereof. For example, expression of the non-native gene in an algal or heterokont cell can result in the algal or heterokont cell producing a greater amount of biomass or a greater amount of one or more biomolecules, such as, without limitation, a lipid, a terpenoid, a polyketide, a protein, a peptide, one or more amino acids, a carbohydrate, an alcohol, a nucleic acid, one or more nucleotides, nucleosides, or nucleobases, a vitamin, a cofactor, a hormone, an antioxidant, or a pigment or colorant.

A recombinant microorganism having a non-native gene encoding a polypeptide having a CHORD, CHORD-derived, or SKP1 polypeptide can comprise, e.g., any of the nucleic acid molecules described herein that encode a polypeptide that includes a CHORD, CHORD-derived, or SKP1 polypeptide or functional domain thereof. Further, the recombinant host cells may comprise any of the constructs or vectors described herein. In some aspects, the nucleic acid sequence encoding the polypeptide can be heterologous with respect to the recombinant host cell, and can be a gene encoding a CHORD, CHORD-derived, or SKP1 polypeptide derived from any species, including a plant, animal, or microbial species, or a variant thereof. Alternatively, the gene encoding a CHORD, CHORD-derived, or SKP1 polypeptide may be homologous with respect to the host organism. For example, the non-native CHORD, CHORD-derived, or SKP1 gene may be a CHORD, CHORD-derived, or SKP1 gene of the same species as the host microorganism and is introduced into the recombinant microorganism in an expression cassette that allows regulated expression or overexpression of the introduced homologous CHORD, CHORD-derived, or SKP1 gene. Alternatively, the CHORD, CHORD-derived, or SKP1 non-native gene may be endogenous to the microorganism and a heterologous promoter may be introduced into the host microorganism such that it becomes juxtaposed with and operably linked to the endogenous CHORD, CHORD-derived, or SKP1 gene to effect overexpression and/or regulated expression.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof "Transient transformation" is intended to mean that a polynucleotide is introduced into the organism and does not integrate into the genome or otherwise become established and stably inherited by successive generations.

Genetic transformation can result in stable insertion and/or expression of transgenes from either the nucleus or the plastid, and in some cases can result in transient expression of transgenes. For example, genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell*, 2010; and Gong et al., *J. Ind. Microbiol. Biotechnol.*, 2011). Non-limiting examples of such useful transformation methods include agitation of cells in the presence of glass beads or silicon carbide whiskers as reported by, for example, Dunahay, *Biotechniques*, 15(3):452-460, 1993; Kindle, *Proc. Natl. Acad. Sci. USA.*, 1990; Michael and Miller, *Plant J.*, 13, 427-435, 1998. Electroporation techniques have been successfully used for genetic transformation of several microalgal species including *Nannochloropsis* sp. (see, e.g., Chen et al., *J. Phycol.*, 44:768-76, 2008), *Chlorella* sp. (see, e.g., Chen et al., *Curr. Genet.*, 39:365-370, 2001; Chow and Tung, *Plant Cell Rep.* Vol. 18, No. 9, 778-780, 1999), *Chlamydomonas* (Shimogawara et al., *Genetics*, 148: 1821-1828, 1998), *Dunaliella* (Sun et al., *Mol. Biotechnol.*, 30(3): 185-192, 2005). Microprojectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.*, 252:572-579, 1996), *Cyclotella* and *Navicula* (Dunahay et al., J. Phycol., 31:1004-1012, 1995), *Cylindrotheca* (Fischer et al., J. Phycol., 35:113-120, 1999), and *Chaetoceros* sp. (Miyagawa-Yamaguchi et al., *Phycol. Res.* 59: 113-119, 2011), as well as green algal species such as *Chlorella* (El-Sheekh, *Biologia Plantarum*, Vol. 42, No. 2: 209-216, 1999), and *Volvox* species (Jakobiak et al., *Protist*, 155:381-93, 2004). Additionally, *Agrobacterium*-mediated gene transfer techniques can also be useful for genetic transformation of microalgae, as has been reported by, for example, Kumar, *Plant Sci.*, 166(3):731-738, 2004, and Cheney et al., *J. Phycol.*, Vol. 37, Suppl. 11, 2001.

A transformation vector as described herein will typically comprise a marker gene that confers a selectable or scorable phenotype on target host cells, e.g., algal cells. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocydin, bleomycin (see, for example, Apt et al., 1996, supra; Fischer et al., 1999, supra; Fuhrmann et al., *Plant J.*, 19, 353-61, 1999, Lumbreras et al., Plant J., 14(4):441-447, 1998; Zaslayskaia et al., *J. Phycol.*, 36:379-386, 2000), spectinomycin (Cerutti et al., Genetics, 145: 97-110, 1997; Doetsch et al., *Curr. Genet.*, 39, 49-60, 2001; Fargo, *Mol. Cell. Biol.*, 19:6980-90, 1999), streptomycin (Berthold et al., *Protist,* 153:401-412, 2002), paromomycin (Jakobiak et al., *Protist,* supra.; Sizova et al., *Gene,* 277:221-229, 2001), nourseothricin (Zaslayskaia et al., 2000, supra), G418 (Dunahay et al., 1995, supra; Poulsen and Kroger, *FEBS Lett.*, 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paramomycin and neomycin resistance (Sizova et al., 2001, supra). Other fluorescent or chromogenic markers that have been used include luciferase (Falciatore et al., *J. Mar. Biotechnol.*, 1: 239-251, 1999; Fuhrmann et al., *Plant Mol. Biol.*, 2004; Jarvis and Brown, Curr. Genet., 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.*, 1:165-169, 1994), β-galactosidase (Gan et al., *J. Appl. Phycol.*, 15:345-349, 2003; Jiang et al., *Plant Cell Rep.*, 21:1211-1216, 2003; Qin et al., *High Technol. Lett.*, 13:87-89, 2003), and green fluorescent protein (GFP) (Cheney et al., 2001, supra; Ender et al., *Plant Cell,* 2002, Franklin et al., *Plant J.*, 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.*, 18:778-780, 1999; Jarvis and Brown, *Curr. Genet.*, 317-321, 1991; Lohuis and Miller, *Plant J.*, 13:427-435, 1998). The SV40 promoter from simian virus has also reported to be active in several algae (Gan et al., *J. Appl. Phycol.*, 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.*, 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.*, 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.*, 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, FEBS Lett 272:

3413-3423, 2005), thus gene expression can be switched off or on when microalgal cells are grown in the presence of ammonium/nitrate. Additional algal promoters that can find use in the constructs and transformation systems provided herein include those disclosed in U.S. Patent Appl. Pub. No. US 2013/0023035; U.S. Patent Application Pub. No. US 2013/0323780, filed Jun. 1, 2012; U.S. Patent Application Pub. No. US 2014/0154806, filed Dec. 4, 2012; and U.S. Patent Application Pub. No. US 2014/0363892, filed Jun. 11, 2013.

Host microorganisms or cells can be either untransformed cells or cells that are already transfected with at least one nucleic acid molecule. For example, a host cell that includes a non-native gene as provided herein that encodes a CHORD, CHORD-derived, or SKP1 gene, homolog, or variant can further include one or more genes that may confer any desirable trait, such as, but not limited to, increased production of biomolecules of interest, such as one or more proteins, pigments, alcohols, or lipids. For example, for production of lipid, a host cell (such as but not limited to an algal or heterokont host cell) can optionally include one or more non-native genes encoding polypeptides that functions in lipid biosynthesis, including, but not limited to, polypeptides that encode enzymes for the production of fatty acids, fatty acid derivatives, and/or glycerolipids including, but not limited to, diacylglycerol acyltransferase (DGAT) gene, a glycerolphosphate acyltransferase (GPAT) gene, a lysophosphatidic acid acyltransferase (dehydrogenase) (LPAAT) gene, a phosphatidic acid phosphatase (PAP) gene, and/or a monoacylglycerol acyltransferase (MGAT) gene.

Suitable host cells to be modified using the materials and methods according to the present invention include, but are not limited to, bacteria, protists, microalgae, phytoplankton, heterokonts, fungi, and protozoa. The process can be used, for example, with algal species that are important or interesting for aquaculture, or for the production of biomass used in producing liquid fuel molecules and other chemicals.

Heterokont species considered for use in the invention include, but are not limited to, Bacillariophytes, Eustigmatophytes, Labrinthulids, and Thraustochytrids. In some examples, the strain may be a species of *Labryinthula, Labryinthuloides, Thraustochytrium, Schizochytrium, Aplanochytrium, Aurantiochytrium, Japonochytrium, Diplophrys,* or *Ulkenia*.

Algal species suitable for the method of the invention include microalgae such as, for example, a species of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phceodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*.

In some embodiments of the present application, preferred microorganisms to genetically engineer include, but are not limited to, photosynthetic organisms such as cyanobacteria, algae, diatoms, and the like. Non-limiting examples of exemplary species include, for instance, eustigmatophytes or diatoms such as, for example, a species of *Amphora, Chaetoceros, Cyclotella, Eustigmatos, Fragilaria, Fragilaropsis, Monodus, Nannochloropsis, Navicula, Nitzschia, Pavlova, Phceodactylum, Thalassiosira,* or *Vischeria*. In some embodiments, members of the genus *Nannochloropsis* such as, but are not limited to, *N. gaditana, N. granulata, N. limnetica, N. oceanica, N. oculata,* and *N. sauna* are transformed with or overexpress a nucleic acid molecule as provided herein that encodes a CHORD, CHORD-derived, CHORD-like, SKP1, or SKP1-like polypeptide.

A microorganism that includes a non-native nucleic acid molecule as provided herein that includes a nucleic acid sequence encoding a SKP1 polypeptide can demonstrate overexpression of a SKP1 polypeptide, for example, can demonstrate a higher level of a SKP1 transcript as compared to a control microorganism that does not include the non-native nucleic acid molecule. A microorganism that includes a non-native nucleic acid molecule as provided herein that includes a nucleic acid sequence encoding a CHORD-derived polypeptide can demonstrate overexpression of a CHORD-derived polypeptide, for example, can demonstrate a higher level of a CHORD transcript as compared to a control microorganism that does not include the non-native nucleic acid molecule.

A microorganism that includes a non-native gene as provided herein can have improved productivity, especially lipid, such as FAME, and biomass, such as AFDW or TOC, when compared with a control microorganism that does not include the non-native gene encoding a CHORD, CHORD-derived, or SKP1 polypeptide. Higher productivity can be demonstrated by measuring growth rates, for example, using a cytometer, or by measuring optical density at wavelengths higher than 700 nm, for example, at 730 or 750 nm. Ash free dry weight can also be measured, as provided in the Examples herein. Production of various biomolecules can be assessed by extraction of algal biomass, partial or substantial purification of the product of the biomolecule of interest, and quantitation of the product by any means known in the art, such as but not limited to, chemical or biochemical analysis, spectroscopic or immunological detection, and/or activity assays.

Methods of Producing Algal Products

Also provided herein are methods of producing biomass or at least one bioproduct by culturing microbial cells having a modulated growth characteristic, such as the host cells disclosed herein. The methods include culturing a microbial cell as disclosed herein that includes a non-native gene encoding a CHORD, CHORD-derived, or SKP1 protein, such as a nucleic acid molecule as disclosed herein that encodes a CHORD, CHORD-derived, or SKP1 polypeptide, in a suitable medium to provide an algal culture and recovering biomass or at least one bioproduct from the culture.

Heterotrophic or mixotrophic culture media can include a reduced carbon source that can be, for example, a sugar, organic acid, carbohydrate, alcohol, aldehyde, ketone, amino acids, peptides, etc. Various monosaccharides such as glucose, oligosaccharides, polysaccharides, cellulosic material, xylose, and arabinose, disaccharides, such sucrose, saturated or unsaturated fatty acids, succinate, lactate, acetate, ethanol, etc., or mixtures thereof may be used.

The microorganism in some examples can be a microalga. The algal culture can optionally be a photoautotrophic culture, in which the culture medium preferably does not include a substantial amount of reduced carbon, that is, the culture does not include reduced carbon in a form or at a level that can be used by the algae for growth.

Algae may be cultured in any suitable vessel, including flasks or bioreactors, where the algae may be exposed to artificial or natural light. The culture comprising algal cells with modulated growth characteristics may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the host cells provided herein having modulated growth characteristics can achieve enhanced growth as demonstrated, for example, by higher cell density of the culture over time, for example, over a period of a week or more, with respect to a culture wild type algal cells of the same strain that are not modulated in growth characteristics. For example, a host cell of the invention as described herein may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press, for media and methods for culturing algae. Algal media recipes can also be found at the websites of various algal culture collections, including, as non-limiting examples, the UTEX Culture Collection of Algae (www.sbs.utexas.edu/utex/media.aspx); Culture Collection of Algae and Protozoa (www.ccap.ac.uk); and Katedra Botaniky (bot-any.natur.cuni.cz/algo/caup-media.html).

The culture methods can optionally include inducing expression of one or more genes for the production of a product, such a but not limited to a protein that participates in the production of a lipid, one or more proteins, antioxidants, or pigments, and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms having a modulated growth characteristic as described herein can be cultured in a fermenter or bioreactor, where the bioreactor can optionally be a "photobioreactor" equipped with an artificial light source, and/or having one or more walls that is transparent enough to light, including sunlight, to enable, facilitate, and/or maintain photosynthetic microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, recombinant photosynthetic microorganisms or host cells may be grown in ponds, canals, sea-based growth containers, trenches, raceways, channels, or the like, or combinations thereof. As with standard bioreactors, a source of inorganic carbon (such as, but not limited to, CO2, bicarbonate, carbonate salts, and the like), including, but not limited to, air, CO2-enriched air, flue gas, or the like, or combinations thereof, can be supplied to the culture. When supplying flue gas and/or other sources of inorganic that may contain CO in addition to CO2, it may be necessary to pre-treat such sources such that the CO level introduced into the (photo)bioreactor do not constitute a dangerous and/or lethal dose with respect to the growth, proliferation, and/or survival of the microorganisms.

Biomass of the microorganism culture can be recovered by harvesting the microorganism from the medium, for example, by filtering, settling, centrifugation, or combinations thereof. In biomass production embodiments according to the invention, the amount of the biomass produced and/or recovered by the method described herein, measured as ash free dry weight (AFDW) can advantageously be at least about 0.05 g per liter of culture, for example at least about 0.1 g, at least about 0.2 g, at least about 0.3 g, at least about 0.4 g, at least about 0.5 g, at least about 0.6 g, at least about 0.7 g per liter of culture, at least about 1 g per liter of culture, at least about 1.5 g per liter of culture, at least about 2 g per liter of culture, at least about 2.5 g per liter of culture, or at least about 5 g per liter of culture. Although many times the goal can be to produce and/or recover as much biomass as possible, in some instances the amount of the biomass produced and/or recovered by the method described herein, measured as ash free dry weigh (AFDW) can be limited to about 15 g or less per liter of culture, for example about 12 g or less per liter of culture, about 10 g or less per liter of culture, about 5 g or less per liter of culture, about 2 g or less per liter of culture, about 1 g or less per liter of culture, or about 0.5 g or less per liter of culture.

Biomass can be harvested, for example, by centrifugation or filtering. The biomass may be dried and/or frozen. Further products may be isolated from biomass, such as, for example, lipids or one or more proteins. Thus, also provided in an aspect of the invention is an algal biomass comprising an algal host cell having modulated growth and/or phenotypic characteristics, such as any of the recombinant host cells disclosed herein, for example, an algal host cell comprising a nucleic acid molecule of the invention wherein elevated expression of the nucleic acid molecule results in higher biomass, such as AFDW or TOC, productivity.

Biomass can be used in any of a number of ways, for example, it can be processed for use as a biofuel by generating syngas from the biomass, can be supplied to an anaerobic digester for production of one or more alcohols, or the biomass can be extracted to provide algal lipids, such as but not limited to monoglycerides, diglycerides, or triglycerides, fatty acid alkyl esters, fatty acids, and/or fatty acid derivatives.

The host algal cell as described herein can include one or more non-native genes encoding a polypeptide for the production of a product, such as, but limited to, a lipid, a colorant or pigment, an antioxidant, a vitamin, a nucleotide, an nucleic acid, an amino acid, a hormone, a cytokine, a peptide, a protein, or a polymer. For example, a non-native gene can encode an enzyme, metabolic regulator, cofactor, carrier protein, or transporter.

In some embodiments, products such as fatty acids and fatty acid derivatives can be recovered from culture by recovery means known to those of ordinary skill in the art, such as by whole culture extraction, for example, using organic solvents. In some cases, recovery of fatty acids or fatty acid derivatives (such as fatty acid esters) can be enhanced by homogenization of the cells, as provided in the examples herein. When fatty acids are sufficiently released from the microorganisms into the culture medium, the recovery method can be adapted to efficiently recover only the released fatty acids, only the fatty acids produced and stored within the microorganisms, or both the produced and released fatty acids.

In further embodiments, products such as but not limited to free fatty acids and fatty acid derivatives that are secreted/released into the culture medium by the recombinant microorganisms described above can be recovered in a variety of ways. A straightforward isolation method, e.g., by partition using immiscible solvents, may be employed. Additionally or alternately, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acids can then be eluted from the particulate adsorbents, e.g., by the use of an appropriate solvent. In such circumstances, one isolation method can include carrying out evaporation of the solvent, followed by further processing of the isolated fatty acids and lipids, to yield chemicals and/or fuels that can be used for a variety of commercial purposes.

Some embodiments of the invention concern methods that comprise culturing an algal host cell as described herein that further includes at least one non-native gene encoding a polypeptide that participates in the production of a product, to produce biomass or at least one algal product. Products such as lipids and proteins can be recovered from culture by recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending U.S. Patent Application Publication 2013/entitled "Solvent Extraction of Products from Algae", filed on Feb. 29, 2012, which is incorporated herein by reference in its entirety.

The discussion of the general methods given herein is intended for illustrative purposes only. Other alternative methods and embodiments will be apparent to those of skill in the art upon review of this disclosure, and are to be included within the spirit and purview of this application.

Additionally or alternatively to any of the above-disclosed embodiments, the invention encompasses the following embodiments:

Embodiment 1 is a recombinant microorganism that includes a non-native nucleic acid molecule that includes a nucleic acid sequence encoding a SKP1 polypeptide, wherein the nucleic acid sequence encoding the SKP1 polypeptide is operably linked to a heterologous promoter, wherein the recombinant microorganism has greater biomass productivity and/or greater lipid productivity than a control microorganism that does not include the non-native nucleic acid molecule.

Embodiment 2 is a recombinant microorganism according to embodiment 1, wherein
  the heterologous promoter, which is optionally a promoter derived from the host microorganism species, is operably linked to the nucleic acid sequence encoding the SKP1 polypeptide on a nucleic acid molecule construct transformed into the host; or
  the heterologous promoter is an endogenous promoter of the host genome, wherein the nucleic acid sequence encoding the SKP1 polypeptide is transformed into the host microorganism such that it integrates into the genome to become operably linked to the endogenous host promoter.

Embodiment 3 is a recombinant microorganism according to embodiment 1 or 2, wherein any one or more of the following are fulfilled:
  the microorganism is a heterokont or alga;
  the amino acid sequence of the SKP1 polypeptide has at least 65%, at least 70%, at least 75%, at least 80%, at least 85%, at least 90%, at least 95%, or between 95% and 100% identity to a SKP1 polypeptide selected from the group consisting of SEQ ID NO:28, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90;
the SKP1 polypeptide include one or both of a SKP1 family dimerization domain and a SKP1 family dimerization domain; and
the amino acid sequence of the SKP1 polypeptide has at least 65%, at least 70%, at least 75%, at least 80%, at least 85%, at least 90%, at least 95%, or between 95% and 100% identity to a SKP1 polypeptide of the host microorganism.

Embodiment 4 is a recombinant microorganism according to any of embodiments 1-3, wherein:
the recombinant microorganism is a labyrinthylomycete and the SKP1 polypeptide has at least 65%, at least 70%, at least 75%, at least 80%, at least 85%, at least 90%, at least 95%, or between 95% and 100% identity to a SKP1 polypeptide of a labyrinthulomycete species, optionally wherein the SKP1 polypeptide has at least 65%, at least 70%, at least 75%, at least 80%, at least 85%, at least 90%, at least 95%, or between 95% and 100% identity to SEQ ID NO:73 or SEQ ID NO:74;
the recombinant microorganism is a diatom and the SKP1 polypeptide has at least 65%, at least 70%, at least 75%, at least 80%, at least 85%, at least 90%, at least 95%, or between 95% and 100% identity to a SKP1 polypeptide of a diatom species, optionally wherein the SKP1 polypeptide has at least 65%, at least 70%, at least 75%, at least 80%, at least 85%, at least 90%, at least 95%, or between 95% and 100% identity to SEQ ID NO:65, SEQ ID NO:70, SEQ ID NO:71, SEQ ID NO:72, SEQ ID NO:75, SEQ ID NO:76, SEQ ID NO:77, SEQ ID NO:78, SEQ ID NO:79, SEQ ID NO:80, and SEQ ID NO:81;
the recombinant microorganism is a eustigmatophyte species and the SKP1 polypeptide has at least 65%, at least 70%, at least 75%, at least 80%, at least 85%, at least 90%, at least 95%, or between 95% and 100% identity to a SKP1 polypeptide of a eustigmatophyte species, optionally wherein the SKP1 polypeptide has at least 65%, at least 70%, at least 75%, at least 80%, at least 85%, at least 90%, at least 95%, or between 95% and 100% identity to SEQ ID NO:28, SEQ ID NO:68, and SEQ ID NO:69; or
the recombinant microorganism is chlorophyte alga and the SKP1 polypeptide has at least 65%, at least 70%, at least 75%, at least 80%, at least 85%, at least 90%, at least 95%, or between 95% and 100% identity to a SKP1 polypeptide of a chlorophyte species, optionally wherein the SKP1 polypeptide has at least 65%, at least 70%, at least 75%, at least 80%, at least 85%, at least 90%, at least 95%, or between 95% and 100% identity to SEQ ID NO:66, SEQ ID NO:67, SEQ ID NO:82, SEQ ID NO:83, SEQ ID NO:84, SEQ ID NO:85, SEQ ID NO:86, SEQ ID NO:87, SEQ ID NO:88, SEQ ID NO:89, or SEQ ID NO:90.

Embodiment 5 is a recombinant microorganism that includes a non-native nucleic acid molecule that includes a nucleic acid sequence encoding a CHORD-derived polypeptide comprising at least a portion of a CHORD domain, wherein the nucleic acid sequence encoding the CHORD-derived polypeptide is operably linked to a heterologous promoter, wherein the recombinant microorganism has greater biomass productivity and/or greater lipid productivity than a control microorganism that does not include the non-native nucleic acid molecule.

Embodiment 6 is a recombinant microorganism according to embodiment 5, wherein
the heterologous promoter is an endogenous promoter of the host genome, wherein the nucleic acid sequence encoding the CHORD-derived polypeptide is transformed into the host microorganism such that it integrates into the genome to become operably linked to the endogenous promoter; or
the heterologous promoter is operably linked to the nucleic acid sequence encoding the CHORD-derived polypeptide on a nucleic acid molecule construct transformed into the host microorganism.

Embodiment 7 is a recombinant microorganism according to Embodiment 6, wherein the CHORD-derived polypeptide comprises a portion of a CHORD domain of a naturally-occurring CHORD polypeptide or an amino acid sequence having at least 80% identity thereto, optionally wherein the portion of a CHORD domain or amino acid sequence having at least 80% identity thereto is at least 60% of the contiguous amino acids of a CHORD domain of a naturally-occurring CHORD polypeptide or is at least 36, 37, 38, 39, of 40 amino acids of a CHORD domain of a naturally-occurring CHORD polypeptide, optionally wherein the CHORD domain has at least 80%, at least 85%, at least 90%, at least 95%, at least 96%, at least 97%, at least 98%, at least 99%, or 100% identity to SEQ ID NO:4.

Embodiment 8 is recombinant microorganism according to Embodiment 6 or Embodiment 7, wherein the CHORD-derived polypeptide comprises a CHORD domain or portion thereof or an amino acid sequence having at least 80% identity thereto and further wherein the CHORD domain or portion thereof or an amino acid sequence having at least 80% identity thereto is fused to a heterologous amino acid sequence, optionally wherein the CHORD-derived polypeptide comprises an amino acid sequence having at least 65%, at least 70%, at least 75%, at least 80%, at least 85%, at least 90%, at least 95%, at least 96%, at least 97%, at least 98%, or at least 99% identity to SEQ ID NO:4, SEQ ID NO:99, or SEQ ID NO:100.

Embodiment 9 is a recombinant microorganism according to any of Embodiments 1-8, wherein the recombinant microorganism has increased biomass productivity with respect to a control microorganism cultured under identical conditions, wherein the conditions are batch, semicontinuous, or continuous culture.

Embodiment 10 is a recombinant microorganism according to embodiment 9, wherein the recombinant microorganism is an alga and the culture conditions under which increased productivity is demonstrated are photoautotrophic.

Embodiment 11 is a method of producing biomass or at least one bioproduct, comprising culturing the microorganism of any of claims 1-10 in a suitable culture medium to produce biomass or at least one bioproduct, optionally further including recovering biomass or at least one bioproduct from the culture.

Embodiment 12 is a method according to Embodiment 11, wherein the culture conditions are batch, semicontinuous, or continuous culture.

Embodiment 13 is a method according to embodiment 11 or 12, wherein the recombinant microorganism is an alga and the culture conditions are photoautotrophic.

Embodiment 14 is a biomass comprising a recombinant microorganism according to any of embodiments 1-9.

EXAMPLES

Applicants have identified and isolated from the algal strain *Nannochloropsis gaditana* two genes whose altered expression confer increased productivity, for example increased productivity of biomass and lipid, in microorganisms. These discoveries were made by identifying genes encoding cell cycle regulatory family members in the genome of the algal strain *Nannochloropsis* WT-3730, constructing vectors designed to alter gene expression, transforming them into *Nannochloropsis,* and analyzing the resulting algal lines for increased productivity, especially increased productivity of lipid, such as FAME, and biomass, such as AFDW or TOC.

Media Used in Examples

The following media are used in the Examples.

PM066 medium includes nitrate as the sole nitrogen source. PM066 medium included 10 mM nitrate (NO3) and 0.417 mM phosphate (PO4) along with trace metals and vitamins in Instant Ocean salts. PM066 media was made by adding 5.71 ml of a 1.75 M NaNO3 stock solution (148.7 g/L), and 5.41 ml of a 77 mM K2HPO4.3H2O stock solution (17.57 g/L) to 981 mls of Instant Ocean salts solution (35 g/L) along with 4 ml of Chelated Metals Stock Solution and ml of 4 ml Vitamin Stock Solution. Chelated Metals Stock Solution was prepared by adding to 400 mls of water 2.18 g Na2EDTA.2H2O; 1.575 g FeCl3.6H2O; 500 µl of 39.2 mM stock solution (0.98 g/100 ml) CuSO4.5H2O; 500 µl of 77.5 mM stock solution (2.23 g/100 ml) ZnSO4.7H2O; 500 µl of 42.0 mM stock solution (1.00 g/100 ml) CoCl2.6H2O; 500 µl of 910.0 mM stock solution (18.0/100 ml) MnCl2.4H2O; 500 µl of 26.0 mM stock solution (0.63 g/100 ml) Na2MoO4.2H2O; bringing up to 500 ml final volume, and filter sterilizing. Vitamin Stock Solution was prepared by adding to 400 mls of water 0.05 g Thiamine HCl; 500 µl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

PM074 is a nitrogen replete medium that is 10× F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM NaNO3, 0.361 mM NaH2PO4.H2O, 10× F/2 Trace metals, and 10× F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

Example 1

Insertional Mutagenesis of *Nannochloropsis Gaditana*

A wild type *Nannochloropsis gaditana* strain, WT-3730, which is a subcultured isolate of the *N. gaditana* strain CCMP1894, obtained from the Provasoli-Guillard National Center for Marine Algae and Microbiota (NCMA, Maine, U.S.A.), formerly the Culture Collection of Marine Phytoplankton (CCMP), was used as a wild type background for insertional mutagenesis and genetic manipulation. A construct that included a resistance gene was transformed into *Nannochloropsis gaditana* cells. The construct (SEQ ID NO:57) included the *Aspergillus blasticidin* resistance gene codon-optimized for *Nannochloropsis* expression (SEQ ID NO:98), operably linked to the *Nannochloropsis* TCTP promoter (SEQ ID NO:97) as described in U.S. Patent Publication No. 20140220638, filed Dec. 6, 2013, incorporated herein by reference in its entirety. *Nannochloropsis gaditana* cells were transformed by electroporation essentially as described in U.S. Patent Publication No. 20140220638.

Example 2

Screen and Isolation of Increased Lipid Mutants

Initially, random insertion tagged libraries of transformed *Nannochloropsis* were screened for increased lipid content using fluorescence activated cell sorting (FACS) techniques coupled with a fluorescent neutral lipid specific dye, BODIPY 505/515 (Life Technologies). Antibiotic resistant colonies appearing on transformation plates were resuspended into liquid culture and acclimated to low light intensities, stained with BODIPY, and sorted by flow cytometry using a BD FACSAria II flow cytometer (BD Biosciences, San Jose, Calif.) such that high BOPDIPY fluorescence cells were selected. BODIPY staining was performed by treating 1 ml of cells with a final concentration of 12.5% glycerol and 0.1 ug/ml BODIPY. In general, approximately 0.5 to 2% of the total population of cells was selected as having the highest BODIPY fluorescence from this first screening procedure. In some instances, two successive rounds of sorting based on increased BODIPY fluorescence were performed. Sorted cells were pooled and grown up in 25 ml batch cultures in nitrogen-replete medium, normalized by cell number, and assessed for TOC and FAME levels. Flasks (25 cm2) containing approximately 30 ml PM066 nitrogen replete medium were inoculated with sorted cells and cultured in an Adaptis growth chamber, shaking at approximately 130 rpm in an environment containing 1% CO2 enriched air and exposed to approximately 274 µE·m-2·s-1 light on a 16 h light (at 30° C.): 8 h dark (at 25° C.) cycle.

FAME analysis was performed on 2 mL samples that were dried using a GeneVac HT-4X. To the dried pellets the following was added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 µL of glass beads (425-600 nm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were vortexed for five minutes at 2 krpm and finally centrifuged for 3 minutes at 1 krpm. The heptane layer was sampled using a Gerstel MPS Autosampler. Quantitation used the 80 µg of C23:0 FAME internal standard.

Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The four point calibration range was from 2 ppm to 200 ppm corresponding to 20-2000 ppm for non-diluted cultures with a correlation coefficient of r2>0.999.

Batches with increased TOC and FAME compared to wild type were plated onto PM066 plates containing 100 µg/mL blasticidin and incubated under constant light (~80 µmol photons m-2 sec-1) until individual colonies appeared (about 2-3 weeks). Recovered individual colonies were further assessed for productivity improvements as described in the following example.

Example 3

Lipid Productivity Assessment of Clones Having Increased Lipid Production

Seven high lipid producing isolates were assessed in a batch growth assay to test lipid productivities. In this assay, triplicate 225 cm2 flasks for each strain were inoculated with algae to provide a culture density of 0.15 OD 730 nm in a total volume of 500 mL of PM066 medium that includes 8.8 mM nitrate as the nitrogen source. Stir bars were added to each flask, and stoppers having a syringe filter for air/CO2 delivery at a rate of 100 ml/min and a clave connector for sampling were fitted to the flasks, which were given random positions along the 16-flask rack. The stir plates beneath the rack were operated at 450 rpm. The LED light bank provided a 16:8 light regime designed to provide 1800 µE·m-2·s-1 for 16 hours, followed by 8 hours of darkness. The temperature varied from 25° C. to 34° C. Samples (typically 2 mLs) were removed on days 3, 5, 6, 7, 8, 9, and 10 for TOC and FAME analysis. After Day 5, all seven high lipid containing isolates were clearly outperforming wild type in FAME productivity (FIG. 1). By Day 10, strain GE-5877 had a 62% increase in volumetric FAME productivity compared to wild type WE-3730 (FIG. 1 and Table 1).

TABLE 1

FAME Productivity Values and Percent Improvements over WE-3730 on Day 10 of the Batch Growth Assay

| Strain | Day 10 FAME (mg/L) | % Increase over WT |
|---|---|---|
| GE-5870 | 112.1 | 40% |
| GE-5871 | 93.5 | 17% |
| GE-5873 | 107.3 | 34% |
| GE-5874 | 112.1 | 40% |
| GE-5875 | 114.5 | 43% |
| GE-5876 | 92.0 | 15% |
| GE-5877 | 129.4 | 62% |
| WE-3730 | 80.1 | — |

Example 4

Genotyping of Increased Lipid Mutants

Seven strains with confirmed increased lipid phenotypes were sequenced to identify the causative mutation. Whole genomic DNA of *Nannochloropsis gaditana* mutants were used for Nextera DNA library preparation according to the recommended protocol (Illumina Inc., San Diego, Calif.). The libraries were sequenced by paired-end sequencing on an Illumina MiSeq instrument. In each of the seven cases, a single vector integration event occurred between the third and fourth exon in a gene coding for a CHORD (cysteine and histidine rich domain) protein product (referred to as gene 3266 or "CHORD-3266" (SEQ ID NO:1)). Since all seven of the mutant isolates were essentially identical except for SNPs in non-coding regions, strain GE-5877 was picked for a more detailed characterization (the sequence of the disrupted 3266 locus is provided as SEQ ID NO:56).

Example 5

Physiological Assessment of GE-5877

Figure 2A:
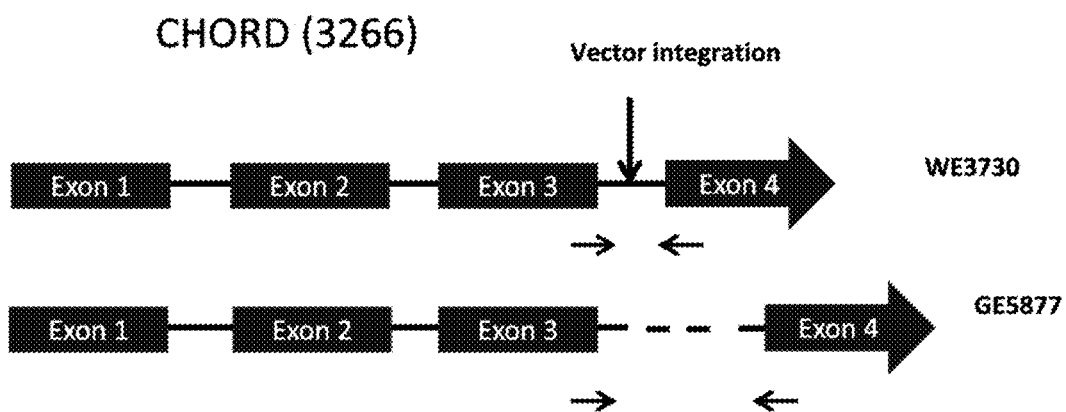
FIGS. 2A-2G provide characterization information for strain GE-5877.
Figure 2B:
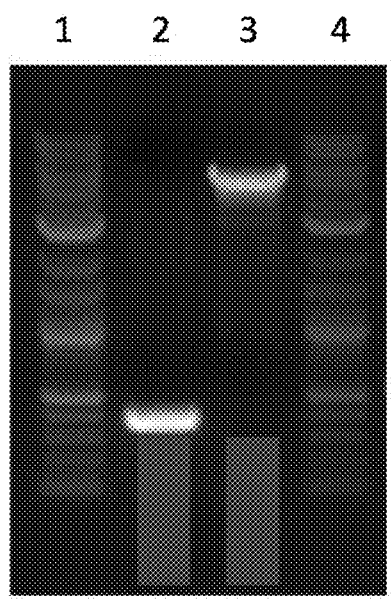
Figures 2C, 2D, 2E:
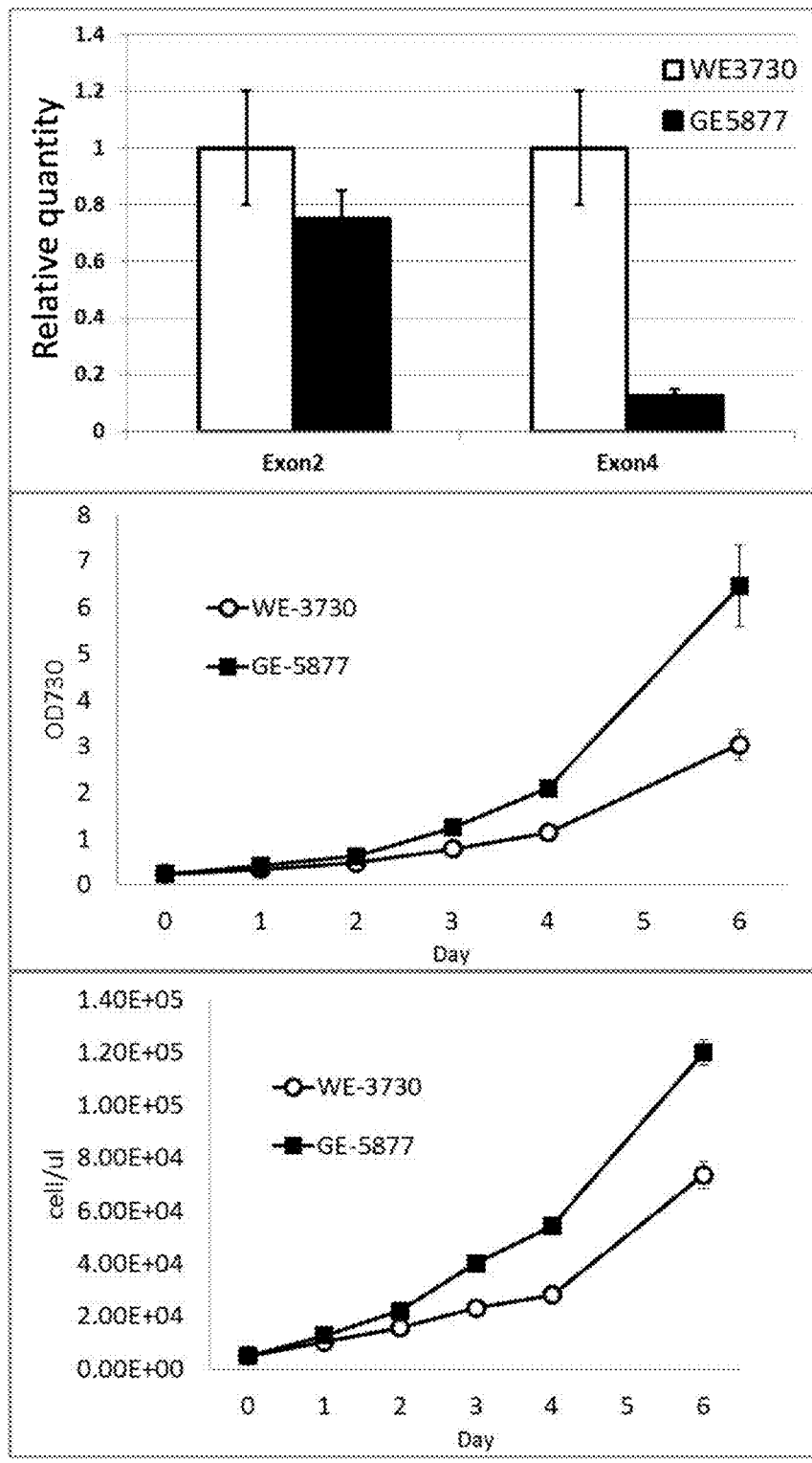
Figures 2F, 2G:
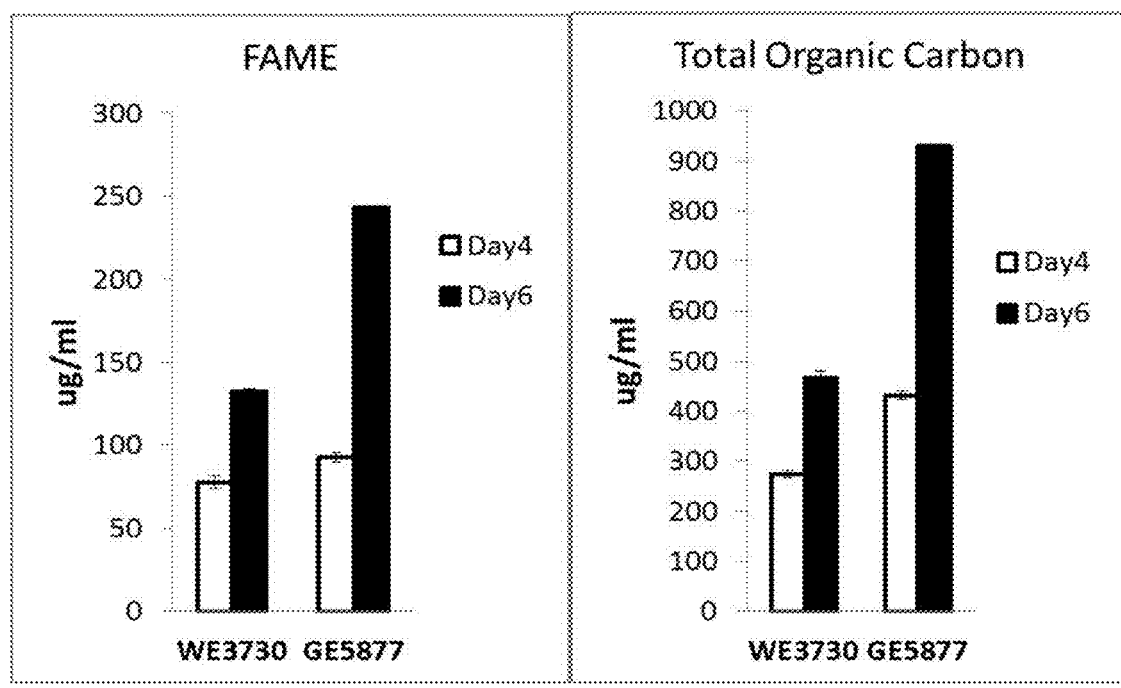

GE5877 and wild type strain WE3730 were grown in shake flasks with approximately 100 µE light on a 16:8 diel cycle for six days. Samples were taken throughout the culture period for cell counts, OD730, FAME, TOC, and polynucleotide extraction. Polynucleotide extraction, polymerase chain reaction (PCR), and quantitative real-time PCR (qRT-PCR) were performed essentially as disclosed in U.S. Patent Publication Nos. 20150191515 and 20150183838, both of which are incorporated by reference in their entireties. Sequencing results initially revealed the mutagenesis vector was inserted between exon 3 and exon 4 of the CHORD-3266 locus (Example 4). PCR using primers (SEQ ID NO:58 and SEQ ID NO:59) flanking the insertion site confirmed the presence of the vector (FIG. 2A). qRT-PCR indicated that the lesion caused by the vector integration interferes with transcription of the full length CHORD gene (FIGS. 2A and 2B). qRT-PCR amplification was performed using sequence specific primers for exon 2 (SEQ ID NO:60 and SEQ ID NO:61) and exon 4 (SEQ ID NO:62 and SEQ ID NO:63). qRT-PCR products that resulted from primer pairs amplifying exon 2 versus primer pairs amplifying exon 4 revealed different transcript levels corresponding to these two regions of the disrupted CHORD-3266 gene (FIG. 2C). These results indicated two separate transcripts were being produced. GE5877 outperformed WE3730 in cell density measured by both optical density (FIG. 2D) and cell counts (FIG. 2E), and was superior to the wild type strain in both biomass and FAME productivity (FIGS. 2E and 2F; Table 2), most likely driven by the reduction in generation time as seen by cell counts over the time course (FIG. 2E).

TABLE 2

FAME ug/mL and Total Organic Carbon (TOC) ug/mL Content of WE-3730 and GE-5877 Batch Growth Cultures

| | FAME Day 4 | FAME Day 6 | TOC Day 4 | TOC Day 6 |
|---|---|---|---|---|
| WE-3730 | 77.7 | 132 | 275 | 467 |
| GE-5877 | 92.7 | 243 | 432 | 929 |
| % increase | 19% | 84% | 57% | 99% |

Example 6

Transcriptomics Analysis of GE-5877

GE5877 and wild type strain WE3730 were grown in shake flasks with approximately 100 µE 16:8 diel cycle for six days as described in Example 5. After a week of acclimation, both wild type and CHORD knockout GE5877 were inoculated to an OD730 of 0.25 (t=0) in biological triplicates and were harvested for RNA extractions three hours after inoculation, when both strains were at essentially equal densities and similar acclimation states.

To isolate total RNA, 10 mLs of algal cell culture was spun down at 4000×g for 5 minutes and the supernatant was decanted. The pellet was resuspended in 1.8 mL Buffer A (5 mL TLE Grinding Buffer, 5 mL phenol, 1 mL 1-bromo-3-chloropropane and 20 nt mercaptoethanol, where TLE Grinding Buffer includes 9 mL of 1M Tris pH 8, 5 mL of 10% SDS, 0.6 mL of 7.5 M LiCl, and 0.45 M EDTA, in a final volume of 50 mL) and transferred to a 2 mL microcentrifuge tube containing approximately 0.5 mL of 200 μm zirconium beads. The tube was vortexed vigorously for 5 min at 4° C. and then centrifuged for 2 min at 11.8×g. The aqueous layer was then removed and pipetted into a new 2 mL tube, to which 1 mL 25:24:1 phenol extraction buffer (25 mL phenol pH 8 or 5.1; 24 mL 1-bromo-3-chloropropane, and 1 mL isoamyl alcohol) was added and the tube was shaken vigorously and centrifuged for 2 min at 11.8×g. After centrifugation, the aqueous layer was removed and pipetted into a new 2 mL centrifuge tube, to which 1 ml 1-bromo-3-chloropropane was added. The tube was shaken and again centrifuged for 2 min at 11.8×g. The aqueous layer was removed to a new tube and 0.356 volumes of 7.5 M LiCl was added. The tube was inverted 10-12 times and stored at −20° C. overnight. The next day, samples were allowed to come to room temperature without mixing and were centrifuged at 16,000×g for 30 minutes. The supernatant was removed and the pellet was washed with 1 mL of ice cold 80% ethanol. The tube was centrifuged for 30 min at 16,000×g and allowed to air dry after the supernatant had been removed. Finally, the RNA pellet was resuspended in 50 μl ultrapure water. The RNA quality was assessed by on-chip gel electrophoresis using an Agilent 2100 Bioanalyzer and RNA6000 LabChip according to manufacturer instructions.

Next-generation sequencing libraries were prepared from the isolated RNA utilizing the TruSeq Stranded mRNA Sample Prep Kit (Illumina) following manufacturer instructions. The TruSeq libraries were sequenced using sequencing-by-synthesis (Illumina MiSeq) to generate 100 bp paired-end reads using the mRNA-Seq procedure (described in Mortazavi et al. (2008) Nature Methods 5:621-628). Mappable reads were aligned to the *N. gaditana* reference genome sequence using TopHat (tophat.cbcb.umd.edu/). Expression levels were computed for every annotated using the Cuffdiff component of the Cufflinks software (cufflinks.cbcb.umd.edu). Differential expression analysis was performed using the R package edgeR (McCarthy et al. (2012) Nucl. Acids Res. 40:doi:10/1093/nar/gks042)). Expression levels in units of fragments per kilobase of transcript per million mapped reads (FPKM) were reported for every gene in each sample using standard parameters. FPKM is a measure of relative transcriptional levels that normalizes for differences in transcript length.

Global analysis of the CHORD knockout strain GE-5877 against the wild type (WE-3730) transcriptome revealed that the majority of differentially regulated genes were down-regulated in strain with respect to wild type (FIG. 3A). Out of the approximately 3,000 genes identified with statistically significant expression levels across all replicates, only 3.5% were upregulated more than 2-fold in the mutant compared to wild type, while 20% were down-regulated less than 2-fold. Analysis of Gene Ontology categories (which provide a controlled vocabulary of terms for describing gene product characteristics and their functions, see: geneontology.org) revealed that the relatively small subset of up-regulated genes was enriched with genes involved in cell cycle progression and mitosis (FIG. 3B). Indeed, processes like "M/G1 transition of mitotic cell cycle" and cellular components such as the "kinetochore" and "proteasome complex" that play critical roles in cell division, were amongst the top 10 Gene Ontology categories enriched for upregulated genes. These expression profiles were consistent with the increased growth rate observed for the CHORD knockout and suggest that cell cycle control is de-regulated in this mutant.

Example 7

Recapitulation of GE-5877 Mutation

Figure 4A:
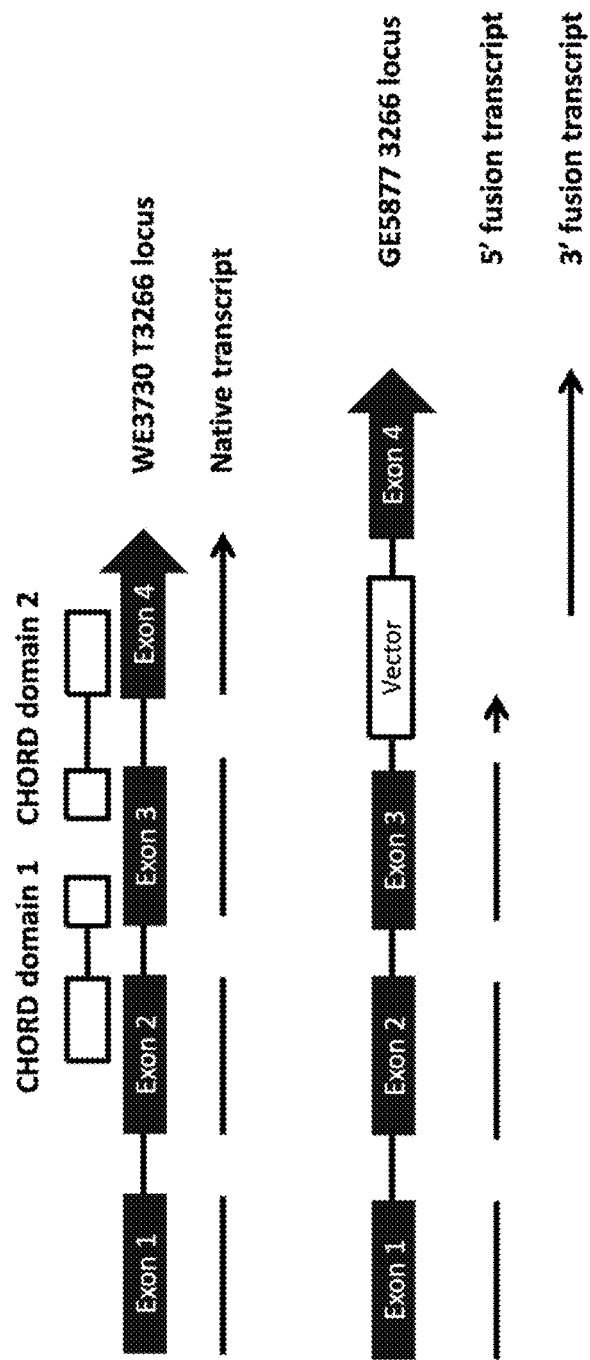
FIGS. 4A-4C depict further characterization of strain GE-5877.
Figure 4B:
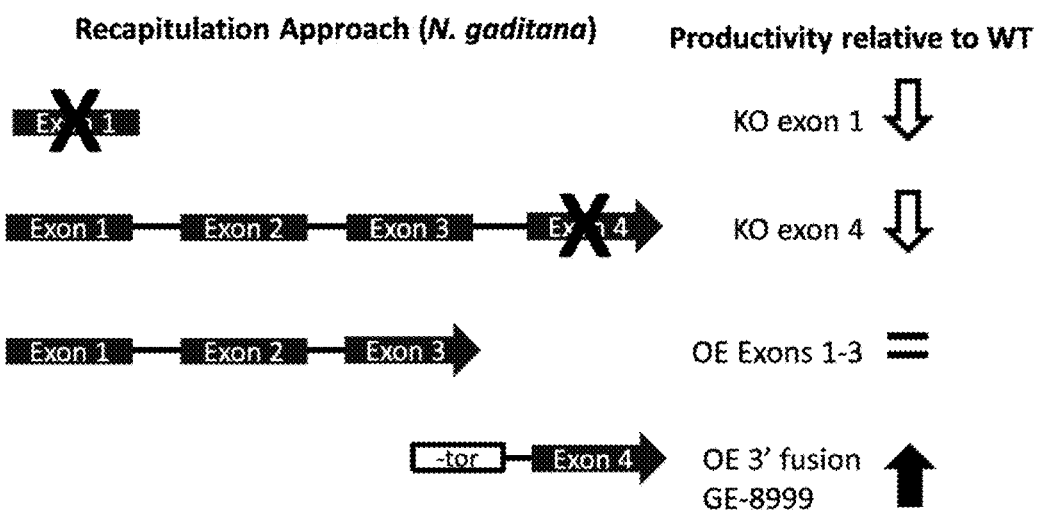
Figure 4C:
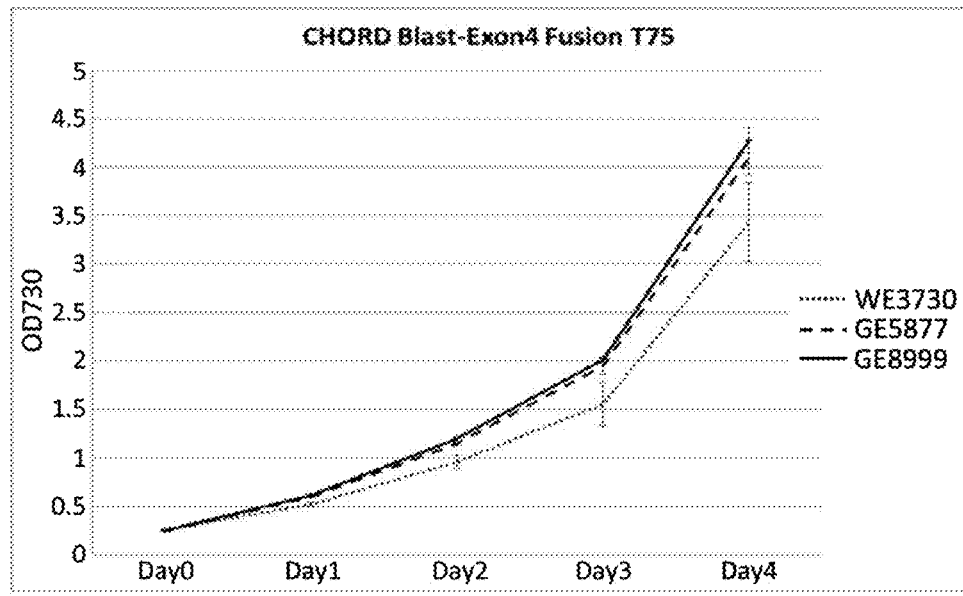
Figure 5:
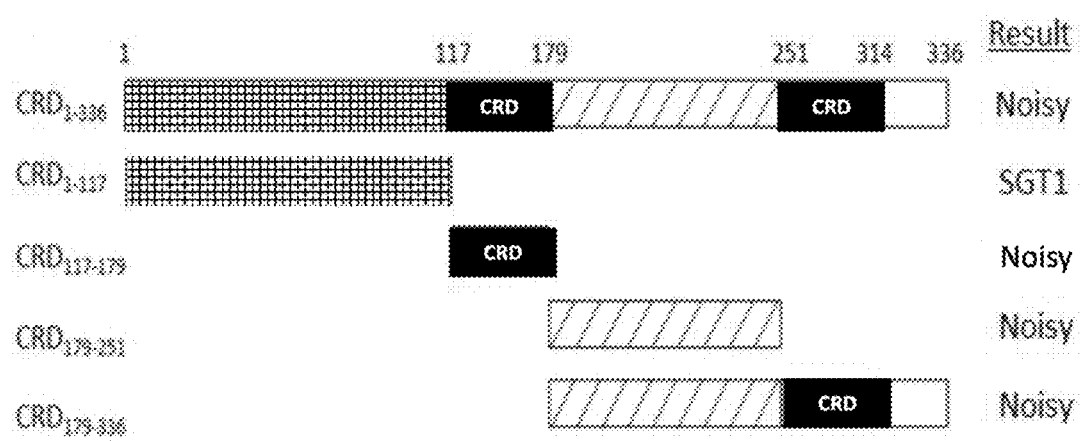
FIG. 5 provides a cartoon depicting modular structure of full length CHORD-3266 protein (CRD1-336) and the different peptides (CRD1-117, CRD117-179, CRD179-251 and CRD179-336) used as bait in Y2H screens and the outcome for each screen.

Transcriptomics data obtained in Example 6 revealed that strain GE-5877 expressed two mutant CHORD transcripts—the first spanning exons 1-3 (SEQ ID NO:2) and the second beginning in the 3' region of the inserted blasticidin gene and spanning the remainder of intron 4 and exon 4 (SEQ ID NO:3) (FIG. 4A). In an attempt to recapitulate the GE-5877 phenotype, gene knock-out and overexpression approaches were both employed in the *Nannochloropsis gaditana* WE-3730 background strain. Inserting an antibiotic-resistance marker into exon 1 or exon 4 did not recapitulate the increased growth rate phenotype (FIG. 4B). Similarly, overexpressing genomic DNA spanning exons 1-3 did not result in the desired phenotype (FIG. 4B). Surprisingly, overexpression of the transcript product of the 3' end of the vector and spanning intron 4 and exon 4 (expression construct provided as SEQ ID NO:64), as in strain GE-8999, did result in an improved growth rate similar to the original GE-5877 mutant phenotype (FIGS. 4B and 4C; Table 3). This truncated and mutated transcript (SEQ ID NO:3) encoded a fusion polypeptide (SEQ ID NO:100) which contained the amino acid sequence encoded by exon 4 (SEQ ID NO:99) which included the last 40 out of 65 amino acids of the second CHORD domain (61% of CHORD domain 2, i.e., 61% of SEQ ID NO:4). These results support that overexpression of exon 4 (that includes approximately 60% of CHORD domain 2) fused to a heterologous sequence is sufficient to increase biomass compared to a wild type strain expressing a non-altered CHORD-3266 gene transcript.

TABLE 3

Optical Density (OD) of Strains after Four Days of Batch Growth

| Strain | OD730 on Day 4 | % increase over WE-3730 |
|---|---|---|
| WE-3730 | 3.43 | — |
| GE-5877 | 4.10 | 19% |
| GE-8999 | 4.28 | 25% |

Example 8

Yeast Two Hybrid Experiments

Total *Nannochloropsis* RNA was isolated independently from cultures from grown in four different conditions which were later pooled: standard nitrogen replete conditions, nitrogen deprivation, phosphorus deprivation, and high light intensity. For making cDNA to screen in the Yeast Two Hybrid assay, RNA was isolated by removing 10 mLs from the algal cell culture, which was then spun down at 4000×g for 5 minutes and the supernatant was decanted. The pellet was resuspended in 1.8 mL Buffer A (5 mL TLE Grinding Buffer, 5 mL phenol, 1 mL 1-bromo-3-chloropropane and 20

μL mercaptoethanol, where TLE Grinding Buffer includes 9 mL of 1M Tris pH 8, 5 mL of 10% SDS, 0.6 mL of 7.5 M LiCl, and 0.45 M EDTA, in a final volume of 50 mL) and transferred to a 2 mL microcentrifuge tube containing approximately 0.5 mL of 200 μm zirconium beads. The tube was vortexed vigorously for 5 min at 4° C. and then centrifuged for 2 min at 11.8×g. The aqueous layer was then removed and pipetted into a new 2 mL tube, to which 1 mL 25:24:1 phenol extraction buffer (25 mL phenol pH 8 or 5.1; 24 mL 1-bromo-3-chloropropane, and 1 mL isoamyl alcohol) was added and the tube was shaken vigorously and centrifuged for 2 min at 11.8×g. After centrifugation, the aqueous layer was removed and pipetted into a new 2 mL centrifuge tube, to which 1 ml 1-bromo-3-chloropropane was added. The tube was shaken and again centrifuged for 2 min at 11.8×g. The aqueous layer was removed to a new tube and 0.356 volumes of 7.5 M LiCl was added. The tube was inverted 10-12 times and stored at −20° C. overnight. The next day, samples were allowed to come to room temperature without mixing and were centrifuged at 16,000×g for 30 minutes. The supernatant was removed and the pellet was washed with 1 mL of ice cold 80% ethanol. The tube was centrifuged for 30 min at 16,000×g and allowed to air dry after the supernatant had been removed. Finally, the RNA pellet was resuspended in 50 μl ultrapure water. The RNA quality was assessed by on-chip gel electrophoresis using an Agilent 2100 Bioanalyzer and RNA6000 LabChip according to manufacturer instructions.

The cDNA library was synthesized using the Make Your Own "Mate & Plate™" Library System User Manual as a guideline (Clontech, Mountain View, Calif.). However, instead of using the SMART III Oligo provided by the kit, a modified 5' primer that takes advantage of a previously described splice leader identified in *Nannochloropsis* (see US Patent Application Publication 2014/0186842, "*Nannochloropsis* Spliced Leader Sequences and Uses Therefor" filed Dec. 5, 2013, incorporated herein in its entirety) was used for first strand synthesis (SEQ ID NO:5). A modified 3' primer was also used for second strand synthesis (SEQ ID NO:6). Both modified 5' and 3' primers contained sequence extensions that added nucleotide sequences compatible with the yeast expression vector pGADT7-rec (Clontech) to allow for subsequent cloning by circular polymerase extension cloning (cpec; see for example Quan & Tij an (2009) PLoS One 4(7): e6441). After cloning of the second strand cDNA into pGAD-T7-rec, the resulting library was transformed into *E. coli*. Approximately 750,000 colonies were obtained which represents at least 25-fold coverage of the *Nannochloropsis* transcriptome. Low redundancy of the library was verified by sequencing and the library was transformed into yeast strain Y2HGold (Clontech). The final yeast expression library consisted of more than 2 million colonies.

To identify potential protein binding partners, CHORD protein fragments were used in a yeast-two hybrid (Y2H) screen. Coding sequence for CHORD-3266 encoding full length CHORD protein (SEQ ID NO:22) was divided into its different domains: CRD1-117 (SEQ ID NO:23), CRD117-179 (SEQ ID NO:24), CRD179-251 (SEQ ID NO:25), and CRD179-336 (SEQ ID NO:26). Each domain was used as bait in the Y2H screen (FIG. 5A) (see, for example, Chien et al. (1991) Proc. Natl. Acad. Sci. 88: 9578-9582; Guarente (1993) Proc. Natl. Acad. Sci. 90: 1639-1641; Rutisjmu & Golemis (2008) Biotechniques 44: 655-662). The full length sequence and individual domains were each amplified using sequence specific primers containing overhanging sequence for cloning into the yeast-two-hybrid plasmids: CRD1-336 (SEQ ID NO:15 and SEQ ID NO:16) CRD1-117 (SEQ ID NO:15 and SEQ ID NO:17), CRD117-179 (SEQ ID NO:18 and SEQ ID NO:19), CRD179-251(SEQ ID NO:20 and SEQ ID NO:21), and CRD179-336 (SEQ ID NO:20 and SEQ ID NO:16).

The coding sequence fragments of CHORD-3266 were amplified from cDNA using forward primer and reverse primers as described in the previous paragraph. The individual fragments were cloned into the bait vector pGBKT7 (Clontech) by circular polymerase extension cloning and transformed into *E. coli*. Upon sequence confirmation it was transformed into yeast strain Y187 (Clontech) and screened for interactions against the *Nannochloropsis* cDNA library cloned into the prey vector as described above.

The prey library was screened for by mating of the library-containing (prey) strain with each individual bait strain (i.e., a strain expressing CRD1-117) according to the Matchmaker™ Gold Yeast Two-Hybrid System User Manual (Clontech). A mating efficiency of ~4.5% was achieved for the CRD1-117 screen (good mating efficiencies are usually between 3-5%). Based on these numbers, it is estimated that more than 10 million interactions were tested.

Some of the CHORD domains resulted in multiple false positives, but one domain (CRD1-117) was more selective and only a few positive clones were retrieved based on their growth and blue color on selective media, which resulted from the interaction of the expressed proteins with CRD1-117 and the subsequent activation of auxotrophic markers and a reporter gene. After subtraction of false positives from the other domain hits, one hit remained which was unique to this domain: the gene encoding SGT1 (SEQ ID NO:27) encoded at *N. gaditana* genome locus Naga_100120g12; Genbank Accession AZIL01000354.1. This gene is commonly referred to as "suppressor of G2 allele of skp1" because it was discovered in a genetic suppressor screen aimed at suppressing skp1-4, a mutant with defects in yeast kinetochore function (Hieter et al. 1999 Nature 402:362-363). SGT1 is an essential component of the yeast kinetochore assembly pathway and has been associated to a number of different biological roles in different organisms. Furthermore, mammalian SGT1 is known to interact with an Hsp90 chaperone and melusin, the human homolog of CHORD-3266. Similarly, the *Arabidopsis* CHORD-3266 homolog, RAR1, is also known to bind *Arabidopsis* SGT1 (Takahashi et al. (2003) PNAS USA 100:11777-11782). Given that there is precedent in the literature for CHORD-3266 homologs binding to SGT1 proteins, the observed interaction by Y2H was likely to be an interaction that occurs in vivo.

In order to determine whether SGT1 (SEQ ID NO:27) and Skp1 were members of the same pathway, we tested whether *Nannochloropsis* SGT1 was capable of binding to *Nannochloropsis* Skp1 by Y2H. Two different Skp1 proteins were identified in *Nannochloropsis*, SKP1-8611 (polynucleotide SEQ ID NO:9 and polypeptide SEQ ID NO:28) and Skp1-7479 (SEQ ID NO:29 encoded at *N. gaditana* genome locus Naga_100005g56, Genbank Accession AZIL01000936). Protein coding sequences were amplified using sequence specific primers for SGT1 (SEQ ID NO:30 and SEQ ID NO:31), SKP-8611 (SEQ ID NO:32 and SEQ ID NO:33), and SKP-7479 (SEQ ID NO:34 and SEQ ID NO:35) and cloned into the prey and bait vectors as described above. These constructs were used in a direct yeast-two hybrid assay and both resulted in positive interactions with SGT1 by Y2H (FIG. 5B).

Example 9

Over-Expression of SKP1 in *Nannochloropsis Gaditana*

Figure 7:
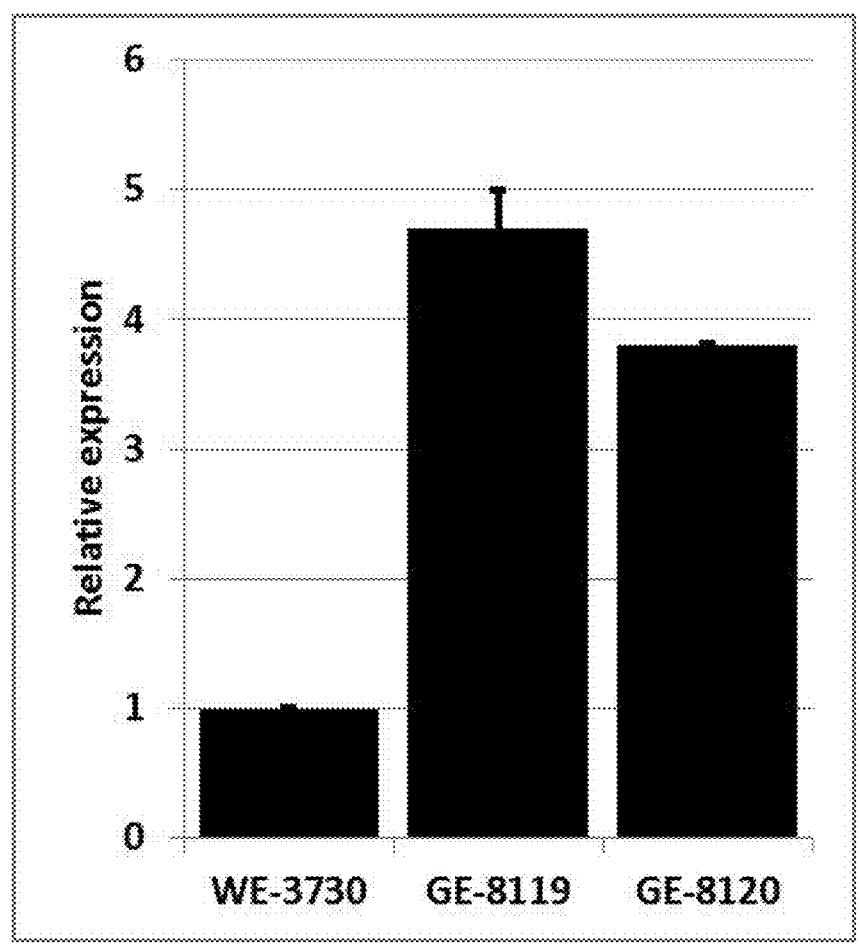
FIG. 7 provides a bar graph depicting steady-state mRNA levels of SKP1-8611 transcript in SKP1-8611 overexpressing strains GE-8119 and GE-8120 compared to wild type strains WE-3730 as determined by qRT-PCR.
Figure 8A:
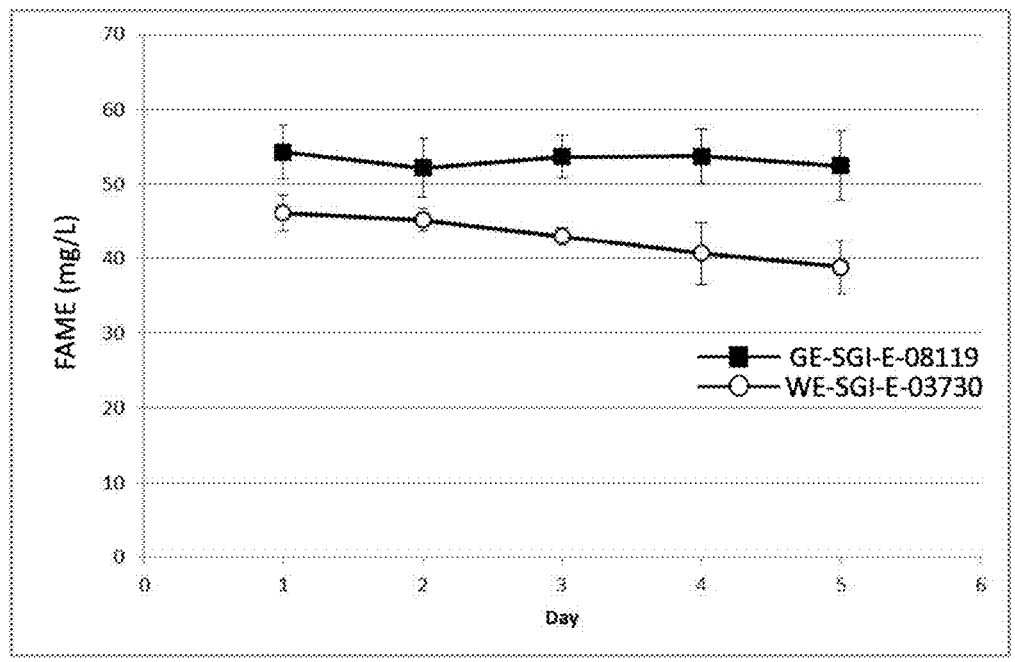
FIGS. 8A-8D provide line graphs depicting FAME and TOC values in two independent semi-continuous productivity assays of GE-8119 and WE-3730 at a 30% daily dilution rate.
Figure 8B:
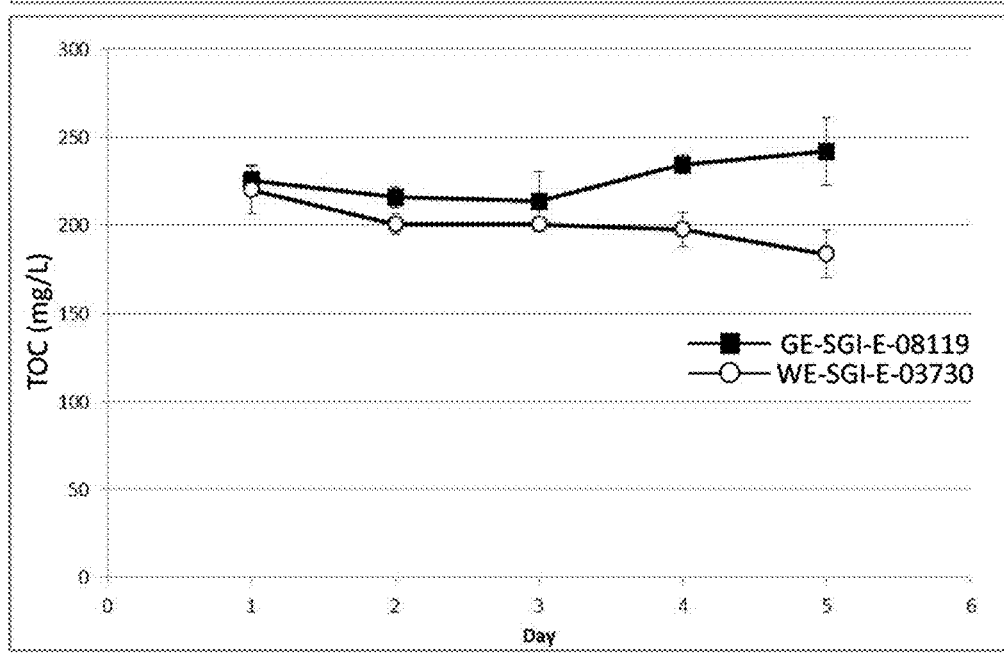
Figure 8C:
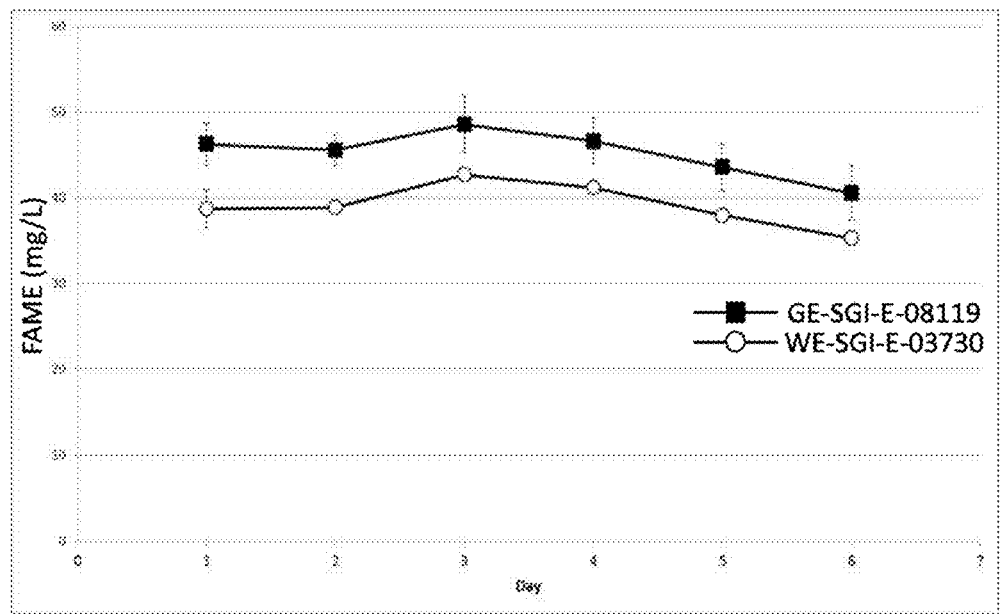
Figure 8D:
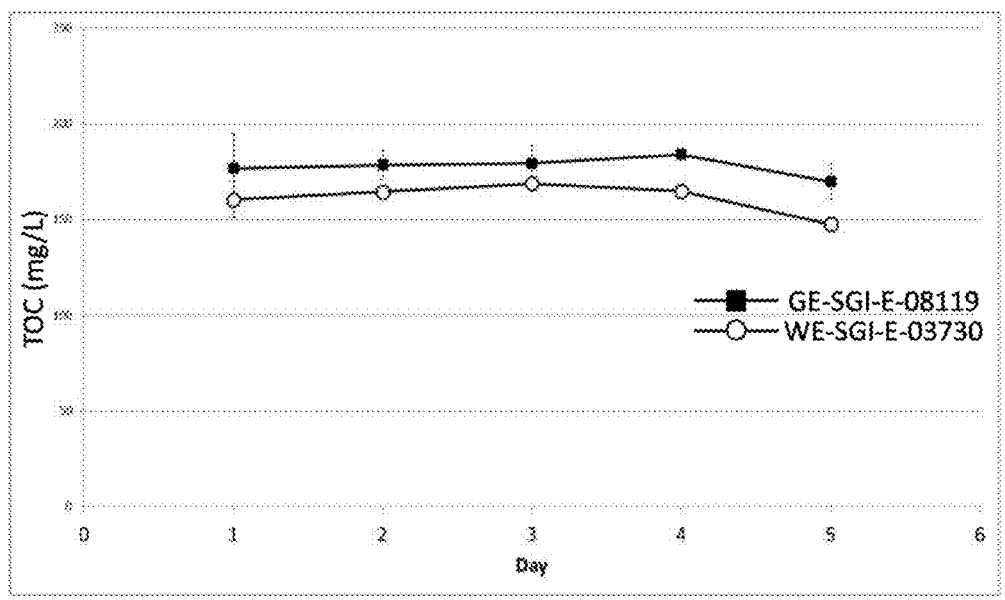

Guided by the transcriptomics and Y2H data the SKP-Cullin-F-box E3 ubiquitin-ligase complex, a key component of the ubiquitin-proteasome system, was targeted for manipulation. SKP1-8611 (SEQ ID NO:9, encoding SEQ ID NO:28; FIG. 6) was overexpressed based on the positive regulatory role it has on the cell cycle. Primers (SEQ ID NO:7 and SEQ ID NO:8) were used to PCR amplify SKP1-8611 (SEQ ID NO:9) which was then cloned into a vector containing the 5901 promotor (SEQ ID NO:103) and T9 terminator (SEQ ID NO:104) to generate a SKP1-8611 overexpression vector (SEQ ID NO:10). Transformation of the SKP1-8611 overexpression vector (SEQ ID NO:10) into *Nannochloropsis* was performed by electroporation. Colonies were recovered on PM74 agar plates containing 500 µg/mL hygromycin antibiotic and PCR-screened to confirm the presence of the SKP1-8611 overexpression construct. Positive strains GE-8119 and GE-8120 were subjected to qRT-PCR analysis to confirm overexpression of the SKP1 transcript.

qRT-PCR experiments were performed to assess the steady-state mRNA levels of the SKP1-8611 transgenes in the *Nannochloropsis* transgenic lines GE-8119 and GE-8120, as compared to a wild-type control line. Total RNA was isolated essentially as described in Example 8. Isolated RNA was converted to cDNA using a commercial reverse transcriptase according to the manufacturer's protocol. For PCR, Ssofast EvaGreen Supermix (Bio-Rad, Hercules, Calif.) was used along with gene-specific primers. The PCR reaction was carried out on C1000 Thermal Cycler coupled with a CFX Real-time System (BioRad). Primer and cDNA concentrations were according to the manufacturer's recommendation. SKP1-8611 transcript was PCR amplified using sequence specific primers (SEQ ID NO:11 and SEQ ID NO:12). Transcript levels for each sample were normalized against a housekeeping gene with consistent expression levels under different culture conditions, specifically T5001704 which was amplified using sequence specific primers (SEQ ID NO:13 and SEQ ID NO:14). Relative expression levels were calculated using the ddCT method using BioRad's CFX Manager software. FIG. 7 shows normalized expression values plotted on the y-axis relative to wild-type (WT), where expression of SKP1-8611 was equal to 1 for WE-3730. The error bars represent the standard error for three technical replicates. Strains GE-8119 and GE-8120 were found to over-express the SKP1-8611 transgene at levels approximated 4-5 fold over the wild-type parent (FIG. 7).

Example 10

Productivity Assessment of Strain GE-8119

The confirmed SKP1 over-expression lines GE-8119 was tested for FAME and TOC levels to determine whether over-expression of the cDNA sequence encoding SKP1 also resulted in increased productivity. In this semicontinuous culture assay, triplicate 225 cm² flasks for each strain were inoculated with algae to provide a culture density of 0.15 OD 730 nm in a total volume of 500 mL of PM074 medium. Stir bars were added to each flask, and stoppers having a syringe filter for air/CO₂ delivery at a rate of 100 ml/min and a clave connector for sampling were fitted to the flasks, which were given random positions along the 16-flask rack. The stir plates beneath the rack were operated at 450 rpm. The LED light bank provided a programed sinusoidal 16:8 light regime designed to steadily ramp up to a peak of 2000 $\mu E \cdot m^{-2} \cdot s^{-1}$ and back down to 0 $\mu E \cdot m^{-2} \cdot s^{-1}$ over 16 hours, followed by 8 hours of darkness. The temperature varied from 25° C. to 34° C. Cultures were diluted 30% daily to achieve semi-continuous growth and, once cultures reached a steady growth state, samples (typically 2 mLs) were removed each day over 5-6 days for TOC and FAME analysis. FIG. 7 summarizes the results of experiments assessing productivity level of fatty acid methyl esters (FAME, FIG. 8) and total organic carbon (TOC, FIG. 8) values GE-8119 and wildtype WE-3730. Transgenic line GE-8119 over-expressing SKP1 was found to also outperform the wild-type in both FAME and TOC productivity (FIG. 8, Table 4).

TABLE 4

FAME and TOC Productivity of SKP1-Overexpressing Line
GE-8119 Compared to Wild Type in Semicontinuous Culture

|  | Run 1 (6 day avg ± SD) | | Run 2 (6 day avg ± SD) | |
| --- | --- | --- | --- | --- |
|  | FAME (mg/L) | TOC (mg/L) | FAME (mg/L) | TOC (mg/L) |
| WE-3730 | 42.7 ± 3.0 | 200 ± 13 | 39.1 ± 2.5 | 161 ± 8 |
| GE-8119 | 53.2 ± 0.9 | 226 ± 12 | 45.2 ± 2.7 | 178 ± 5 |
|  | (25% inc) | (12% inc) | (15% inc) | (10% inc) |

Example 11

Additional Cell Cycle Genes

Based on transcriptomics and yeast-two-hybrid data from Examples 6 and 8, additional members of the SKP-Cullin-F box E3 ubiquitin-ligase complex and other cell cycle regulator genes were targeted for knock out or overexpression (Table 5). These additional targets were SGT1 (polypeptide SEQ ID NO:27), SKP1-7479 (polypeptide SEQ ID NO:29), SKP2-6789 (polypeptide SEQ ID NO:36), CDC25 (polypeptide SEQ ID NO:37), FBW7-1 (polypeptide SEQ ID NO:38), FBW7-2 (polypeptide SEQ ID NO:39), FBW7-3 (polypeptide SEQ ID NO:40), FBW7-4 (polypeptide SEQ ID NO:41), FBW7-5 (polypeptide SEQ ID NO:51), Wee1-1 (polypeptide SEQ ID NO:43), Wee1-2 (polypeptide SEQ ID NO:44), Wee1-3 (polypeptide SEQ ID NO:45), Wee1-4 (polypeptide SEQ ID NO:46), Wee1-5 (polypeptide SEQ ID NO:47), Cyclin-6855 (SEQ ID NO:48), Cyclin-3560 (polypeptide SEQ ID NO:49), Cyclin-9008 (polypeptide SEQ ID NO:50), Cyclin-4163 (polypeptide SEQ ID NO:51), CDKA1-3735 (polypeptide SEQ ID NO:52), CDKA1-864 (polypeptide SEQ ID NO:53), CDKA1-9049 (polypeptide SEQ ID NO:54), and CDKA1-8325 (polypeptide SEQ ID NO:55). Each strain was assessed for increased FAME productivity on a batch growth assay as described in Example 5. Of the tested mutants, only SKP-8611 overexpressing lines GE-8119 and GE-8120 (that included gene SEQ ID NO:9 encoding polypeptide SEQ ID NO:28) demonstrated increased FAME productivities compared to WE-3730 (Table 5). As increased biomass productivities of GE-8119 and GE-8120 with respect to wild type cells were reflected in higher volumetric FAME productivities in these batch assays, the inability to detect higher FAME productivity in any of the additional mutants was also considered to be indicative of the lack of increased overall biomass productivity.

TABLE 5

Altering Expression of Genes of the SKP-Cullin-F Box E3 Ubiquitin-Ligase Complex and Cell Cycle Regulator Genes in *Nannochloropsis*

| Gene Name | Gene number | Protein SEQ ID NO: | Genetic Manipulation | % WT FAME |
|---|---|---|---|---|
| Skp1-8611 | 8611 | 28 | Overexpression | 125 |
| Skp1-7479 | 7479 | 29 | Overexpression | 100 |
| SGT1 | 1852 | 27 | Knockout | 100 |
| SGT1 | 1852 | 27 | RNAi | 100 |
| Skp2 (gDNA) | 6789 | 36 | Overexpression | 100 |
| Skp2 (CDNA1) | 6789 | 36 | Overexpression | 100 |
| Skp2 (CDNA2) | 6789 | 36 | Overexpression | 100 |
| CDC25 | 9451 | 37 | Overexpression | 100 |
| FBW7-1 | 2293 | 38 | Knockout | 100 |
| FBW7-2 | 284 | 39 | Knockout | 100 |
| FBW7-3 | 4601 | 40 | Knockout | 100 |
| FBW7-4 | 3015 | 41 | Knockout | 100 |
| FBW7-5 | 4195 | 42 | Knockout | 100 |
| Wee1-1 | 6397 | 43 | Knockout | 100 |
| Wee1-2 | 4623 | 44 | Knockout | 100 |
| Wee1-3 | 8521 | 45 | Knockout | 100 |
| Wee1-4 | 7374 | 46 | Knockout | 100 |
| Wee1-5 | 9810 | 47 | Knockout | 100 |
| Cyclin-6855 | 6855 | 48 | Overexpression | 100 |
| Cyclin-3560 | 3560 | 49 | Overexpression | 100 |
| Cyclin-9008 | 9008 | 50 | Overexpression | 100 |
| Cyclin-4163 | 4163 | 51 | Overexpression | 100 |
| CDKA1 | 3735 | 52 | Overexpression | 100 |
| CDKA1 | 864 | 53 | Overexpression | 100 |
| CDKA1 | 9049 | 54 | Overexpression | 100 |
| CDKA1 | 8325 | 55 | Overexpression | 100 |

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

Headings within the application are solely for the convenience of the reader, and do not limit in any way the scope of the invention or its embodiments.

All publications and patent applications mentioned in this specification are herein incorporated by reference to the same extent as if each individual publication or patent application was specifically and individually indicated to be incorporated by reference.

What is claimed is:

1. A recombinant algal microorganism transformed with a non-native nucleic acid molecule that comprises a heterologous promoter operably linked to a nucleic acid sequence encoding an algal CHORD-derived polypeptide, wherein the algal CHORD-derived polypeptide includes at least a portion of a cysteine and histidine rich domain (CHORD), wherein the algal CHORD-derived polypeptide comprises an amino acid sequence having at least 90% amino acid sequence identity to the amino acid sequence as set forth in SEQ ID NO: 99, wherein said algal CHORD-derived polypeptide is obtained from a polypeptide having at least 95% amino acid sequence identity to SEQ ID NO: 22, and wherein overexpression of said algal CHORD-derived polypeptide from said heterologous promoter increases biomass in the recombinant algal microorganism as compared to a control algal microorganism of the same species that does not comprise the non-native nucleic acid molecule.

2. A recombinant algal microorganism according to claim 1, wherein the CHORD-derived polypeptide comprises the amino acid sequence as set forth in SEQ ID NO: 99.

3. The recombinant algal microorganism of claim 1, wherein the algal microorganism is a *Nannochloropsis*.

* * * * *

SEQUENCE LISTING

```
<160> NUMBER OF SEQ ID NOS: 104

<210> SEQ ID NO 1
<211> LENGTH: 1327
<212> TYPE: DNA
<213> ORGANISM: Nannochloropsis gaditana
<220> FEATURE:
<221> NAME/KEY: misc_feature
<223> OTHER INFORMATION: CHORD-3266 coding sequence

<400> SEQUENCE: 1
atgaaactct atgtgcacta cgaggaggct ggtcaggatg aaaaggcatt gacgcttaag      60
ttgactctgc ccaaaagctg ggcggagcag ccgttgcttc aagtactgga gctgttcatc     120
gaatcctaca acaagaaaaa gaccggtcta cctcccttgg acaaagactt tgtccacatg     180
gaaaaagctg ggtaagtcct tactcgtgac agcgttccct ttctccagac tagacgccta     240
atagtgttct aatgtaccac tgggacacgc ctcgctgcct gtgcaccatg ctccatactc     300
aacgctgcta cagggcgta atccttccag tcggcaacat tgtgagcgac atgttgagcg      360
atagagatga tttgtatatc agatccgggc cagggcctgc tcgtgggaag attgcccatc     420
tcagttcgcc cccaaacgcg cacgcttcga gtgagtcgag cacaggattg ttgcgctgca     480
aaaactatgg atgcaatcag tcattttcgg aagaaaacaa ttcagaagag gcgtgccgct     540
ttcacaaggc accccccgtc tttcatgata cgaagaaagg gtggtcgtgc tgcgcgaagc     600
gagtatatga ctgggacgag ttccatacgg taagcgtgga agtgttcgtt ctcggcccca     660
ggactttgtt ttgaggcaat tggtgtactt taattggcgg ataaagggag gactcacaac     720
tttcgatatt caccgtctcc agatcgaggg gtgcaccaca ggacggcaca gtctcatcga     780
tccgaaggaa attttcgcgc cgtcccccac cctggctgca gccgcgcagg ccgagagggg     840
```

| agattgcagc aatacgtcaa gcgctgctac agtcatcaag agcattgatg aattcaatca | 900 |
| gtcgaatcca aatgccgccg ctgcatgcaa aacagcagcc tcgatgacgc tggcgggcac | 960 |
| gcgctgcacc gtcaaaccgg acgggtctgc cacctgtttg aacaaaggct gccaaaagga | 1020 |
| ctacttgctc aaggagaatc acccctctgc atgtcggtaa ggacaccgcg ctcgatggaa | 1080 |
| tcgtgagctt tacgttccca cgccaacact tcgccatttc tcctcccttc ctttctttag | 1140 |
| ctaccacgca gccggcccg tcttccacga cgcgggtaaa tactggtcat gttgccctgg | 1200 |
| aacggtcaag tacgacttcg acgactttct caagatccct ggatgcatgc tcagtagtca | 1260 |
| ttacgacgga agccaggaga gcctggaggc gttcactaga cacgccaaaa cgtctgaggg | 1320 |
| cacatga | 1327 |

<210> SEQ ID NO 2
<211> LENGTH: 821
<212> TYPE: DNA
<213> ORGANISM: Nannochloropsis gaditana
<220> FEATURE:
<221> NAME/KEY: misc_feature
<223> OTHER INFORMATION: CHORD-3266 5' fusion transcript

<400> SEQUENCE: 2

| atgaaactct atgtgcacta cgaggaggct ggtcaggatg aaaaggcatt gacgcttaag | 60 |
| ttgactctgc ccaaaagctg gcggagcag ccgttgcttc aagtactgga gctgttcatc | 120 |
| gaatcctaca acaagaaaaa gaccggtcta cctcccttgg acaaagactt tgtccacatg | 180 |
| gaaaaagctg ggggcgtaat ccttccagtc ggcaacattg tgagcgacat gttgagcgat | 240 |
| agagatgatt tgtatatcag atccgggcca gggcctgctc gtgggaagat tgcccatctc | 300 |
| agttcgcccc caaacgcgca cgcttcgagt gagtcgagca caggattgtt gcgctgcaaa | 360 |
| aactatggat gcaatcagtc attttcggaa gaaaacaatt cagaagaggc gtgccgcttt | 420 |
| cacaaggcac cccccgtctt tcatgatacg aagaaagggt ggtcgtgctg cgcgaagcga | 480 |
| gtatatgact gggacgagtt ccatacgatc gagggtgca ccacaggacg gcacagtctc | 540 |
| atcgatccga aggaaatttt tcgcgccgtcc cccaccctgg ctgcagccgc gcaggccgag | 600 |
| aggggagatt gcagcaatac gtcaagcgct gctacagtca tcaagagcat tgatgaattc | 660 |
| aatcagtcga atccaaatgc cgccgctgca tgcaaaacag cagcctcgat gacgctggcg | 720 |
| ggcacgcgct gcaccgtcaa accggacggg tctgccacct gtttgaacaa aggctgccaa | 780 |
| aaggactact tgctcaagga gaatcacccc tctgcatgtc g | 821 |

<210> SEQ ID NO 3
<211> LENGTH: 420
<212> TYPE: DNA
<213> ORGANISM: Nannochloropsis gaditana
<220> FEATURE:
<221> NAME/KEY: misc_feature
<223> OTHER INFORMATION: CHORD-3266 3' fusion transcript

<400> SEQUENCE: 3

| atgggcagcc cacagcggtt ggcatcaggg agttgcttcc ctctggctac gtctgggagg | 60 |
| gttgaaattc actggccgtc gttttacaac gtcgtaactg ggaaaaccct ggcgttaccc | 120 |
| aacttaatcg ccttgcagca catccccctt tcgccagtgg caaacagcta taatcgtgag | 180 |
| ctttacgttc ccacgccaac acttcgccat ttctcctccc ttcctttctt tagctaccac | 240 |
| gcagccggcc ccgtcttcca cgacgcgggt aaatactggt catgttgccc tggaacggtc | 300 |
| aagtacgact tcgacgactt tctcaagatc cctggatgca tgctcagtag tcattacgac | 360 | ggaagccagg agagcctgga ggcgttcact agacacgcca aaacgtctga gggcacatga    420

<210> SEQ ID NO 4
<211> LENGTH: 65
<212> TYPE: PRT
<213> ORGANISM: Nannochloropsis gaditana
<220> FEATURE:
<221> NAME/KEY: misc_feature
<223> OTHER INFORMATION: CHORD-3266 domain2

<400> SEQUENCE: 4

Gly Ser Ala Thr Cys Leu Asn Lys Gly Cys Gln Lys Asp Tyr Leu Leu
1               5                   10                  15

Lys Glu Asn His Pro Ser Ala Cys Arg Tyr His Ala Ala Gly Pro Val
            20                  25                  30

Phe His Asp Ala Gly Lys Tyr Trp Ser Cys Cys Pro Gly Thr Val Lys
        35                  40                  45

Tyr Asp Phe Asp Asp Phe Leu Lys Ile Pro Gly Cys Met Leu Ser Ser
    50                  55                  60

His
65

<210> SEQ ID NO 5
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' primer MCA-1185

<400> SEQUENCE: 5
ttccacccaa gcagtggtat caacgcagag tggcctaagg gaaaacaaca g             51

<210> SEQ ID NO 6
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for Y2H library second strand synthesis

<400> SEQUENCE: 6
gtatcgatgc ccaccctcta gaggccgagg cggccgacac ggtacccgct ttttttttt    60

<210> SEQ ID NO 7
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-P6317-5901PRO-8611-F

<400> SEQUENCE: 7
gtttttcttt ggcaggcaaa catgcaagca tcccaaaaga cgtc                    44

<210> SEQ ID NO 8
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-P6317-8611-T9-R

<400> SEQUENCE: 8
ctatgcacct tcccccttga ctcttagctt gagttgctgt tgc                          43

<210> SEQ ID NO 9
<211> LENGTH: 1918
<212> TYPE: DNA
<213> ORGANISM: Nannochloropsis gaditana
<220> FEATURE:
<221> NAME/KEY: misc_feature
<223> OTHER INFORMATION: SKP-8611 coding sequence
<220> FEATURE:
<221> NAME/KEY: misc_feature
<222> LOCATION: (1136)..(1136)
<223> OTHER INFORMATION: n is a, c, g, or t

<400> SEQUENCE: 9

| | |
|---|---|
| atgcaagcat cccaaaagac gtccgatgtg caagaggagg atggtccgcc caaatacatt | 60 |
| acattacaag cccgagatgg cacgctcgac gagccagtgg acgcccgcat tctcttgccg | 120 |
| tccgacctcc tgcgaagcat gctccccgaa aagtgtaagc tgcgaagtga atgcacaaaa | 180 |
| gagataggag ccatgttcta ttttggtgtc gtttttgggg ttgtgtgact gattttgtcc | 240 |
| cgtacgaagg gcgtgtctgt ctctcctttt tgaggatgtg tcgatatacg tctcgtcctt | 300 |
| tttatcaatt cttatcgggt tcgtccactc ccaaacggct tgcatttcag tgtccgaaat | 360 |
| tgaggacgat ttccagatac cgctgcaggg agttgacaag gccgtactgg agaaggtagg | 420 |
| gtggaaggga aattaggatg gggagaggaa gggagatgga taggagagga taacaatgcc | 480 |
| gtatttcatt ttgtttcctt gtcttatcat ggtaggtggt agagtattta catctttatc | 540 |
| gcgaagagcc gatgtacaag atcgagaagg taatcgaggg agggaggggag ggaggggggg | 600 |
| agggagaggg gagggaaggg agagggggaaa ggaggaggga tcaattcctc attctgggcg | 660 |
| tgtacctcac tctctctcct tctccttcat tttcaagccc ttgaacaaag tgaagctgta | 720 |
| cgacctggtt caaccccaat acgatcagtt catcaatgcc cttcattaca agacgatatt | 780 |
| ccagatcatc gatgcggtgc gcttcctccc ttccttcatt tctccctccc ttcctctctt | 840 |
| ctccctccct tcttccctcc caccctccct cccttctccc tcccctcttc cttcccacct | 900 |
| cccttctttc ctctttccct ttcttcctcc ctttctcccc cttgcccat tctctctttg | 960 |
| ttcttttcct gttttcccct cgcctccttc cctgacttcc tttcgagttt ttgtgttaat | 1020 |
| atgtatatat atatatacaa tttttaacta tatatatata atcttaaccct caaagcgtat | 1080 |
| ccctagcggt cttagctgac atgtgcaaat cacagaatcc cttcttaccc ctcctncct | 1140 |
| cgacccatcc ctcgcccgtt cttctcgcgg ccttcttgca aaccactcgt ggtagacatg | 1200 |
| gtccaatcct ttccgcctcc cccttccccc ctccctctgt cccttcctcc tcccctgcg | 1260 |
| tcttgctcct tgactgtcta ctccaggcga atttcctggg aatcgagccc ctccttccc | 1320 |
| tctcgttatc gtgggtggcc ttcgtcctta aaggtaccac tgggaagaag gagtggaggg | 1380 |
| aggagtggag gagtcaaagg agggagatga acacatgag gcaatactcg aacaagaatt | 1440 |
| aagacctccc tggcatcgaa ttttggcgc ccgtgcctcg gccggtctca acaccacctc | 1500 |
| ctcctcccgc cctcccgccc atatatccct cttgataatc cttgtttccc gatagggcct | 1560 |
| actgtggaag agttcaagaa actgttcacg atccataacg attttacgcc ggaggtgagg | 1620 |

```
gaaaaacgag tggattgagg gggagagggg agaaggaaga gagcagggat cgctaggagg       1680
tagcacacgt cggcgggtgt ggtgtggcat ttccccgttc ccctccctca tgtggtcgag       1740
tttcattcga tttcataatg tcttttgacc ccccgttctc cttcctcgca cggtcgcggc       1800
cttctcctta caggaggagg ctatcttcag gcgcgagtac ctccttccgc gccggaatcg       1860
ggcgacaagc gagggcggga gggagagagg cgcgtctggc aacagcaact caagctaa        1918

<210> SEQ ID NO 10
<211> LENGTH: 19193
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SKP-8611 over-expression vector

<400> SEQUENCE: 10
gctagtgata ataagtgact gaggtatgtg ctcttcttat ctccttttgt agtgttgctc         60
ttattttaaa caactttgcg gttttttgat gactttgcga ttttgttgtt gctttgcagt        120
aaattgcaag atttaataaa aaaacgcaaa gcaatgatta aaggatgttc agaatgaaac        180
tcatggaaac acttaaccag tgcataaacg ctggtcatga aatgacgaag gctatcgcca        240
ttgcacagtt taatgatgac agcccggaag cgaggaaaat aacccggcgc tggagaatag        300
gtgaagcagc ggatttagtt ggggtttctt ctcaggctat cagagatgcc gagaaagcag        360
ggcgactacc gcacccggat atggaaattc gaggacgggt tgagcaacgt gttggttata        420
caattgaaca aattaatcat atgcgtgatg tgtttggtac gcgattgcga cgtgctgaag        480
acgtatttcc accggtgatc ggggttgctg cccataaagg tggcgtttac aaaacctcag        540
tttctgttca tcttgctcag gatctggctc tgaaggggct acgtgttttg ctcgtggaag        600
gtaacgaccc ccagggaaca gcctcaatgt atcacggatg gtaccagat cttcatattc         660 atgcagaaga cactctcctg cctttctatc ttggggaaaa ggacgatgtc acttatgcaa        720
taaagcccac ttgctggccg gggcttgaca ttattccttc ctgtctggct ctgcaccgta        780
ttgaaactga gttaatgggc aaatttgatg aaggtaaact gccccaccgat ccacacctga        840 tgctccgact ggccattgaa actgttgctc atgactatga tgtcatagtt attgacagcg        900
cgcctaacct gggtatcggc acgattaatg tcgtatgtgc tgctgatgtg ctgattgttc        960
ccacgcctgc tgagttgttt gactacacct ccgcactgca gttttcgat atgcttcgtg        1020 atctgctcaa gaacgttgat cttaaagggt tcgagcctga tgtacgtatt ttgcttacca        1080
aatacagcaa tagcaatggc tctcagtccc cgtggatgga ggagcaaatt cgggatgcct        1140
ggggaagcat ggttctaaaa aatgttgtac gtgaaacgga tgaagttggt aaaggtcaga        1200
tccggatgag aactgttttt gaacaggcca ttgatcaacg ctcttcaact ggtgcctgga        1260
gaaatgctct ttctatttgg gaacctgtct gcaatgaaat tttcgatcgt ctgattaaac        1320
cacgctggga gattagataa tgaagcgtgc gcctgttatt ccaaaacata cgctcaatac        1380
tcaaccggtt gaagatactt cgttatcgac accagctgcc ccgatggtgg attcgttaat        1440
tgcgcgcgta ggagtaatgg ctcgcggtaa tgccattact ttgcctgtat gtggtcggga        1500
tgtgaagttt actcttgaag tgctccgggg tgatagtgtt gagaagacct ctcgggtatg        1560
gtcaggtaat gaacgtgacc aggagctgct tactgaggac gcactggatg atctcatccc        1620 ttctttttcta ctgactggtc aacagacacc ggcgttcggt cgaagagtat ctggtgtcat        1680
```

```
agaaattgcc gatgggagtc gccgtcgtaa agctgctgca cttaccgaaa gtgattatcg   1740
tgttctggtt ggcgagctgg atgatgagca gatggctgca ttatccagat tgggtaacga   1800
ttatcgccca acaagtgctt atgaacgtgg tcagcgttat gcaagccgat tgcagaatga   1860
atttgctgga atatttctg cgctggctga tgcggaaaat atttcacgta agattattac    1920
ccgctgtatc aacaccgcca aattgcctaa atcagttgtt gctctttttt ctcaccccgg   1980
tgaactatct gcccggtcag gtgatgcact tcaaaaagcc tttacagata aagaggaatt   2040
acttaagcag caggcatcta accttcatga gcagaaaaaa gctggggtga tatttgaagc   2100
tgaagaagtt atcactcttt taacttctgt gcttaaaacg tcatctgcat caagaactag   2160
tttaagctca cgacatcagt ttgctcctgg agcgacagta ttgtataagg gcgataaaat   2220
ggtgcttaac ctggacaggt ctcgtgttcc aactgagtgt atagagaaaa ttgaggccat   2280
tcttaaggaa cttgaaaagc cagcaccctg atgcgaccac gttttagtct acgtttatct   2340
gtctttactt aatgtccttt gttacaggcc agaaagcata actggcctga atattctctc   2400
tgggcccact gttccacttg tatcgtcggt ctgataatca gactgggacc acggtcccac   2460
tcgtatcgtc ggtctgatta ttagtctggg accacggtcc cactcgtatc gtcggtctga   2520
ttattagtct gggaccacgg tcccactcgt atcgtcggtc tgataatcag actgggacca   2580
cggtcccact cgtatcgtcg gtctgattat tagtctggga ccatggtccc actcgtatcg   2640
tcggtctgat tattagtctg gaccacggt cccactcgta tcgtcggtct gattattagt    2700
ctggaaccac ggtcccactc gtatcgtcgg tctgattatt agtctgggac acggtcccac   2760 tcgtatcgt cggtctgatt attagtctgg gaccacgatc ccactcgtgt tgtcggtctg    2820
attatcggtc tgggaccacg gtcccacttg tattgtcgat cagactatca gcgtgagact   2880
acgattccat caatgcctgt caagggcaag tattgacatg tcgtcgtaac ctgtagaacg   2940
gagtaacctc ggtgtgcggt tgtatgcctg ctgtggattg ctgctgtgtc ctgcttatcc   3000
acaacatttt gcgcacggtt atgtggacaa aatacctggt tacccaggcc gtgccggcac   3060
gttaaccggg ctgcatccga tgcaagtgtg tcgctgtcga cgagctcgcg agctcggaca   3120
tgaggttgcc ccgtattcag tgtcgctgat ttgtattgtc tgaagttgtt tttacgttaa   3180
gttgatgcag atcaattaat acgatacctg cgtcataatt gattatttga cgtggtttga   3240
tggcctccac gcacgttgtg atatgtagat gataatcatt atcactttac gggtcctttc   3300
cggtgatccg acaggttacg gggcggcgac ctcgcgggtt ttcgctattt atgaaaattt   3360
tccggtttaa ggcgtttccg ttcttcttcg tcataactta atgttttat ttaaaatacc    3420 ctctgaaaag aaaggaaacg acaggtgctg aaagcgagct ttttggcctc tgtcgtttcc   3480
tttctctgtt tttgtccgtg gaatgaacaa tggaagtccg agctcatcgc taataacttc   3540
gtatagcata cattatacga agttatattc gatgcgcccg ggcgcctatt tccgagtgca   3600
tgtcccagtc gaaggacgcc tgggggggtga tgcaaggata catcgatcat ttggccgtgc   3660 atttgtcaa ccgggtaagg tggattacgg agaatcttcg tttctttcct cctcttctct    3720
tagtggcctt ccctcctttt tttttcattt gtttcctttc ccgtgcctgt ttgcacggca   3780 aaatttcct ctttccacct taacgtcctt cctcttctcc tttcttcctg ccctccccc    3840 gattcctctc cccccttcct cccctccctc cctcccagt cgtggaaacc gacgtcatcc    3900
ggagcaacgg cggcctggtc gtgaccgtt cggtccactc ctggctcacg ggccgccggg    3960
agcccatcct cgccctctcc ctcgactcct cagaccctcg agtcctcttc tcttcctcg    4020 gcgccgactt gagcctgagc ccggagggcg gggtggaggg cgggcacggc acctgccgta   4080
```

```
tgtccaacga cgtggaaaac accgtcaccg cctgtgcccc cgtcctggac gaggcgtcgg   4140
gggaaatccg ggaataccga aaaccccga gcaccttcca caccggcaag catttcccgc   4200
accggatcgg acagttggcc gcccaccatg gagacgagaa aatttgggc gtgtggcctc    4260 gaaagacgat cgttatccag gcggggtccc gtgagggagg cagcaatgtg caatacggac   4320
attccgacgg catgcagttc ccccccttgc accgcctcga agaagcccgc ccggtcgcct   4380
cggaggatac cggcgtgtcc tcggtattaa acggcacact cggcgctgaag gaactggcgg   4440 ccttgtcctt cttggacgcg ggggaggcgg agacctcgac ggggatggaa agagaggagg   4500
ttgtcatggc ggatccggcg tcggtatcgg aggatcaact ttcggtgttt ttgagcaagt   4560
tcgtcctccc cctctggttc cgcttccagg aaacggtctc cttgcgaggc atccgccttt   4620
tgaaattcaa cctctcgccg ttgactttct ccccgcaacg gccggacgcc tcgggctttt   4680
ccatgcttgg cctgggggag ggcgggcggg agggtctatt caatctgacc gaccttcaaa   4740
cgatgccatc ttttctgagc acgccacaat ttcacggtga gaaccaggga gggacgcgtg   4800
gggagggtga tggatgggga agaaacaggt gggagggtaa ggtaacgcga gagcgtaggg   4860
ttccacgtca tctctctctc tacattcttg cccctttcaat ccttcacacc gtgggacatg   4920
agagaacaag cgtgttcctt gtgcccactc ccggcccctc cccgcccgc ccttccctcc    4980 ccatcgcctt cttccaggat acccctccct gcgaaagctt ccctgtctgg ccagcctcag   5040
gttgtcggag atcgggaaga ggcaggccgc ccgaggaagc tacttggcgg tggagcccta   5100
caccggtacg gacaagacag aggaatgcac aggcggggagg acgggggat taaagggatg     5160 gggcaagtta aggaagcttc aatatcctgg atccggggg gcgggcgtgg gcgagtcggg     5220
gagggctcca gacgaggttt ggtcttctcg gtcgccgaaaa ttcggcccct tcctgccgca    5280
tcgcggaatt cccacgtctt ccaccctcat cacatgacgc ctccccaatc ttccttcct    5340 ttcctctccca cctcctatca ttgccttgtc cctccgtcct cctcacgctc ttcttccctc   5400
ctcatcactg tccttccttc cctcctcatc ccaacacacc tcttttcct tcctcctcgg    5460 cccctccctt tgcccctcctg acctccacct tcctcccctc ctcatccctc cttaccttcca  5520 ccttcctccc ctcctcatcc cttcttacct cgaccttcct tccctcctca tccctcctta   5580
cctcgacctt ccttccctcc tcatccctcc tttcctccac cctccctcca cctcaccgct   5640
cttcaccttc cttcttccct cctcctcctc cctccttcct tccatctccc ctcctccttc   5700 ccgcccctc acccgtaggc aagacaatga gcgcccacat tgccatgcaa gtctctggcg   5760
ccatcaaaac cgcctccggg aacggaccca gctatgacat ctggtaaggg agggagggag   5820
ggagggaggg aggaaggaag ggagggaggg agggagggag ggagggaggg aggtagaatg   5880
acacaacgtc gagtgcgaag gtcgccctcc ccctcgcaac gagccgtgcc aggaacagga   5940
ccttaccttc tcctcccct tgtccttccc atcccatcac ccccgcctcg ctccttccct    6000
ccttatcccc tcctccctcc ttcccacctc atcaggcacc atcaggtata cccgccgag   6060 atcgtcccca ccttgtggat ggctcaatct gccgaggttg ccctgcgga tgcccgtacc    6120 ttccacgata aaatctatcg ctctgccagc atcttggccg atatcaggcg ctactccttc   6180 atcggggaa taacggcctt ggccctgggg ctcttgcttg tgcttgggag ctgttggtgg    6240
gcgaggaagg gagggaggga gggagggagg gagggaggga gggagggagg gaggaggcag   6300
gacgtggaag cggcggtgga gatgcaggag agagggggagg gaggaggagg agggaggaag   6360
ccggggaaga aggatctctt cggagcgaga cgtccagtgc cggccgttta agcgccgtcc   6420
```

```
gttacttcgc aacggctgta ttttttaaatt tgaaatttaa aagggggagt ctggaggcgt    6480
agagaccctg gggcctgggc gttcggctct gtcattgttc gcgtgcgtgg ccgtgccact    6540
ggttctttcc agctttaggg ggaagaaggg agggagggag ggagggaggg agggaagtag    6600
gaaaggaagg agcggggaag ttcatgggac tgagagcgtg agaagaagag agggaaggcg    6660
gggagttcag tcataccatg tctcgtctct tggggaagga gaggtggagg gacgttggga    6720
tggcgggggtg gagccacagt gggaggagaa agacgtttat ggaaagatct agaaccttcg    6780
gcgaaagtgt aggaaaaact ccagggctgg gtgcctctca cagcaagcct tcaaccgggg    6840
gagaaagatt tcaaatttca aaacagaaga ggaagacttc gcagtcgtaa cggctcccca    6900
acggttgaaa cgccctgggt cccttccagc ctcatcacgt gcattttctc tttctttcct    6960
ccctccttcc tcctcctccc cgctctcccc ttccctcttc ctcaagcttt tctttggcat    7020
cctaccgccc ctaccttcac ctcttcacgc actcacacct tccagatcca tgcgatcgca    7080
acaagttttg atttttgtgt tgtcgtattt ttacgcagga aaatgtcaga gccgatacat    7140
tcgagctacc tggggttgtc ttttttaagag tcccagcatt tgttcacct acgatagtgc    7200
atggctgcaa gtaaattcat tttgcgataa ccacaaaact agccaattta cgaatctgtg    7260
aagaagtttt tcgcgttcta cggtcctctt gtagtaaccc atcgatgttg cttcaagata    7320
tgggcgctgg tcgatggaaa aaccacagg actagttaaa atcatagatt ccacgaaatt    7380
attaaaatat tattttcat gccctgcggt ccgtgaagac tgcgagcacg cgccttagga    7440
gatgagagcc tctcgacatc tcctgcatac atctgcagac gacaagagag catcaggggc    7500
taagggaggc atggaatagc gtcgacacat cgacagctca ttccatattc tctctaagtt    7560
cccctgtgga gcgattgctt cgatcagtga agatcacctg gcccttttcct cgttgaaagt    7620
gaggctcagg acgtcggaa ggtattgtat tggtacgctt tgacgtagcc ttctcgttga    7680
cactttgact tgcatacgac ccttgtggcg acggctgcat ttgtgcgctg ttgctccaag    7740
aactatgcat cgaaggcaca cgccctggaa gccccgacac ctctgtttga gacactgctt    7800
caaatcactt gagcaggact cacaatgaga gtacatcgta ttgggtttgg cggccgccgt    7860
atggtcgacg gttgctcgga tggggggggc ggggagcgat ggaggagga agatcaggta    7920
aggtctcgac agactagaga agcacgagtg caggtataag aaacagcaaa aaaaagtaat    7980
gggcccaggc ctggagaggg tatttgtctt gtttttcttt ggccaggaac ttgttctcct    8040
ttcttcgttt ctaggacccc gatccccgct cgcatttctc tcttcctcag ccgaagcgca    8100
gcggtaaagc atccatttta tcccaccgaa agggcgctcc cagccttcgt cgagcggaac    8160
cggggttaca gtgcctcact cctttgcacg cggtcgggtg ctcggcctac ggttgcccga    8220
gtccgcaagc acctcaacac agccgtctgt ccacaccgca gccgaccggc gtgcgatttg    8280
ggtccgaccc accgtcccag ccccgctgcg gactatcgcg tcgcagcggc cctgcgccca    8340
cgcggcgtcg tcgaagttgc cgtcgacgag agactggtaa agctgatcga gtccgatacg    8400
caacatatag gcgcggagtc gtggggagcc ggccagctcc gggtgcctcc gttcaaagta    8460
gcgtgtctgc tgctccatgc acgccaacca gggacgccag aagaatatgt tcgccacttc    8520
gtattggcta tcaccaaaca tcgcttcgga ccagtcgatg acagcagtaa tccgaccatt    8580
gtctgtaagt acgttattgc tgccgaaatc cgcgtgcacc aggtgcctga cctcagggca    8640
atcctcggcc cacaacatga gttcgtccag tgcttgggcc acggatgcag acacggtgtc    8700
atccatgact gtctgccaat gatagacgtg aggatcggca atggcgcaga tgaagtctcg    8760
ccaggtcgtg tactgcccga tgccctgggg cccaaaaggt ccaaagccgg acgtctgaga    8820
```

```
cagatctgcg gcagcgatcg cgtccatggc ctcggccacg ggttgcaaaa cggcaggcaa    8880
ttcagtttcg ggcagatctt gcaacgtcac tccctgggct cggcgcgaga tgcagtacgt    8940
gagagattcg ctaaactccc caatgtccag tacctctggt atggggagag cggcggaggc    9000
gaaatgacgg tagacatacc gatccttgta gaacccgtcc gcacaactat taaccctcaa    9060
cacgtatccc cgaccccta cgtcaaacga gaacgcccta ctctcctctc cctcgctcag    9120
ttgcatcaag tcggagacag agtcgaactt ctcaataagg aatttctcca cggacgtagc    9180
ggtcagttcc ggtttcttcc ccatcgagct cggtacccgg ggatccatga ttgttgtatt    9240
atgtacctat gtttgtgatg agacaataaa tatgagaaga gaacgttgcg gccactttt     9300 tctccttcct tcgcgtgctc atgttggtgg tttgggaggc agaagatgca tggagcgcca    9360
cacattcggt aggacgaaac agcctccccc acaaagggac catgggtagc taggatgacg    9420
cacaagcgag ttcccgctct cgaagggaaa cccaggcatt tccttcctct tttcaagcca    9480
cttgttcacg tgtcaacaca attttggact aaaatgcccc tcggaactcg gcaggcctcc    9540
ctctgctccg ttgtcctggt cgccgagaac gcgagaccgt gccgcatgcc atcgatctgc    9600
tcgtctgtac tactaatcgt gtgcgtgttc gtgcttgttt cgcacgaaat tgtcctcgtt    9660
cggccctcac aacggtggaa atcggtgcta gaataaagtg aggtggctta tttcaatggc    9720
ggccgtcatc atgcgggatc aactgaagta cggcgggttc tcgagatttc atcgtgctcg    9780
tccagagcag gtgttttgcc tgcagctctt catgtttagg ggtcatgatt tcatctgata    9840
tgccgtaaga aaaccaatat tcacttctca attttccatg gaaaggtgaa ggcctaggtt    9900
gtgtgcgagg caacgactgg ggagggatcg caacattctt gctaacctcc cctctatctt    9960
ggccgctgtg aatcggcata tttaccgggc tgaattgaga agtgttttg agggaattaa    10020 aaggtggctg tcttgcaagc ttggcttcag tgcctgctta attcgaaccg atccagcttg    10080
tgatgaggcc ttcctaagcc tggtagtcag aagcgacatg gcgctataaa tttcgtctca    10140
gttggagagt agaaaagcat gattcgaaca cggttttcaa ctgccaaaga tatctccatt    10200
gtttccttca atctgtacac ctgcacggtg caccagttgg tacggcatat tatggtttaa    10260
taagcataca tcatatgaat acaattcagc ttaaatttat catacaaaga tgtaagtgca    10320
gcgtgggtct gtaacgatcg ggcgtaattt aagataatgc gagggaccgg gggaggtttt    10380
ggaacggaat gaggaatggg tcatggccca taataataat atgggtttgg tcgcctcgca    10440
cagcaaccgt acgtgcgaaa aaggaacaga tccatttaat aagttgaacg ttattctttc    10500
ctatgcaatg cgtgtatcgg aggcgagagc aagtcatagg tggctgcgca caataattga    10560
gtctcagctg agcgccgtcc gcgggtggtg tgagtggtca tcctcctccc ggcctatcgc    10620
tcacatcgcc tctcaatggt ggtggtgggg cctgatatga cctcaatgcc gacccatatt    10680
aaaacccagt aaagcattca ccaacgaacg aggggctctt tgtgtgtgt tttgagtatg     10740 attttacacc tctttgtgca tctctctggt cttccttggt tcccgtagtt tgggcatcat    10800
cactcacgct tccctcgacc ttcgttcttc ctttacaacc ccgacacagg tcagagttgg    10860
agtaatcaaa aaaggggtgc acgaatgaga tacattagat tttgacagat atccttttac    10920
tggagagggt tcaagggatc aaatgaacag cgggcgttgg caatctaggg agggatcgga    10980
ggttggcagc gagcgaaagc gtgtccatcc ttttggctgt cacacctcac gaaccaactg    11040
ttagcaggcc agcacagatg acatacgaga atctttatta tatcgtagac cttatgtgga    11100
tgacctttgg tgctgtgtgt ctggcaatga acctgaaggc ttgatagga ggtggctccc     11160
```

```
gtaaacccctt tgtcctttcc acgctgagtc tcccccgcac tgtcctttat acaaattgtt   11220
acagtcatct gcaggcggtt tttctttggc aggcaaacat gcaagcatcc caaaagacgt   11280
ccgatgtgca agaggaggat ggtccgccca aatacattac attacaagcc cgagatggca   11340
cgctcgacga gccagtggac gcccgcattc tcttgccgtc cgacctcctg cgaagcatgc   11400
tccccgaaaa gttgtccgaa attgaggacg atttccagat accgctgcag ggagttgaca   11460
aggccgtact ggagaaggtg gtagagtatt tacatcttta tcgcgaagag ccgatgtaca   11520
agatcgagaa gcccttgaac aaagtgaagc tgtacgacct ggttcaaccc caatacgatc   11580
agttcatcaa tgcccttcat tacaagacga tattccagat catcgatgcg gcgaatttcc   11640
tgggaatcga gcccctcctt tccctctcgt tatcgtgggt ggccttcgtc cttaaagggc   11700
ctactgtgga agagttcaag aaactgttca cgacccataa cgattttacg ccggaggagg   11760
aggctatctt caggcgcgag tacctccttc cgcgccggaa tcgggcgaca agcgagggcg   11820
ggagggagag aggcgggtct ggcaacagca actcaagcta agagtcaagg gggaaggtgc   11880
atagtgtgca acaacagcat taacgtcaaa gaaaactgca cgttcaagcc cgcgtgaacc   11940
tgccggtctt ctgatcgcct acatatagca gatactagtt gtactttttt ttccaaaggg   12000
aacattcatg tatcaatttg aaataaacat ctatcctcca gatcaccagg gccagtgagg   12060
ccggcataaa ggacggcaag gaaagaaaag aaagaaagaa aaggacactt atagcatagt   12120
ttgaagttat aagtagtcgc aatctgtgtg cagccgacag atgcttttt tttccgtttg   12180 gcaggaggtg tagggatgtc gaagaccagt ccagctagta tctatcctac aagtcaatca   12240
tgctgcgaca aaaatttctc gcacgaggcc tctcgataaa caaaacttta aaagcacact   12300
tcattgtcat gcagagtaat aactcttccg cgtcgatcaa tttatcaatc tctatcattt   12360
ccgccccttt ccttgcatag agcaagaaaa gcgacccgga tgaggataac atgtcctgcg   12420
ccagtagtgt ggcattgcct gtctctcatt tacacgtact gaaagcataa tgcacgcgca   12480
taccaatatt tttcgtgtac ggagatgaag agacgcgaca cgtaagatca cgagaaggcg   12540
agcacggttg ccaatggcag acgcgctagt ctccattatc gcgttgttcg gtagcttgct   12600
gcatgtcttc agtggcacta tatccactct gcctcgtctt ctacacgagg ccacatcgg   12660 tgcaagttcg aaaaatcata tctcaatctt cagatccttt ccagaaacgg tgctcaggcg   12720
ggaaagtgaa ggttttctac tctagtggct accccaattc tctccgactg tcgcagacgg   12780
tccttcgttg cgcacgcacc gcgcactacc tctgaaattc gacaaccgaa gttcaatttt   12840
acatctaact tctttcccat tctctcacca aaagcctagc ttacatgttg gagagcgacg   12900
agagcggcct gcccgccatg gagatcgagt gccgcatcac cggcaccctg aacggcgtgg   12960
agttcgagct ggtgggcggc ggagagggca cccccgagca gggccgcatg accaacaaga   13020
tgaagagcac caaaggcgcc ctgaccttca gcccctacct gctgagccac gtgatgggct   13080
acggcttcta ccacttcggc acctaccccc gcggctacga gaacccttc ctgcacgcca   13140 tcaacaacgg cggctacacc aacacccgca tcgagaagta cgaggacggc ggcgtgctgc   13200
acgtgagctt cagctaccgc tacgaggccg ccgcgtgat cggcgacttc aaggtgatgg   13260
gcaccggctt ccccgaggac agcgtgatct tcaccgacaa gatcatccgc agcaacgcca   13320
ccgtggagca cctgcacccc atgggcgata acgatctgga tggcagcttc acccgcacct   13380
tcagcctgcg cgacggcggc tactacagct ccgtggtgga cagccacatg cacttcaaga   13440
gcgccatcca ccccagcatc ctgcagaacg gggccccat gttcgccttc cgccgcgtgg   13500
aggaggatca cagcaacacc gagctgggca tcgtggagta ccagcacgcc ttcaagaccc   13560
```

```
cggatgcaga tgccggtgaa gaataagggt gggaaggagt cggggagggt cctggcagag   13620
cggcgtcctc atgatgtgtt ggagacctgg agagtcgaga gcttcctcgt cacctgattg   13680
tcatgtgtgt ataggttaag ggggcccact caaagccata agacgaaca caaacactaa    13740 tctcaacaaa gtctactagc atgccgtctg tccatcttta tttcctggcg cgcctatgct   13800
tgtaaaccgt tttgtgaaaa aattttaaa ataaaaagg ggacctctag ggtccccaat     13860
taattagtaa tataatctat taaaggtcat tcaaaaggtc atccagtcga ccaattctca   13920
tgtttgacag cttatcatcg aatttctgcc attcatccgc ttattatcac ttattcaggc   13980
gtagcaacca ggcgtttaag ggcaccaata actgccttaa aaaaattacg ccccgccctg   14040
ccactcatcg cagtactgtt gtaattcatt aagcattctg ccgacatgga agccatcaca   14100
aacggcatga tgaacctgaa tcgccagcgg catcagcacc ttgtcgcctt gcgtataata   14160
tttgcccatg gtgaaaacgg gggcgaagaa gttgtccata ttggccacgt ttaaatcaaa   14220
actggtgaaa ctcacccagg gattggctga gacgaaaaac atattctcaa taaacccttt   14280
agggaaatag gccaggtttt caccgtaaca cgccacatct tgcgaatata tgtgtagaaa   14340
ctgccggaaa tcgtcgtggt attcactcca gagcgatgaa aacgtttcag tttgctcatg   14400
gaaaacggtg taacaagggt gaacactatc ccatatcacc agctcaccgt ctttcattgc   14460
catacgaaat tccggatgag cattcatcag gcgggcaaga atgtgaataa aggccggata   14520
aaacttgtgc ttattttct ttacggtctt taaaaaggcc gtaatatcca gctgaacggt     14580
ctggttatag gtacattgag caactgactg aaatgcctca aaatgttctt tacgatgcca   14640
ttgggatata tcaacggtgg tatatccagt gatttttttc tccattttag cttccttagc   14700
tcctgaaaat ctcgataact caaaaaatac gcccggtagt gatcttattt cattatggtg   14760
aaagttggaa cctcttacgt gccgatcaac gtctcatttt cgccaaaagt tggcccaggg   14820
cttcccggta tcaacaggga caccaggatt tatttattct gcgaagtgat cttccgtcac   14880
aggtatttat tcgcgataag ctcatggagc ggcgtaaccg tcgcacagga aggacagaga   14940
aagcgcggat ctgggaagtg acggacagaa cggtcaggac ctggattggg gaggcggttg   15000
ccgccgctgc tgctgacggt gtgacgttct ctgttccggt cacaccacat acgttccgcc   15060
attcctatgc gatgcacatg ctgtatgccg gtataccgct gaaagttctg caaagcctga   15120
tgggacataa gtccatcagt tcaacggaag tctacgcgaa ggttttttgcg ctggatgtgg   15180 ctgcccggca ccgggtgcag tttgcgatgc cggagtctga tgcggttgcg atgctgaaac   15240
aattatcctg agaataaatg ccttggcctt tatatgaaaa tgtggaactg agtggatatg   15300 ctgttttttgt ctgttaaaca gagaagctgg ctgttatcca ctgagaagcg aacgaaacag   15360
tcgggaaaat ctcccattat cgtagagatc cgcattatta atctcaggag cctgtgtagc   15420
gtttatagga agtagtgttc tgtcatgatg cctgcaagcg gtaacgaaaa cgatttgaat   15480
atgccttcag gaacaataga aatcttcgtg cggtgttacg ttgaagtgga gcggattatg   15540
tcagcaatgg acagaacaac ctaatgaaca cagaaccatg atgtggtctg tcctttaca    15600 gccagtagtg ctcgccgcag tcgagcgaca gggcgaagcc ctcgagctgg ttgccctcgc   15660
cgctgggctg gcggccgtct atggccctgc aaacgcgcca gaaacgccgt cgaagccgtg   15720
tgcgagacac cgcggccggc cgccggcgtt gtggatacct cgcggaaaac ttggccctca   15780
ctgacagatg aggggcggac gttgacactt gaggggccga ctcacccggc gcggcgttga   15840
cagatgaggg gcaggctcga tttcggccgg cgacgtggag ctggccagcc tcgcaaatcg   15900
```

```
gcgaaaacgc ctgattttac gcgagtttcc cacagatgat gtggacaagc ctggggataa    15960
gtgccctgcg gtattgacac ttgaggggcg cgactactga cagatgaggg gcgcgatcct    16020
tgacacttga ggggcagagt gctgacagat gaggggcgca cctattgaca tttgaggggc    16080
tgtccacagg cagaaaatcc agcatttgca agggtttccg cccgttttc ggccaccgct    16140 aacctgtctt ttaacctgct tttaaaccaa tatttataaa ccttgttttt aaccagggct    16200
gcgccctgtg cgcgtgaccg cgcacgccga agggggtgc cccccttct cgaaccctcc    16260 cggtcgagtg agcgaggaag caccagggaa cagcacttat atattctgct tacacacgat    16320
gcctgaaaaa acttcccttg gggttatcca cttatccacg gggatatttt tataattatt    16380 tttttatag ttttagatc ttctttttta gagcgccttg taggccttta ccatgctgg    16440 ttctagagaa ggtgttgtga caaattgccc tttcagtgtg acaaatcacc ctcaaatgac    16500
agtcctgtct gtgacaaatt gcccttaacc ctgtgacaaa ttgccctcag aagaagctgt    16560 ttttcacaa agttatccct gcttattgac tcttttttat ttagtgtgac aatctaaaaa    16620
cttgtcacac ttcacatgga tctgtcatgg cggaaacagc ggttatcaat cacaagaaac    16680
gtaaaaatag cccgcgaatc gtccagtcaa acgacctcac tgaggcggca tatagtctct    16740
cccgggatca aaaacgtatg ctgtatctgt tcgttgacca gatcagaaaa tctgatggca    16800
ccctacagga acatgacggt atctgcgaga tccatgttgc taaatatgct gaaatattcg    16860
gattgacctc tgcggaagcc agtaaggata tacggcaggc attgaagagt ttcgcgggga    16920
aggaagtggt tttttatcgc cctgaagagg atgccggcga tgaaaaaggc tatgaatctt    16980
ttccttggtt tatcaaacgt gcgcacagtc catccagagg gctttacagt gtacatatca    17040
acccatatct cattcccttc tttatcgggt tacagaaccg gtttacgcag tttcggctta    17100
gtgaaacaaa agaaatcacc aatccgtatg ccatgcgttt atacgaatcc ctgtgtcagt    17160
atcgtaagcc ggatggctca ggcatcgtct ctctgaaaat cgactggatc atagagcgtt    17220
accagctgcc tcaaagttac cagcgtatgc ctgacttccg ccgccgcttc ctgcaggtct    17280
gtgttaatga gatcaacagc agaactccaa tgcgcctctc atacattgag aaaaagaaag    17340
gccgccagac gactcatatc gtattttcct tccgcgatat cacttccatg acgacaggat    17400
agtctgaggg ttatctgtca cagatttgag ggtggttcgt cacatttgtt ctgacctact    17460
gagggtaatt tgtcacagtt ttgctgtttc cttcagcctg catggatttt ctcatacttt    17520
ttgaactgta attttaagg aagccaaatt tgagggcagt ttgtcacagt tgatttcctt    17580
ctctttccct tcgtcatgtg acctgatatc ggggggttagt tcgtcatcat tgatgagggt    17640
tgattatcac agtttattac tctgaattgg ctatccgcgt gtgtacctct acctggagtt    17700
tttcccacgg tggatattc ttcttgcgct gagcgtaaga gctatctgac agaacagttc    17760
ttctttgctt cctcgccagt tcgctcgcta tgctcggtta cacggctgcg gcgagcatca    17820
cgtgctataa aaataattat aatttaaatt tttaatata aatatataaa ttaaaaatag    17880
aaagtaaaaa aagaaattaa agaaaaaata gttttttgttt tccgaagatg taaaagactc    17940 taggggggatc gccaacaaat actacctttt atcttgctct tcctgctctc aggtattaat    18000
gccgaattgt ttcatcttgt ctgtgtagaa gaccacacac gaaaatcctg tgattttaca    18060
ttttacttat cgttaatcga atgtatatct atttaatctg cttttcttgt ctaataaata    18120
tatatgtaaa gtacgctttt tgttgaaatt ttttaaacct ttgttatttt tttttcttc    18180 attccgtaac tcttctacct tctttattta ctttctaaaa tccaaataca aaacataaaa    18240
ataaataaac acagagtaaa ttcccaaatt attccatcat taaaagatac gaggcgcgtg    18300
```

```
taagttacag gcaagcgatc ctagtacact ctatattttt ttatgcctcg gtaatgattt    18360
tcattttttt ttttccacct agcggatgac tcttttcttt tcttagcgat tggcattatc    18420
acataatgaa ttatacatta tataaagtaa tgtgatttct tcgaagaata tactaaaaaa    18480
tgagcaggca agataaacga aggcaaagat gacagagcag aaagccctag taaagcgtat    18540
tacaaatgaa accaagattc agattgcgat ctctttaaag ggtggtcccc tagcgataga    18600
gcactcgatc ttcccagaaa aagaggcaga agcagtagca gaacaggcca cacaatcgca    18660
agtgattaac gtccacacag gtataggggtt tctggaccat atgatacatg ctctggccaa    18720
gcattccggc tggtcgctaa tcgttgagtg cattggtgac ttacacatag acgaccatca    18780
caccactgaa gactgcggga ttgctctcgg tcaagctttt aaagaggccc tactggcgcg    18840
tggagtaaaa aggtttggat caggatttgc gcctttggat gaggcacttt ccagagcggt    18900
ggtagatctt tcgaacaggc cgtacgcagt tgtcgaactt ggtttgcaaa gggagaaagt    18960
aggagatctc tcttgcgaga tgatcccgca ttttcttgaa agctttgcag aggctagcag    19020
aattaccctc cacgttgatt gtctgcgagg caagaatgat catcaccgta gtgagagtgc    19080
gttcaaggct cttgcggttg ccataagaga agccacctcg cccaatggta ccaacgatgt    19140
tccctccacc aaaggtgttc ttatgtagtt ttacacagga gtctggactt gac           19193
```

<210> SEQ ID NO 11
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-SKP-8611-RT-F SKP qRT

<400> SEQUENCE: 11
accccaatac gatcagttca tc                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-SKP-8611-RT-R SKP qRT

<400> SEQUENCE: 12
cttccacagt aggcccttta ag                                              22

<210> SEQ ID NO 13
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-RT-1704-F housekeeping qRT

<400> SEQUENCE: 13
gaggaagcgg aagaggatg                                                  19

<210> SEQ ID NO 14
<211> LENGTH: 20

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-RT-1704-R housekeeping qRT

<400> SEQUENCE: 14
tcaagtacca gttccacacg                                                 20

<210> SEQ ID NO 15
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-Chord-pGB-F for FL CHORD Y2H

<400> SEQUENCE: 15
catggaggcc gaattcatga aactctatgt gcactac                              37

<210> SEQ ID NO 16
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-Chord-pGB-R for FL CHORD Y2H

<400> SEQUENCE: 16
gcaggtcgac ggatcctcat gtgccctcag acgttttg                             38

<210> SEQ ID NO 17
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-pGB-ChDom1-R for Y2H

<400> SEQUENCE: 17
gcaggtcgac ggatcctcac aacaatcctg tgctcgactc a                         41

<210> SEQ ID NO 18
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer JLC-pGB-CRD117-179 for Y2H

<400> SEQUENCE: 18
catggaggcc gaattcatgt tgcgctgcaa aaactatg                             38

<210> SEQ ID NO 19
<211> LENGTH: 41
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: Primer JLC-pGB-ChDom1-R for Y2H

<400> SEQUENCE: 19
gctgcaggtc gacggatcct cagtgccgtc ctgtggtgca c                     41

<210> SEQ ID NO 20
<211> LENGTH: 40
<212> TYPE: DNA
<213> ORGANISM: Artificial Sequence
<220> FEATURE:
<223> OTHER INFORMATION: Synthetic

<400> SEQUENCE: 20
catggaggcc gaattcatga gtctcatcga tccgaaggaa                       40

<210> SEQ ID NO 21
<211> LENGTH: 38
<212> TYPE: DNA
<213> ORGANISM: Artificial Sequence
<220> FEATURE:
<223> OTHER INFORMATION: Synthetic

<400> SEQUENCE: 21
gcaggtcgac ggatcctcag tccggtttga cggtgcag                         38

<210> SEQ ID NO 22
<211> LENGTH: 335
<212> TYPE: PRT
<213> ORGANISM: Nannochloropsis gaditana
<220> FEATURE:
<221> NAME/KEY: misc_feature
<223> OTHER INFORMATION: Full length CHORD T3266 CRD1-336

<400> SEQUENCE: 22
```

Met Lys Leu Tyr Val His Tyr Glu Glu Ala Gly Gln Asp Glu Lys Ala
1               5                   10                  15

Leu Thr Leu Lys Leu Thr Leu Pro Lys Ser Trp Ala Glu Gln Pro Leu
            20                  25                  30

Leu Gln Val Leu Glu Leu Phe Ile Glu Ser Tyr Asn Lys Lys Thr
        35                  40                  45

Gly Leu Pro Pro Leu Asp Lys Asp Phe Val His Met Glu Lys Ala Gly
    50                  55                  60

Gly Val Ile Leu Pro Val Gly Asn Ile Val Ser Asp Met Leu Ser Asp
65                  70                  75                  80

Arg Asp Asp Leu Tyr Ile Arg Ser Gly Pro Gly Pro Ala Arg Gly Lys
                85                  90                  95

Ile Ala His Leu Ser Ser Pro Pro Asn Ala His Ala Ser Ser Glu Ser
            100                 105                 110

Ser Thr Gly Leu Leu Arg Cys Lys Asn Tyr Gly Cys Asn Gln Ser Phe
        115                 120                 125

Ser Glu Glu Asn Asn Ser Glu Glu Ala Cys Arg Phe His Lys Ala Pro
    130                 135                 140

Pro Val Phe His Asp Thr Lys Lys Gly Trp Ser Cys Cys Ala Lys Arg
145                 150                 155                 160

Val Tyr Asp Trp Asp Glu Phe His Thr Ile Glu Gly Cys Thr Thr Gly
                165                 170                 175

Arg His Ser Leu Ile Asp Pro Lys Glu Ile Phe Ala Pro Ser Pro Thr
            180                 185                 190

```
Leu Ala Ala Ala Ala Gln Ala Glu Arg Gly Asp Cys Ser Asn Thr Ser
            195                 200                 205

Ser Ala Ala Thr Val Ile Lys Ser Ile Asp Glu Phe Asn Gln Ser Asn
210                 215                 220

Pro Asn Ala Ala Ala Cys Lys Thr Ala Ala Ser Met Thr Leu Ala
225                 230                 235                 240

Gly Thr Arg Cys Thr Val Lys Pro Asp Gly Ser Ala Thr Cys Leu Asn
            245                 250                 255

Lys Gly Cys Gln Lys Asp Tyr Leu Lys Glu Asn His Pro Ser Ala
                260                 265                 270

Cys Arg Tyr His Ala Ala Gly Pro Val Phe His Asp Ala Gly Lys Tyr
            275                 280                 285

Trp Ser Cys Cys Pro Gly Thr Val Lys Tyr Asp Phe Asp Phe Leu
            290                 295                 300

Lys Ile Pro Gly Cys Met Leu Ser Ser His Tyr Asp Gly Ser Gln Glu
305                 310                 315                 320

Ser Leu Glu Ala Phe Thr Arg His Ala Lys Thr Ser Glu Gly Thr
                325                 330                 335

<210> SEQ ID NO 23
<211> LENGTH: 117
<212> TYPE: PRT
<213> ORGANISM: Nannochloropsis gaditana
<220> FEATURE:
<221> NAME/KEY: misc_feature
<223> OTHER INFORMATION: CHORD protein amino acids 1-117

<400> SEQUENCE: 23

Met Lys Leu Tyr Val His Tyr Glu Glu Ala Gly Gln Asp Glu Lys Ala
1               5                   10                  15

Leu Thr Leu Lys Leu Thr Leu Pro Lys Ser Trp Ala Glu Gln Pro Leu
            20                  25                  30

Leu Gln Val Leu Glu Leu Phe Ile Glu Ser Tyr Asn Lys Lys Lys Thr
        35                  40                  45

Gly Leu Pro Pro Leu Asp Lys Asp Phe Val His Met Glu Lys Ala Gly
    50                  55                  60

Gly Val Ile Leu Pro Val Gly Asn Ile Val Ser Asp Met Leu Ser Asp
65                  70                  75                  80

Arg Asp Asp Leu Tyr Ile Arg Ser Gly Pro Gly Pro Ala Arg Gly Lys
                85                  90                  95

Ile Ala His Leu Ser Ser Pro Pro Asn Ala His Ala Ser Ser Glu Ser
            100                 105                 110

Ser Thr Gly Leu Leu
        115

<210> SEQ ID NO 24
<211> LENGTH: 63
<212> TYPE: PRT
<213> ORGANISM: Nannochloropsis gaditana
<220> FEATURE:
<221> NAME/KEY: misc_feature
<223> OTHER INFORMATION: CHORD protein amino acids 117-179

<400> SEQUENCE: 24

Leu Arg Cys Lys Asn Tyr Gly Cys Asn Gln Ser Phe Ser Glu Glu Asn
1               5                   10                  15

Asn Ser Glu Glu Ala Cys Arg Phe His Lys Ala Pro Pro Val Phe His
            20                  25                  30
```

```
Asp Thr Lys Gly Trp Ser Cys Cys Ala Lys Arg Val Tyr Asp Trp
             35                  40                  45

Asp Glu Phe His Thr Ile Glu Gly Cys Thr Thr Gly Arg His Ser
 50                  55                  60
```

<210> SEQ ID NO 25
<211> LENGTH: 71
<212> TYPE: PRT
<213> ORGANISM: Nannochloropsis gaditana
<220> FEATURE:
<221> NAME/KEY: misc_feature
<223> OTHER INFORMATION: CHORD protein amino acids 179-251

<400> SEQUENCE: 25

```
Leu Ile Asp Pro Lys Glu Ile Phe Ala Pro Ser Pro Thr Leu Ala Ala
 1               5                  10                  15

Ala Ala Gln Ala Glu Arg Gly Asp Cys Ser Asn Thr Ser Ser Ala Ala
             20                  25                  30

Thr Val Ile Lys Ser Ile Asp Glu Phe Asn Gln Ser Asn Pro Asn Ala
             35                  40                  45

Ala Ala Ala Cys Lys Thr Ala Ala Ser Met Thr Leu Ala Gly Thr Arg
 50                  55                  60

Cys Thr Val Lys Pro Asp Gly
 65                  70
```

<210> SEQ ID NO 26
<211> LENGTH: 156
<212> TYPE: PRT
<213> ORGANISM: Nannochloropsis gaditana
<220> FEATURE:
<221> NAME/KEY: misc_feature
<223> OTHER INFORMATION: CHORD protein amino acids 179-336

<400> SEQUENCE: 26

```
Leu Ile Asp Pro Lys Glu Ile Phe Ala Pro Ser Pro Thr Leu Ala Ala
 1               5                  10                  15

Ala Ala Gln Ala Glu Arg Gly Asp Cys Ser Asn Thr Ser Ser Ala Ala
             20                  25                  30

Thr Val Ile Lys Ser Ile Asp Glu Phe Asn Gln Ser Asn Pro Asn Ala
             35                  40                  45

Ala Ala Ala Cys Lys Thr Ala Ala Ser Met Thr Leu Ala Gly Thr Arg
 50                  55                  60

Cys Thr Val Lys Pro Asp Gly Ser Ala Thr Cys Leu Asn Lys Gly Cys
 65                  70                  75                  80

Gln Lys Asp Tyr Leu Leu Lys Glu Asn His Pro Ser Ala Cys Arg Tyr
             85                  90                  95

His Ala Ala Gly Pro Val Phe His Asp Ala Gly Lys Tyr Trp Ser Cys
            100                 105                 110

Cys Pro Gly Thr Val Lys Tyr Asp Phe Asp Asp Phe Leu Lys Ile Pro
            115                 120                 125

Gly Cys Met Leu Ser Ser His Tyr Asp Gly Ser Gln Glu Ser Leu Glu
            130                 135                 140

Ala Phe Thr Arg His Ala Lys Thr Ser Glu Gly Thr
145                 150                 155
```

<210> SEQ ID NO 27
<211> LENGTH: 390
<212> TYPE: PRT
<213> ORGANISM: Nannochloropsis gaditana
<220> FEATURE:

```
<221> NAME/KEY: misc_feature
<223> OTHER INFORMATION: SGT1 1852 polypeptide

<400> SEQUENCE: 27

Met Glu Gln Ala Gln Leu Ala Phe Met Asp Glu Asp Tyr Ala Thr Ala
1               5                   10                  15

Asp Glu Leu Phe Ser Ala Tyr Ile Ala Thr His Pro Asp Asp Ala Thr
            20                  25                  30

Ala Leu Val Ser Arg Ala Ala Val His Leu Lys Leu Asn Gln Pro Ser
        35                  40                  45

Gln Ala Leu His Asp Ala Glu Ala Ala Ser Leu Lys Ser Asp Phe
    50                  55                  60

Glu Val Ala Trp Tyr Arg Gln Gly Val Ala Ala Phe Ala Leu Glu Asp
65              70                  75                  80

Phe Ser Arg Ala Lys Glu Ala Phe Met Arg Gly Arg Ala Leu Leu Gly
                85                  90                  95

Asp Arg Pro Glu Pro Gln Gly Arg Arg Tyr Asp Val Trp Leu Arg Lys
            100                 105                 110

Thr Thr Leu Glu Leu Gly Glu His Asp Glu Gln Gly Met Thr Val Val
        115                 120                 125

Ala Glu Gly Gly Arg Lys Glu Leu Arg Gln Glu Gly Ala Lys Gly
    130                 135                 140

Ile Glu Ala Thr Val Pro Arg Ser Gln Pro Ser Pro Thr His Pro Pro
145                 150                 155                 160

Ser Ser Ala Pro Ala Ile Pro Ala Gly His Val Lys Phe Gln Phe Tyr
                165                 170                 175

Gln Thr Thr Ser Tyr Val Thr Val Thr Ile Leu Tyr Lys Gly Leu Arg
            180                 185                 190

Glu Glu Asp Ala Asn Val Ser Val Gln Pro Arg His Leu Lys Val Ser
        195                 200                 205

Val Gly Ala Asp Gly Asp Val Leu Phe Asp Arg Ala Leu Phe Glu Thr
    210                 215                 220

Val Val Pro Glu Glu Ser Thr Ser Lys Ile Phe Ala Thr Lys Ile Glu
225                 230                 235                 240

Val Lys Leu Arg Lys Ala Met Glu Gly Leu Thr Trp Pro Glu Leu Cys
                245                 250                 255

Ala Leu Ser Pro Gly Ala Ala Ser Val His Thr Val Ser Ala Pro
            260                 265                 270

Thr Pro Asp Ser His Ala Thr Ala Leu Pro Ser Leu Ala Gln Gly Pro
        275                 280                 285

Ala Thr Ala Pro Ser Ser Lys Pro Leu Arg Pro Tyr Ala Ser Thr Lys
    290                 295                 300

Asp Trp Gly Ala Val Glu Lys Glu Ile Ser Lys Glu Leu Glu Ser Glu
305                 310                 315                 320

Lys Pro Glu Gly Asp Glu Ala Leu Asn Thr Leu Phe Arg Asp Ile Tyr
                325                 330                 335

Ala Lys Gly Ser Asp Glu Thr Arg Arg Ala Met Val Lys Ser Phe Gln
            340                 345                 350

Thr Ser Gly Gly Thr Val Leu Ser Thr Asn Trp Glu Glu Val Gly Lys
        355                 360                 365

Lys Asp Tyr Glu Lys Glu Glu Arg Lys Ala Pro Glu Gly Met Glu
    370                 375                 380

Trp Arg Lys Trp Gly Val
385                 390
```

<210> SEQ ID NO 28
<211> LENGTH: 200
<212> TYPE: PRT
<213> ORGANISM: Nannochloropsis gaditana
<220> FEATURE:
<221> NAME/KEY: misc_feature
<223> OTHER INFORMATION: SKP-8611 polypeptide

<400> SEQUENCE: 28

```
Met Gln Ala Ser Gln Lys Thr Ser Asp Val Gln Glu Glu Asp Gly Pro
1               5                   10                  15

Pro Lys Tyr Ile Thr Leu Gln Ala Arg Asp Gly Thr Leu Asp Glu Pro
            20                  25                  30

Val Asp Ala Arg Ile Leu Leu Pro Ser Asp Leu Leu Arg Ser Met Leu
        35                  40                  45

Pro Glu Lys Leu Ser Glu Ile Glu Asp Asp Phe Gln Ile Pro Leu Gln
    50                  55                  60

Gly Val Asp Lys Ala Val Leu Lys Val Val Glu Tyr Leu His Leu
65                  70                  75                  80

Tyr Arg Glu Glu Pro Met Tyr Lys Ile Glu Lys Pro Leu Asn Lys Val
                85                  90                  95

Lys Leu Tyr Asp Leu Val Gln Pro Gln Tyr Asp Gln Phe Ile Asn Ala
            100                 105                 110

Leu His Tyr Lys Thr Ile Phe Gln Ile Ile Asp Ala Ala Asn Phe Leu
        115                 120                 125

Gly Ile Glu Pro Leu Leu Ser Leu Ser Leu Ser Trp Val Ala Phe Val
    130                 135                 140

Leu Lys Gly Pro Thr Val Glu Glu Phe Lys Lys Leu Phe Thr Ile His
145                 150                 155                 160

Asn Asp Phe Thr Pro Glu Glu Ala Ile Phe Arg Arg Glu Tyr Leu
                165                 170                 175

Leu Pro Arg Arg Asn Arg Ala Thr Ser Glu Gly Gly Arg Glu Arg Gly
            180                 185                 190

Ala Ser Gly Asn Ser Asn Ser Ser
        195                 200
```

<210> SEQ ID NO 29
<211> LENGTH: 172
<212> TYPE: PRT
<213> ORGANISM: Nannochloropsis gaditana
<220> FEATURE:
<221> NAME/KEY: misc_feature
<223> OTHER INFORMATION: SKP-7479 polypeptide

<400> SEQUENCE: 29

```
Met Gly Asp Lys Ala Lys Gly Ala Glu Ser Gly Lys Val Val His Leu
1               5                   10                  15

Val Ser Gln Glu Gly Asp Gln Tyr Glu Val Glu Val Ser Val Cys Lys
            20                  25                  30

Met Ser Glu Leu Val Lys Thr Met Leu Pro Asp Asp Asp Ser Ser
        35                  40                  45

Glu Thr Gln Glu Ile Pro Leu Pro Asn Val Lys Asn Asn Val Leu Ala
    50                  55                  60

Lys Val Ile Glu Phe Cys Lys His His Lys Glu Asp Pro Met Asn Asp
65                  70                  75                  80

Ile Glu Lys Pro Leu Lys Ser Ala Asn Met His Glu Val Val Gln Asp
                85                  90                  95
```

```
Trp Tyr Ala Asn Phe Val Asn Val Asp Gln Glu Leu Leu Phe Glu Leu
            100                 105                 110

Ile Leu Ala Ala Asn Tyr Met Asp Ile Lys Pro Leu Leu Asp Leu Thr
        115                 120                 125

Cys Ala Thr Val Ala Ser Met Ile Lys Gly Lys Thr Pro Glu Glu Ile
    130                 135                 140

Arg Arg Thr Phe Asn Ile Thr Asn Asp Phe Thr Pro Glu Glu Ala
145                 150                 155                 160

Gln Val Arg Glu Glu Asn Lys Trp Cys Glu Glu Val
                165                 170

<210> SEQ ID NO 30
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer SGTI Y2H

<400> SEQUENCE: 30
catatggcca tggaggccga attcatggag caggcgcagc ttgcattc        48

<210> SEQ ID NO 31
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SGTI Y2H

<400> SEQUENCE: 31
gctgcaggtc gacggatccc cctacacccc ccacttccgc cactc           45

<210> SEQ ID NO 32
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SKP-8611 Y2H

<400> SEQUENCE: 32
catggaggcc agtgaattcc acatgcaagc atcccaaaag acgtcc          46

<210> SEQ ID NO 33
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SKP-8611 Y2H

<400> SEQUENCE: 33
gatcccgtat cgatgcccac ccgttagctt gagttgctgt tgccag          46

<210> SEQ ID NO 34
<211> LENGTH: 44
```

<210> SEQ ID NO 34
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SKP-7479 Y2H

<400> SEQUENCE: 34
catggaggcc agtgaattcc acatgggtga caaagcgaag ggag          44

<210> SEQ ID NO 35
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SKP-7479 Y2H

<400> SEQUENCE: 35
gatcccgtat cgatgcccac ccgtcacacc tcctcacacc acttg          45

<210> SEQ ID NO 36
<211> LENGTH: 646
<212> TYPE: PRT
<213> ORGANISM: Nannochloropsis gaditana
<220> FEATURE:
<221> NAME/KEY: misc_feature
<223> OTHER INFORMATION: SKP2-6789 polypeptide

<400> SEQUENCE: 36

Met Gly Gly Ile Phe Phe Lys Gly Leu Glu Glu Gly Arg Asp Glu
1               5                   10                  15

Gly Gly Val Gly Gly Arg Ser Ser Arg His Tyr Glu Asp Ala Ala Cys
            20                  25                  30

Pro Ser Arg Ser Arg Leu Ala Val Asp Glu Glu Asp Glu Ser Glu Ala
        35                  40                  45

Thr Ser Ile Asn Leu Ser Ser Glu Ala Ser Val His Arg Phe Leu Gln
    50                  55                  60

Glu Gln Tyr Ser Leu Ala Arg Gly Gly Arg Cys Arg Arg Cys Arg Pro
65                  70                  75                  80

Ala Glu Gly Asn Gly Glu Ile Met Ser Leu Ile Asp Leu Cys Ile Asp
                85                  90                  95

Ser Ile Cys Gln Asn Ile Leu Cys Tyr Glu Val Pro Pro Ser Phe Asp
            100                 105                 110

Val Leu Pro Pro Asp Leu Val Arg Arg Ile Phe Asp Ser Leu Thr Ser
        115                 120                 125

His Lys Ala Leu Thr Lys Leu Thr Leu Leu Pro Leu Arg Tyr Cys Asp
    130                 135                 140

Val Thr Arg Leu Asp Leu Ser Pro Cys Lys Gly Val Thr Asp Gln Trp
145                 150                 155                 160

Leu Arg Pro Phe Thr Asp Lys Thr Leu Thr His Leu Cys Leu Ala Phe
                165                 170                 175

Cys Asn Ala Ile Thr Asp Ala Gly Leu Leu Asn Leu Thr Glu Leu Gly
            180                 185                 190

Gly Leu Gln Val Ala Asp Leu Thr Ala Cys Ala Gly Leu Arg Thr Gly
        195                 200                 205

Gly Leu Ala Ala Phe Arg Glu Ser Trp Ser Met Thr Ser Leu Thr Leu
        210                 215                 220

```
Asn Gly Cys Arg Asn Leu Thr Asp Glu Ala Val Lys Pro Leu Ala Tyr
225                 230                 235                 240

Leu Ser Ala Leu Gln His Leu Arg Leu Arg Gly Cys Trp Gln Leu Ser
                245                 250                 255

Asp Ala Ala Leu Asn Ala Leu Ala Pro Leu Met Pro Gln Leu Lys Thr
            260                 265                 270

Leu Asp Val Asn Ala Cys Arg Gln Phe Ser Ser Thr Ser Ile Ser Phe
        275                 280                 285

Cys Val Gly Lys Met Arg Glu Ile Arg His Leu Asp Leu Gly Tyr Cys
    290                 295                 300

Pro Arg Gly Val Gly Gly Ala Leu Glu Val Leu Thr Arg Gly Pro
305                 310                 315                 320

Ala Pro Thr Thr Leu Gln Val Leu Ile Leu Asp Ser Ser Arg Ser Leu
                325                 330                 335

Ser Asn Ala Asp Leu Phe Ser Leu Gly Lys Phe Arg Cys Leu Gln Arg
            340                 345                 350

Leu Ser Leu Arg Asn Cys Thr Thr Ile Ser Asp Ala Gly Leu Cys Gln
        355                 360                 365

Leu Pro Ser Ser Leu Glu Thr Leu Asp Ala Ser His Cys Arg Gly Val
    370                 375                 380

Arg Arg Leu Pro Ala Gln Ser Leu Pro Cys Leu Arg Ser Val Asn Phe
385                 390                 395                 400

Ala His Ser Gly Leu Arg Asp Ser Asp Val Gly Ser Leu Ala Val Phe
                405                 410                 415

Pro Ala Leu Val Asn Ile Asn Leu Asp Ser Cys Ser Ile Gly Asn Ser
            420                 425                 430

Gly Leu Val Ser Leu Leu Pro Leu Lys Lys Leu Lys Arg Leu Asn Leu
        435                 440                 445

Ala Asp Thr Gly Val Ser Asn Gly Gly Met Asp Val Leu Ala Lys Leu
    450                 455                 460

Ser Ser Leu Ser Val Ile Ser Leu Phe Tyr Thr Ser Ile Ser Asp Ser
465                 470                 475                 480

Gly Val Arg Gln Leu Ser Val Leu Gln Asn Leu Thr Asp Leu Asn Leu
                485                 490                 495

Asp Asn Arg Asp Leu Thr Asp Thr Ser Leu Leu His Leu Ser Ser Leu
            500                 505                 510

Thr Lys Leu Arg Arg Leu Asp Met Phe Ser Ser Arg Val Ser Asp Val
        515                 520                 525

Gly Leu Cys Phe Ile Thr Ser Leu Val Glu Leu Val Asp Leu Glu Ile
    530                 535                 540

Cys Gly Gly Arg Ile Thr Asp Lys Gly Leu Glu Tyr Ile Ser Gln Leu
545                 550                 555                 560

Pro Ser Leu Gln Arg Leu Asn Val Ser Gln Asn Val Gln Ile Ser Asn
                565                 570                 575

Ser Gly Leu His His Leu Ala Ser Leu Lys Asp Leu Glu Ala Leu Asn
            580                 585                 590

Val Ser His Ser Gln Val Ala Ala Pro Gly Ala Leu Lys Pro Leu Cys
        595                 600                 605

Arg Leu Arg Gly Leu Lys Ile Leu Ala Val Asn Gly Cys Arg Gly Met
    610                 615                 620

Asp Asp Thr Thr Leu His Gln Ile Gln Ser Ser Leu Pro Asn Leu Arg
625                 630                 635                 640
```

Thr Val Arg Ala Val Ser
                645

<210> SEQ ID NO 37
<211> LENGTH: 303
<212> TYPE: PRT
<213> ORGANISM: Nannochloropsis gaditana
<220> FEATURE:
<221> NAME/KEY: misc_feature
<223> OTHER INFORMATION: CDC25-9451 polypeptide

<400> SEQUENCE: 37

Met Val Tyr Pro Pro Val His Ser Val Thr Gly Leu Tyr Thr Pro Leu
1               5                   10                  15

Trp Lys Thr Phe Gly Ala Trp Cys Met Pro Gly His Pro Ser Ser Ser
            20                  25                  30

Leu Arg Val Arg Pro Asp Ser Cys Asn Phe Phe Arg Gly Ala Phe Pro
        35                  40                  45

Arg Pro Phe Leu Phe Ala Arg Tyr Phe Arg Ser Ser Ser Ala Leu Leu
    50                  55                  60

Leu Phe Leu Thr Ile Pro Leu Ser Tyr Cys Phe Val Arg Pro Pro Gly
65                  70                  75                  80

Pro Phe Ser Ile Ala Ser Leu Cys Pro Ser Trp Gly Thr Arg Ser Ile
                85                  90                  95

Val Ser Asn Phe Pro Arg Pro Asp Ala Arg Arg Ala Phe Thr Thr Phe
            100                 105                 110

Ser Gly Thr Asp Val His Leu Ala Met Ser Ser Ser Val Ser His
        115                 120                 125

Ala Leu Ser Gly Pro Ala Tyr Ile Glu Gln Glu Leu Leu Ala Ile
    130                 135                 140

Leu His Ala Arg Arg Gly Glu Arg Ser Leu Lys Leu Gln Ile Leu
145                 150                 155                 160

Asp Val Arg Asp Asp Tyr Thr Gly Gly Glu Arg Thr Gly Gly Leu
                165                 170                 175

Ala Lys Leu Pro Gly Ala Ile Asn Val Pro Ser Glu Asp Trp Arg Asp
            180                 185                 190

Glu Glu Arg Val Val Ala Leu Ala Glu Ser Leu Lys Asp His Asp Met
        195                 200                 205

Ile Val Leu His Cys Met Leu Ser Gln Val Arg Gly Pro Phe Cys Ser
    210                 215                 220

Ala Arg Leu Met Ala His Phe Ser Cys Ala Val Gly Glu Asp Gly Gly
225                 230                 235                 240

Ala Ala Thr Lys Gln Glu Arg Asn Gln Ser Ser Gly Arg Asn Asp Gly
                245                 250                 255

Glu Glu Thr Leu Pro Ala Asn Glu Ser Lys Lys Glu Arg Arg Arg Glu
            260                 265                 270

Gln Gly Val Pro Gln Val Leu Val Leu Arg Gly Gly Phe Gln Gly Trp
        275                 280                 285

Tyr Ala Arg Tyr Arg Glu Glu Ile Gly Met Val Glu Pro Cys Glu
    290                 295                 300

<210> SEQ ID NO 38
<211> LENGTH: 2071
<212> TYPE: PRT
<213> ORGANISM: Nannochloropsis gaditana
<220> FEATURE:
<221> NAME/KEY: misc_feature
<223> OTHER INFORMATION: FBW7.1-2293 polypeptide

<400> SEQUENCE: 38

```
Met Ala His Ser Ile Leu Ala Lys Gly Cys Asp Thr Met Glu Glu Gln
1               5                   10                  15
Ser Gln Glu Gly Asp His Arg Ala Gly Pro Gly Val Lys Glu Ser Ile
            20                  25                  30
Gly Ser Ser Leu Arg Ala Ser Asn Gly Ala Ala Asp Ala Asn Gly Val
        35                  40                  45
Leu Glu Val Arg Val Ile Glu Ala Thr Asp Leu Ile Glu Arg Pro Arg
    50                  55                  60
Glu Arg Lys Gln Arg Ser Phe Phe Ala Gly Met Ala Glu Ser Ser Gly
65                  70                  75                  80
Val Met Ser Arg Ala Glu Tyr Gly Trp Pro Tyr Val Thr Ile Arg Ala
                85                  90                  95
Gly Arg Asp Ala Pro Arg Arg Thr Met Pro Gly Ile Met Ser Met Gln
            100                 105                 110
Ala Glu Glu Asp Arg Arg Gly Ser His Asn Asn Ala Gly Leu Ser Ser
        115                 120                 125
Gly Met Val Ala Trp His Glu Asp Phe Val Phe Gly Pro Val Ser Ser
    130                 135                 140
Arg Glu Glu Val Val Thr Cys Tyr Met His Arg Arg Ser Ala Gly
145                 150                 155                 160
Pro Asp Gly Arg Ser Ala Gln Cys Ser Val Gly Asp Val His Ile
                165                 170                 175
Pro Val Asn Arg Leu Pro Glu Gly His Ala Ile Glu Gln Trp Tyr Gln
            180                 185                 190
Leu Leu Pro Gln Gln Glu Thr Pro Arg Glu Asp Glu Leu Gly Arg Ser
        195                 200                 205
Arg Pro Arg Pro Ser Arg Lys Gly Val Val Ser Lys Ala Ala Ile Lys
    210                 215                 220
Leu Arg Leu Tyr Tyr Gln Val Arg Asp Pro Ala Phe Ala Pro Arg Gly
225                 230                 235                 240
Glu Gly Ala Val Ala Phe Val Gly Pro Glu Thr Met Gly Arg Thr Gln
                245                 250                 255
Arg Ile Gly Ala Glu Gly Val Ser Ala Thr Tyr Pro Ser Pro Ser Ser
            260                 265                 270
Thr Thr Gly Ala Ser Gly Leu Asp Thr Pro Arg Ser Ala Gln Glu Ser
        275                 280                 285
Gln Ser Gln Asp Glu Gln Gln Arg Gln Val Met Leu Ser Ser Ala Gly
    290                 295                 300
Gly Gly Leu Leu Ser Ser Ala Pro Gly Thr Glu Gly Gly Thr Gly Asp
305                 310                 315                 320
Pro Val Glu Gly Ala Ser Pro Arg Arg Leu Pro Thr Pro Ser Ser Met
                325                 330                 335
Ala Glu Leu Ala Gln Glu Glu Leu Pro Thr Gly Leu Val Asp Tyr Phe
            340                 345                 350
Cys Ile Met Gly Pro Arg Leu Asp Glu Ala Thr Gly Leu Pro Ser Leu
        355                 360                 365
His Asn Gly Ala Ile Leu Leu Arg His Pro Val Glu Asp Lys Ala Gly
    370                 375                 380
Gln Pro Leu Pro Asp Ser Pro Gln Phe Phe Cys Phe Pro Ala Gly Met
385                 390                 395                 400
Ala Leu Ala Tyr Gly Pro Ser Pro Pro Lys Pro Ala Pro Leu Ala Tyr
```

```
            405                 410                 415
Thr Phe Val Ile Lys His Ser Gly Val Ser Ser Tyr Gly Val Cys Leu
            420                 425                 430

His Phe His Arg Arg Trp Glu Gln Leu Ser Lys Asn Val Leu Ser Pro
            435                 440                 445

Ser Val Gly Leu Leu Gly Val Thr Gly Asp Thr Ser Gln Glu His Asp
450                 455                 460

Arg Pro Ser Gly Gln Glu Asp Pro Lys Gln Gln Gly Thr Thr Val Trp
465                 470                 475                 480

Ala Pro Val Cys Phe Cys Leu Leu Thr Arg Val Pro Val Val Gln Pro
                485                 490                 495

Leu Leu Asn Trp Leu Val His Ala Tyr Asp His Met Asp Arg Leu Leu
                500                 505                 510

Pro Pro Thr Tyr Asp Ala Leu Leu Gly Asp Pro Leu Asp Pro Ala Ser
            515                 520                 525

Val Pro Gly Ala His Leu Thr Asp Leu Leu Arg Thr His Ile Val Gln
530                 535                 540

Leu Thr Leu Glu Val Pro Leu Pro Ile Pro Gly Ala Leu Gly Val Gln
545                 550                 555                 560

Phe Asp Phe Leu Gly Arg Pro Ile Thr Cys Arg Leu Ala Gly Pro Gly
                565                 570                 575

Ala Leu Pro Ser Leu Cys Tyr Pro Leu Ser Pro Phe Leu Arg Thr Phe
                580                 585                 590

Ser Ala Arg Asn Val Leu Ala Leu Val Ala Ala Leu Thr Glu Ser
                595                 600                 605

Lys Val Leu Leu His Ser His Asp Leu Ser Val Leu Pro Val Met Ala
610                 615                 620

Glu Ser Leu Leu Ser Leu Ile Tyr Pro Leu Gln Trp Gln His Pro Tyr
625                 630                 635                 640

Leu Val Pro Leu Pro Arg Glu Leu Leu Val Val Glu Thr Pro Thr
                645                 650                 655

Asn Tyr Ile Leu Gly Val His Thr Glu Trp Leu Ala Asp Val Pro Arg
                660                 665                 670

Asp Ser Leu Lys Asp Val Val Cys Val Asp Cys Asp Ser Gly Ala Val
                675                 680                 685

Arg Leu Pro Pro Arg Pro Phe Asn Pro Pro Ser Phe Pro Pro Ser Val
                690                 695                 700

Leu Tyr Pro Leu Leu Arg Arg Leu Arg Gly Thr Val Tyr Pro Met Leu
705                 710                 715                 720

Thr Arg Leu Asp Ser Ala Ser Ser Arg Val Ser Leu Asp Asp Leu Pro
                725                 730                 735

Ile Ile Ser Thr Ser Ala Pro Ser Glu Ile Ser Pro Ala Ser Glu Glu
                740                 745                 750

Glu Leu Arg Arg Leu Phe Leu Arg Cys Leu Ala Tyr Leu Leu Ser Gly
                755                 760                 765

Tyr His Asp Cys Val Phe Tyr Ile Asp Pro Asn Ser Pro Ile Phe Asn
            770                 775                 780

Arg Ala Arg Phe Leu Ala Glu Tyr Ala Pro Ala Glu Asp His Ala Phe
785                 790                 795                 800

Leu Ser Arg Leu Leu Asp Thr Gln Ser Phe Gln Ala Phe Leu Glu Asn
                805                 810                 815

Gln Asp Gly Pro Ser Ile Asn Leu Phe Arg Arg Thr Leu Phe Gln Ala
                820                 825                 830
```

```
Phe Ser Arg Ala Thr Ser Arg Pro Pro Ser Pro Leu Pro Gly Glu Thr
        835                 840                 845
Thr Ser Ser Pro Ala Ala Ser Thr Ser Phe Pro Ser Leu Lys Lys Cys
    850                 855                 860
Pro Ala Asp Phe Arg Ile Leu Met Glu Glu Glu Ser Gly Asn Glu
865                 870                 875                 880
Trp Leu Glu Thr Pro Gly Ala Gly His Arg Glu Thr His Gly Glu Ala
                885                 890                 895
Trp Glu Gln Arg Pro Ser Ala Gly Arg Gly Glu Glu Cys Glu Val
            900                 905                 910
Lys Leu Met Leu Lys Ile Pro Pro Pro Leu Tyr Gly Glu Thr Glu
            915                 920                 925
Glu Asp Glu Ser Glu Ser Asp Gly Ser Val Asp Glu Cys Asp Pro
    930                 935                 940
Ala Thr Thr Arg Gly Glu Glu Ala Val Pro Gly Gly Arg Arg Glu Phe
945                 950                 955                 960
Arg Phe Asp Gly Asp Gln Asp Gln Lys Ala Glu Gly Trp Glu Gly Val
                965                 970                 975
Ser Glu Glu Arg Asp Val Ser Gly Arg Gln Arg Thr Ser Val Arg Phe
            980                 985                 990
Asn Leu Gly Glu Leu Glu Asn Pro  Gly Glu Ser Lys Gly  Asp Arg Gly
            995                 1000                1005
Asp Ser  Glu Val Met Ser  Ser Asp Arg Met Ala Asn  Thr Ile Thr
     1010                 1015                1020
Ala Ser  Glu Gly Leu Ser  Thr Val Val Ser Ala Glu  Ser Asn Arg
     1025                 1030                1035
His Lys  Glu Lys Arg Ala Lys  Ala Lys Lys Ala Arg  Arg Pro Leu
     1040                 1045                1050
Asn Leu  Pro Gly Leu Ala Val  Gly Ser Pro Pro Thr  Arg Ser Ser
     1055                 1060                1065
Leu Glu  Gly Thr Phe Gly Glu  Ala Asp Leu Asp Ala  Leu Met Arg
     1070                 1075                1080
Lys Thr  Met Asn Leu Thr Gly  Ala Thr Tyr Gly Arg  Asn Val Pro
     1085                 1090                1095
Ala Ala  Ser His Thr Gly Gly  Tyr Thr Cys Gly Asp  Glu Gly Asp
     1100                 1105                1110
Ser Met  Asp Ser Ser Val Val  Pro Ala Arg Thr Val  Asp Leu Asp
     1115                 1120                1125
Ser Gly  Tyr Gln Gly Gly Ala  Ala Glu Ala Lys Gly  Pro Thr Asn
     1130                 1135                1140
Ala Ala  Thr Gly Val Ala Trp  Arg Lys Ala Arg Arg  Trp Ser Val
     1145                 1150                1155
Glu Ala  Ala Ala Gly Met Met  Asp Val Thr Val Arg  Asp Val Ala
     1160                 1165                1170
Arg Ala  Phe Gly Leu Asn Phe  Asp Leu Gln Arg Val  Met Thr Arg
     1175                 1180                1185
Gly His  Thr Ile Phe Gly Phe  Phe Asp Asp Val Pro  Pro Ser Trp
     1190                 1195                1200
Gly Arg  Glu Gln Gly Ser Lys  Gly Gly Glu Gly Cys  Arg Glu Gly
     1205                 1210                1215
Arg Ala  Thr Glu Gly Ser Trp  Leu Gly Lys Glu Asp  Asp Gly Leu
     1220                 1225                1230
```

```
Glu Lys Asp Gly Ala Gly Ala Gln Thr Gly Val Leu Ser Gly Asp
    1235                1240                1245

Met Ala Lys Leu Asn Arg Cys Leu Ala Glu Ala Phe Ser Thr Glu
    1250                1255                1260

Lys Pro Ser Lys Glu Leu Phe Arg Glu Val Glu Ile Ala Phe Arg
    1265                1270                1275

Ala Arg Gly Val Arg Thr Arg Phe Leu Ala Ile Leu Ser Gln Pro
    1280                1285                1290

Arg Ser Lys Arg Met Ile Gln Arg His Gln Phe Leu Ile Gly Gly
    1295                1300                1305

Gly Thr Ser Gly His Phe Arg Val His Ser Thr Gly Phe Glu Ala
    1310                1315                1320

Leu Met Gln Leu Ala Ser Ala Val Cys Asp Ala Cys Val Val Asp
    1325                1330                1335

Arg Asp Phe Pro Thr Ala His Ala Leu Leu Gln Leu Met Gly Lys
    1340                1345                1350

Tyr Tyr Arg Val Leu Glu Gly Gly Gly Gly Asn His Ala Trp
    1355                1360                1365

Ala Ala Ala Thr Leu Arg Gln Gly Glu Gly Gly Ala Gly Ala Gln
    1370                1375                1380

Gln Gln His Lys Glu Phe Leu Ser Ser Arg Leu Arg His His Gln
    1385                1390                1395

Ile Tyr Gln Cys Val Glu Leu Trp Met His Val Leu Glu Glu Gln
    1400                1405                1410

Leu Gly Ala Gly Lys Gly Pro Thr Ala Thr Arg Arg Asp Ser Thr
    1415                1420                1425

Asn Val Asn Ser Val Asn Gly Phe Lys Leu Ala Lys Ala Pro Gly
    1430                1435                1440

Ala Lys Thr Thr Asn Arg Asp Leu Pro Ser Val Ala Glu Ala Asp
    1445                1450                1455

Asp Pro Ser Ser Val Gly Thr Val Asp Val Lys Ala Gly Gly Lys
    1460                1465                1470

Gly Lys Gly Ser Ala Leu Gly Gln Gly Glu Ala Ala Ala Glu Glu
    1475                1480                1485

Thr Pro Gly Ser Glu Met Asp Asp Ala Glu Val Asp Pro Arg Lys
    1490                1495                1500

Phe Ile Leu Arg Val Lys Ser Ile Leu Ala Glu Met His Gly Val
    1505                1510                1515

Gly Met Pro Asp His Arg Ala Leu Ala Phe Val Gly Arg Ile Cys
    1520                1525                1530

Glu Val His Glu Ala Gly Met Glu Ser Lys Gln Ala Leu Val Arg
    1535                1540                1545

Leu Val Gln Lys Ile Trp Gly Ile Ser Pro Ala Pro Thr Pro Gln
    1550                1555                1560

Gln Met Phe Ile Ser Gln Glu Pro Val Asn Arg Gly Glu Ser Val
    1565                1570                1575

Gly Ser Asp Ala Pro Arg Pro Ala Ala Ser Ser Ser Ser Ser Ser
    1580                1585                1590

Thr Ser Pro Ala Trp Thr Ser Pro Glu Gly Ile Ala Pro Met Val
    1595                1600                1605

Pro Pro Arg Arg Val Ser Phe Gln Gly Val Gly Ser Glu Ile Gly
    1610                1615                1620

Arg Arg Ser Ser Asp Ser Ile Gly Asp Ser Val Arg Lys Asn Ser
```

```
              1625                1630                1635

Thr Leu Leu Asn Asp Leu Arg Gly Pro Ser Pro Ser Pro Ser Phe
         1640                1645                1650

Ser Ser Thr Val Ser Ser Ser Ser Gly Ala Arg Leu His Arg
         1655                1660                1665

Ser Thr Ser Pro Ile Ser His Leu Met Gly Met Gly Leu Gly
         1670                1675                1680

Leu Gly Met Gly Ser Ala Ala Pro Pro Glu Ala Ser Met His Arg
         1685                1690                1695

Gly Pro Val Leu Ser Val Asp Val Asp Ala Ala Gly Ser Val Gly
         1700                1705                1710

Val Ser Gly Gly Ala Asp Lys Leu Leu Ile Val Tyr Ser Leu Gln
         1715                1720                1725

Gln Arg Ser Arg Ile Thr Ser Phe Ser Gly His Thr Gly Pro Val
         1730                1735                1740

Thr Cys Val Lys Ile Phe Arg Asp His Ala Asn Asp Pro Leu Val
         1745                1750                1755

Ala Ser Ala Ser Met Asp Ser Thr Leu Arg Ile Trp Lys Leu Gly
         1760                1765                1770

Gly Gly Gly Gly Asp Pro Gly Ala Phe Thr Gly Ala Arg Leu
         1775                1780                1785

Leu Ser Ser Phe Thr Thr Ala Lys Asp Val Arg His Ile Leu Thr
         1790                1795                1800

Gly His Ala Lys Gly Ile Val Cys Leu Asp Lys Cys Glu Asp Leu
         1805                1810                1815

Gln Leu Leu Ala Thr Gly Ala Met Asp Arg Ala Val Lys Leu Trp
         1820                1825                1830

Asn Val Ser Gln Gly Arg Asn Thr Ala Thr Leu Ile Gly His Thr
         1835                1840                1845

Arg Thr Val Asn Ser Leu Arg Phe Met Asp Gln Ser Gln Gly Tyr
         1850                1855                1860

Arg Ile Leu Ser Ala Gly Gln Asp Arg Thr Met Ile Leu Trp Asp
         1865                1870                1875

Ser Gly Arg Gly Ser Cys Ile Arg Val Phe Lys Gly His Glu Ser
         1880                1885                1890

Trp Ile Arg Gln Val Glu Ala Trp Gly Arg Asp Leu Ala Val Thr
         1895                1900                1905

Ala Ser Asn Asp Arg Thr Leu Arg Val Trp Asp Leu Arg Val His
         1910                1915                1920

Asn Cys Val Gln Lys Leu Ala Glu His Lys Gly Ala Val Thr Cys
         1925                1930                1935

Met Gln Val Ser Lys Glu Gln Asp Ala Pro Val Val Tyr Ser Gly
         1940                1945                1950

Ser Thr Asp Ser Thr Val Lys Ile Trp Asp Leu Arg Gly Gly Gly
         1955                1960                1965

Gly Arg Cys Thr Ala Thr Leu Glu Gly His Ala Glu Ala Val Thr
         1970                1975                1980

Gly Leu Ala Leu Glu Ser Pro Met Ala Ala Gly Ile Gly Lys Ser
         1985                1990                1995

Lys Asn Gly Gly Gly Ser Lys Leu Val His Gln Lys Leu Val Ser
         2000                2005                2010

Val Gly Glu Asp Lys Arg Val Val Glu Trp Asp Thr Arg Thr Gly
         2015                2020                2025
```

```
Ala Leu Leu Gln Ser Arg Met Gly His Ser Asp Gly Ile Ser Cys
    2030                2035                2040

Val Gln Val Ser Lys Tyr Gly Val Ile Val Thr Gly Ser Trp Asp
    2045                2050                2055

Ala Ser Val Arg Leu Trp Glu Gly Ile Gln Ile Ser Val
    2060                2065                2070

<210> SEQ ID NO 39
<211> LENGTH: 544
<212> TYPE: PRT
<213> ORGANISM: Nannochloropsis gaditana
<220> FEATURE:
<221> NAME/KEY: misc_feature
<223> OTHER INFORMATION: FBW7.2-284 polypeptide

<400> SEQUENCE: 39

Met Gly Arg Ser Leu Leu Pro His Pro Ser Ser Leu Met Leu Ser His
1               5                   10                  15

Pro Ser Ser Arg Leu Leu Ser Ile Met Thr Thr Ser Leu Ala Asp Met
            20                  25                  30

Ile Leu Gly Asn Arg Lys Arg Thr Cys Asp Leu Tyr Thr Ala Glu Met
        35                  40                  45

Thr Ser Gly Thr Thr Pro Pro Phe Leu Pro Ala Gln Lys Leu Lys Val
    50                  55                  60

Ala Val Lys Val Asp Gln Glu Tyr Lys Ile Pro Cys Ser Ser Pro Thr
65                  70                  75                  80

Val His Thr Ser Ser Thr Lys Gln Glu Ser Glu Ala Thr Ser Ala Pro
                85                  90                  95

Gly Asn Glu Glu Thr Arg His Arg Gly Pro Ser Val Leu Ala Gly Gln
            100                 105                 110

Gly Lys Ala Lys Gly Glu Ala Thr Asp Thr Leu Asn Ile Leu Asn Ser
        115                 120                 125

Leu Arg Asn Glu Glu Ala Glu Arg Glu Leu Arg Gln Tyr Arg Gly Lys
    130                 135                 140

Tyr Gly Gly Ser Arg Ala Ala Ser Arg Gly Ala Leu Val Ala Tyr Lys
145                 150                 155                 160

Gly Asn Asp Ala Gly Gly Ala Met Val Ser Arg Ser Asn Lys Arg Asp
                165                 170                 175

Gly Arg Thr Pro Pro Gly Ala Ala Ala Ala Ala Ala Gly Ile Gly
            180                 185                 190

Asn Ser Ser Ala Leu Ala Leu His Arg Thr Pro Ala Lys Val Pro Thr
        195                 200                 205

Pro Thr Trp His Ala Pro Trp Lys Leu His Ala Val Val Ala Gly His
    210                 215                 220

Leu Gly Trp Val Arg Ala Val Ala Phe Asp Pro Ala Asn Glu Trp Phe
225                 230                 235                 240

Val Thr Gly Ser Ala Asp Arg Thr Ile Lys Val Trp Asp Leu Ala Lys
                245                 250                 255

Cys Ala Ala Gly Ala Glu Gly Gly Leu Arg Leu Thr Leu Thr Gly His
            260                 265                 270

Ile Ser Ala Val Arg Ala Leu Ala Val Ser Asn Arg His Pro Tyr Leu
        275                 280                 285

Phe Ser Val Ala Glu Asp Lys Thr Val Lys Cys Trp Asp Leu Glu Gln
    290                 295                 300

Asn Lys Val Ile Arg His Tyr His Gly His Leu Ser Gly Val Tyr Ser
```

```
                305                 310                 315                 320
Leu Ala Leu His Pro Thr Leu Asp Val Leu Thr Gly Gly Arg Asp
                325                 330                 335
Ser Val Ala Arg Val Trp Asp Met Arg Thr Lys Met Gln Val His Val
                340                 345                 350
Leu Gly Gly His Thr Asn Thr Val Gly Ala Leu Ala Thr Asn Ser Val
                355                 360                 365
Asp Pro Gln Ile Ile Thr Gly Ser Tyr Asp Ser Thr Ile Lys Leu Trp
                370                 375                 380
Asp Ile Val Ala Gly Lys Ser Met Ala Thr Leu Thr Asn His Lys Lys
385                 390                 395                 400
Ala Val Arg Asp Leu Lys Val His Pro Lys Glu Leu Ser Phe Val Ser
                405                 410                 415
Gly Ala Gln Asp Asn Leu Lys Arg Trp Gln Val Arg Asp Gly Lys Phe
                420                 425                 430
Leu Lys Asn Leu Ser Gly His Asn Ala Val Ile Asn Thr Leu Ala Ile
                435                 440                 445
Asn Glu Asp Asn Val Leu Val Ser Cys Gly Asp Asn Gly Ser Leu Arg
                450                 455                 460
Phe Trp Asp Tyr Gln Thr Gly Tyr Cys Phe Gln Arg Leu Glu Thr Ile
465                 470                 475                 480
Val Gln Pro Gly Ser Leu Asp Cys Glu Ala Gly Ile Tyr Ala Ser Ala
                485                 490                 495
Phe Asp Met Ser Gly Thr Arg Phe Leu Thr Cys Glu Ala Asp Lys Thr
                500                 505                 510
Val Lys Ile Trp Lys Glu Asp Ala Glu Ala Ser Pro Glu Thr His Pro
                515                 520                 525
Ile Asp Met Glu Ala Trp Lys Gln Glu Cys Leu Ser His Lys Arg Trp
                530                 535                 540
```

<210> SEQ ID NO 40
<211> LENGTH: 437
<212> TYPE: PRT
<213> ORGANISM: Nannochloropsis gaditana
<220> FEATURE:
<221> NAME/KEY: misc_feature
<223> OTHER INFORMATION: FBW7.3-4601 polypeptide

<400> SEQUENCE: 40

```
Met Leu Thr Glu Arg Gln Lys Ala Asp Leu His Val Ala Ile Leu Glu
1               5                   10                  15
Tyr Leu Arg Asp Glu Gly Asp Ser Leu Ala Lys Thr Ala Glu Leu Phe
                20                  25                  30
Ala Leu Glu Thr Gly Leu Glu Ala Ala Val Pro Lys Leu Thr Gly
                35                  40                  45
Thr Leu Glu Lys Lys Trp Ser Ala Val Val Arg Leu Gln Lys Lys Leu
50                  55                  60
Met Glu Leu Glu Glu Arg Met Leu Val Ala Glu Gln Glu Leu Lys Ala
65                  70                  75                  80
Tyr Arg Gly His Ser His Met Gly Gly Thr Arg Ala Pro Ala Ala Gly
                85                  90                  95
Asp Asp Arg Asn Leu Pro Arg Ala Pro Ala Ile Arg Ser Phe Leu Gly
                100                 105                 110
His Arg Gly Gly Val Thr Cys Leu Ala Met His Pro Ile Phe Ala Leu
                115                 120                 125
```

```
Leu Val Ser Gly Ser Asp Asp Ala Thr Ile Lys Thr Trp Asp Leu Glu
    130                 135                 140

Ser Gly Ala His Glu Leu Thr Leu Lys Gly His Thr Asn Gly Val Gln
145                 150                 155                 160

Ala Val Val Phe Asn Arg Ala Gly Thr Leu Leu Ala Ser Cys Ser Ser
                165                 170                 175

Asp Leu Ser Ile Lys Leu Trp Asn Phe Gln Ser Pro Ser Thr Ala Pro
            180                 185                 190

Glu Cys Val Arg Thr Leu Arg Gly His Asp His Thr Ile Ser Gly Leu
        195                 200                 205

Ala Phe Ile Gly Pro Thr Asp Ala Gln Leu Ala Ser Cys Ser Arg Asp
    210                 215                 220

Thr Thr Val Arg Leu Trp Glu Val Ser Thr Gly Phe Cys Gln Arg Ser
225                 230                 235                 240

Leu Val Gly Ala His Thr Asp Trp Val Arg Cys Ile Ala Thr Ser Ala
                245                 250                 255

Asp Gly Ala Leu Leu Ala Ser Gly Gly Ser Asp Arg Leu Val Ala Val
            260                 265                 270

Trp Ala Leu Asp Thr Cys Ala Pro Val Ala Val Leu Arg Glu His Ser
        275                 280                 285

His Val Val Glu Ala Val Ala Phe Pro Pro Gly Val Ala Val Lys
    290                 295                 300

Ile Asp Gly Asn Lys Gly Gly Ser Thr Gly Leu Gly Ser Glu Asn Gly
305                 310                 315                 320

Glu Ala Ser Ala Gly Leu Gln Ser Gln Gly Ser Ala Glu Glu Ala Tyr
                325                 330                 335

Leu Val Ser Gly Ser Arg Asp Lys Thr Ile Met Leu Trp Asn Ala Arg
            340                 345                 350

Thr Gly Gln Cys Leu Leu Arg Leu Ala Asp His Glu Asn Trp Val Arg
        355                 360                 365

Ser Val Arg Phe His Pro Ser Gly Gln Phe Leu Leu Ser Val Ser Asp
    370                 375                 380

Asp Arg Ser Leu Arg Val Phe Asp Ile Ala Lys Ala Arg Cys Ile Arg
385                 390                 395                 400

Ser Leu Pro Asp Ala His Glu Gln Phe Val Ser Ala Leu Ala Gln His
                405                 410                 415

Pro Thr Leu Pro Tyr Leu Ala Thr Gly Ser Val Asn Arg Glu Ile Lys
            420                 425                 430

Leu Trp Glu Cys Arg
        435

<210> SEQ ID NO 41
<211> LENGTH: 544
<212> TYPE: PRT
<213> ORGANISM: Nannochloropsis gaditana
<220> FEATURE:
<221> NAME/KEY: misc_feature
<223> OTHER INFORMATION: FBW7.4-3015 polypeptide

<400> SEQUENCE: 41

Met Gly Phe Phe Tyr Phe Phe Tyr Leu Thr Leu Gln Arg Thr Arg Arg
1               5                   10                  15

Phe Leu Glu Thr Thr Ser Pro Val Thr Leu Leu Arg Thr Pro Ser Met
            20                  25                  30

Thr Ser Glu Ala Leu Pro Pro Ala Ser Glu Leu His Val Thr Lys
        35                  40                  45
```

```
Lys Ala Lys Lys Leu Pro Thr Leu Pro Gly Ser Met Val Gln Phe
 50                  55                  60
Gln Asp Ala Thr Gly Lys Gln Thr Gly Pro Arg Ile Asp Leu Pro Thr
 65                  70                  75                  80
Asp Ser Thr Pro Ala Gln Leu Glu Leu Ile Asn Glu Leu Arg Lys
                 85                  90                  95
Ala Thr Asp Pro Thr Glu Glu Ser Gln Gly Lys Val Pro Tyr Ser Cys
                100                 105                 110
Tyr Ile Asn Asp Val Glu Val Leu Asp Ser Leu Arg Asp Thr Leu Glu
                115                 120                 125
Ser Gln Gly Ile Val Asn Gly Glu Ala Val Ile Asn Ile Asn Tyr Gln
            130                 135                 140
Pro Leu Ala Val Phe Arg Val Arg Pro Val Val Arg Cys Thr Asp Thr
145                 150                 155                 160
Met Pro Gly His Thr Glu Ala Val Ile His Val Ser Phe Ser Pro Asp
                165                 170                 175
Gly Arg Arg Leu Ala Ser Gly Gly Asp Thr Thr Val Arg Phe Trp
                180                 185                 190
Asp Thr Gly Thr Ser Leu Pro Lys Phe Thr Cys Arg Gly His Arg His
            195                 200                 205
His Val Leu Cys Thr Ala Trp Ser Pro Asp Gly Ser Arg Phe Ala Ser
    210                 215                 220
Ala Asp Lys Ala Gly Glu Ile Arg Leu Trp Asp Pro Ala Thr Gly Leu
225                 230                 235                 240
Ala Val Gly Gln Pro Leu Gln Gly His Lys Gln His Ile Thr Ser Leu
                245                 250                 255
Ala Trp Glu Pro Leu His Leu Asn Arg Gly Lys Gly Glu Arg Leu Ala
                260                 265                 270
Ser Ser Ser Lys Asp Gly Thr Val Arg Val Trp Asn Val Arg Thr Gly
            275                 280                 285
Ala Cys Leu Thr Thr Leu Ala Gln His Thr Asn Ser Val Glu Cys Cys
            290                 295                 300
Lys Trp Gly Gly Gln Gly Val Leu Tyr Thr Gly Ser Arg Asp Arg Thr
305                 310                 315                 320
Val Lys Ile Trp Ala Leu Gln Gly Arg Asp Gly Glu Ala Gly Phe Gly
                325                 330                 335
Lys Leu Val Lys Thr Leu Val Gly His Gly His Arg Ile Asn Thr Leu
                340                 345                 350
Ala Leu Asn Thr Asp Tyr Val Leu Arg Thr Gly Pro Phe Asp His Thr
            355                 360                 365
Gly Ser Leu Ala Leu Asp Ala Ala Ser Pro Met Glu Ala Ala Glu Ala
    370                 375                 380
Lys Tyr Arg Lys Phe Leu Glu Gly Ser Glu Gly Arg Glu Arg Leu Val
385                 390                 395                 400
Ser Gly Ser Asp Asp Phe Thr Leu Phe Leu Trp Asp Pro Leu Gly Glu
                405                 410                 415
Glu Gly Gly Lys Lys Pro Leu Ala Arg Met Thr Gly His Gln Gln Ala
                420                 425                 430
Val Asn His Ile Ser Phe Ser Pro Asp Gly Arg Tyr Val Ala Ser Ala
            435                 440                 445
Ser Phe Asp Lys Lys Val Lys Thr Trp Asp Gly Arg Thr Gly Arg Phe
450                 455                 460
```

```
Leu Ser Thr Leu Val Gly His Val Gly Ala Val Tyr Met Val Ala Trp
465                 470                 475                 480

Ser Pro Asp Ser Arg Leu Leu Val Ser Ala Ser Lys Asp Ser Thr Leu
                485                 490                 495

Lys Leu Trp Asp Val Ala Lys Gly Ala Lys Ala Lys Glu Thr Leu Pro
                500                 505                 510

Gly His Met Asp Glu Val Tyr Ala Leu Asp Trp Ala Pro Asn Gly Ala
                515                 520                 525

Ser Val Ala Ser Gly Ser Lys Asp Arg Thr Ile Lys Ile Trp Arg Ala
530                 535                 540

<210> SEQ ID NO 42
<211> LENGTH: 601
<212> TYPE: PRT
<213> ORGANISM: Nannochloropsis gaditana
<220> FEATURE:
<221> NAME/KEY: misc_feature
<223> OTHER INFORMATION: FBW7.5-4195 polypeptide

<400> SEQUENCE: 42

Met Thr Gly Pro Ser Thr Arg Asn Ser Ser Leu Thr Ala Ala His
1               5                   10                  15

Trp Arg Thr Ser Val Leu Asn Ala Leu Gln Gln Asn Asp Val Glu
                20                  25                  30

Val Glu Pro Phe Arg Gly Ile Ile Leu Ser Tyr Thr Asp Leu Ala Arg
                35                  40                  45

Gln Asn Gln Val Leu Lys Ala His Val Asp His Gln Glu Lys Glu Leu
                50                  55                  60

Val Thr Leu Arg His Glu Ala Leu Glu Gln Ser Asp Ser Arg Gly Gln
65                  70                  75                  80

Gly Gly Ala Gly Ala Cys Gly Ala Lys Asp Glu Gln Thr Arg Lys Leu
                85                  90                  95

Gln Ser Lys Val Gln Arg Leu Gln Glu Glu Leu Thr Asp Lys Leu Arg
                100                 105                 110

Leu Glu Val Gln Gly Thr Thr Ser Gln Leu Asn Met Ser Lys Glu Ile
                115                 120                 125

Gln Asp Leu Phe Gln Lys Trp Gln Leu Ser Arg Ala Glu Ala Glu Lys
                130                 135                 140

Leu Arg Thr Glu Val Asp Gly Phe Arg Ala Arg Glu Ala Thr Leu Glu
145                 150                 155                 160

Ala Gln Ala Gly Met Ala Thr Arg Asp Leu Glu Ile Val Gln Glu Glu
                165                 170                 175

Leu Lys Arg Val Arg Ala Arg Leu Asn Thr Val Glu Lys Glu Tyr Leu
                180                 185                 190

Asp Val Arg Arg Gln Asn Glu Glu Leu Val Arg Arg Met Val Gly Glu
                195                 200                 205

Lys Ser His Asn Ala Glu Glu Met Asn Arg Met Thr Glu Leu Val Glu
                210                 215                 220

Arg Met Arg Ala Gln Leu Lys Ala Arg Asn Leu Glu Ile Glu Ser Thr
225                 230                 235                 240

Gln Ala Val Ala Ala Asp Ile Glu Ile Glu Ala Pro Ser Ser Gly
                245                 250                 255

Leu Arg Thr Asp Glu Leu Pro Ser His Cys Asn Gln Gln Phe Arg Ala
                260                 265                 270

His Ala Ala Asp Val Asn Asp Leu Val Tyr Cys Asp Thr Gly Gln Trp
                275                 280                 285
```

Leu Ala Thr Ala Gly Gly Asp Gly Lys Val Arg Val Trp Glu Ala Gly
            290                 295                 300

Ser Gly Arg Leu Lys Ala Thr Leu His Gly Gln Asp Val Met Leu Gly
305                 310                 315                 320

Leu Asp Phe Arg Gly Asp Phe Val Val Gly Ser Ser Asp His Thr
                325                 330                 335

Cys Lys Leu Trp Ser Leu Ala Ser Gly Arg Leu His Arg Thr Phe Val
                340                 345                 350

Gly His Ser Gly Asn Val Tyr Ala Val Lys Leu Ile Ala Gly Asp Leu
            355                 360                 365

Arg Ala Val Leu Thr Gly Gly Ala Asp Arg Thr Ile Arg Leu Trp Asp
370                 375                 380

Val Gly Arg Ala Ser Cys Arg Gln Val Leu Arg Ser Gly Ser Thr Cys
385                 390                 395                 400

Asn Gly Leu Asp Ile Gly Leu Asp Gly His Ala Pro Val Ser Ala His
                405                 410                 415

Gln Asp Gly Gly Leu Arg Phe Trp Asp Leu Arg Ala Gly Asn Pro Thr
            420                 425                 430

Met Ile Val Arg Ala Phe Glu Thr Gln Ala Thr Ser Val Gln Tyr Gly
                435                 440                 445

Gln Asn Phe Thr Ala Leu Ala Asn Ser Arg Asp Asn Ala Leu Lys Ile
450                 455                 460

Ile Asp Thr Arg Thr Phe Glu Thr Leu His Val Leu Arg His Glu Asp
465                 470                 475                 480

Tyr Arg Thr Phe Leu Asn Trp Ser Arg Ala Cys Phe Ser Pro Ser Ser
                485                 490                 495

Ser Tyr Val Ala Ala Gly Ser Ala Thr Gly Gln Leu Phe Val Trp Glu
            500                 505                 510

Thr Ala Ser Gly Glu Met Lys Ser Ile Leu Ser His Ala Pro Asp Ser
                515                 520                 525

Arg His Ser Phe Ser Ser Pro Glu His Asp Glu Leu Arg Cys Gln
530                 535                 540

Gly Met Ser Leu Ser Ala Ser Gly Asp Arg Ile Arg Thr Ser Ser Glu
545                 550                 555                 560

Ala Leu Glu Gly Ser Thr Ser Gly Ala Gly Gln Arg Gly Gly Gly
                565                 570                 575

Gly Ile Ile Ser Cys Ala Trp Lys Ala Ser Arg Leu Ser Ala Cys Thr
            580                 585                 590

Arg Ser Gly Asn Val Cys Ile Trp Ser
            595                 600

<210> SEQ ID NO 43
<211> LENGTH: 578
<212> TYPE: PRT
<213> ORGANISM: Nannochloropsis gaditana
<220> FEATURE:
<221> NAME/KEY: misc_feature
<223> OTHER INFORMATION: Wee1.1-6397 polypeptide

<400> SEQUENCE: 43

Met Thr His Ser Leu Pro Leu Tyr Leu Phe Glu Lys Val Met Ser Leu
1               5                   10                  15

Val Leu Asp Pro Arg Asn Leu Ile Ser Pro Cys Pro Phe Leu Ser Thr
            20                  25                  30

Ser His Thr Ala Thr Gln Met Ser Ser Met Met Met Asp Leu Asp Asp

```
                35                  40                  45
Asp Asp Gly Pro Leu Lys Met Glu Asp Gly Gly Ser Gly Gly Ser
 50                  55                  60

Pro Gly Gly Ser Asp Asp Tyr Ile Leu Pro Arg Pro Ser Pro Gly
 65                  70                  75                  80

Gly Leu Gln Arg Thr Phe Thr Pro Val Asp Tyr Glu Thr Thr Cys
                 85                  90                  95

Ser Pro Leu Pro Pro Leu Pro Pro Ser Ser Ser Thr Ser Ser Asp
                100                 105                 110

Tyr Lys Arg Asn Gly Arg Ala Asn Cys Asp Phe His Leu Ser Arg Pro
                115                 120                 125

Ile Ala Ser Pro Phe Ser Gly Arg Asn Ser Gln His Gln Pro His Ser
                130                 135                 140

Ala Pro Met Gly Pro Pro Gln Ala His Leu Arg Glu Asn Ile Asn Arg
145                 150                 155                 160

Asp Leu Lys Arg Gly Tyr Ala Met Gln Asp Glu Leu Gly Lys Asn Tyr
                165                 170                 175

Phe Leu Asp Glu Ser Pro Ser Asp Val Met Ala Phe Pro Pro Pro Thr
                180                 185                 190

Pro Tyr Lys Pro Ala His Pro Gly Tyr Ala Pro Ala Ser Ala Thr Arg
                195                 200                 205

Thr Pro Ser Ser Leu His Arg His Pro His Glu Pro His Ser His His
210                 215                 220

His Pro Thr His Ser Ser Lys Arg Asn Gly Arg Gly Ser Asn Pro Cys
225                 230                 235                 240

Ser Thr Asp Lys His Arg Gly Ser Gly Ala Gly Pro Gly Ser Ser Gly
                245                 250                 255

Arg Arg Thr Ser Leu His Glu Gly His Gly Pro Thr Thr Pro Val Ser
                260                 265                 270

Arg Phe Gln Thr Asp Phe Asp Val Val Arg Val Ile Gly Ser Gly Cys
                275                 280                 285

Phe Gly Glu Val Tyr Arg Val Arg Ser Arg Val Asp Gly Val Glu Tyr
290                 295                 300

Ala Val Lys Cys Thr Arg Arg Phe Arg Gly Pro Ala Asp Arg Asn
305                 310                 315                 320

Arg Tyr Leu Gln Glu Val Lys Ala Leu Ala Lys Val Cys Ala Ala Asp
                325                 330                 335

Ser Ser Glu Glu Val Leu His Val Val Arg Tyr His Gln Ala Trp Ile
                340                 345                 350

Glu Asp Glu Arg Leu Phe Met Gln Thr Glu Leu Cys Glu Glu Ser Leu
                355                 360                 365

Asp Gly Ala Leu Arg Ala Gly Glu Lys Met Gly Phe Glu Glu Val Phe
                370                 375                 380

Asp Phe Met Arg Gln Met Leu Leu Ala Leu Asp Val Leu His Arg His
385                 390                 395                 400

Gly Leu Val His Leu Asp Val Lys Pro Gly Asn Ile Phe Ile Lys Ala
                405                 410                 415

Gly Val Tyr Lys Leu Gly Asp Phe Gly Leu Val Ala Ser Val Asn Ser
                420                 425                 430

Ser Asp Gly Leu Gly Asp Ser Leu Val Glu Gly Asp Ser Arg Tyr Met
                435                 440                 445

Ser Ala Glu Leu Leu Gln Asp Gly Pro Lys Asp Leu Thr Lys Cys Asp
                450                 455                 460
```

```
Ile Phe Ser Leu Gly Ala Thr Val Tyr Glu Met Gly Arg Gly Arg Ala
465                 470                 475                 480

Leu Pro Pro Asn Gly Glu Glu Trp His Ala Leu Arg Ser Gly His Pro
            485                 490                 495

Pro Ser Leu Lys Gly Glu Pro Ala Val Leu Val Ser Asp Leu Met Arg
        500                 505                 510

Val Leu Ala Gln Met Met Ala Arg Glu Pro Ser Gln Arg Pro Ser Ala
            515                 520                 525

Ala Val Leu Leu Thr His Pro Arg Leu Arg Ser Lys Leu Glu Arg Glu
530                 535                 540

Leu Leu Gln Glu Lys Met Lys Ser Lys Lys Leu Val Lys Ala Leu Val
545                 550                 555                 560

Gln Asn Gln Gln Gln Ser Lys Gly Arg Lys Leu Glu Arg Thr Gln
                565                 570                 575

Thr Tyr
```

<210> SEQ ID NO 44
<211> LENGTH: 596
<212> TYPE: PRT
<213> ORGANISM: Nannochloropsis gaditana
<220> FEATURE:
<221> NAME/KEY: misc_feature
<223> OTHER INFORMATION: Wee1.2-4623 polypeptide

<400> SEQUENCE: 44

```
Met Gly Leu Asp Asp Phe Glu Val Ile Gln Gly Leu Gly Lys Gly Ala
1               5                   10                  15

Phe Ala Arg Val Asp Lys Val Lys Arg Lys Ile Asp Gly Lys Val Tyr
            20                  25                  30

Ala Leu Lys Arg Val Asn Ile Ser Thr Ile Pro Pro Lys Asp Leu Glu
        35                  40                  45

Asp Ser Leu Asn Glu Ile Arg Ile Leu Ala Ser Phe Lys His Pro Arg
    50                  55                  60

Leu Ile Arg Trp Tyr Glu Thr Phe Val Glu Asn Ala Lys Glu Glu Leu
65                  70                  75                  80

Cys Ile Val Met Glu Leu Cys Pro Tyr Gly Asp Leu Glu Gln Lys Ile
                85                  90                  95

Lys Arg His Lys His Arg Lys Gln Tyr Ile Asp Glu Arg Glu Ile Trp
            100                 105                 110

Val Tyr Ala Val Asn Leu Leu Glu Gly Leu Ala Ala Leu His Ser Lys
        115                 120                 125

Gly Val Val His Arg Asp Leu Lys Pro Ala Asn Cys Leu Ile Asp Ser
130                 135                 140

Gln Gly Cys Val Lys Ile Ala Asp Met Asn Ile Ser Lys Val Ser Lys
145                 150                 155                 160

Gly Gly Asn Met Gln Thr Gln Val Gly Thr Pro Tyr Phe Ile Cys Pro
                165                 170                 175

Glu Ile Tyr Leu Lys Arg Pro Tyr Thr Ser Thr Ser Asp Ile Trp Ser
            180                 185                 190

Leu Gly Gly Val Leu Tyr Asn Leu Ala Ala Leu Arg Pro Pro Phe Leu
        195                 200                 205

Ala Asp Asn Ile Gln Asn Leu Arg Arg Val Val Ile Arg Gly Ser Phe
    210                 215                 220

Asp Pro Leu Pro Ser Val Phe Gly Gln Ser Leu Thr Thr Leu Ile Gly
225                 230                 235                 240
```

```
Gln Leu Leu Gln Ile Asn Pro Ser Asp Arg Pro Glu Ala Lys Glu Ile
                245                 250                 255

Leu Lys Asp Pro Leu Val Glu Arg His Lys Tyr Leu Leu His Pro
            260                 265                 270

Leu Pro Ala Gly Gln Glu Ala Glu Gly Glu Met Leu Pro Thr Ile
        275                 280                 285

Arg Val Ala Ser Asp Lys Glu Gly Thr Lys Thr Ile Arg Leu Pro Gly
    290                 295                 300

Pro Ala Tyr Glu Glu Glu Thr Gly Ala Gly Thr Arg Ala Gly Lys
305                 310                 315                 320

Glu Arg Gly Ala Arg Asp Arg Pro Pro Ser Pro Arg Ser Pro Thr Ser
                325                 330                 335

Val Phe Val Ser Ser Pro Arg Ala Lys Asp Lys Ala Asn Ser Pro
            340                 345                 350

Ala Ser His Pro Ala Arg Glu Ser Thr Ser Pro Ser Asn Ser Ser Ala
                355                 360                 365

Gly Ser Ala Ala Arg Thr Glu Pro Ala Pro Arg Val Gln Ser Ser Pro
    370                 375                 380

Pro Ala Asp Ala Pro Arg Arg Pro Pro Arg Ser Ser Pro Pro Ser
385                 390                 395                 400

Ser Pro Pro Thr Ser Pro Ser Gln Leu Pro Met Gly Gly Arg Leu Ser
                405                 410                 415

Pro Leu Lys Thr Pro Ser Pro Thr Gln Met Phe Pro Ser Phe Pro Phe
                420                 425                 430

Ala Ser Pro Lys Val Gly Gly Ser Lys Pro Ser Ser Pro Ser Asn Gly
            435                 440                 445

Thr Ser Thr Ala Pro Thr Ala Ala Pro Gly Ser Pro Arg Ser Gly
            450                 455                 460

Ser Pro Leu Ser Ser Leu Leu Pro Ala Leu Gln Asp Met Gly Arg Asp
465                 470                 475                 480

Met Val Arg His Leu Pro Val Arg Pro Pro Gly Met Lys Val Ser Lys
                485                 490                 495

Glu Glu Lys Ala Arg Leu Ala Ala Ile Ala Ala Gly Glu Tyr Gly Gly
            500                 505                 510

Gly Ala Val Phe Ile Asp Thr Gly Tyr Asp Asp Val Gly Asp Val
        515                 520                 525

Ala Gly Ser Pro Ala Thr Ser Thr Ser Val Gly Gly Lys Ala Lys Arg
    530                 535                 540

Ser Ser Ile Gln Arg Val Phe Asp Gly Glu Gly Leu Pro Ser Phe Pro
545                 550                 555                 560

Thr Leu Glu Ala Phe Pro Val Ala Glu Val Lys Asn Phe Phe Ala Asn
                565                 570                 575

Ala Asn Gly Arg Arg Thr Pro Pro Gly Glu Lys Pro Asp Met Glu
            580                 585                 590

Glu Trp Arg Leu
        595

<210> SEQ ID NO 45
<211> LENGTH: 505
<212> TYPE: PRT
<213> ORGANISM: Nannochloropsis gaditana
<220> FEATURE:
<221> NAME/KEY: misc_feature
<223> OTHER INFORMATION: Wee1.3-8521 polypeptide
```

```
<400> SEQUENCE: 45

Met Gly Ile Glu Gln Phe Glu Ile Leu Lys Ser Leu Gly Glu Gly Ala
1               5                   10                  15

Phe Ala Ser Val His Lys Val Thr Arg Leu Val Asp Gly Lys Thr Tyr
            20                  25                  30

Ala Leu Lys Lys Val Asp Val Ser Leu Asp Asp Lys Glu Leu Leu
        35                  40                  45

Ser Ala Leu Asn Glu Ile Arg Leu Leu Ala Ser Phe Gly His Pro Arg
50                  55                  60

Ile Val Arg Leu His Glu Thr Phe Met Asp Gly Asn Asn Leu Cys Ile
65                  70                  75                  80

Val Met Glu Tyr Cys Gly Trp Gly Asp Leu Ala Met Lys Ile Lys Arg
                85                  90                  95

Tyr Val Lys Arg Arg Glu Tyr Ile Asp Glu Arg Val Ile Trp Val Tyr
            100                 105                 110

Met Ile Gln Ile Leu Glu Gly Leu Lys Ala Leu His Glu Arg Asn Val
        115                 120                 125

Leu His Arg Asp Leu Lys Pro Ala Asn Cys Phe Leu Ala Glu Asp Gly
130                 135                 140

Ser Ile Lys Ile Gly Asp Met Asn Val Ser Lys Val Met Lys Asp Gly
145                 150                 155                 160

Asn Ala Lys Thr Gln Ile Gly Thr Pro Tyr Tyr Met Ser Pro Glu Ile
                165                 170                 175

Trp Ala Arg Arg Pro Tyr Asn His Ala Thr Asp Ile Trp Ser Leu Gly
            180                 185                 190

Cys Leu Ile Tyr Glu Leu Cys Ala Leu Arg Pro Pro Phe Leu Gly Asn
        195                 200                 205

Asn Met Ser Glu Leu Lys Thr Ala Val Leu Gly Gly Asn Phe Asn Pro
210                 215                 220

Val Pro Ser Val Tyr Ser Lys Asp Leu Gly Ser Val Ile Ala Arg Met
225                 230                 235                 240

Leu Leu Ala Ala Ala Arg Asp Arg Pro Ser Ala Ala Glu Ala Leu Ala
                245                 250                 255

Tyr Pro Glu Val Asn Ala Arg Lys Cys Leu Val Lys Asn Val Leu Arg
            260                 265                 270

Glu Glu Glu Leu Tyr Thr Lys Gly Gly Lys Gly Gly Tyr Gly Ala Glu
        275                 280                 285

Asp Ala Leu Met Pro Thr Ile His Ile Gly Ser Leu Arg Glu Leu Gly
290                 295                 300

Ile Lys Leu Pro Gly Pro Ser Tyr Pro Ser Asp Gly Pro Pro Thr Pro
305                 310                 315                 320

Thr Thr Pro Ile Met Leu Ala His Asp Ala Ser Pro Val Asn Glu Lys
                325                 330                 335

Ala Thr Leu Ala Ser Pro Ile His His Arg Gln Lys His Glu Gln Glu
            340                 345                 350

Phe Pro Ala Ser Gly Ser Pro Ser His His Arg Arg Ala Gly Leu Pro
        355                 360                 365

Gly Ala Lys Ser Glu Ser His Ser Pro Leu Ser Pro Ser Ile Pro Pro
370                 375                 380

Ile Asp Lys Gly Arg Gln Gln Ser Pro Val Gly Ser Leu Asp Arg
385                 390                 395                 400

Asp Leu Ser Gly Ala Lys Glu Arg Gly Ser Ala Ser Tyr Pro Gln Asp
                405                 410                 415
```

```
Arg Arg Arg Val Pro Thr Pro Pro Asn Gly Ala Pro Ala Lys Pro
            420             425             430

Leu Pro Ile Gly Arg Ile Pro Ser His Gly Lys Gly Ser Ala Ala
            435             440             445

Ser Ser Ser Leu Pro Val Leu Lys Ile Lys Thr Ser Ser Gly Ser
450                 455                 460

Gly His Val Thr Pro Val Gly Val Gly Asp Glu Tyr Ser Met Leu
465                 470                 475                 480

Pro Arg Thr Glu Gln Lys Asn Ser Val Lys Asn Val Leu Gln Ala Val
                485             490             495

Gln Lys Glu Ile Ser Arg Pro Pro Tyr
            500             505

<210> SEQ ID NO 46
<211> LENGTH: 289
<212> TYPE: PRT
<213> ORGANISM: Nannochloropsis gaditana
<220> FEATURE:
<221> NAME/KEY: misc_feature
<223> OTHER INFORMATION: Wee1.4-7374 polypeptide

<400> SEQUENCE: 46

Met Asn Gly Gly Lys Arg Gly Glu Gly Gly Gly Tyr Asp Gly Ser Glu
1               5                   10                  15

Ala Cys Leu Leu Arg Val Ala Arg Asp Val Gly Ala Leu Asp Phe
            20                  25                  30

Met His Ser Arg Gly Ile Val His Met Asp Val Lys Pro Gly Asn Ile
            35                  40                  45

Phe Ile Ala Ala Asp Gly Ser Phe Lys Leu Gly Asp Leu Gly His Ala
        50                  55                  60

Ile Lys Ala Asp Gly Ser Met His Val Leu Glu Gly Asp Glu Arg Tyr
65                  70                  75                  80

Leu Ser Met Glu Val Leu Lys Gly Leu Asp Leu Phe Lys Leu Ser Ala
                85                  90                  95

Gly Lys Glu Val Pro Pro Tyr Arg Thr Ile Leu Glu Pro Asn Asp Ile
            100                 105                 110

Phe Gly Leu Gly Ala Ser Leu Tyr Glu Ala Trp Ser Arg Val Pro Leu
        115                 120                 125

Ala Gly Ala Gly Pro Glu Phe Leu Ala Val Arg Glu Gly Arg Leu Thr
130                 135                 140

His Leu Pro Ser Asn Gly Glu Lys Ser Val Ser Glu Gly Phe Glu Arg
145                 150                 155                 160

Phe Leu Arg Asn Leu Leu Ala Pro Arg Gly Glu Asp Arg Pro Thr Ala
                165                 170                 175

Ala Glu Val Val Gly Arg Ala Met Gly Leu Leu Gly Ala Gly Ser Gly
            180                 185                 190

Gly Arg His His Ala His Gly Trp Glu Gly Gly Trp Gln Thr Gln Ala
        195                 200                 205

Ala Glu Asp Thr Asp Asn Gly Ser Pro Arg Ala Ser Arg Arg Gln Glu
    210                 215                 220

Glu Asp His His Phe Ser Asp Ala Lys Gly Arg Ala Ala Ala Ala Val
225                 230                 235                 240

Ala Ala Ala Ala Ala Gly Ala Gln Ser Glu Leu Asn Arg Asp Ala Pro
                245                 250                 255

Leu Arg Val Pro Phe Ala Cys Glu Leu Pro Glu Cys Gln Ala Arg Gln
```

```
                    260                 265                 270
Gln Arg Ile Arg Ala Leu Glu Thr Met Ile Leu Ser Leu Thr Gly Glu
            275                 280                 285
Gly

<210> SEQ ID NO 47
<211> LENGTH: 540
<212> TYPE: PRT
<213> ORGANISM: Nannochloropsis gaditana
<220> FEATURE:
<221> NAME/KEY: misc_feature
<223> OTHER INFORMATION: Wee1.5-9810 polypeptide

<400> SEQUENCE: 47

Met Tyr Ser Gln Ala Ser Ser Gln Phe Ser Gln Glu Asp Tyr Leu Thr
1               5                   10                  15

Pro Ala Thr Gln Asp His Thr Ser Ala Pro Phe Leu Pro Pro His Tyr
            20                  25                  30

Ala Ile Ala Ser Pro Ser Ile Lys Lys Ser Arg Pro Ser Arg
        35                  40                  45

Arg Gly Ser Asn Gly Ala Ala Thr Arg His Gln Ala Met Met Met Ser
    50                  55                  60

Val Leu Pro Glu Gly Ile Pro Leu Pro Asn Gly Gly His Ala Ile Asn
65                  70                  75                  80

His Lys Ser Pro Arg Asp Ala Leu Pro Pro Met Gln Val His Pro Gly
                85                  90                  95

Pro Ile Leu His Ala Gly Asp Thr His Arg Ser Leu Gly Lys Ala Gln
            100                 105                 110

Gly Ser His Ala Ser Asn Ser Thr Leu Pro Ser Ser Leu Gly Arg Glu
        115                 120                 125

Glu Gly Asn Pro Ser Pro Pro Thr Pro Ser Lys Leu Arg Glu Arg Val
    130                 135                 140

Asp Arg Arg Leu Asp Pro Arg His Lys Pro Leu Asn Arg Asp Leu His
145                 150                 155                 160

Gly Leu Pro Ala Ser Pro Leu His Ser Arg Ala Ser Leu Gly Ser Ala
                165                 170                 175

Ser Val Leu Arg Ala Arg Asp Ala Ser Leu Gly Leu Thr Ser Ser Ser
            180                 185                 190

Ser Ser Ser Ala Ser Ser Ser Ala Ser Pro Pro Ser Ala Ser Phe
        195                 200                 205

Leu Pro Pro Arg Gly Pro Gly Pro Asp Ala Leu Gly Pro Gly Leu Asp
    210                 215                 220

Leu Pro His Pro His Arg Ser Asp Glu Lys Arg Gly Ser Ser Phe Gln
225                 230                 235                 240

Ser Leu Ser Gln Ser Val Val Asp Cys Phe Gly Ser Leu Arg Val His
                245                 250                 255

Gly Pro Ser Pro Glu Glu Val Pro Asn Glu Ser Lys Gly Lys Gly Ala
            260                 265                 270

Leu Gly Phe Gln Gly Ala Arg Gly Glu Glu Gly Glu Glu Gly Gly
        275                 280                 285

Glu Gly Glu Gly Trp Ala Met Gln Ser Ser Gln Asp Met Ala Gly Gly
    290                 295                 300

Phe Arg Leu Lys Ser Val Gly Ala Val Trp Asp Glu Glu Gly Ala
305                 310                 315                 320

Glu Met Glu Ala Gly Gly Gly Leu Arg Gly Glu Gly Glu Gly Glu Arg
```

-continued

```
                325                 330                 335
Gly Arg Gln Arg Ala Met Thr Gly Gly Pro Ile Ser Leu Asp Ala Trp
            340                 345                 350
Gly Gly Arg Gly Gly Arg Glu Asp Glu Ala Gly Gly Glu Val Val
        355                 360                 365
His Val Val Ser Ile Pro Ala Cys Asn Pro Asn Pro Phe Gly Pro Pro
    370                 375                 380
Ser Ser Arg Ala Ser Glu Asp Leu Pro Glu Gly Arg Lys Arg Thr Arg
385                 390                 395                 400
Gln Arg Lys Ile Lys Ile Pro Cys Ser Arg Gly Thr Gly Glu Gly Gly
                405                 410                 415
Arg Glu Gly Ala Gly Gly Gly Glu Gly Glu Val Ser Arg Tyr Leu
            420                 425                 430
Leu Glu Phe Glu Gln Leu Glu Thr Ile Gly Ala Gly Arg Phe Ser Leu
            435                 440                 445
Val His Lys Val Arg Lys Arg Leu Asp Gly Trp Val Tyr Ala Ile Lys
    450                 455                 460
Arg Ser Arg His Ser Leu Val Ser Glu Gly Glu Lys Glu Gly Ala Met
465                 470                 475                 480
Arg Glu Val Tyr Ala Leu Ala Leu Gln Gly Cys Pro His Leu Val
                485                 490                 495
Arg Tyr Met Ser Ala Trp Met Glu Ala Ser Tyr Leu Phe Ile Gln Thr
            500                 505                 510
Glu Tyr Cys Pro Gly Gly Cys Leu Glu Arg Ala Val Phe Asp Ser Val
        515                 520                 525
Arg Ala Arg Gly Gln Gly Ala Gly Glu Gly Pro Gly
    530                 535                 540

<210> SEQ ID NO 48
<211> LENGTH: 518
<212> TYPE: PRT
<213> ORGANISM: Nannochloropsis gaditana
<220> FEATURE:
<221> NAME/KEY: misc_feature
<223> OTHER INFORMATION: Cyclin-6855 polypeptide

<400> SEQUENCE: 48

Met Val His Ser Lys Arg Lys Ala Leu Glu Asp Ile Thr Ala Val Ala
1               5                   10                  15
Leu Ser Gly Ser Gln Pro Phe Arg Ala Ala Tyr Asp Thr Gly Gly Lys
            20                  25                  30
His Lys Arg Ala Cys Ile Asp Thr Val Asn Gln Thr Ser Lys Arg Arg
        35                  40                  45
Val Pro Asp Ala Pro Cys Arg Val Thr Arg Arg Ser Ala Leu Ala
    50                  55                  60
Ala Phe Ser Leu Thr Thr Asp Gly Pro Ala Gln Asp Gly Lys Ala Thr
65                  70                  75                  80
Phe Arg Arg Leu Tyr Ser Thr Arg Ser Cys Pro Asn Val Glu Ile Asn
                85                  90                  95
Cys Pro Val Pro Ala Ser Ser Lys Val Lys Asp Asp Lys Asp Ser Asp
            100                 105                 110
Ala Asp Leu His Leu Ala Cys Lys Glu Ala Leu Ala Met Glu Glu Ile
        115                 120                 125
Ser Gly Ser Pro Asp Arg Arg Pro Thr Asp Glu Pro Val Ala Leu Pro
    130                 135                 140
```

```
Ser Ser Ala Ser Gln Ser Asp Ser Glu Val Asn Thr Gly Leu Glu
145                 150                 155                 160

His His Leu Ser Asp Ala Thr Ser Phe Pro Phe Ser Ser Ser Leu Ser
                165                 170                 175

Ser Ser Thr Leu Pro Val Gly Ile Ile Asp Ile Asp Glu Thr Gln Gly
            180                 185                 190

Ser Ser Gln His Pro Arg Ser His Leu Leu Pro His Gln Val Gly Lys
        195                 200                 205

Ala Ser His Lys Gln Ser Asp Asn Val Ile Val Pro Arg Ser Ser Asn
    210                 215                 220

Leu Ala Leu Thr Asp Gly Thr Pro Gln Arg Leu Ala Ser Tyr Ser Arg
225                 230                 235                 240

Asp Tyr Phe Ala Tyr Leu Arg Glu Arg Glu Glu Gln Gln Asp Arg
                245                 250                 255

Pro Leu Pro Asp Tyr Met Ser Arg Ile Gln Gly Gly Ala Leu Thr Gln
                260                 265                 270

Asp Met Arg Ala Leu Leu Val Asp Trp Leu Val Thr Val Cys Glu Glu
            275                 280                 285

Cys Glu Leu Met Pro Ser Thr Leu Tyr His Cys Val Glu Leu Ile Asp
290                 295                 300

Arg Ala Leu Ser Lys Leu Gln Val Pro Lys Glu Gln Leu Gln Cys Met
305                 310                 315                 320

Gly Cys Ala Cys Leu Phe Ile Ala Cys Lys Phe Glu Thr Thr Val
                325                 330                 335

Pro Ser Leu Glu Glu Phe Thr Tyr Met Ala Ala Glu Ser Phe Ser Lys
            340                 345                 350

Lys Gln Leu Thr Asp Leu Glu Leu Arg Val Val Glu Ala Leu Ser Phe
        355                 360                 365

Arg Leu Ser Thr Val Thr Ala Tyr Asn Phe Leu Ser Arg Phe Thr Leu
    370                 375                 380

Ala Ala Gly Ser Gly Pro Arg Glu Thr Ala Leu Val Tyr Tyr Phe Ser
385                 390                 395                 400

Glu Leu Ser Leu Leu His Tyr Glu Phe Leu Gly Phe Ser Pro Ser Ile
                405                 410                 415

Arg Ala Ala Ala Leu Tyr Leu Ala Arg Gln Thr Leu Ala Val Ser
                420                 425                 430

Asn Thr Asp Ser Ala Arg Arg Ala Glu Glu Arg Asn Ile Trp Thr
            435                 440                 445

Pro Thr Ile Ala Phe Tyr Thr Gly Tyr Ser Pro Ala Thr Thr Leu Pro
        450                 455                 460

Leu Gln Glu Cys Val Arg Leu Arg Arg Ala His Ala Gly Val Glu
465                 470                 475                 480

Tyr Ser Pro Tyr Glu Ala Leu Lys Leu Lys Tyr Gly Ala Pro Ala Leu
                485                 490                 495

Leu His Val Gly Asp Ile Ala Cys Val Glu Glu Lys Asp Leu Gly Ala
            500                 505                 510

Thr Ile Leu Asn Leu Asn
        515
```

<210> SEQ ID NO 49
<211> LENGTH: 688
<212> TYPE: PRT
<213> ORGANISM: Nannochloropsis gaditana
<220> FEATURE:
<221> NAME/KEY: misc_feature
<223> OTHER INFORMATION: Cyclin-3560 polypeptide

<400> SEQUENCE: 49

```
Met Arg Lys Arg Arg His Asp Asp Ser Ser Gln Asn Ser Glu Val Ala
1               5                   10                  15

Leu Ser Ser Gln Val Lys Arg Ala Val Asn Pro Arg Ser Thr Arg Ser
            20                  25                  30

His Ser Arg Ser Thr Asp Lys Gly Ile Ser Asp Glu Ala Lys Lys Asn
        35                  40                  45

Gln Phe Ser Ala Pro Asp Ser Lys Ser Ala Ala Ser Arg Pro Ser Arg
    50                  55                  60

Gly Gln Phe Ser Leu Lys His Ala Arg Glu Pro Ala Thr Glu Gln
65                  70                  75                  80

Asn Leu Val Asn Gln Ser Arg Asp Ser Pro Arg Pro Met Gln Pro
                85                  90                  95

Cys Pro Val His Cys His Gly Ala Met Glu Asp Met Asp Ser Ile Ser
            100                 105                 110

Ser Thr Asn Thr Thr Lys Arg Asn Val Glu Gly Arg Pro Ser Leu Ile
            115                 120                 125

Ile Leu Gln Thr Gln Cys Leu Glu Ala Ile Leu Gln Asn Leu Thr Pro
    130                 135                 140

Ile Ser Arg Ser Pro Ser Ala Pro Pro Val Leu Leu Ala Glu Arg
145                 150                 155                 160

Leu Ala Leu Arg Lys Leu Gly Leu Gln Leu Met Ala Leu Thr Ala Pro
                165                 170                 175

Asp Asp Gly Glu Asn Ser Gly Phe Pro Leu Ser Tyr Ala Gly Ala Glu
            180                 185                 190

His Ala Gly Val Asp Met Val Ser Ala Ser Glu Glu Glu Arg Glu Glu
        195                 200                 205

Arg Arg Gly Glu Ala Ser Lys Ala Phe Ala Pro Leu Cys Gly Arg Gly
    210                 215                 220

Ile Ala Ile Asp Glu Ser Ser Thr Tyr Asn Gly Leu Ser Ser Thr Asp
225                 230                 235                 240

Asn Gly Ala Gln Arg Ser Gly Asn Arg Pro Ser Arg Leu Ser Ser Ser
                245                 250                 255

Ser Ser Ile Pro Ala Ala Ser Leu Ser Ser Pro Ser Leu Ser Leu Lys
            260                 265                 270

Arg Pro Ser Ser Val Met Arg Ala Phe Arg Tyr Lys Cys Gly Pro Cys
        275                 280                 285

Pro Lys His Ala Ser Tyr Asp Leu Pro Arg Thr Ile Lys Gly Asn Pro
    290                 295                 300

Gly Gly Ile Thr Arg Ala Gly Lys Pro Pro Asp Asp Gly Leu Leu Val
305                 310                 315                 320

Leu Pro Glu Ser Val Trp Gln His Ala Phe Ser Phe Val Pro Ala His
                325                 330                 335

Asp Leu Leu Ser Val Met Leu Thr Ala Arg Pro Phe Cys Ser Met Ala
            340                 345                 350

Glu Pro Phe Lys Gly Phe Tyr Phe His Trp Asn Leu Arg Ala Ala Glu
        355                 360                 365

Ser Leu Gln Ser Leu Arg Pro Tyr Ile Ser Lys Leu Arg His Leu Asn
    370                 375                 380

Ala Lys Met Arg Ala Ile Leu Leu Asp Trp Val Thr Asp Val His Gln
385                 390                 395                 400
```

```
Ser Leu Ser Phe Ala Pro Ala Thr Leu Tyr Arg Thr Ala Gln Val Leu
                405                 410                 415

Asp Gln Phe Leu Ser Arg Thr Glu Asn Val Thr Arg Glu Lys Leu Gln
            420                 425                 430

Leu Val Gly Val Thr Ala Phe Met Val Ala Lys Gly Val Glu His
        435                 440                 445

Thr Pro Pro Asp Pro Asp Cys Ala Tyr Trp Thr Asp Asn Ala Tyr
    450                 455                 460

Ser Gly Leu Glu Val Ser Ser Met Glu Ala Arg Leu Leu Lys Val Leu
465                 470                 475                 480

Ser Gln Ser Pro Phe Arg Pro Pro Ser Leu Pro Pro Thr Ala Gln Asp
                485                 490                 495

Phe Leu Thr Leu Tyr Leu Lys Glu Val Gly Ala Gly Lys Leu Ala Ser
            500                 505                 510

Cys Arg Ala Gln Tyr Tyr Cys Glu Arg Thr Leu Gln Glu His Asp Met
        515                 520                 525

Leu Ser Phe Pro Pro Ser Leu Ile Ala Ala Ser Val Ile Leu Ala
    530                 535                 540

Leu Lys Ser Ser Pro Ile Pro Val Val His Pro Cys Ser Thr Gln
545                 550                 555                 560

Lys Pro Lys Ser Trp Thr Glu Ala Val Ala His Tyr Ser Gly Tyr Ser
                565                 570                 575

Asp Thr Lys Val Ala Ala Cys Ala Arg Arg Ile Cys Gln His Val Arg
            580                 585                 590

His Thr Val Thr Thr Leu Ser Gly Arg Lys Leu Asp Ala Val Lys Arg
        595                 600                 605

Lys Tyr Ala Asn Gly Leu Phe Leu Ala Val Ser Arg Met Glu Pro Pro
610                 615                 620

Thr Trp Gly Gly Gly Pro Gly Glu Asp Ala Glu Lys Ala Glu Gly Gly
625                 630                 635                 640

Gly Gly Gln Glu Glu Gly Gly Glu Ile Ser Asn Ala Glu Gly Gly Asn
                645                 650                 655

Ala Pro Gly Gly Asp Glu Val Asp Val Glu Glu Ala Gly Glu Glu Gly
            660                 665                 670

Asn Gly Asp Gly Gly Met Gly Gly Asp Val Glu Gly Gly Leu Glu Val
        675                 680                 685

<210> SEQ ID NO 50
<211> LENGTH: 729
<212> TYPE: PRT
<213> ORGANISM: Nannochloropsis gaditana
<220> FEATURE:
<221> NAME/KEY: misc_feature
<223> OTHER INFORMATION: Cyclin-9008 polypeptide

<400> SEQUENCE: 50

Met Tyr Gly Leu Asn Lys Ala Cys Glu Asp Ser Val Leu Ala Ala Ala
1               5                   10                  15

Cys His Glu Thr Leu Glu Met Glu Asp Leu Glu Ala Leu Ala Thr Cys
            20                  25                  30

Ala Lys Ser Thr Tyr Ser Gly Asp Val Gly Gly Asp Thr Trp Ile Gln
        35                  40                  45

Ser Arg Arg Pro Ser Arg Ser Ser Phe Tyr Leu Lys Thr Gly Leu Phe
    50                  55                  60

Leu Pro Pro Asp Val Thr Leu His Asn Met Lys His Tyr Gly Arg Arg
65                  70                  75                  80
```

```
His Phe Leu Lys Met Arg Glu Ser Glu Met His Ile Tyr Ala Cys Asp
            85                  90                  95

Pro Cys Tyr Glu Arg Gln Ile Glu Leu Arg Pro Asp Met Arg Ala
        100                 105                 110

Gln Leu Val Asp Trp Leu Met Glu Val Cys Ala Asn Phe Ser Val His
        115                 120                 125

Arg Arg Thr Phe Gln Ala Ala Val Asn His Cys Asp Arg Tyr Leu Ser
130                 135                 140

Leu Cys Ala Arg Gly Phe Pro Lys Gln Arg Leu Gln Leu Leu Ala Ile
145                 150                 155                 160

Thr Ala Leu Phe Val Ala Ala Lys Met Asp Glu Val Tyr Pro Pro Lys
                165                 170                 175

Ala His Asp Leu Ala Glu Ala Thr Ala Gly Ala Phe His Ala Arg Asp
            180                 185                 190

Leu Val Val Phe Glu Gln Asp Leu Leu Thr Thr Leu Ser Trp Asn Leu
            195                 200                 205

Thr Pro Pro Thr Pro Asp Asp Trp Ala Glu Trp Tyr Phe Leu Ala Phe
            210                 215                 220

Leu Glu Arg Gly Leu Pro Ala Ala Thr Glu Met Lys Ala Ala Ser
225                 230                 235                 240

Ala Pro Ser Leu Ser Gln Gln Asp Leu Pro Ser Leu Ala Leu Leu Gln
                245                 250                 255

His Leu Pro Thr Gly Ile Ala Gln Lys Val Gln Val Leu Leu Asp Leu
            260                 265                 270

Ala Leu Leu Asp Val Thr Ser Ile His Phe Phe Pro Ser Met Leu Ala
            275                 280                 285

Ala Ala Gly Leu Tyr Val Leu Leu Pro Pro Val Phe Tyr Pro Ala Leu
            290                 295                 300

Ala Leu Ala Thr Gly Tyr Pro Pro Asn Asp Lys Ala Leu Glu His Cys
305                 310                 315                 320

Lys Ala Tyr Leu Thr Phe Leu Ala Thr Gly Leu Phe Asp Ser Ser Leu
                325                 330                 335

Pro Leu Gln Ala Leu Pro Leu Ser Arg Arg His Leu Gln His Gly Gln
            340                 345                 350

Pro Gly Gln Arg Ala Gly Gly Phe Gly Trp Thr Pro Glu Ala Ser
            355                 360                 365

Glu Ala Ala Gln Ser Gly Val Pro Leu Trp Asp Lys His Ser Leu Gln
370                 375                 380

Ser His Pro Ser Arg Leu Leu Pro His Leu Leu Gly Arg Ile Ser Ala
385                 390                 395                 400

Ile Ser Asp His Cys Asp Asp Leu Pro Pro Leu Pro His Ala Pro
                405                 410                 415

Lys Thr Gln Gly Ala Gln Ala Asp Asn Pro Ala Gly Asn Ala Ala Ala
                420                 425                 430

Leu Ala Thr Ser Ser Leu Ser Pro Cys Ser Ser Ala Ser Pro Ser
                435                 440                 445

Ala Ser Thr Leu Pro Ser Ala Thr Arg Ala Pro Ala Ala Leu Ala Asp
            450                 455                 460

Leu Val Thr Pro Ile His Ala Lys Ala Arg Leu Leu Ser Pro Leu Pro
465                 470                 475                 480

Ser Phe Leu Gly Tyr Arg Ser Val Ser Ser Lys Asn Leu Ile Ala Gly
                485                 490                 495
```

-continued

```
Arg Lys Gly Arg Cys Asp Glu Trp Glu Asp Gly Ala Met Phe Met
            500                 505                 510
Glu Thr Leu Glu Met Trp Pro Met Asp Glu Ser Glu Asn Gly Glu Glu
515                 520                 525
Thr Glu Glu Glu Glu Glu Glu Glu Gly Gly Ala Glu Glu
        530                 535                 540
Glu Glu Glu Lys Gly Gly Ala Glu Glu Glu Gly Arg Lys Gly
545                 550                 555                 560
Met Asp Glu Asp Ile Phe Gly His Ser Leu Glu Leu His Glu Trp
                565                 570                 575
Glu Ser Gly Arg Arg Gly Arg Glu Arg Lys Ala Gly Arg Cys Gly Leu
            580                 585                 590
Gly Gln Asp Lys Gly Arg Gly Ala Gly Pro Gln Ser Leu Arg Leu Glu
            595                 600                 605
Ala Leu Asp Gly Glu Ala Ser Glu Asn Glu Leu Gly Trp Ser Met Ala
            610                 615                 620
Thr Thr Val Asp Pro Gln Thr Thr Arg Asp Ser Val Phe Ser Phe Phe
625                 630                 635                 640
Ser Leu Glu Gly Thr Glu Gly Gly Gln Asp Gly Gly His Gly Leu Gly
                645                 650                 655
Ser Gly Arg Gly Ser Glu Glu Met Leu Gly Trp Gln His Glu Val Arg
            660                 665                 670
Glu Arg Phe Gly Glu Asp Cys Thr Asn Thr Gln Glu Ser Cys Gly Glu
            675                 680                 685
Gly Glu Glu Leu Glu Glu Met Arg Asn Val Ala Leu Ser Ser Pro Cys
690                 695                 700
Leu Thr Pro Ile Phe Cys Pro Asp Glu Ala Lys Val Ala Ser Gly Leu
705                 710                 715                 720
Gly Ala Ser Ala Thr Thr Thr Ala Pro
                725

<210> SEQ ID NO 51
<211> LENGTH: 463
<212> TYPE: PRT
<213> ORGANISM: Nannochloropsis gaditana
<220> FEATURE:
<221> NAME/KEY: misc_feature
<223> OTHER INFORMATION: Cyclin-4163 polypeptide

<400> SEQUENCE: 51

Met His Ala Thr Arg Ser Glu Ala Ala Thr Phe His Gly Lys His Ser
1               5                   10                  15
Ser Ala His Glu His Glu Ala Leu Ala Thr Asp Asp Gly Pro Gln Gly
            20                  25                  30
Pro Asp Cys Leu Gly Pro Leu Ile Lys Pro Gly Val Ser Thr Arg Ser
        35                  40                  45
Gly Leu Ala Ser Gly Ala Ser Arg Arg Ala Leu Gly Asp Ile Thr Asn
    50                  55                  60
Asn Arg Gly Ala Pro Ser Gly Lys Pro Gly Gln His Asn Thr Ser Lys
65                  70                  75                  80
Pro Met Thr Arg Ala Met Trp Ala Thr Ala Ala Gly Glu Gly Pro
                85                  90                  95
Leu Pro Gly Ala Thr Ser Ser Val Gly Leu Ala Ser Val Ala Pro Pro
            100                 105                 110
Pro Val Leu Tyr Glu Gln Pro Leu Pro Ala Leu Gln Lys Ser Asp Met
        115                 120                 125
```

```
Asp Gly Lys Arg Arg Glu Ala Val Asp Asp Met Asp Leu Ile Gln
        130                 135                 140

Glu Val Glu Glu Ile Asp Met His Ile Glu Glu Ala Ser Glu Met Pro
145                 150                 155                 160

Gln Glu Ala Ile Gln Ala Glu Ser Gln Glu Ala Leu Gly Ala Ile Ile
                165                 170                 175

Glu Asp Leu Gln Gly Met Thr Leu Lys Tyr Ser Thr Ala Arg Pro Val
            180                 185                 190

Leu Gly Leu Gly Val Asp Asp Ile Asp Ala Leu Asp Ala Ser Asn Pro
        195                 200                 205

Leu Ala Cys Val Asp Tyr Val Glu Ser Gln Tyr Ser His Tyr Arg Glu
210                 215                 220

Lys Glu Cys Arg Pro Gly Tyr Asp Pro Gly Tyr Met Lys Lys Gln Pro
225                 230                 235                 240

Tyr Ile Asn Val Arg Met Arg Ala Ile Leu Val Asp Trp Leu Val Glu
                245                 250                 255

Val His Tyr Lys Phe Lys Cys Cys Pro Glu Thr Leu Tyr Leu Thr Val
            260                 265                 270

Asn Leu Ile Asp Arg Phe Leu Asp Arg Lys Gln Val Pro Arg Pro Lys
        275                 280                 285

Leu Gln Leu Val Gly Val Thr Ala Phe Leu Ile Ala Cys Lys Tyr Glu
290                 295                 300

Glu Ile Tyr Pro Pro Glu Val Lys Glu Leu Val Tyr Met Thr Asp Ala
305                 310                 315                 320

Ala Tyr Thr Arg Lys Gln Ile Ile Asp Met Glu Ala Phe Met Leu Ala
                325                 330                 335

Thr Leu Lys Phe Gln Val Thr Val Cys Thr Thr His Cys Phe Leu Val
            340                 345                 350

Arg Phe Leu Lys Ala Gly His Ala Asp Asn Lys Leu Tyr Phe Leu Ala
        355                 360                 365

Ser Tyr Ile Ala Glu Arg Thr Leu Gln Glu Val Asp Val Leu Cys Phe
370                 375                 380

Leu Pro Ser Met Val Ala Ala Ala Val Tyr Leu Ala Arg Lys Asn
385                 390                 395                 400

Cys Gly Met Arg Ser Trp Ser Pro Thr Leu Asn His Tyr Thr Lys Tyr
                405                 410                 415

Ser Glu Glu Ala Leu Leu Pro Cys Leu Arg Val Leu Ser Pro Trp Leu
            420                 425                 430

Asn Ser Arg Ser Gln Thr Leu Gln Ala Ile Arg Lys Lys Tyr Gly Ala
        435                 440                 445

Ala Lys Phe Met Met Val Ser Ser Leu Glu Leu Thr Gly Val Val
450                 455                 460

<210> SEQ ID NO 52
<211> LENGTH: 397
<212> TYPE: PRT
<213> ORGANISM: Nannochloropsis gaditana
<220> FEATURE:
<221> NAME/KEY: misc_feature
<223> OTHER INFORMATION: CDKA1-3735 polypeptide

<400> SEQUENCE: 52

Met Glu Arg Tyr Gln Lys Leu Glu Lys Ile Gly Glu Gly Thr Tyr Gly
1               5                   10                  15

Val Val Phe Lys Ala Lys Asp Arg Val Thr Asn Glu Ile Leu Ala Leu
```

```
            20                  25                  30
Lys Lys Ile Arg Leu Glu Ala Glu Asp Glu Gly Ile Pro Ser Thr Ala
            35                  40                  45

Ile Arg Glu Ile Ser Leu Leu Lys Glu Leu Gln His Pro Asn Ile Val
        50                  55                  60

Arg Leu Tyr Asp Val Val His Thr Glu Arg Lys Leu Thr Leu Val Phe
 65                  70                  75                  80

Glu Tyr Leu Asp Gln Asp Leu Lys Lys Tyr Leu Asp Thr Cys Glu Ser
                    85                  90                  95

Gly Leu Asp Leu Pro Val Leu Gln Ser Phe Leu Tyr Gln Leu Leu His
                100                 105                 110

Gly Val Ala Phe Cys His Asp His Arg Val Leu His Arg Asp Leu Lys
                115                 120                 125

Pro Gln Asn Leu Leu Ile Asn Arg Glu Gly Leu Lys Leu Ala Asp
            130                 135                 140

Phe Gly Leu Ala Arg Ala Phe Gly Ile Pro Val Arg Ser Tyr Thr His
145                 150                 155                 160

Glu Val Val Thr Leu Trp Tyr Arg Ala Pro Asp Val Leu Met Gly Ser
                165                 170                 175

Arg Lys Tyr Ser Thr Pro Val Asp Ile Trp Ser Ile Gly Cys Ile Phe
                180                 185                 190

Ala Glu Met Ala Asn Gly Arg Pro Leu Phe Ala Gly Ser Ser Glu Ser
                195                 200                 205

Asp Gln Leu Asp Arg Ile Phe Arg Ala Leu Gly Thr Pro Thr Glu Gly
            210                 215                 220

Met Tyr Pro Gly Ile Val Glu Leu Pro Glu Phe Gln Lys Val Lys Asn
225                 230                 235                 240

Gln Phe Pro Arg Tyr Ser Pro Leu Glu Ser Trp Ala Pro Leu Val Pro
                245                 250                 255

Thr Leu Pro Pro Val Gly Ile Asp Leu Leu Gly Lys Met Leu Thr Phe
                260                 265                 270

Asp Pro Ala Lys Arg Val Ser Ala Arg Asp Ala Leu Ser His Pro Phe
            275                 280                 285

Phe Gly Asp Ile His Ala His Gly His Ala His Pro Ala Gln Ile Glu
        290                 295                 300

Pro Gly Met Thr Ala Gly Gly Arg Gly Gly Ile Pro Pro Tyr Ser Ile
305                 310                 315                 320

His His Pro Pro His Gln His His Ile His Gln Gln Pro Ser Gln Gln
                325                 330                 335

Gln His Phe Gln His Gly Pro Met His Ser Val His Pro Gln Gly Ser
            340                 345                 350

His His Pro Thr Gln Ala His Gly Ala Ser Leu Ala Leu Gly Pro Pro
            355                 360                 365

His Ala Gly His Pro Ala Gln Gln Pro Ser Ser Met Ala Pro Ala Ala
            370                 375                 380

Val Gly Asp Val Gly Leu Ala Gly Trp Glu Ala Arg Gly
385                 390                 395

<210> SEQ ID NO 53
<211> LENGTH: 334
<212> TYPE: PRT
<213> ORGANISM: Nannochloropsis gaditana
<220> FEATURE:
<221> NAME/KEY: misc_feature
<223> OTHER INFORMATION: CDKA1-864 polypeptide
```

<400> SEQUENCE: 53

Met Asp Arg Phe Thr Asn Ile Gln Gln Ile Gly Glu Gly Thr Tyr Gly
1               5                   10                  15

Ile Val Tyr Lys Gly Tyr Met Lys Gly Pro Gly Ser Ala Thr Thr Ser
            20                  25                  30

Ser Asn Gly Glu Leu Ile Ala Leu Lys Gln Ile Arg Leu Ala Asp Glu
        35                  40                  45

Asp Glu Gly Val Pro Ser Thr Ala Ile Arg Glu Ile Ser Leu Leu Lys
    50                  55                  60

Glu Leu Ser His Pro Asn Val Val Thr Leu Lys Asp Val Ile Tyr Ala
65                  70                  75                  80

Asp Asn Arg Leu Tyr Leu Val Phe Glu Tyr Leu Asp Gln Asp Leu Lys
                85                  90                  95

Arg Tyr Met Asp Gly Cys Lys Thr Gly Leu Asp Ser Thr Leu Val Lys
            100                 105                 110

Ser Tyr Leu His Gln Met Ile Gln Gly Val Ala Phe Cys His Ser His
        115                 120                 125

Arg Val Leu His Arg Asp Leu Lys Pro Gln Asn Leu Leu Ile Asp Arg
130                 135                 140

Gln Gly Arg Leu Lys Leu Ala Asp Phe Gly Leu Ala Arg Ala Phe Asn
145                 150                 155                 160

Val Pro Leu Arg Gln Tyr Thr Arg Glu Val Val Thr Leu Trp Tyr Arg
                165                 170                 175

Ala Pro Glu Ile Leu Leu Gly Ala Glu His Tyr Ser Thr Pro Val Asp
            180                 185                 190

Thr Trp Ser Ile Gly Cys Ile Phe Ala Glu Met Leu Asn Lys Glu Pro
        195                 200                 205

Leu Phe Pro Gly Asp Ser Glu Ile Asp Glu Leu Phe Arg Ile Phe Arg
    210                 215                 220

Val Leu Gly Thr Pro Asn Asp Glu Ile Trp Pro Lys Val Thr Glu Leu
225                 230                 235                 240

Pro Asn Tyr Lys Thr Gln Phe Pro Lys Trp Lys Arg Gln Ser Leu Asp
                245                 250                 255

Arg Asn Val Ser Arg Leu Cys Ala Asp Gly Leu Asp Leu Leu Ser Val
            260                 265                 270

Cys Ala Thr Ser Lys Lys Leu Ser Trp Arg Ala Lys Glu Val Val Ile
        275                 280                 285

Asn Thr Leu Pro His Phe Phe Leu Ser Tyr Leu Pro Lys Arg Leu Leu
    290                 295                 300

Thr Tyr Glu Pro Thr Ala Arg Ile Thr Cys Arg Glu Ala Gln Asp His
305                 310                 315                 320

Ala Tyr Phe Ala Gly Leu Gly Ala Cys Lys Asp Arg Met Val
                325                 330

<210> SEQ ID NO 54
<211> LENGTH: 303
<212> TYPE: PRT
<213> ORGANISM: Nannochloropsis gaditana
<220> FEATURE:
<221> NAME/KEY: misc_feature
<223> OTHER INFORMATION: CDKA1-9049 polypeptide

<400> SEQUENCE: 54

Met His Ile Tyr Leu Arg Tyr Gln Lys Ile Glu Lys Asn Gly Gly Gly
1               5                   10                  15

-continued

```
Asn Leu Gly Glu Gly Thr Tyr Gly Val Val Tyr Lys Ala Arg Asp Lys
             20                  25                  30

Gln Thr Asn Asp Ile Val Ala Leu Lys Arg Ile Arg Leu Glu Met Glu
         35                  40                  45

Asp Glu Gly Ile Pro Ser Thr Ala Leu Arg Glu Ile Ser Leu Leu Gln
     50                  55                  60

Glu Leu Arg His Pro Cys Ile Val Glu Leu Leu Asp Cys Val Gln Ser
 65                  70                  75                  80

Glu Gly Arg Leu Tyr Leu Val Phe Glu Phe Val Asp Arg Asp Leu Lys
                 85                  90                  95

Lys Tyr Met Glu Ala Gln Pro Gly Thr Leu Ser Arg Gly Val Val Lys
            100                 105                 110

Ser Phe Leu Phe Gln Ile Phe His Gly Leu Ala Phe Cys His Ala Arg
        115                 120                 125

Gly Ile Met His Arg Asp Leu Lys Pro Gln Asn Leu Leu Val Ser Lys
    130                 135                 140

Glu Gly Arg Leu Lys Ile Ala Asp Phe Gly Leu Ala Arg Ala Phe Val
145                 150                 155                 160

Pro Pro Ile Arg Pro Leu Thr His Glu Val Val Thr Leu Trp Tyr Arg
                165                 170                 175

Pro Pro Glu Ile Leu Leu Gly Ser Gln Thr Tyr Ala Pro Pro Val Asp
            180                 185                 190

Val Trp Ala Cys Gly Ala Ile Phe Val Glu Leu Leu Cys Lys Arg Ala
        195                 200                 205

Met Phe Gln Gly Asp Ser Glu Val Asp Gln Leu Phe Lys Ile Phe Arg
    210                 215                 220

Ser Leu Gly Thr Pro Ser Glu Glu Thr Trp Pro Gly Val Thr Ala Leu
225                 230                 235                 240

Gln Asp Trp Asn Pro Ala Phe Pro Val Trp Pro Val Lys Leu Thr
                245                 250                 255

Lys Tyr Cys Pro Ser Ile Asp Glu Ala Gly Leu Asp Leu Leu Glu Lys
            260                 265                 270

Leu Val Val Leu Asp Pro Lys Ser Arg Ile Ser Ala Lys Thr Ala Leu
        275                 280                 285

Tyr His Arg Tyr Phe Asp Asp Leu Asp Lys Gln Gln Phe Arg Gln
    290                 295                 300
```

<210> SEQ ID NO 55
<211> LENGTH: 528
<212> TYPE: PRT
<213> ORGANISM: Nannochloropsis gaditana
<220> FEATURE:
<221> NAME/KEY: misc_feature
<223> OTHER INFORMATION: CDKA1-8325 polypeptide

<400> SEQUENCE: 55

```
Met Thr Ser Ile Cys Glu Glu Cys Glu Glu Met Pro Ala Ala Met Arg
  1               5                  10                  15

Cys Glu Asp Cys Asp Leu Ile Tyr Cys Leu Pro Cys Ala Lys His Phe
             20                  25                  30

His Ala Lys Gly Asn Arg Ala Lys His Val Leu Asp Phe Phe Pro Ser
         35                  40                  45

Gln Asn Cys Gly Asn Leu Ala Gln Asp Asp Gly Thr Glu Ser Met Leu
     50                  55                  60

Ser Thr Ser Ser Ser Leu Thr Arg Arg Arg Ser Gly Ser Gly Ala Leu
```

-continued

```
                65                  70                  75                  80
Leu Gly Pro Pro Leu Arg Gln Thr Thr Pro Gln Ser Gln Gln Lys Arg
                            85                  90                  95

Arg Ser Arg Leu Pro Leu Gly Ile Pro Thr Ala Asn Ile Met Ala Glu
                100                 105                 110

Asn Ala Thr Gln Thr Ala Val Val Lys Ser Val Thr Gly Pro Gln
                115                 120                 125

Tyr Pro Gln Thr Thr Val Leu Gly Val Asn Gln Asn His Asn Gly Gly
            130                 135                 140

Ser Gly Arg Arg Ser Ser Thr Leu Lys Thr Pro Thr Thr Thr Ala Thr
145                 150                 155                 160

Glu Ser His Ala Cys Arg Met Ser Gly Ser Asn Leu Gly Gln Gly Pro
                    165                 170                 175

Asp Ser Ser Ile Ser Ser Met Lys Trp Ser Ala Ser Asp Phe Val Val
                180                 185                 190

Gly Arg Pro Leu Gly Arg Gly Lys Phe Gly Asn Val Tyr Leu Ala Arg
                195                 200                 205

Glu Ser Arg Thr Ser Lys Ser Val Ala Leu Lys Val Ile Phe Lys Asn
            210                 215                 220

Ser Leu Thr Gly Gly Lys Ser Phe Asn Leu Leu Arg Arg Glu Val Glu
225                 230                 235                 240

Ile Gln Ile Arg Leu Arg His Pro His Ile Leu Arg Leu Tyr Gly Tyr
                    245                 250                 255

Phe His Asp Pro Lys Ser Cys Phe Leu Val Leu Glu Trp Ala Ser Gly
                260                 265                 270

Gly Glu Leu Tyr Lys His Leu Lys Ala Leu Pro Glu Asn Arg Leu Glu
            275                 280                 285

Glu Ser Leu Ala Ala Gln Tyr Met Arg Gln Val Ala Leu Ala Val Gln
290                 295                 300

Tyr Leu His Ala Cys His Val Ile His Arg Asp Ile Lys Pro Glu Asn
305                 310                 315                 320

Leu Leu Leu Ala Gly Asp Leu Pro Pro Ser Ala Ala Pro Ala Thr Ala
                325                 330                 335

Gly Ser His Gly Arg Arg Ser Ser Gly Ser Thr Gly Val Gly Val Ala
                340                 345                 350

Gly Val Leu Pro Ala Asp His Val Leu Lys Leu Cys Asp Phe Gly Trp
            355                 360                 365

Ala Val His Ala Pro Pro Asp Gln His Trp Arg Gln Thr Leu Cys
370                 375                 380

Gly Thr Ala Glu Tyr Leu Ser Pro Glu Met Val Ala Gly Lys Pro Tyr
385                 390                 395                 400

Asp Tyr Thr Val Asp Val Trp Ala Leu Gly Ile Leu Ala Tyr Glu Leu
                405                 410                 415

Leu Gln Gly Lys Thr Pro Phe Tyr Val Pro Glu Gly Glu Asn Arg Gly
                420                 425                 430

Ala Val Ser Met Asp Arg Gly Glu Arg Glu Gly Gly Gly Gly
            435                 440                 445

Lys Gly Val Gly Val Ala Ala Ala Val Ala Ala Thr Glu Asp
450                 455                 460

Gly Asp Met Lys Lys Gly Arg Glu Val Tyr Ala Arg Ile Ala Ala
465                 470                 475                 480

Tyr Glu Gly Ala Leu Thr Phe Pro His Pro Val Ser Val Glu Ala Arg
                485                 490                 495
```

```
Ser Phe Val Asn Ala Leu Leu Val Pro Asp Pro Gln Asp Arg Val Ser
            500                 505                 510

Leu Asp Ala Val Leu Arg His Pro Trp Leu Met Glu Glu Glu Asp Val
        515                 520                 525

<210> SEQ ID NO 56
<211> LENGTH: 5457
<212> TYPE: DNA
<213> ORGANISM: Nannochloropsis gaditana
<220> FEATURE:
<221> NAME/KEY: misc_feature
<223> OTHER INFORMATION: disrupted CHORD-3266 locus in strain GE-5877

<400> SEQUENCE: 56
atgaaactct atgtgcacta cgaggaggct ggtcaggatg aaaaggcatt gacgcttaag      60
ttgactctgc ccaaaagctg gcggagcag ccgttgcttc aagtactgga gctgttcatc     120
gaatcctaca acaagaaaaa gaccggtcta cctcccttgg acaaagactt tgtccacatg     180
gaaaaagctg ggtaagtcct tactcgtgac agcgttccct ttctccagac tagacgccta     240
atagtgttct aatgtaccac tgggacacgc ctcgctgcct gtgcaccatg ctccatactc     300
aacgctgcta caggggcgta atccttccag tcggcaacat tgtgagcgac atgttgagcg     360
atagagatga tttgtatatc agatccgggc cagggcctgc tcgtgggaag attgcccatc     420
tcagttcgcc cccaaacgcg cacgcttcga gtgagtcgag cacaggattg ttgcgctgca     480
aaaactatgg atgcaatcag tcattttcgg aagaaaacaa ttcagaagag gcgtgccgct     540
ttcacaaggc accccccgtc tttcatgata cgaagaaagg gtggtcgtgc tgcgcgaagc     600
gagtatatga ctgggacgag ttccatacgg taagcgtgga agtgttcgtt ctcggcccca     660
ggactttgtt ttgaggcaat tggtgtactt taattggcgg ataaagggag gactcacaac     720
tttcgatatt caccgtctcc agatcgaggg gtgcaccaca ggacggcaca gtctcatcga     780
tccgaaggaa atttcgcgc cgtcccccac cctggctgca gccgcgcagg ccgagagggg     840
agattgcagc aatacgtcaa gcgctgctac agtcatcaag agcattgatg aattcaatca     900
gtcgaatcca aatgccgccg ctgcatgcaa acagcagcc tcgatgacgc tggcgggcac     960
gcgctgcacc gtcaaaccgg acgggtctgc cacctgtttg aacaaaggct gccaaaagga    1020
ctacttgctc aaggagaatc acccctctgc atgtcggtaa ggacaccgcg ctcgatggat    1080
atcataatac gatgggtatt atgggtctgg cgtaatagcg aagaggcccg caccgatcgc    1140
ccttcccaac agttgcgcag cctgaatggc gaatggcgcc tgatgcggta ttttctcctt    1200
acgcatctgt gcggtatttc acaccgcata tggtgcactc tcagtacaat ctgctctgat    1260
gccgcatagt taagccagcc ccgacacccg ccaacacccg ctgacgcgcc ctgacgggct    1320
tgtctgctcc cggcatccgc ttacagacaa gctgtgaccg tctccgggag ctgcatgtgt    1380
cagaggtttt caccgtcatc accgaaacgc gcgagacgaa agggcctcgt gatacgccta    1440
tttttatagg ttaatgtcat gataataatg gtttcttaga cgtcaggtgg cacttttcgg    1500
ggaaatgtgc gcggaacccc tatttgttta ttttttctaaa tacattcaaa tatgtatccg    1560
ctcatgagac aataaccctg ataaatgctt caataatatt gaaaaggaa gagtatgagt    1620 attcaacatt tccgtgtcgc ccttattccc ttttttgcgg cattttgcct tcctgttttt    1680
gctcacccag aaacgctggt gaaagtaaaa gatgctgaag atcagttggg tgcacgagtg    1740
ggttacatcg aactggatct caacagcggt aagatccttg agagttttcg ccccgaagaa    1800
cgttttccaa tgatgagcac ttttaaagtt ctgctatgtg gcgcggtatt atcccgtatt    1860
```

```
gacgccgggc aagagcaact cggtcgccgc atacactatt ctcagaatga cttggttgag    1920
tactcaccag tcacagaaaa gcatcttacg gatggcatga cagtaagaga attatgcagt    1980
gctgccataa ccatgagtga taacactgcg gccaacttac ttctgacaac gatcggagga    2040
ccgaaggagc taaccgcttt tttgcacaac atggggatc atgtaactcg ccttgatcgt     2100
tgggaaccgg agctgaatga agccatacca aacgacgagc gtgacaccac gatgcctgta    2160
gcaatggcaa caacgttgcg caaactatta actggcgaac tacttactct agcttcccgg    2220
caacaattaa tagactggat ggaggcggat aaagttgcag gaccacttct gcgctcggcc    2280
cttccggctg gctggtttat tgctgataaa tctggagccg gtgagcgtgg gtctcgcggt    2340
atcattgcag cactggggcc agatggtaag ccctcccgta tcgtagttat ctacacgacg    2400
gggagtcagg caactatgga tgaacgaaat agacagatcg ctgagatagg tgcctcactg    2460
attaagcatt ggtaactgtc agaccaagtt tactcatata ctttagat tgatttaaaa      2520 cttcattttt aatttaaaag gatctaggtg aagatccttt ttgataatct catgaccaaa    2580
atcccttaac gtgagttttc gttccactga gcgtcagacc ccgtagaaaa gatcaaagga    2640
tcttcttgag atcctttttt tctgcgcgta atctgctgct tgcaaacaaa aaaaccaccg    2700
ctaccagcgg tggtttgttt gccggatcaa gagctaccaa ctcttttcc gaaggtaact      2760 ggcttcagca gagcgcagat accaaatact gttcttctag tgtagccgta gttaggccac    2820
cacttcaaga actctgtagc accgcctaca tacctcgctc tgctaatcct gttaccagtg    2880
gctgctgcca gtggcgataa gtcgtgtctt accgggttgg actcaagacg atagttaccg    2940
gataaggcgc agcggtcggg ctgaacgggg ggttcgtgca cacagcccag cttggagcga    3000
acgacctaca ccgaactgag atacctacag cgtgagctat gagaaagcgc cacgcttccc    3060
gaagggagaa aggcggacag gtatccggta agcggcaggg tcggaacagg agagcgcacg    3120
agggagcttc cagggggaaa cgcctggtat ctttatagtc ctgtcgggtt tcgccacctc    3180
tgacttgagc gtcgattttt gtgatgctcg tcagggggc ggagcctatg gaaaaacgcc      3240
agcaacgcgg ccttttttacg gttcctggcc ttttgctggc cttttgctca catgttcttt    3300
cctgcgttat cccctgattc tgtggataac cgtattaccg cctttgagtg agctgatacc    3360
gctcgccgca gccgaacgac cgagcgcagc gagtcagtga gcgaggaagc ggaagagcgc    3420
ccaatacgca aaccgcctct ccccgcgcgt tggccgattc attaatgcag ctggcacgac    3480
aggtttcccg actggaaagc gggcagtgag cgcaacgcaa ttaatgtgag ttagctcact    3540
cattaggcac cccaggcttt acactttatg cttccggctc gtatgttgtg tggaattgtg    3600
agcggataac aatttcacac aggaaacagc tatgaccatg attacgccaa gcttgcatgc    3660
ctgcaggtcg actctagagc gtgcaggtgt acagattgaa ggaaacaatg gagatatctt    3720
tggcagttga aaaccgtgtt cgaatcatgc tcttctactc tccaactgag acgaaattta    3780
tagcgccatc tcgcttctga ctaccaggct taggaaggcc tcatcacaag ctggatcggt    3840
tcgaattaag caggcactga agccaagctt gcaagacagc cacctttaa ttctctcaaa      3900 acactttctc aattcagccc ggtaaatatg ccgattcaca gcggccaaga tagaggggag    3960
gttagcaaga atgttgcgat ccctccccag tcgttgcctc gcacacaacc taggacttca    4020
cctttccatg gaaaattgag aagtgaatat tggttttctt acggcatatc agatgaaatc    4080
atgaccccta acatgaaga gctgcaggca aacacctgc tctggacgag cacgatgaaa       4140
tctcgagaac ccgccgtact tcagttgatc ccgcatgatg acggccgcca ttgaaataag    4200
```

```
ccacctcact ttattctagc accgatttcc accgttgtga gggccgaacg aggacaattt    4260
cgtgcgaaac aagcacgaac gcgcacacga ttagtaggac agacgagcag atcgatggca    4320
tgcggcacgg tctcgcgttc tcggcgacca ggacaacgga gcagagggag gcctgccgag    4380
ttccgagggg cattttagtc ccaaaattgt gttgacacgt gaacaagtgg cttgaaaaga    4440
ggaaggaaat gcctgggttt cccttcgaga gcgggaactc gcttgtgcgt catcctagct    4500
acccatggtc cctttgtggg ggaggctgtt tcgtcctacc gaatgtgtgg cgctccatgc    4560
atcttctgcc tcccaaacca ccaacatgag cacgcgaagg aaggagaaaa aagtggccgc    4620
aacgttctct tctcatattt attgtctcat cacaaacata ggtacataat acaacaatca    4680
tggatccccg ggtaccgagc tcgatggcca agcctttgtc ccaagaggaa tccacgctga    4740
tcgaacgtgc aactgcgacc atcaacagca tacctattag cgaggactac tcggtggcca    4800
gtgcagccct ctcgtccgac ggtcggatct ttaccggcgt gaatgtatat catttcaccg    4860
gagggccatg cgcggagctc gtggtcctcg gaacggccgc tgcggctgct gccggaaatc    4920
tgacgtgcat agtggccatc gggaacgaaa accgcggcat tctgtctccg tgcgggcgat    4980
gtcggcaggt gctgcttgac ttgcacccgg ggatcaaggc aattgtcaaa gattccgatg    5040
ggcagcccac agcggttggc atcagggagt tgcttccctc tggctacgtc tgggagggtt    5100
gaaattcact ggccgtcgtt ttacaacgtc gtgactggga aaaccctggc gttacccaac    5160
ttaatcgcct tgcagcacat ccccctttcg ccagtggcaa acagctataa tcgtgagctt    5220
tacgttccca cgccaacact tcgccatttc tcctcccttc ctttctttag ctaccacgca    5280
gccgcccccg tcttccacga cgcgggtaaa tactggtcat gttgccctgg aacggtcaag    5340
tacgacttcg acgactttct caagatccct ggatgcatgc tcagtagtca ttacgacgga    5400
agccaggaga gcctggaggc gttcactaga cacgccaaaa cgtctgaggg cacatga       5457
```

<210> SEQ ID NO 57
<211> LENGTH: 4118
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Vector used in insertional mutagenesis

<400> SEQUENCE: 57

```
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagcttgc     240
atgcctgcag gtcgactcta gagcgtgcag gtgtacagat gaaggaaac aatggagata     300 tctttggcag ttgaaaaccg tgttcgaatc atgctcttct actctccaac tgagacgaaa     360
tttatagcgc catctcgctt ctgactacca ggcttaggaa ggcctcatca caagctggat     420
cggttcgaat taagcaggca ctgaagccaa gcttgcaaga cagccacctt ttaattctct     480
caaaacactt tctcaattca gcccggtaaa tatgccgatt cacagcggcc aagatagagg     540
ggaggttagc aagaatgttg cgatccctcc ccagtcgttg cctcgcacac aacctaggac     600
ttcacctttc catggaaaat tgagaagtga atattggttt tcttacgcca tatcagatga     660
aatcatgacc cctaaacatg aagagctgca ggcaaaacac ctgctctgga cgagcacgat     720
```

```
gaaatctcga gaacccgccg tacttcagtt gatcccgcat gatgacggcc gccattgaaa    780
taagccacct cactttattc tagcaccgat ttccaccgtt gtgagggccg aacgaggaca    840
atttcgtgcg aaacaagcac gaacgcgcac acgattagta ggacagacga gcagatcgat    900
ggcatgcggc acggtctcgc gttctcggcg accaggacaa cggagcagag ggaggcctgc    960
cgagttccga ggggcatttt agtcccaaaa ttgtgttgac acgtgaacaa gtggcttgaa   1020
aagaggaagg aaatgcctgg gtttcccttc gagagcggga actcgcttgt gcgtcatcct   1080
agctacccat ggtccctttg tgggggaggc tgtttcgtcc taccgaatgt gtggcgctcc   1140
atgcatcttc tgcctcccaa accaccaaca tgagcacgcg aaggaaggag aaaaaagtgg   1200
ccgcaacgtt ctcttctcat atttattgtc tcatcacaaa cataggtaca taatacaaca   1260
atcatggatc cccgggtacc gagctcgatg gccaagcctt tgtcccaaga ggaatccacg   1320
ctgatcgaac gtgcaactgc gaccatcaac agcatcccta ttagcgagga ctactcggtg   1380
gccagtgcag ccctctcgtc cgacggtcgg atctttaccg gcgtgaatgt atatcatttc   1440
accggagggc catgcgcgga gctcgtggtc tcggaacgg ccgctgcggc tgctgccgga   1500
aatctgacgt gcatagtggc catcgggaac gaaaaccgcg gcattctgtc tccgtgcggg   1560
cgatgtcggc aggtgctgct tgacttgcac ccggggatca aggcaattgt caaagattcc   1620
gatgggcagc ccacagcggt tggcatcagg gagttgcttc cctctggcta cgtctgggag   1680
ggttgaaatt cactggccgt cgttttacaa cgtcgtgact gggaaaaccc tggcgttacc   1740
caacttaatc gccttgcagc acatccccct ttcgccagac ccataatacc cataatagct   1800
gtttgccact ggcgtaatag cgaagaggcc cgcaccgatc gcccttccca acagttgcgc   1860
agcctgaatg gcgaatggcg cctgatgcgg tattttctcc ttacgcatct gtgcggtatt   1920
tcacaccgca tatggtgcac tctcagtaca atctgctctg atgccgcata gttaagccag   1980
ccccgacacc cgccaacacc cgctgacgcg ccctgacggg cttgtctgct cccggcatcc   2040
gcttacagac aagctgtgac cgtctccggg agctgcatgt gtcagaggtt ttcaccgtca   2100
tcaccgaaac gcgcgagacg aaagggcctc gtgatacgcc tatttttata ggttaatgtc   2160
atgataataa tggtttctta gacgtcaggt ggcacttttc ggggaaatgt gcgcggaacc   2220
cctatttgtt tatttttcta aatacattca aatatgtatc cgctcatgag acaataaccc   2280
tgataaatgc ttcaataata ttgaaaaagg aagagtatga gtattcaaca tttccgtgtc   2340
gcccttattc cctttttgc ggcattttgc cttcctgttt ttgctcaccc agaaacgctg   2400
gtgaaagtaa aagatgctga agatcagttg ggtgcacgag tgggttacat cgaactggat   2460
ctcaacagcg gtaagatcct tgagagtttt cgccccgaag aacgttttcc aatgatgagc   2520
acttttaaag ttctgctatg tggcgcggta ttatcccgta ttgacgccgg caagagcaa    2580
ctcggtcgcc gcatacacta ttctcagaat gacttggttg agtactcacc agtcacagaa   2640
aagcatctta cggatggcat gacagtaaga gaattatgca gtgctgccat aaccatgagt   2700
gataacactg cggccaactt acttctgaca acgatcggag gaccgaagga gctaaccgct   2760
tttttgcaca acatggggga tcatgtaact cgccttgatc gttgggaacc ggagctgaat   2820
gaagccatac caaacgacga gcgtgacacc acgatgcctg tagcaatggc aacaacgttg   2880
cgcaaactat taactggcga actacttact ctagcttccc ggcaacaatt aatagactgg   2940
atggaggcgg ataaagttgc aggaccactt ctgcgctcgg cccttccggc tggctggttt   3000
attgctgata atctggagc cggtgagcgt gggtctcgcg gtatcattgc agcactgggg   3060
ccagatggta agccctcccg tatcgtagtt atctacacga cggggagtca ggcaactatg   3120
```

```
gatgaacgaa atagacagat cgctgagata ggtgcctcac tgattaagca ttggtaactg    3180
tcagaccaag tttactcata tatactttag attgatttaa aacttcattt ttaatttaaa    3240
aggatctagg tgaagatcct ttttgataat ctcatgacca aaatcccctta acgtgagttt   3300 tcgttccact gagcgtcaga ccccgtagaa aagatcaaag gatcttcttg agatcctttt    3360
tttctgcgcg taatctgctg cttgcaaaca aaaaaccac cgctaccagc ggtggtttgt     3420
ttgccggatc aagagctacc aactcttttt ccgaaggtaa ctggcttcag cagagcgcag    3480
ataccaaata ctgttcttct agtgtagccg tagttaggcc accacttcaa gaactctgta    3540
gcaccgccta catacctcgc tctgctaatc ctgttaccag tggctgctgc cagtggcgat    3600
aagtcgtgtc ttaccgggtt ggactcaaga cgatagttac cggataaggc gcagcggtcg    3660
ggctgaacgg ggggttcgtg cacacagccc agcttggagc gaacgaccta caccgaactg   3720
agatacctac agcgtgagct atgagaaagc gccacgcttc ccgaagggag aaaggcggac    3780
aggtatccgg taagcggcag ggtcggaaca ggagagcgca cgagggagct tccaggggga    3840
aacgcctggt atctttatag tcctgtcggg tttcgccacc tctgacttga gcgtcgattt    3900
ttgtgatgct cgtcagggg gcggagccta tggaaaaacg ccagcaacgc ggcctttta     3960 cggttcctgg ccttttgctg gccttttgct cacatgttct ttcctgcgtt atcccctgat    4020
tctgtggata accgtattac cgcctttgag tgagctgata ccgctcgccg cagccgaacg    4080
accgagcgca gcgagtcagt gagcgaggaa gcggaaga                            4118

<210> SEQ ID NO 58
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer flanking CHORD insertion

<400> SEQUENCE: 58
gtcaagcgct gctacagtca tcaagagc                                            28

<210> SEQ ID NO 59
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer flanking CHORD insertion

<400> SEQUENCE: 59
cagggatctt gagaaagtcg tcgaagtcg                                           29

<210> SEQ ID NO 60
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: qRT Primer CHORD exon 2

<400> SEQUENCE: 60
ggatgcaatc agtcattttc gg                                                  22
```

<210> SEQ ID NO 61
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: qRT Primer CHORD exon 2

<400> SEQUENCE: 61
cccagtcata tactcgcttc g                                             21

<210> SEQ ID NO 62
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: qRT Primer CHORD exon 4

<400> SEQUENCE: 62
atactggtca tgttgccctg                                               20

<210> SEQ ID NO 63
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: qRT CHORD exon 4

<400> SEQUENCE: 63
gttttggcgt gtctagtgaa c                                             21

<210> SEQ ID NO 64
<211> LENGTH: 7822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CHORD Exon4 fusion expression vector

<400> SEQUENCE: 64
gcggccgccg tatggtcgac ggttgctcgg atggggggg cggggagcga tggagggagg     60
aagatcaggt aaggtctcga cagactagag aagcacgagt gcaggtataa gaaacagcaa    120
aaaaaagtaa tgggcccagg cctggagagg gtatttgtct tgttttctt tggccaggaa     180 cttgttctcc tttcttcgtt tctaggaccc cgatccccgc tcgcatttct ctcttcctca    240
gccgaagcgc agcggtaaag catccatttt atcccaccga aagggcgctc ccagccttcg    300
tcgagcggaa ccggggttac agtgcctcac tcctttgcac gcggtcgggt gctcggccta    360
cggttgcccg agtccgcaag cacctcaaca cagccgtctg tccacaccgc agccgaccgg    420
cgtgcgattt gggtccgacc caccgtccca gccccgctgc ggactatcgc gtcgcagcgg    480
ccctgcgccc acgcggcgtc gtcgaagttg ccgtcgacga gagactggta aagctgatcg    540
agtccgatac gcaacatata ggcgcggagt cgtggggagc cggccagctc cgggtgcctc    600

```
cgttcaaagt agcgtgtctg ctgctccatg cacgccaacc agggacgcca gaagaatatg      660
ttcgccactt cgtattggct atcaccaaac atcgcttcgg accagtcgat gacagcagta      720
atccgaccat tgtctgtaag tacgttattg ctgccgaaat ccgcgtgcac caggtgcctg      780
acctcagggc aatcctcggc ccacaacatg agttcgtcca gtgcttgggc cacggatgca      840
gacacggtgt catccatgac tgtctgccaa tgatagacgt gaggatcggc aatggcgcag      900
atgaagtctc gccaggtcgt gtactgcccg atgccctggg gcccaaaagg tccaaagccg      960
gacgtctgag acagatctgc ggcagcgatc gcgtccatgg cctcggccac gggttgcaaa     1020
acggcaggca attcagtttc gggcagatct tgcaacgtca ctccctgggc tcggcgcgag     1080
atgcagtacg tgagagattc gctaaactcc ccaatgtcca gtacctctgg tatggggaga     1140
gcggcggagg cgaaatgacg gtagacatac cgatccttgt agaacccgtc cgcacaacta     1200
ttaaccctca acacgtatcc ccgaccccct acgtcaaacg agaacgccct actctcctct     1260
ccctcgctca gttgcatcaa gtcggagaca gagtcgaact tctcaataag gaatttctcc     1320
acggacgtag cggtcagttc cggtttcttc cccatcgagc tcggtacccg gggatccatg     1380
attgttgtat tatgtaccta tgtttgtgat gagacaataa atatgagaag agaacgttgc     1440
ggccactttt ttctccttcc ttcgcgtgct catgttggtg gtttgggagg cagaagatgc     1500
atggagcgcc acacattcgg taggacgaaa cagcctcccc cacaaaggga ccatgggtag     1560
ctaggatgac gcaaagcga gttcccgctc tcgaagggaa acccaggcat ttccttcctc     1620
ttttcaagcc acttgttcac gtgtcaacac aattttggac taaaatgccc ctcggaactc     1680
ggcaggcctc cctctgctcc gttgtcctgg tcgccgagaa cgcgagaccg tgccgcatgc     1740
catcgatctg ctcgtctgta ctactaatcg tgtgcgtgtt cgtgcttgtt tcgcacgaaa     1800
ttgtcctcgt tcggccctca caacggtgga atcggtgct agaataaagt gaggtggctt     1860
atttcaatgg cggccgtcat catgcgggat caactgaagt acggcgggtt ctcgagattt     1920
catcgtgctc gtccagagca ggtgttttgc ctgcagctct tcatgtttag ggtcatgat     1980
ttcatctgat atgccgtaag aaaaccaata ttcacttctc aattttccat ggaaaggtga     2040
aggcctaggt tgtgtgcgag gcaacgactg gggagggatc gcaacattct tgctaacctc     2100
ccctctatct tggccgctgt gaatcggcat atttaccggg ctgaattgag aaagtgtttt     2160
gagggaatta aaaggtggct gtcttgcaag cttggcttca gtgcctgctt aattcgaacc     2220
gatccagctt gtgatgaggc cttcctaagc ctggtagtca gaagcgacat ggcgctataa     2280
atttcgtctc agttggagag tagaaaagca tgattcgaac acggttttca actgccaaag     2340
atatctccat tgtttccttc aatctgtaca cctgcacggt gcaccagttg gtacggcata     2400
ttatggttta aagttgaaaa tgctaacagt gaagtgatat ccttttttaa tggagtgttg     2460
aggtgaagtc tagcatcgta ggggaaaaca ggattctgtg tcttccattc tactccttga     2520
taaagcgaag aaatccgaca aaaccaaaga gattgttcaa gtttaagatt tgtaagcgta     2580
caactatgaa cttcttctct ttgtaggcct gagtggtcgt atgcatacga ttcatgaagt     2640
gaatcagtat cgctggattt tgcttaggag taaagcacaa ctaagaaaat atgctgcctg     2700
gcaggcatcc tgagacatga ggcaagcgac gtagcaattg aatcctaatt taagccaggg     2760
catctgtatg actctgttag ttaattgatg aaccaatgag ctttaaaaaa aaatcgttgc     2820
gcgtaatgta gttttaattc tccgccttga ggtgcggggc catttcggac aaggttcttt     2880
ggacggagat ggcagcatgt gtcccttctc caaattggtc cgtgtggtag ttgagatgct     2940
gccttaaaat tctgctcggt catcctgcct tcgcattcac tcctttcgag ctgtcgggtt     3000
```

```
cctcacgagg cctccgggag cggattgcgc agaaaggcga cccggagaca cagagaccat    3060
acaccgacta aattgcactg gacgatacgg catggcgacg acgatggcca agcattgcta    3120
cgtgattatt cgccttgtca ttcagggaga aatgatgaca tgtgtgggac ggtctttata    3180
tgggaagagg gcatgaaaat aacatggcct ggcgggatgg agcgtcacac ctgtgtatgc    3240
gttcgatcca caagcaactc accatttgcg tcggggcctg tctccaatct gctttaggct    3300
acttttctct aatttagcct attctataca gacagagaca cacagggatc taatgggcag    3360
cccacagcgg ttggcatcag ggagttgctt ccctctggct acgtctggga gggttgaaat    3420
tcactggccg tcgttttaca acgtcgtaac tgggaaaacc ctggcgttac ccaacttaat    3480
cgccttgcag cacatccccc tttcgccagt ggcaaacagc tataatcgtg agctttacgt    3540
tcccacgcca acacttcgcc atttctcctc ccttcctttc tttagctacc acgcagccgg    3600
ccccgtcttc cacgacgcgg gtaaatactg gtcatgttgc cctggaacgg tcaagtacga    3660
cttcgacgac tttctcaaga tccctggatg catgctcagt agtcattacg acggaagcca    3720
ggagagcctg gaggcgttca ctagacacgc caaaacgtct gagggcacat gacgtagagt    3780
caagggggaa ggtgcatagt gtgcaacaac agcattaacg tcaaagaaaa ctgcacgttc    3840
aagcccgcgt gaacctgccg gtcttctgat cgcctacata tagcagatac tagttgtact    3900 ttttttttcca aagggaacat tcatgtatca atttgaaata aacatctatc ctccagatca    3960
ccagggccag tgaggccggc ataaaggacg gcaaggaaag aaaagaaaga aagaaaagga    4020
cacttatagc atagtttgaa gttataagta gtcgcaatct gtgtgcagcc gacagatgct    4080
ttttttttcc gtttggcagg aggtgtaggg atgtcgaaga ccagtccagc tagtatctat    4140
cctacaagtc aatcatgctg cgacaaaaat ttctcgcacg aggcctctcg ataaacaaaa    4200
ctttaaaagc acacttcatt gtcatgcaga gtaataactc ttccgcgtcg atcaatttat    4260
caatctctat catttccgcc ccttccttg catagagcaa gaaaagcgac ccggatgagg    4320
ataacatgtc ctgcgccagt agtgtggcat tgcctgtctc tcatttacac gtactgaaag    4380
cataatgcac gcgcatacca atatttttcg tgtacggaga tgaagagacg cgacacgtaa    4440
gatcacgaga aggcgagcac ggttgccaat ggcagacgcg ctagtctcca ttatcgcgtt    4500
gttcggtagc ttgctgcatg tcttcagtgg cactatatcc actctgcctc gtcttctaca    4560
cgagggccac atcggtgcaa gttcgaaaaa tcatatctca atcttcagat cctttccaga    4620
aacggtgctc aggcgggaaa gtgaaggttt tctactctag tggctacccc aattctctcc    4680
gactgtcgca gacggtcctt cgttgcgcac gcaccgcgca ctacctctga aattcgacaa    4740
ccgaagttca attttacatc taacttcttt cccattctct caccaaaagc ctagcttaca    4800
tgttggagag cgacgagagc ggcctgcccg ccatggagat cgagtgccgc atcaccggca    4860
ccctgaacgg cgtggagttc gagctggtgg gcggcggaga gggcaccccc gagcagggcc    4920
gcatgaccaa caagatgaag agcaccaaag gcgccctgac cttcagcccc tacctgctga    4980
gccacgtgat gggctacggc ttctaccact tcggcaccta cccagcggc tacgagaacc    5040 ccttcctgca cgccatcaac aacggcggct acaccaacac ccgcatcgag aagtacgagg    5100
acggcggcgt gctgcacgtg agcttcagct accgctacga ggccgccgc gtgatcggcg    5160 acttcaaggt gatgggcacc ggcttccccg aggacagcgt gatcttcacc gacaagatca    5220
tccgcagcaa cgccaccgtg gagcacctgc accccatggg cgataacgat ctggatggca    5280
gcttcacccg caccttcagc ctgcgcgacg gcggctacta cagctccgtg gtggacagcc    5340
```

```
acatgcactt caagagcgcc atccacccca gcatcctgca gaacggggc cccatgttcg    5400
ccttccgccg cgtggaggag gatcacagca acaccgagct gggcatcgtg gagtaccagc    5460
acgccttcaa gaccccggat gcagatgccg gtgaagaata agggtgggaa ggagtcgggg    5520
agggtcctgg cagagcggcg tcctcatgat gtgttggaga cctggagagt cgagagcttc    5580
ctcgtcacct gattgtcatg tgtgtatagg ttaaggggc ccactcaaag ccataaagac    5640
gaacacaaac actaatctca acaaagtcta ctagcatgcc gtctgtccat ctttatttcc    5700
tggcgcgcct atgcttgtaa accgttttgt gaaaaattt ttaaaataaa aaggggacc    5760
tctagggtcc ccaattaatt agtaatataa tctattaaag gtcattcaaa aggtcatcca    5820
gacgaaaggg cctcgtgata cgcctatttt tataggttaa tgtcatgata ataatggttt    5880
cttagacgtc aggtggcact tttcggggaa atgtgcgcgg aaccccctatt tgtttatttt    5940
tctaaataca ttcaaatatg tatccgctca tgagacaata accctgataa atgcttcaat    6000
aatattgaaa aaggaagagt atgagtattc aacatttccg tgtcgccctt attccctttt    6060
ttgcggcatt ttgccttcct gttttgctc acccagaaac gctggtgaaa gtaaaagatg    6120
ctgaagatca gttgggtgca cgagtgggtt acatcgaact ggatctcaac agcggtaaga    6180
tccttgagag ttttcgcccc gaagaacgtt ttccaatgat gagcactttt aaagttctgc    6240
tatgtggcgc ggtattatcc cgtattgacg ccgggcaaga gcaactcggt cgccgcatac    6300
actattctca gaatgacttg gttgagtact caccagtcac agaaaagcat cttacgatg    6360
gcatgacagt aagagaatta tgcagtgctg ccataaccat gagtgataac actgcggcca    6420
acttacttct gacaacgatc ggaggaccga aggagctaac cgcttttttg cacaacatgg    6480
gggatcatgt aactcgcctt gatcgttggg aaccggagct gaatgaagcc ataccaaacg    6540
acgagcgtga ccacgatg cctgtagcaa tggcaacaac gttgcgcaaa ctattaactg    6600
gcgaactact tactctagct tcccggcaac aattaataga ctggatggag gcggataaag    6660
ttgcaggacc acttctgcgc tcggcccttc cggctggctg gtttattgct gataaatctg    6720
gagccggtga gcgtgggtct cgcggtatca ttgcagcact ggggccagat ggtaagccct    6780
cccgtatcgt agttatctac acgacgggga gtcaggcaac tatggatgaa cgaaatagac    6840
agatcgctga gataggtgcc tcactgatta gcattggta actgtcagac caagtttact    6900
catatatact ttagattgat ttaaaacttc atttttaatt taaaaggatc taggtgaaga    6960
tcctttttga taatctcatg accaaaatcc cttaacgtga gttttcgttc cactgagcgt    7020
cagacccccg agaaaagatc aaaggatctt cttgagatcc ttttttttctg cgcgtaatct    7080
gctgcttgca acaaaaaaa ccaccgctac cagcggtggt ttgtttgccg gatcaagagc    7140
taccaactct ttttccgaag gtaactggct tcagcagagc gcagatacca atactgtcc    7200
ttctagtgta gccgtagtta ggccaccact tcaagaactc tgtagcaccg cctacatacc    7260
tcgctctgct aatcctgtta ccagtggctg ctgccagtgg cgataagtcg tgtcttaccg    7320
ggttggactc aagacgatag ttaccggata aggcgcagcg tcgggctga acggggggtt    7380
cgtgcacaca gcccagcttg gagcgaacga cctacaccga actgagatac ctacagcgtg    7440
agctatgaga aagcgccacg cttcccgaag ggagaaaggc ggacaggtat ccggtaagcg    7500
gcagggtcgg aacaggagag cgcacgaggg agcttccagg gggaaacgcc tggtatcttt    7560
atagtcctgt cgggtttcgc cacctctgac ttgagcgtcg attttttgtga tgctcgtcag    7620
gggggcggag cctatggaaa aacgccagca acgcggcctt tttacggttc ctggccttt    7680
gctggccttt tgctcacatg ttctttcctg cgttatcccc tgattctgtg gataaccgta    7740
```

```
ttaccgcctt tgagtgagct gataccgctc gccgcagccg aacgaccgag cgcagcgagt    7800
cagtgagcga ggaagcggaa ga                                              7822
```

<210> SEQ ID NO 65
<211> LENGTH: 171
<212> TYPE: PRT
<213> ORGANISM: Cyclotella sp.
<220> FEATURE:
<221> NAME/KEY: misc_feature
<223> OTHER INFORMATION: SKP1-0244 polypeptide

<400> SEQUENCE: 65

```
Met Trp Ala Tyr Asn Gly Ala Asp Thr Gln Ile Ser Arg Glu Gly Val
1               5                   10                  15

Arg Tyr Gln Val Pro Ser Asn Ala Ala Lys Leu Ser Phe Phe Val Ala
            20                  25                  30

Leu Cys Val Asp Asn Glu Asp Ile Glu Asp Gly Gly Asp Thr Asp Gln
        35                  40                  45

Asn Asn Gly Asn Gly Ser Gly Val Val His Glu Ile Pro Leu His Ala
    50                  55                  60

Ile Asn Ser Val Val Leu Ala Lys Ile Val Lys Tyr Met Glu Tyr Tyr
65                  70                  75                  80

Lys Gln Asp Pro Met Gln Lys Ile Ile Thr Leu Phe Thr Ser Ser Arg
                85                  90                  95

Asn Cys Asn Phe Phe Gln Glu Glu Tyr Ala Ile Val Ile Asp Val Asp
            100                 105                 110

Arg Asn Thr Leu Phe Glu Leu His Ala Ala Asp Phe Leu Gly Ile
        115                 120                 125

Gln Pro Leu Leu Glu Leu Thr Ser Leu Ala Val Leu Leu Ser Tyr Met
    130                 135                 140

Trp Val Gly Val Leu Ile Tyr Leu Thr Leu Asp Gly Ile Val Thr Ser
145                 150                 155                 160

Cys Asn Ser Ile His Pro Ala Leu Leu Asp Asn
                165                 170
```

<210> SEQ ID NO 66
<211> LENGTH: 174
<212> TYPE: PRT
<213> ORGANISM: Tetraselmis sp.
<220> FEATURE:
<221> NAME/KEY: misc_feature
<223> OTHER INFORMATION: SKP1-4935 polypeptide

<400> SEQUENCE: 66

```
Met Ala Ala Pro Ser Gln Pro Ser Leu Gly Ser Asp Val Val Arg Leu
1               5                   10                  15

Arg Ser Ala Asp Gly Val Thr His Glu Val Asn Arg Glu Ala Leu Thr
            20                  25                  30

Arg Leu Ser Pro Val Leu Glu Gly Leu Gly Glu Cys Gly Ala Glu
        35                  40                  45

Glu Ala Val Pro Leu Pro Ser Val Gln Gly Arg Glu Leu Gly Arg Val
    50                  55                  60

Ala Glu Phe Cys Arg Gln Trp Asp Ala His Ala Ala Ala Arg Gly
65                  70                  75                  80

Ala Asp Gly Ser Gly Ala Ala Ala Ala Ala Ala Lys Glu Arg
                85                  90                  95

Ala Ala Trp Glu Ala Ala Tyr Leu Ala Pro Leu Asn Ala Asp Asp Leu
```

```
              100                 105                 110
His Asp Leu Leu Ala Ala Asn Phe Leu His Ala Glu Pro Leu Met
        115                 120                 125

Thr Leu Cys Phe Arg Ala Val Gly Asp Ala Met Arg Gly Lys Ala Pro
130                 135                 140

Ala Glu Ile Arg Ala His Phe Gly Ile Pro Asn Asp Phe Glu Pro Gly
145                 150                 155                 160

Glu Glu Asp Ala Ile Arg Arg Glu Asn Gln Arg Tyr Phe Ser
                165                 170

<210> SEQ ID NO 67
<211> LENGTH: 165
<212> TYPE: PRT
<213> ORGANISM: Chlorella vulgaris
<220> FEATURE:
<221> NAME/KEY: misc_feature
<223> OTHER INFORMATION: SKP1-9804 polypeptide

<400> SEQUENCE: 67

Met Arg Ser Ile Ile Leu Arg Ser Cys Asp Gly Ala Asp His Val Val
1               5                   10                  15

Ala Gln Glu Ala Ala Cys Leu Ser Lys Thr Val Gln Ser Leu Leu Glu
                20                  25                  30

Glu Leu Glu Glu Ser Thr Leu Val Val Pro Leu Pro Asn Val Cys Asp
            35                  40                  45

Cys Thr Leu Arg Lys Val Leu Gln Tyr Cys Thr Gln His Thr Ala Leu
        50                  55                  60

Gln Arg Arg Val Thr Asp Ile Ser Asp Glu Leu Arg Thr Arg Glu Met
65                  70                  75                  80

Glu Ala Trp Asp Lys Arg Tyr Ile Met Val Ser Thr Asp Glu Leu Tyr
                85                  90                  95

His Leu Val Met Ala Ala His Tyr Leu Asn Val Pro Gly Leu Leu Glu
                100                 105                 110

Leu Cys Cys Glu Gly Ile Ala Asn Leu Ile Arg Gly Lys Ser Pro Glu
            115                 120                 125

His Val Arg Gln Cys Phe Gly Leu Val Lys Asn Phe Glu Ala Pro Glu
        130                 135                 140

Glu Glu Asn Ile Arg Arg Thr Asn Leu Trp Ala Leu Val Asp Glu Lys
145                 150                 155                 160

Glu Gln Ala Lys Lys
                165

<210> SEQ ID NO 68
<211> LENGTH: 187
<212> TYPE: PRT
<213> ORGANISM: Nannochloropsis gaditana
<220> FEATURE:
<221> NAME/KEY: misc_feature
<223> OTHER INFORMATION: SKP1-9734 polypeptide

<400> SEQUENCE: 68

Met Ala Gly Trp Thr Ser Val Pro Asp Pro Phe Gln Ala Ala Lys Met
1               5                   10                  15

Ser Asp Glu Ala Lys Gly Thr Glu Ser Gly Lys Val Val His Leu Val
                20                  25                  30

Ser Gln Glu Gly Asp Gln Tyr Glu Val Glu Val Ala Val Cys Lys Met
            35                  40                  45

Ser Glu Leu Val Lys Thr Met Leu Pro Asp Asp Asp Asn Thr Asp
```

```
                    50                  55                  60
Thr Gln Glu Ile Pro Leu Pro Asn Val Lys Asn Ser Val Leu Ala Lys
 65                  70                  75                  80

Val Ile Glu Phe Cys Lys His His Lys Asp Asp Pro Met Asn Asp Ile
                     85                  90                  95

Glu Lys Pro Leu Lys Ser Ala Asn Met His Glu Val Val Gln Asp Trp
                100                 105                 110

Tyr Ala Asn Phe Val Asn Val Asp Gln Glu Leu Leu Phe Glu Leu Ile
                115                 120                 125

Leu Ala Ala Asn Tyr Met Asp Ile Lys Pro Leu Leu Asp Leu Thr Cys
130                 135                 140

Ala Thr Val Ala Ser Met Ile Lys Gly Lys Thr Pro Glu Glu Ile Arg
145                 150                 155                 160

Arg Thr Phe Asn Ile Thr Asn Asp Phe Thr Pro Glu Glu Ala Gln
                165                 170                 175

Val Arg Glu Glu Asn Lys Trp Cys Glu Glu Val
                180                 185
```

<210> SEQ ID NO 69
<211> LENGTH: 172
<212> TYPE: PRT
<213> ORGANISM: Nannochloropsis gaditana
<220> FEATURE:
<221> NAME/KEY: misc_feature
<223> OTHER INFORMATION: SKP1-5078 polypeptide

<400> SEQUENCE: 69

```
Met Ser Asp Glu Ala Lys Gly Thr Glu Ser Gly Lys Val Val His Leu
  1               5                  10                  15

Val Ser Gln Glu Gly Asp Gln Tyr Glu Val Glu Val Ala Val Cys Lys
                 20                  25                  30

Met Ser Glu Leu Val Lys Thr Met Leu Pro Asp Asp Asp Asn Thr
             35                  40                  45

Asp Thr Gln Glu Ile Pro Leu Pro Asn Val Lys Asn Ser Val Leu Ala
 50                  55                  60

Lys Val Ile Glu Phe Cys Lys His His Lys Asp Asp Pro Met Asn Asp
 65                  70                  75                  80

Ile Glu Lys Pro Leu Lys Ser Ala Asn Met His Glu Val Val Gln Asp
                 85                  90                  95

Trp Tyr Ala Asn Phe Val Asn Val Asp Gln Glu Leu Leu Phe Glu Leu
                100                 105                 110

Ile Leu Ala Ala Asn Tyr Met Asp Ile Lys Pro Leu Leu Asp Leu Thr
                115                 120                 125

Cys Ala Thr Val Ala Ser Met Ile Lys Gly Lys Thr Pro Glu Glu Ile
130                 135                 140

Arg Arg Thr Phe Asn Ile Thr Asn Asp Phe Thr Pro Glu Glu Ala
145                 150                 155                 160

Gln Val Arg Glu Glu Asn Lys Trp Cys Glu Glu Val
                165                 170
```

<210> SEQ ID NO 70
<211> LENGTH: 169
<212> TYPE: PRT
<213> ORGANISM: Phaeodactylum tricornutum

<400> SEQUENCE: 70

```
Met Met Asp Val Glu Gln Glu Thr Thr Val Asn Leu Ile Ser Lys Asp
```

```
             1               5                  10                 15
Gly Asp Ser Phe Ser Val Pro Leu Ala Val Ala Lys Met Ser Glu Leu
                20                  25                  30

Val Lys Gly Met Ile Asp Glu Asp Ala Glu Asp Glu Gly Asp Lys Ile
                35                  40                  45

Glu Ile Pro Leu Pro Asn Val Lys Ser Gln Val Leu Asn Lys Val Ile
 50                  55                  60

Glu Phe Cys Glu His His Leu Gln Glu Pro Met Thr Glu Ile Glu Lys
 65                  70                  75                  80

Pro Leu Lys Ser Gln Val Met Ala Asp Val Val Gln Lys Trp Tyr Ala
                85                  90                  95

Asp Phe Val Asp Val Glu Gln Val Leu Leu Phe Glu Leu Ile Leu Ala
                100                 105                 110

Ala Asn Tyr Met Asp Ile Lys Pro Leu Leu Asp Leu Thr Cys Ala Thr
                115                 120                 125

Val Ala Gly Met Ile Lys Gly Lys Thr Pro Glu Asp Ile Arg Gln Thr
                130                 135                 140

Phe Gly Ile Gln Asn Asp Phe Ser Pro Glu Glu Ala Gln Val Arg
145                 150                 155                 160

Glu Glu Asn Lys Trp Cys Glu Glu Ala
                165

<210> SEQ ID NO 71
<211> LENGTH: 193
<212> TYPE: PRT
<213> ORGANISM: Fragilariopsis cylindrus
<220> FEATURE:
<221> NAME/KEY: misc_feature
<223> OTHER INFORMATION: SKP1-6453 polypeptide

<400> SEQUENCE: 71

Met Asp Val Glu Asp Ser Lys Glu Thr Ala Ala Ser Thr Ala Asp Thr
 1               5                  10                  15

Ser Ser Ser Gly Val Thr Ile Gln Leu Ile Ser Lys Glu Gly Asp Lys
                20                  25                  30

Phe Pro Val Pro Ile Thr Val Ser Asn Met Ser Glu Leu Val Lys Ser
                35                  40                  45

Met Met Asp Asp Lys Asp Asp Asp Asp Asp Asp Asp Asp Glu Asp
                50                  55                  60

Asp Asp Gly Lys Glu Lys Ile Thr Glu Ile Pro Leu Pro Asn Val Lys
 65                  70                  75                  80

Ser Glu Val Leu Lys Lys Val Ile Glu Phe Cys Glu His His Leu Ala
                85                  90                  95

Glu Pro Met Thr Glu Ile Glu Lys Pro Leu Lys Ser Gln Asn Met Ala
                100                 105                 110

Asp Val Val Gln Lys Trp Tyr Ala Asp Phe Val Asp Leu Glu Gln Val
                115                 120                 125

Leu Leu Phe Glu Leu Ile Leu Ala Ala Asn Tyr Met Asp Ile Lys Pro
130                 135                 140

Leu Leu Asp Leu Thr Cys Ala Thr Val Ala Ser Met Ile Lys Gly Lys
145                 150                 155                 160

Thr Pro Asp Glu Ile Arg Ala Thr Phe Asn Ile Thr Asn Asp Phe Ser
                165                 170                 175

Pro Glu Glu Glu Ala Gln Val Arg Glu Glu Asn Lys Trp Cys Glu Glu
                180                 185                 190
```

Ala

<210> SEQ ID NO 72
<211> LENGTH: 156
<212> TYPE: PRT
<213> ORGANISM: Thalassiosira pseudoana
<220> FEATURE:
<221> NAME/KEY: misc_feature
<223> OTHER INFORMATION: SKP1-7124 polypeptide

<400> SEQUENCE: 72

Ser Lys Glu Gly Asp Thr Phe Pro Val Asp Ile Glu Val Ala Arg Met
1               5                   10                  15

Ser Glu Leu Val Lys Gly Met Leu Glu Asp Asp Ala Asp Asp Asp Glu
            20                  25                  30

Glu Ala Thr Glu Ile Pro Leu Pro Asn Val Lys Ser Thr Val Leu Lys
        35                  40                  45

Lys Val Ile Glu Phe Cys Lys His His Arg Ser Glu Pro Met Thr Glu
50                  55                  60

Ile Glu Lys Pro Leu Lys Ser Ala Ala Met Ala Glu Val Val Gln Lys
65                  70                  75                  80

Trp Tyr Ala Asp Phe Val Asn Val Glu Gln Val Leu Leu Phe Glu Leu
                85                  90                  95

Ile Leu Ala Ala Asn Tyr Met Asp Ile Lys Pro Leu Leu Asp Leu Thr
            100                 105                 110

Cys Ala Thr Val Ala Ser Met Ile Lys Gly Lys Thr Pro Glu Glu Ile
        115                 120                 125

Arg Lys Thr Phe Asn Ile Ala Asn Asp Phe Ser Pro Glu Glu Glu Ala
    130                 135                 140

Gln Val Arg Glu Glu Asn Lys Trp Cys Glu Glu Pro
145                 150                 155

<210> SEQ ID NO 73
<211> LENGTH: 167
<212> TYPE: PRT
<213> ORGANISM: Aplanochytrium kerguelense
<220> FEATURE:
<221> NAME/KEY: misc_feature
<223> OTHER INFORMATION: SKP1-5159 polypeptide

<400> SEQUENCE: 73

Met Glu Thr Glu Ser Leu Ala Ser Arg Ile Tyr Asn Leu Val Ser Gln
1               5                   10                  15

Glu Lys Glu Lys Phe Pro Val Ser Lys Glu Val Ala Glu Met Ser Asn
            20                  25                  30

Leu Val Lys Glu Met Thr Glu Asp Glu Glu Asp Glu Asp Ser Asp Ile
        35                  40                  45

Pro Leu Pro Asn Val Ser Ser Arg Val Leu Lys Lys Val Ile Glu Phe
    50                  55                  60

Cys Gln His His Glu Lys Glu Lys Met Pro Gly Ile Glu Lys Pro Leu
65                  70                  75                  80

Lys Ser Ser Asn Met Ala Glu Val Val Ser Asp Trp Asp Ala Lys Phe
                85                  90                  95

Val Glu Val Glu Gln Glu Leu Leu Phe Gln Leu Ile Leu Ala Ala Asn
            100                 105                 110

Tyr Met Asp Ile Lys Ser Leu Leu Asp Leu Ser Cys Ala Lys Val Ala
        115                 120                 125

Ser Met Ile Lys Gly Lys Thr Pro Glu Glu Ile Arg Lys Thr Phe Asn

```
                130                 135                 140
Ile Thr Asn Asp Phe Thr Pro Glu Glu Glu Cys Thr Val Arg Glu Glu
145                 150                 155                 160

Asn Lys Trp Ser Glu Glu Ser
                165
```

<210> SEQ ID NO 74
<211> LENGTH: 172
<212> TYPE: PRT
<213> ORGANISM: Schizochytrium aggregatum
<220> FEATURE:
<221> NAME/KEY: misc_feature
<223> OTHER INFORMATION: SKP1-0889 polypeptide

<400> SEQUENCE: 74

```
Met Gly Asp Ala Pro Glu Val Gly Ala Thr Lys Gly Met Cys Ala Leu
1               5                   10                  15

Val Ser Gln Glu Gly Lys Arg Tyr Glu Val Ser Arg Glu Thr Ala Met
                20                  25                  30

Gln Ser Met Leu Val Lys Glu Met Val Asp Glu Glu Gly Glu Asp
            35                  40                  45

Ser Val Leu Asp Ile Pro Leu Pro Asn Val Lys Ser Ser Val Leu Glu
        50                  55                  60

Lys Val Ile Glu Phe Cys Ser His His Val Lys Glu Pro Met Pro Asp
65                  70                  75                  80

Ile Glu Lys Pro Leu Lys Ser Ala Asn Met Asn Glu Val Val Ser Glu
                85                  90                  95

Trp Asp Ala Asn Phe Val Asp Leu Asp Gln Ala Leu Phe Glu Leu
            100                 105                 110

Ile Leu Ala Ala Asn Tyr Met Asp Ile Lys Ser Leu Leu Asp Leu Thr
        115                 120                 125

Cys Ala Lys Val Ala Ser Met Ile Lys Gly Lys Ser Pro Glu Glu Ile
    130                 135                 140

Arg Glu Thr Phe Asn Ile Thr Asn Asp Phe Thr Pro Glu Glu Glu Ala
145                 150                 155                 160

Arg Val Arg Glu Glu Asn Lys Trp Cys Glu Arg Ser
                165                 170
```

<210> SEQ ID NO 75
<211> LENGTH: 166
<212> TYPE: PRT
<213> ORGANISM: Cyclotella sp.
<220> FEATURE:
<221> NAME/KEY: misc_feature
<223> OTHER INFORMATION: SKP1-3944 polypeptide

<400> SEQUENCE: 75

```
Met Glu Asp Thr Ala Arg Thr Ile Asn Leu Val Ser Lys Thr Gly Asp
1               5                   10                  15

Lys Tyr Glu Leu Ser Tyr Lys Ala Ala Lys Leu Ser Gln Leu Val Phe
                20                  25                  30

Asp Ala Ser Glu Asn Lys Glu Asp Glu Cys Ser Asp Val Pro Ile
            35                  40                  45

Leu Lys Val Glu Ser Glu Cys Leu Glu Lys Val Glu Phe Leu Lys
        50                  55                  60

His Tyr Glu Gln Glu Pro Leu Lys Glu Ile Lys Ser Pro Leu Glu Asp
65                  70                  75                  80

Asn Thr Phe Glu Gly Val Val Lys Gln Glu Trp Tyr Arg Asn Phe Val
```

```
                    85                  90                  95

Gln Glu Val Asp Ser Pro Met Leu Phe Asp Leu Val Thr Ala Ala Asn
                100                 105                 110

Phe Met Ala Ile Gln Pro Leu Leu Asp Leu Ala Cys Leu Lys Val Ser
            115                 120                 125

Cys Leu Leu Met Gly Lys Ser Ser Glu Glu Ile Arg Ile Ile Leu Asn
130                 135                 140

Ile Pro Gln Met Thr Pro Gln Glu Glu His Ala Arg Arg Glu His
145                 150                 155                 160

Arg Trp Ile Phe Asp Asp
                165

<210> SEQ ID NO 76
<211> LENGTH: 158
<212> TYPE: PRT
<213> ORGANISM: Thalassiosira pseudoana
<220> FEATURE:
<221> NAME/KEY: misc_feature
<223> OTHER INFORMATION: SKP1-8843 polypeptide

<400> SEQUENCE: 76

Ile Lys Leu Ile Ser Arg Ala Gly Asp Ser Phe Glu Leu Pro Tyr Ala
1               5                   10                  15

Ala Ala Ile Leu Ser Gln Thr Val Lys Asp Ala Gln Ser Cys Glu Asp
            20                  25                  30

Asp Glu Glu Asn Glu Asn Pro Asp Asp Val Glu Ile Val Lys Val Glu
        35                  40                  45

Ser Arg Cys Leu Glu Lys Val Val Glu Phe Leu His His Leu Glu
50                  55                  60

Glu Pro Leu Ala Glu Ile Lys Thr Pro Leu Glu Asp Asn Thr Phe Asp
65                  70                  75                  80

Gly Val Val Lys Gln Gln Phe Tyr Arg Asp Phe Val Lys Gly Val Asp
                85                  90                  95

Gln Pro Met Leu Phe Asp Leu Val Thr Ala Ala Asn Phe Met Ala Ile
                100                 105                 110

Gln Pro Leu Leu Asp Leu Thr Cys Leu Gln Val Ser Cys Gln Leu Met
            115                 120                 125

Gly Lys Ser Ala Asp Glu Ile Arg Thr Ile Leu Asn Ile Pro Gln Met
        130                 135                 140

Thr Pro Glu Glu Glu Ala Lys Ala Arg Gln Glu His Arg Trp
145                 150                 155

<210> SEQ ID NO 77
<211> LENGTH: 175
<212> TYPE: PRT
<213> ORGANISM: Phaeodactylum tricornutum
<220> FEATURE:
<221> NAME/KEY: misc_feature
<223> OTHER INFORMATION: SKP1-0332 polypeptide

<400> SEQUENCE: 77

Met Gly Ser Glu Thr Ile Thr Phe Ile Ser Asn Asp Lys Gln Glu Phe
1               5                   10                  15

Asp Leu Pro Phe Glu Ala Ala Lys Thr Ala Gly Leu Val Glu Asp Phe
            20                  25                  30

Phe Glu Ser Ser Asp Asp Asn Glu Gly Asn Asn Asp Gly Gly Lys Pro
        35                  40                  45

Asn Arg Arg Glu Met Glu Phe Pro Arg Val Glu Gly Arg Ile Leu Ser
```

```
            50                  55                  60
Leu Ile Val Asp Phe Leu Lys His His Asn Glu Glu Gln Met Lys Glu
 65                  70                  75                  80

Ile Pro Val Pro Leu Gly Gly Ser Thr Phe Asp Val Met Asp Gln
                 85                  90                  95

Glu Trp Tyr Lys Glu Phe Ala His Ala Leu Ser Gln Asn Lys Thr Leu
                100                 105                 110

Phe Glu Val Leu Thr Ala Ala Asn Tyr Met Asn Ile Lys Pro Leu Leu
                115                 120                 125

Asp Leu Ala Cys Leu Glu Ile Thr Phe Lys Leu Thr Gly Met Ser Ala
                130                 135                 140

Glu Gln Val Arg Val Tyr Leu Asn Leu Pro Gln Leu Thr Ala Glu Gln
145                 150                 155                 160

Glu Ala Glu Ala Arg Glu Arg His Pro Trp Ile Phe Glu Ser His
                165                 170                 175

<210> SEQ ID NO 78
<211> LENGTH: 158
<212> TYPE: PRT
<213> ORGANISM: Phaeodactylum tricornutum
<220> FEATURE:
<221> NAME/KEY: misc_feature
<223> OTHER INFORMATION: SKP1-8957 polypeptide

<400> SEQUENCE: 78

Ser Lys Glu Gly Asp Ala Tyr Glu Val Pro Met Ala Val Ala Lys Met
 1               5                  10                  15

Ser Val Leu Val Ala Asp Thr Phe Asp Ala Asp Glu Asp Asp Glu
                 20                  25                  30

Ala Glu Pro Val Lys Asp Phe Pro Leu Pro Asn Val Thr Ser Gly Val
                 35                  40                  45

Leu Glu Lys Val Ile Glu Phe Cys Lys His Phe Gln Glu Glu Pro Met
             50                  55                  60

Thr Thr Ile Gln Thr Pro Leu Lys Ser Ser Lys Leu Glu Asp Leu Val
 65                  70                  75                  80

Gln Gln Trp Tyr Ala Asp Phe Val Lys Val Pro Lys Thr Leu Leu Phe
                 85                  90                  95

Asp Leu Val Ala Ala Ala Asn Tyr Met Asp Ile Lys Pro Leu Leu Asp
                100                 105                 110

Leu Thr Cys Leu Ala Val Ser Ile Leu Ile Lys Gly Lys Ser Ala Ala
                115                 120                 125

Glu Leu Arg Ser Met Phe Asn Leu Ser Asp Glu Leu Ser His Glu Glu
                130                 135                 140

Glu Ala Gln Met Ala Gln Gly Asn Gln Gln Phe Ala Asp Arg
145                 150                 155

<210> SEQ ID NO 79
<211> LENGTH: 194
<212> TYPE: PRT
<213> ORGANISM: Fragilariopsis cylindrus
<220> FEATURE:
<221> NAME/KEY: misc_feature
<223> OTHER INFORMATION: SKP1-9785 polypeptide

<400> SEQUENCE: 79

Met Asp Glu Glu Asn Gly Ile Val Lys Leu Val Ser Lys Glu Gly Asp
 1               5                  10                  15

Val His Glu Val Pro Ile Asn Val Ala Lys Met Ser Ser Leu Ile Leu
```

```
            20                  25                  30
Ser Thr Leu Asp Asp Glu Glu Asp Asp Asp Asp Glu Glu Thr
        35                  40                  45
Lys Lys His Leu Glu Ile Pro Leu Pro Asn Val Lys Asn Ala Val Leu
 50                  55                  60
Thr Lys Val Ile Glu Tyr Cys Lys His Tyr Thr Asn Asp Glu Ala Met
 65                  70                  75                  80
Thr Gln Ile Gln Thr Pro Leu Lys Ser Ser Lys Ile Glu Asp Leu Val
                85                  90                  95
Gln Thr Trp Tyr Ala Gly Phe Val Asp Val Glu Gln Thr Leu Leu Phe
                100                 105                 110
Glu Leu Val Thr Ala Ala Asn Phe Met Asp Ile Lys Pro Leu Leu Asp
                115                 120                 125
Leu Thr Cys Leu Ala Val Ser Ile Ser Ile Lys Gly Lys Thr Ala Pro
            130                 135                 140
Gln Leu Arg Glu Ile Phe Asn Ile Ser Asn Asp Phe Ser Gln Glu Glu
145                 150                 155                 160
Glu Ala Gln Val Arg Glu Glu Ser Gln Trp Ser Gln Glu Asp Thr Pro
                165                 170                 175
Ala Val Pro Ala Ala Ala Ala Ala Ala Ala Asn Glu Glu Lys
                180                 185                 190
Glu Glu

<210> SEQ ID NO 80
<211> LENGTH: 207
<212> TYPE: PRT
<213> ORGANISM: Cyclotella sp.
<220> FEATURE:
<221> NAME/KEY: misc_feature
<223> OTHER INFORMATION: SKP1-0115 polypeptide

<400> SEQUENCE: 80

Met Leu Leu Trp Val Cys Ala Cys Lys Arg Pro Pro Gln Arg Leu
 1               5                  10                  15
Thr Lys Pro Val Leu Asn Tyr Gln Thr Ile Met Glu Gln Asp Asp Ser
                20                  25                  30
Val Arg Thr Val Lys Leu Ile Ser Asn Glu Gly Glu Ile Phe Lys Val
                35                  40                  45
Pro Leu Glu Ile Ala Lys Leu Ser Asn Leu Val Val Thr Thr Leu Gly
            50                  55                  60
Glu Glu Glu His Asp Asp Asp His Asp Asp Asn Gly Asp Asp Asp Asp
 65                  70                  75                  80
Ala Val Glu Ile Pro Leu Pro Asn Val Lys Ala Ser Val Leu Ala Lys
                85                  90                  95
Val Val Asp Phe Cys Thr His Tyr Lys Glu Glu Pro Met Lys Pro Ile
                100                 105                 110
Thr Thr Pro Leu Glu Ser Met Val Ile Asp Glu Ile Val Gln Thr Phe
            115                 120                 125
Tyr Ala Arg Phe Val Glu Val Asp Gln Val Met Leu Phe Glu Leu Val
            130                 135                 140
Thr Ala Ala Asn Phe Met Asp Ile Lys Pro Leu Leu Asp Leu Thr Cys
145                 150                 155                 160
Leu Ala Val Ser Ile Tyr Ile Lys Gly Lys Ser Pro Asp Glu Ile Arg
                165                 170                 175
Arg Ile Phe Asn Ile Ser Asn Asp Met Ser Gln Gly Asp Gly Gly Gln
```

```
                180               185               190
Val Gly Asp Glu Ser Lys Met Asn Pro Asn Gly Ser Ala Ser His
            195               200               205

<210> SEQ ID NO 81
<211> LENGTH: 176
<212> TYPE: PRT
<213> ORGANISM: Thalassiosira pseudoana
<220> FEATURE:
<221> NAME/KEY: misc_feature
<223> OTHER INFORMATION: SKP1-5712 polypeptide

<400> SEQUENCE: 81

Met Asp Gly Asp Asp Ala His Gly Thr Val Lys Leu Val Ser Lys Glu
1               5                  10                  15

Gly Asp Thr Phe Glu Val Pro Ile Glu Val Ala Lys Leu Ser Asn Leu
                20                  25                  30

Val Val Thr Thr Leu Gly Glu Glu Asp Asp Tyr Asp Asp Asp Asp Asp
            35                  40                  45

Asn Met Val Glu Ile Pro Leu Pro Asn Val Lys Ser Ser Val Leu Ala
        50                  55                  60

Lys Val Ile Glu Tyr Cys Thr His Tyr Asn Gln Asp Pro Met Thr Pro
65                  70                  75                  80

Ile Thr Thr Pro Leu Lys Ser Asn Arg Ile Glu Glu Ile Val Gln Glu
                85                  90                  95

Trp Tyr Ala His Phe Val Asp Val Glu Gln Ile Leu Leu Phe Glu Leu
            100                 105                 110

Val Thr Ala Ala Asn Phe Met Asp Ile Lys Ala Leu Leu Asp Leu Thr
        115                 120                 125

Cys Leu Ala Val Ser Val Leu Ile Lys Gly Lys Ser Ala Glu Glu Ile
    130                 135                 140

Arg Arg Ile Phe Asn Ile Ser Asn Asp Phe Ser Pro Glu Glu Glu Ala
145                 150                 155                 160

Gln Val Ser Lys Glu Asn Gln Phe Thr Asp Gly Thr Ser Ser Ser Ser
                165                 170                 175

<210> SEQ ID NO 82
<211> LENGTH: 158
<212> TYPE: PRT
<213> ORGANISM: Volvox carteri
<220> FEATURE:
<221> NAME/KEY: misc_feature
<223> OTHER INFORMATION: SKP1-3608 polypeptide

<400> SEQUENCE: 82

Met Ser Gly Ser Lys Val Lys Leu Met Ser Ser Asp Thr Gln Met Phe
1               5                  10                  15

Glu Val Asp Glu Glu Ala Ala Phe Gln Ser Gln Thr Val Lys Asn Leu
                20                  25                  30

Val Glu Asp Ala Gly Thr Asp Ala Ile Pro Leu Pro Asn Val Ser
            35                  40                  45

Gly Arg Ile Leu Ala Lys Val Ile Glu Tyr Cys Lys Tyr His Val Glu
        50                  55                  60

Ala Glu Lys Lys Gly Ala Asp Asp Lys Pro Met Lys Thr Glu Asp Glu
65                  70                  75                  80

Val Lys Arg Trp Asp Glu Glu Phe Val Lys Val Asp Gln Ala Thr Leu
                85                  90                  95

Phe Asp Leu Ile Leu Ala Ala Asn Tyr Leu Asn Ile Lys Gly Leu Leu
```

```
              100                 105                 110
Asp Leu Thr Cys Gln Thr Val Ala Gln Met Ile Lys Gly Lys Thr Pro
            115                 120                 125

Glu Glu Ile Arg Lys Thr Phe Asn Ile Lys Asn Asp Phe Thr Pro Glu
        130                 135                 140

Glu Glu Glu Val Arg Arg Glu Asn Gln Trp Ala Phe Asp
145                 150                 155

<210> SEQ ID NO 83
<211> LENGTH: 157
<212> TYPE: PRT
<213> ORGANISM: Chlamydomonas reinhardtii
<220> FEATURE:
<221> NAME/KEY: misc_feature
<223> OTHER INFORMATION: SKP1-6936 polypeptide

<400> SEQUENCE: 83

Met Ala Thr Lys Val Lys Leu Met Ser Ser Asp Ala Gln Met Phe Glu
1               5                  10                  15

Val Asp Glu Asp Val Ala Phe Gln Ser Gln Thr Val Lys Asn Leu Val
            20                  25                  30

Glu Asp Ala Gly Thr Glu Asp Ala Ile Pro Leu Pro Asn Val Ser Gly
        35                  40                  45

Arg Ile Leu Ala Lys Val Ile Glu Tyr Ser Lys Tyr His Val Glu Ala
 50                  55                  60

Glu Lys Lys Gly Ala Asp Asp Lys Pro Thr Lys Thr Glu Asp Asp Val
65                  70                  75                  80

Lys Arg Trp Asp Asp Glu Phe Val Lys Val Asp Gln Ala Thr Leu Phe
                85                  90                  95

Asp Leu Ile Leu Ala Ala Asn Tyr Leu Asn Ile Lys Gly Leu Leu Asp
            100                 105                 110

Leu Thr Cys Gln Thr Val Ala Gln Met Ile Lys Gly Lys Thr Pro Glu
        115                 120                 125

Glu Ile Arg Lys Thr Phe Asn Ile Lys Asn Asp Phe Thr Pro Glu Glu
    130                 135                 140

Glu Glu Glu Val Arg Arg Glu Asn Gln Trp Ala Phe Asp
145                 150                 155

<210> SEQ ID NO 84
<211> LENGTH: 160
<212> TYPE: PRT
<213> ORGANISM: Tetraselmis sp.
<220> FEATURE:
<221> NAME/KEY: misc_feature
<223> OTHER INFORMATION: SKP1-5885 polypeptide

<400> SEQUENCE: 84

Met Ser Glu Lys Val Lys Leu Arg Ser Ala Asp Gly Glu Met Phe Glu
1               5                  10                  15

Val Asp Ala Asp Val Ala Phe Ser Ser Leu Thr Val Lys Asn Met Ile
            20                  25                  30

Glu Asp Thr Gly Ala Ser Ala Pro Val Pro Val Pro Asn Val Asn Ser
        35                  40                  45

Lys Val Leu Ser Lys Ile Ile Glu Tyr Cys Ser Tyr His Val Asp Gln
    50                  55                  60

Glu Arg Arg Ser Lys Asp Ala Asp Asp His Thr Arg Arg Gln Ile Glu
65                  70                  75                  80

Asp Glu Thr Ser Lys Trp Asp Lys Asp Tyr Ile Cys Val Asp Gln Ala
```

```
                85                  90                  95
Val Leu Tyr Glu Leu Ile Leu Ala Ala Asn Phe Leu Asn Ile Lys Gly
            100                 105                 110
Leu Leu Asp Leu Cys Cys Gln Thr Val Ala Asp Ile Ile Lys Gly Lys
            115                 120                 125
Thr Pro Glu Gln Ile Arg Gln Tyr Phe His Ile Lys Asn Asp Phe Thr
    130                 135                 140
Pro Glu Glu Glu Glu Val Arg Lys Glu Asn Gln Trp Ala Phe Glu
145                 150                 155                 160
```

<210> SEQ ID NO 85
<211> LENGTH: 158
<212> TYPE: PRT
<213> ORGANISM: Chlorella vulgaris
<220> FEATURE:
<221> NAME/KEY: misc_feature
<223> OTHER INFORMATION: SKP1-2686 polypeptide

<400> SEQUENCE: 85

```
Met Ala Gln Lys Val Thr Leu Val Ser Ser Asp Ser Gln Asp Tyr Thr
1               5                   10                  15
Val Thr Glu Glu Val Ala Phe Met Ser Glu Thr Val Lys Asn Thr Leu
            20                  25                  30
Glu Glu Thr Gly Gly Glu Asp Thr Lys Val Pro Leu Pro Asn Val His
        35                  40                  45
Ser Lys Ile Leu Ser Lys Val Leu Glu Tyr Cys Asn Phe His Val Asp
    50                  55                  60
Ala Ser Lys Lys Asn Thr Asp Asp Lys Pro Ala Lys Thr Glu Glu Glu
65                  70                  75                  80
Val Lys Thr Trp Asp Ser Asp Phe Val Lys Val Asp Gln Ala Thr Leu
                85                  90                  95
Phe Glu Leu Ile Leu Ala Ala Asn Tyr Leu Asn Ile Lys Ser Leu Leu
            100                 105                 110
Asp Leu Gly Cys Leu Thr Val Ala Asn Met Ile Lys Gly Lys Thr Pro
        115                 120                 125
Glu Glu Ile Arg Lys Thr Phe Asn Ile Pro Asn Asp Phe Thr Pro Glu
    130                 135                 140
Glu Glu Glu Glu Val Arg Arg Glu Asn Gln Trp Ala Phe Glu
145                 150                 155
```

<210> SEQ ID NO 86
<211> LENGTH: 159
<212> TYPE: PRT
<213> ORGANISM: Parachlorella sp.
<220> FEATURE:
<221> NAME/KEY: misc_feature
<223> OTHER INFORMATION: SKP1-2323 polypeptide

<400> SEQUENCE: 86

```
Met Ala Glu Gln Lys Val Lys Leu Val Ser Ser Asp Gly Gln Val Phe
1               5                   10                  15
Glu Val Glu Glu Asp Val Ala Lys Gln Ser Val Thr Leu Gln Asn Thr
            20                  25                  30
Met Asp Glu Ile Asp Ala Ala Asp Glu Gln Ile Pro Leu Pro Asn Val
        35                  40                  45
Ser Gly Lys Ile Leu Ala Lys Val Val Glu Tyr Cys Lys Tyr His Val
    50                  55                  60
Glu Ala Glu Gln Lys Asp Glu His Gly Lys Ala Ala Lys Ser Glu Asp
```

```
                65                  70                  75                  80
Glu Val Lys Thr Trp Asp Thr Glu Phe Cys Lys Val Asp Gln Gly Thr
                    85                  90                  95

Leu Phe Glu Leu Ile Leu Ala Ala Asn Tyr Leu Asn Ile Lys Thr Leu
                100                 105                 110

Leu Asp Leu Thr Cys Leu Thr Val Ala Asn Met Ile Lys Gly Lys Thr
                115                 120                 125

Pro Glu Glu Ile Arg Lys Thr Phe Asn Ile Glu Asn Asp Phe Thr Pro
130                 135                 140

Glu Glu Glu Glu Glu Val Arg Arg Glu Asn Gln Trp Ala Phe Glu
145                 150                 155

<210> SEQ ID NO 87
<211> LENGTH: 168
<212> TYPE: PRT
<213> ORGANISM: Parachlorella sp.
<220> FEATURE:
<221> NAME/KEY: misc_feature
<223> OTHER INFORMATION: SKP1-2322 polypeptide

<400> SEQUENCE: 87

Met Tyr Gln Met Gln Lys Val Cys Ser Arg Arg Val Val Gln Val Lys
1               5                   10                  15

Leu Val Ser Ser Asp Gly Gln Val Phe Glu Val Glu Glu Asp Val Ala
                20                  25                  30

Lys Gln Ser Val Thr Leu Gln Asn Thr Met Asp Glu Ile Asp Ala Ala
            35                  40                  45

Asp Glu Gln Ile Pro Leu Pro Asn Val Ser Gly Lys Ile Leu Ala Lys
        50                  55                  60

Val Val Glu Tyr Cys Lys Tyr His Val Glu Ala Glu Gln Lys Asp Glu
65                  70                  75                  80

His Gly Lys Ala Ala Lys Ser Glu Asp Glu Val Lys Thr Trp Asp Thr
                85                  90                  95

Glu Phe Cys Lys Val Asp Gln Gly Thr Leu Phe Glu Leu Ile Leu Ala
                100                 105                 110

Ala Asn Tyr Leu Asn Ile Lys Thr Leu Leu Asp Leu Thr Cys Leu Thr
            115                 120                 125

Val Ala Asn Met Ile Lys Gly Lys Thr Pro Glu Glu Ile Arg Lys Thr
        130                 135                 140

Phe Asn Ile Glu Asn Asp Phe Thr Pro Glu Glu Glu Glu Glu Val Arg
145                 150                 155                 160

Arg Glu Asn Gln Trp Ala Phe Glu
                165

<210> SEQ ID NO 88
<211> LENGTH: 182
<212> TYPE: PRT
<213> ORGANISM: Parachlorella sp.
<220> FEATURE:
<221> NAME/KEY: misc_feature
<223> OTHER INFORMATION: SKP1-0087 polypeptide

<400> SEQUENCE: 88

Met Phe Trp Trp Thr Thr Phe Ser His Leu Ser Leu Arg Cys Arg Tyr
1               5                   10                  15

Pro Arg Gln Arg Tyr Gly Arg Thr Lys Val Val Gln Val Lys Leu Val
                20                  25                  30

Ser Ser Asp Gly Gln Val Phe Glu Val Glu Glu Asp Val Ala Lys Gln
```

```
                35                  40                  45
Ser Val Thr Leu Gln Asn Thr Met Asp Glu Ile Asp Ala Ala Asp Glu
 50                  55                  60

Gln Ile Pro Leu Pro Asn Val Ser Gly Lys Ile Leu Ala Lys Val Val
 65                  70                  75                  80

Glu Tyr Cys Lys Tyr His Val Glu Ala Glu Gln Lys Asp Glu His Gly
                 85                  90                  95

Lys Ala Ala Lys Ser Glu Asp Glu Val Lys Thr Trp Asp Thr Glu Phe
            100                 105                 110

Cys Lys Val Asp Gln Gly Thr Leu Phe Glu Leu Ile Leu Ala Ala Asn
        115                 120                 125

Tyr Leu Asn Ile Lys Thr Leu Leu Asp Leu Thr Cys Leu Thr Val Ala
130                 135                 140

Asn Met Ile Lys Gly Lys Thr Pro Glu Glu Ile Arg Lys Thr Phe Asn
145                 150                 155                 160

Ile Glu Asn Asp Phe Thr Pro Glu Glu Glu Glu Val Arg Arg Glu
                165                 170                 175

Asn Gln Trp Ala Phe Glu
            180

<210> SEQ ID NO 89
<211> LENGTH: 157
<212> TYPE: PRT
<213> ORGANISM: Chlorella sp.
<220> FEATURE:
<221> NAME/KEY: misc_feature
<223> OTHER INFORMATION: SKP1-0684 polypeptide

<400> SEQUENCE: 89

Met Thr Glu Lys Val Lys Leu Leu Ser Ser Asp Thr Gln His Phe Glu
  1               5                  10                  15

Val Asp Ala Glu Val Ala Lys Gln Ser Val Thr Ile Leu Asn Thr Ile
             20                  25                  30

Glu Glu Ile Gly Ser Asp Glu Val Ile Pro Val Pro Asn Val Asn Ser
         35                  40                  45

Lys Ile Leu Ser Lys Val Ile Glu Tyr Cys Ser Phe His Val Ala Ala
 50                  55                  60

Glu Lys Lys Asp Glu His Gly Lys Thr Gly Lys Thr Glu Asp Glu Ile
 65                  70                  75                  80

Lys Ala Phe Asp Ala Glu Phe Thr Lys Val Asp Gln Gly Val Leu Phe
                 85                  90                  95

Glu Leu Ile Leu Ala Ala Asn Tyr Leu Asn Ile Lys Ser Leu Leu Asp
            100                 105                 110

Leu Thr Cys Leu Thr Val Ala Asn Met Ile Lys Gly Lys Thr Pro Glu
        115                 120                 125

Glu Ile Arg Lys Thr Phe Asn Ile Glu Asn Asp Phe Thr Pro Glu Glu
    130                 135                 140

Glu Glu Glu Val Arg Arg Glu Asn Gln Trp Ala Phe Glu
145                 150                 155

<210> SEQ ID NO 90
<211> LENGTH: 175
<212> TYPE: PRT
<213> ORGANISM: Tetraselmis sp.
<220> FEATURE:
<221> NAME/KEY: misc_feature
<223> OTHER INFORMATION: SKP1-9377 polypeptide
```

<400> SEQUENCE: 90

```
Val Ala Ala Pro Glu Val Arg Asn Ser Ser Phe Thr Gln Arg Thr Tyr
1               5                   10                  15

Thr Met Ala Glu Thr Lys Val Lys Leu Arg Ser Ser Asp Glu Gln Met
            20                  25                  30

Phe Glu Val Glu Glu Asp Val Ala Phe Glu Ser Leu Thr Val Lys Asn
        35                  40                  45

Met Ile Glu Asp Thr Gly Thr Glu Ala Pro Ile Pro Leu Pro Asn Val
    50                  55                  60

Ser Ser Lys Ile Leu Ala Lys Val Ile Glu Tyr Cys Lys Tyr His Val
65                  70                  75                  80

Asp Ala Arg Lys Lys Thr Asp Ala Asp Lys Pro Ser Lys Leu Asp Asp
                85                  90                  95

Asp Val Lys Ala Trp Asp Met Glu Phe Val Lys Val Asp Gln Gly Thr
            100                 105                 110

Leu Phe Glu Leu Ile Leu Ala Ala Asn Tyr Leu Asn Ile Lys Thr Leu
        115                 120                 125

Leu Asp Leu Thr Cys Leu Thr Val Ala Asn Met Ile Lys Gly Lys Thr
    130                 135                 140

Pro Glu Glu Ile Arg Lys Thr Phe Asn Ile Lys Asn Asp Phe Thr Pro
145                 150                 155                 160

Glu Glu Glu Glu Glu Val Arg Lys Glu Asn Gln Trp Ala Phe Glu
                165                 170                 175
```

<210> SEQ ID NO 91
<211> LENGTH: 252
<212> TYPE: PRT
<213> ORGANISM: Tetraselmis sp.
<220> FEATURE:
<221> NAME/KEY: misc_feature
<223> OTHER INFORMATION: CHORD polypeptide

<400> SEQUENCE: 91

```
Met Ala Glu Asp Ala Ala Asn Gly Ala Ala Ala Leu Ala Ala Ala Leu
1               5                   10                  15

Ser Pro Gly Val Gly Lys Leu Ser Leu Gly Gly Leu Gly Thr Gln Ser
            20                  25                  30

Pro Ala Gln Ala Gly Pro His Thr Cys His Arg Met Gly Cys Gly Glu
        35                  40                  45

Lys Phe Asp Pro Ala Ala Asn Ser Asp Ser Ser Cys Arg Tyr His Pro
    50                  55                  60

Asn Pro Pro Tyr Phe His Asp Gly Met Lys Glu Trp Thr Cys Cys Lys
65                  70                  75                  80

Lys Lys Ser His Asp Phe Gly Glu Phe Met Ala Ile Pro Gly Cys Thr
                85                  90                  95

Thr Gly Arg His Ser Ser Glu Lys Pro Glu Lys Pro Ala Ala Lys Pro
            100                 105                 110

Val Pro Ala Ala Ala Ala Pro Pro Val Ala Ser Thr Pro Ala Ala Ala
        115                 120                 125

Ser Thr Cys Leu Arg Cys Ala Gln Gly Phe Phe Cys Ser Asp His Ala
    130                 135                 140

Gly Val Pro Ala Val Val Pro Val Ser Val Ala Ala Ala Ala Pro Val
145                 150                 155                 160

His Pro Gln Val Glu Pro Ala Pro Lys Val Ala Arg Pro Ala Pro Val
                165                 170                 175
```

```
Pro Asp Ala Asp Gly Asn Leu Val Cys Arg His Phe Ala Cys Gly Asn
            180                 185                 190

Lys Tyr Lys Glu Gly Glu Asn His Gly Glu Ala Cys His His Pro
        195                 200                 205

Gly Pro Ala Val Phe His Asp Arg Gln Lys Gly Trp Gly Cys Cys Asn
        210                 215                 220

Lys Phe Glu Arg Asp Phe Asp Ala Phe Leu Ala Ile Pro Pro Cys Ala
225                 230                 235                 240

Tyr Gly Glu His Asp Ala Ala Phe Glu Gly Thr Phe
                245                 250

<210> SEQ ID NO 92
<211> LENGTH: 358
<212> TYPE: PRT
<213> ORGANISM: Nannochloropsis gaditana
<220> FEATURE:
<221> NAME/KEY: misc_feature
<223> OTHER INFORMATION: CHORD polypeptide

<400> SEQUENCE: 92

Met Lys Leu Tyr Phe His Tyr Glu Glu Thr Asp Asp Ala Gly Asp Val
1               5                   10                  15

Glu Glu Ala Lys Ala Leu Thr Leu Lys Leu Thr Leu Pro Lys Ser Trp
            20                  25                  30

Val Gly Gln Pro Leu Leu Gln Val Leu Glu Leu Phe Leu Glu Asn Tyr
        35                  40                  45

Asn Asn Lys Lys Ala Arg Leu Glu Pro Leu Asp Ile Ser Gly Val His
    50                  55                  60

Leu Glu Lys Ala Asp Gly Met Lys Ile His Thr Thr Asp Ile Val Met
65                  70                  75                  80

Asp Ile Leu Ser Asp Arg Asp Val Tyr Val Lys His Gly Ala Glu
                85                  90                  95

Gln Pro Ala Lys Ala Lys Arg Thr Pro Pro Ser Ser Ser Ser Ser Ser
            100                 105                 110

Ser Ser Ser Ser Ser Ser Ser Ser Ser Ser Ser Ile Pro Gly
        115                 120                 125

Ala Thr Thr Glu Gly Ser Thr Gly Leu Leu Arg Cys Lys Asn Tyr Gly
    130                 135                 140

Cys Asn Gln Ser Phe Ala Gln Glu Thr Asn Thr Glu Ser Ala Cys Arg
145                 150                 155                 160

Phe His Arg Ala Pro Pro Val Phe His Asp Thr Lys Lys Gly Trp Ala
                165                 170                 175

Cys Cys Thr Lys Arg Val Tyr Asp Trp Asp Glu Phe His Thr Ile Glu
            180                 185                 190

Gly Cys Ala Thr Gly Arg His Ser Thr Leu Asp Pro Lys Glu Val Phe
        195                 200                 205

Ala Pro Ser Pro Thr Leu Ala Ala Ala Asn Gln Ala Gly Ala Asn Gly
    210                 215                 220

Gly Ser Asp Ala Pro Gly Ala Ser Ser Thr Ala Leu Lys Ser Ile Glu
225                 230                 235                 240

Asp Tyr Asn Gln Ala Asn Pro Asp Ala Ala Thr Ala Ala Lys Ser Ala
                245                 250                 255

Ala Ser Ser Val Thr Lys Pro Gln Ala Arg Cys Thr Val Lys Ala Asp
            260                 265                 270

Gly Ser Ala Thr Cys Leu Asn Lys Gly Cys Gln Lys Glu Phe Gln Val
        275                 280                 285
```

```
Lys Glu Asn His Pro Thr Ala Cys Cys Tyr His Ala Ser Gly Pro Val
            290                 295                 300

Phe His Asp Ala Gly Lys Phe Trp Ser Cys Cys Pro Gly Val Ile Lys
305                 310                 315                 320

Tyr Asp Phe Glu Glu Phe Leu Lys Ile Pro Gly Cys Met Val Ser Ser
                325                 330                 335

His Leu Asp Gly Ser Glu Glu Ser Ser Arg Phe Phe Glu Ser His Ala
            340                 345                 350

Arg Lys Arg Glu Asp Arg
            355

<210> SEQ ID NO 93
<211> LENGTH: 301
<212> TYPE: PRT
<213> ORGANISM: Phaeodactylum tricornutum
<220> FEATURE:
<221> NAME/KEY: misc_feature
<223> OTHER INFORMATION: CHORD polypeptide

<400> SEQUENCE: 93

Met Lys Val Leu Leu His Tyr Glu Asp Asn Glu Asp Ser Ser Leu His
1               5                   10                  15

Lys Ser Leu Lys Ile Thr Leu Pro Lys Ser Trp Lys Thr Gly Pro Thr
            20                  25                  30

Ser Arg Leu Leu Thr Gln Phe Leu Glu Ser Tyr Asn Ala Asn Glu Ser
        35                  40                  45

Phe Arg Ser Asn Pro Leu Thr Glu Ala Thr Met His Leu Glu Thr Arg
50                  55                  60

Ser Ile Ser Thr Glu Ser Gly Pro Thr Val Ser Gly Arg Val Ala Leu
65                  70                  75                  80

Ala Ser Asp Ala Val Val Asp Val Ile Ala Asp Arg Ala Asp Ile
                85                  90                  95

Tyr Ile Val His Gly Pro Ser Arg Thr Leu Gln Asp Met Ala Asp Glu
                100                 105                 110

Val Ala Glu Ala Lys Arg Gln Lys Ala Glu Arg Leu Lys Gly Ser Val
            115                 120                 125

Ala Cys Leu His Phe Gly Cys Gln Asn Arg Phe Pro Lys Gly Gly Pro
        130                 135                 140

Tyr Pro Asp Cys Arg Tyr His Lys Ala Pro Val Phe His Glu Thr
145                 150                 155                 160

Ala Lys Phe Trp Ser Cys Cys Pro Asn Lys Lys Ala Tyr Asp Trp Glu
                165                 170                 175

Thr Phe Gln Ala Ile Pro Gly Cys Glu Thr Gly Thr Cys Thr Asp Val
                180                 185                 190

Arg Glu Glu Gly Asp Asp Gly Lys Gln Phe Leu Gly Gly Ser Asp Leu
            195                 200                 205

Arg Glu Lys Thr Glu Ala Val Pro Leu Lys Ser Ile Asp Asp Phe Asn
        210                 215                 220

Lys Ala Gln Thr Ser Gly Glu Ala Ala Pro Ile Leu Glu Arg Leu Glu
225                 230                 235                 240

Thr Val Leu Leu Gln Leu Gly Val Glu Lys Glu Leu Phe Gln Gln Val
                245                 250                 255

Val His Gly Met Lys Val Asn Leu Glu Ala Gln Thr Ala Asn Glu Ala
                260                 265                 270

Glu Leu Met Glu Ala Val Lys Asn Glu Leu Gly Gly Lys Leu Lys Ala
```

Ala Ile Lys Ala Val Ala Val Glu Gln Leu Arg Ile Lys
            290                 295                 300

<210> SEQ ID NO 94
<211> LENGTH: 297
<212> TYPE: PRT
<213> ORGANISM: Navicula sp.
<220> FEATURE:
<221> NAME/KEY: misc_feature
<223> OTHER INFORMATION: CHORD polypeptide

<400> SEQUENCE: 94

Met Lys Val Leu Leu His Tyr Glu Asp Asn Glu Asn Thr Ala Leu His
1               5                   10                  15

Lys Ser Leu Lys Ile Thr Leu Pro Lys Ser Trp Lys Thr Gly Pro Ser
            20                  25                  30

Ser Lys Leu Leu Asp Gln Phe Val Glu Ser Tyr Asn Gly Asn Glu Thr
        35                  40                  45

Leu Gly Ala Asn Asn Pro Leu Asp Ala Ser Arg Leu His Leu Ala Leu
    50                  55                  60

Lys Gln Pro Asp Asn Ser Phe Arg Leu Ile Ala Ser Asp Ala Thr Ala
65                  70                  75                  80

Val Asp Asp Ile Pro Asp Arg Ala Asp Val Tyr Ile Arg His Gly Ala
                85                  90                  95

Ser Lys Thr Lys Gln Asp Ile Ala Thr Glu Gln Arg Arg Ala Gln Glu
            100                 105                 110

Ala Leu Glu Leu Ala Arg Lys Asp Ser Val Ala Cys Thr His Phe Gly
        115                 120                 125

Cys Arg Asn Arg Phe Pro Lys Asn Gly Pro Phe Pro Glu Cys Arg Tyr
    130                 135                 140

His Lys Ala Pro Pro Val Phe His Glu Thr Ala Lys Phe Trp Ser Cys
145                 150                 155                 160

Cys Pro Gln Lys Lys Ala Tyr Asp Trp Glu Asp Phe Gln Asn Ile Pro
                165                 170                 175

Gly Cys Met Thr Gly Ile Cys Thr Ala Val Lys Glu Thr Glu Gly Lys
            180                 185                 190

Gln Phe Leu Gly Gly Thr Asp Leu Arg Glu Asn Ala Glu Val Ala Thr
        195                 200                 205

Leu Lys Ser Ile Asp Asp Phe Asn Lys Ser Gln Ala Ala Gly Gly Ser
    210                 215                 220

Ala Ala Ala Pro Val Leu Glu Arg Leu Ala Gly Val Leu Glu Glu Leu
225                 230                 235                 240

Gly Ile Glu Lys Glu Leu Phe Gln Gln Val Thr Asn Gly Ile Arg Asp
                245                 250                 255

Glu Lys Arg Lys Ser Gly Ile Ile Thr Ser Glu Ala Glu Leu Leu Asp
            260                 265                 270

Gln Val Lys Glu Glu Leu Gly Ala Lys Leu Lys Ala Ala Val Lys Ala
        275                 280                 285

Ile Ala Val Glu Gln Leu Arg Ile Lys
    290                 295

<210> SEQ ID NO 95
<211> LENGTH: 287
<212> TYPE: PRT
<213> ORGANISM: Thalassiosira pseudonana
<220> FEATURE:

<221> NAME/KEY: misc_feature
<223> OTHER INFORMATION: CHORD polypeptide

<400> SEQUENCE: 95

Met Lys Val Phe Leu Arg Tyr Glu Glu Asn Asp Asp Glu Ser Thr His
1               5                   10                  15

Lys Thr Leu Lys Ile Thr Leu Pro Lys Ser Trp Lys Thr Gly Pro Thr
            20                  25                  30

Ser Arg Leu Leu Asp Gln Phe Val Glu Ser Tyr Asn Gly Gly Lys Glu
        35                  40                  45

Gly Glu Ala Asn Pro Leu Asp Ala Ser Thr Leu His Leu Ser Ile Arg
    50                  55                  60

Arg Pro Ala Ser Thr Thr Val Arg Thr Ser Ser Ala Ser Ala Asp Asp
65                  70                  75                  80

Gly Ala Thr Val Leu Lys Glu Leu Pro Ser Asp Gly Ile Ile Val Glu
                85                  90                  95

Thr Ile Glu Asp Arg Asp Asp Val Tyr Val Cys His Gly Pro Ser Leu
            100                 105                 110

Thr Ser Thr Glu Met Asn Ala Glu Arg Gln Ala Lys Ile Asp Lys Glu
        115                 120                 125

Lys Glu Glu Lys Lys Asn Leu Ser Gln Cys Val His Phe Gly Cys Asn
    130                 135                 140

Asn Arg Phe Pro Lys Gly Gly Pro Tyr Pro Asp Cys Lys Tyr His Ser
145                 150                 155                 160

Gly Pro Pro Val Phe His Glu Thr Ala Lys Phe Trp Ser Cys Cys Pro
                165                 170                 175

Asp Lys Lys Ala Tyr Asp Trp Glu Gly Phe Gln Cys Leu Pro Thr Cys
            180                 185                 190

Gln Ser Gly Pro Lys Leu Lys Ser Ile Asp Asp Phe Asn Ala Ser Ile
        195                 200                 205

Ala Ala Gly Gly Ser Glu Gly Ala Pro Val Leu Glu Arg Leu Arg Ser
    210                 215                 220

Val Leu Gly Glu Leu Gly Val Glu Asn Glu Leu Phe Asp Gln Val Phe
225                 230                 235                 240

Glu Gly Val Lys Lys Glu Val Arg Glu Lys Asn Gly Val Asp Cys Glu
                245                 250                 255

Asp Ala Lys Val Leu Asp Glu Ala Ala Gln Met Leu Gly Gly Lys Leu
            260                 265                 270

Lys Ser Ala Met Lys Ala Ile Ala Val Glu Gln Leu Arg Ile Ser
        275                 280                 285

<210> SEQ ID NO 96
<211> LENGTH: 313
<212> TYPE: PRT
<213> ORGANISM: Cyclotella sp.
<220> FEATURE:
<221> NAME/KEY: misc_feature
<223> OTHER INFORMATION: CHORD polypeptide

<400> SEQUENCE: 96

Met Lys Val Phe Leu Arg Tyr Glu Glu Asn Asp Asp Glu Ser Thr His
1               5                   10                  15

Lys Thr Leu Lys Ile Thr Leu Pro Lys Ser Trp Lys Thr Gly Pro Thr
            20                  25                  30

Ser Arg Leu Leu Asp Gln Phe Ile Glu Ser Tyr Asn Ala Gly Lys Glu
        35                  40                  45

Gly Glu Ala Asn Pro Leu Glu Ala Asn Ala Met His Leu Ser Val Arg
 50                  55                  60

Arg Arg Ile Ser Thr Asn Gly Ser Asn Ser Asp Asp Thr Ile Leu
 65                  70                  75                  80

Lys Asp Leu Pro Ser Asp Gly Ile Val Val Glu Leu Ile Ser Asp Arg
             85                  90                  95

Asp Asp Val Tyr Val Cys His Gly Pro Ser Arg Thr Ser Ser Glu Ile
             100                 105                 110

Asn Ser Glu Arg Glu Ala Gln Leu Lys Lys Glu Lys Glu Lys Lys
         115                 120                 125

Asn Gln Ser Gln Cys Val His Phe Gly Cys Asn Lys Arg Phe Pro Lys
 130                 135                 140

Gly Gly Pro Tyr Pro Glu Cys His Tyr His Ser Gly Pro Pro Val Phe
 145                 150                 155                 160

His Glu Thr Ala Lys Phe Trp Ser Cys Cys Pro Asp Lys Lys Ala Tyr
             165                 170                 175

Asp Trp Glu Ser Phe Gln Ser Leu Pro Thr Cys Gln Ser Gly Thr Cys
             180                 185                 190

Thr Asp Val Arg Glu Glu Ser Asp Ala Pro Arg Lys Glu Phe Leu Gly
             195                 200                 205

Gly Cys Asp Leu Arg Glu Gln Ile Ser Ala Gly Pro Lys Leu Arg Ser
             210                 215                 220

Ile Asp Asp Phe Asn Ala Ser Val Ala Ala Gly Ser Glu Arg Ala
 225                 230                 235                 240

Pro Val Ala Val Arg Leu Arg Ser Val Leu Glu Glu Leu Gly Val Glu
             245                 250                 255

Asn Glu Leu Phe Asp Gln Val Phe Asp Gly Ile Lys Lys Gln Val Lys
             260                 265                 270

Glu Lys Asn Gly Asp Thr Ala Asp Gly Asp Asp Ala Arg Val Val Asp
         275                 280                 285

Glu Ala Val Lys Ile Leu Gly Thr Lys Leu Lys Ser Ala Met Lys Ser
     290                 295                 300

Ile Ala Val Glu Gln Leu Arg Ile Arg
305                 310

<210> SEQ ID NO 97
<211> LENGTH: 1003
<212> TYPE: DNA
<213> ORGANISM: Nannochloropsis gaditana
<220> FEATURE:
<221> NAME/KEY: misc_feature
<223> OTHER INFORMATION: TCTP promoter

<400> SEQUENCE: 97
cgtgcaggtg tacagattga aggaaacaat ggagatatct ttggcagttg aaaaccgtgt     60
tcgaatcatg ctcttctact ctccaactga gacgaaattt atagcgccat ctcgcttctg    120
actaccaggc ttaggaaggc ctcatcacaa gctggatcgg ttcgaattaa gcaggcactg    180
aagccaagct tgcaagacag ccaccttta attctctcaa acactttct caattcagcc    240 cggtaaatat gccgattcac agcggccaag atagagggga ggttagcaag aatgttgcga    300
tccctcccca gtcgttgcct cgcacacaac ctaggacttc acctttccat ggaaaattga    360
gaagtgaata ttggttttct tacggcatat cagatgaaat catgacccct aaacatgaag    420
agctgcaggc aaaacacctg ctctggacga gcacgatgaa atctcgagaa cccgccgtac    480
ttcagttgat cccgcatgat gacggccgcc attgaaataa gccacctcac tttattctag    540

```
caccgatttc caccgttgtg agggccgaac gaggacaatt tcgtgcgaaa caagcacgaa    600
cgcgcacacg attagtagga cagacgagca gatcgatggc atgcggcacg gtctcgcgtt    660
ctcggcgacc aggacaacgg agcagaggga ggcctgccga gttccgaggg gcattttagt    720
cccaaaattg tgttgacacg tgaacaagtg gcttgaaaag aggaaggaaa tgcctgggtt    780
tcccttcgag agcgggaact cgcttgtgcg tcatcctagc tacccatggt cccttttgtgg   840 gggaggctgt ttcgtcctac cgaatgtgtg gcgctccatg catcttctgc ctcccaaacc    900
accaacatga gcacgcgaag gaaggagaaa aaagtggccg caacgttctc ttctcatatt    960
tattgtctca tcacaaacat aggtacataa tacaacaatc atg                     1003
```

<210> SEQ ID NO 98
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Aspergillus blasticidin resistance gene codon optimized for Nannochloropsis gaditana

<400> SEQUENCE: 98

```
atggccaagc tttgtccca agaggaatcc acgctgatcg aacgtgcaac tgcgaccatc    60
aacagcatac ctattagcga ggactactcg gtggccagtg cagccctctc gtccgacggt    120
cggatcttta ccggcgtgaa tgtatatcat ttcaccggag ggccatgcgc ggagctcgtg    180
gtcctcggaa cggccgctgc ggctgctgcc ggaaatctga cgtgcatagt ggccatcggg    240
aacgaaaacc gcggcattct gtctccgtgc gggcgatgtc ggcaggtgct gcttgacttg    300 caccogggga tcaaggcaat tgtcaaagat tccgatgggc agcccacagc ggttggcatc    360
agggagttgc ttccctctgg ctacgtctgg gagggttga                          399
```

<210> SEQ ID NO 99
<211> LENGTH: 61
<212> TYPE: PRT
<213> ORGANISM: Nannochloropsis gaditana
<220> FEATURE:
<221> NAME/KEY: misc_feature
<223> OTHER INFORMATION: Amino acid sequence of CHORD exon 4

<400> SEQUENCE: 99

```
Tyr His Ala Ala Gly Pro Val Phe His Asp Ala Gly Lys Tyr Trp Ser
 1               5                  10                  15

Cys Cys Pro Gly Thr Val Lys Tyr Asp Phe Asp Asp Phe Leu Lys Ile
                20                  25                  30

Pro Gly Cys Met Leu Ser Ser His Tyr Asp Gly Ser Gln Glu Ser Leu
            35                  40                  45

Glu Ala Phe Thr Arg His Ala Lys Thr Ser Glu Gly Thr
        50                  55                  60
```

<210> SEQ ID NO 100
<211> LENGTH: 139
<212> TYPE: PRT
<213> ORGANISM: Nannochloropsis gaditana
<220> FEATURE:
<221> NAME/KEY: misc_feature
<223> OTHER INFORMATION: CHORD 3' fusion vector-intron-exon 4 amino acid sequence

<400> SEQUENCE: 100

-continued

```
Met Gly Ser Pro Gln Arg Leu Ala Ser Gly Ser Cys Phe Pro Leu Ala
1               5                   10                  15

Thr Ser Gly Arg Val Glu Ile His Trp Pro Ser Phe Tyr Asn Val Val
                20                  25                  30

Thr Gly Lys Thr Leu Ala Leu Pro Asn Leu Ile Ala Leu Gln His Ile
            35                  40                  45

Pro Leu Ser Pro Val Ala Asn Ser Tyr Asn Arg Glu Leu Tyr Val Pro
        50                  55                  60

Thr Pro Thr Leu Arg His Phe Ser Ser Leu Pro Phe Phe Ser Tyr His
65                  70                  75                  80

Ala Ala Gly Pro Val Phe His Asp Ala Gly Lys Tyr Trp Ser Cys Cys
                85                  90                  95

Pro Gly Thr Val Lys Tyr Asp Phe Asp Asp Phe Leu Lys Ile Pro Gly
            100                 105                 110

Cys Met Leu Ser Ser His Tyr Asp Gly Ser Gln Glu Ser Leu Glu Ala
        115                 120                 125

Phe Thr Arg His Ala Lys Thr Ser Glu Gly Thr
        130                 135

<210> SEQ ID NO 101
<211> LENGTH: 68
<212> TYPE: PRT
<213> ORGANISM: Nannochloropsis gaditana
<220> FEATURE:
<221> NAME/KEY: misc_feature
<223> OTHER INFORMATION: SKP tetramerization domain

<400> SEQUENCE: 101

Lys Tyr Ile Thr Leu Gln Ala Arg Asp Gly Thr Leu Asp Glu Pro Val
1               5                   10                  15

Asp Ala Arg Ile Leu Leu Pro Ser Asp Leu Leu Arg Ser Met Leu Pro
                20                  25                  30

Glu Lys Leu Ser Glu Ile Glu Asp Phe Gln Ile Pro Leu Gln Gly
            35                  40                  45

Val Asp Lys Ala Val Leu Glu Lys Val Val Tyr Leu His Leu Tyr
        50                  55                  60

Arg Glu Glu Pro
65

<210> SEQ ID NO 102
<211> LENGTH: 68
<212> TYPE: PRT
<213> ORGANISM: Nannochloropsis gaditana
<220> FEATURE:
<221> NAME/KEY: misc_feature
<223> OTHER INFORMATION: SKP dimerization domain

<400> SEQUENCE: 102

Ile Asn Ala Leu His Tyr Lys Thr Ile Phe Gln Ile Ile Asp Ala Ala
1               5                   10                  15

Asn Phe Leu Gly Ile Glu Pro Leu Leu Ser Leu Ser Leu Ser Trp Val
                20                  25                  30

Ala Phe Val Leu Lys Gly Pro Thr Val Glu Glu Phe Lys Lys Leu Phe
            35                  40                  45

Thr Ile His Asn Asp Phe Thr Pro Glu Glu Glu Ala Ile Phe Arg Arg
        50                  55                  60

Glu Tyr Leu Leu
65
```

-continued

```
<210> SEQ ID NO 103
<211> LENGTH: 1000
<212> TYPE: PRT
<213> ORGANISM: Nannochloropsis gaditana
<220> FEATURE:
<221> NAME/KEY: misc_feature
<223> OTHER INFORMATION: 5901 promoter sequence

<400> SEQUENCE: 103

Ala Ala Thr Ala Ala Gly Cys Ala Thr Ala Cys Ala Thr Cys Ala Thr
1               5                   10                  15

Ala Thr Gly Ala Ala Thr Ala Cys Ala Ala Thr Thr Cys Ala Gly Cys
            20                  25                  30

Thr Thr Ala Ala Ala Thr Thr Ala Thr Cys Ala Thr Ala Cys Ala
        35                  40                  45

Ala Ala Gly Ala Thr Gly Thr Ala Ala Gly Thr Gly Cys Ala Gly Cys
    50                  55                  60

Gly Thr Gly Gly Thr Cys Thr Gly Thr Ala Ala Cys Gly Ala Thr
65                  70                  75                  80

Cys Gly Gly Gly Cys Gly Thr Ala Ala Thr Thr Ala Ala Gly Ala
                85                  90                  95

Thr Ala Ala Thr Gly Cys Gly Ala Gly Gly Ala Cys Cys Gly Gly
            100                 105                 110

Gly Gly Gly Ala Gly Gly Thr Thr Thr Gly Gly Ala Ala Cys Gly
        115                 120                 125

Gly Ala Ala Thr Gly Ala Gly Gly Ala Ala Thr Gly Gly Thr Cys
    130                 135                 140

Ala Thr Gly Gly Cys Cys Cys Ala Thr Ala Ala Thr Ala Ala Thr Ala
145                 150                 155                 160

Ala Thr Ala Thr Gly Gly Gly Thr Thr Thr Gly Gly Thr Cys Gly Cys
                165                 170                 175

Cys Thr Cys Gly Cys Ala Cys Ala Gly Cys Ala Ala Cys Cys Gly Thr
            180                 185                 190

Ala Cys Gly Thr Gly Cys Gly Ala Ala Ala Ala Gly Gly Ala Ala
        195                 200                 205

Cys Ala Gly Ala Thr Cys Cys Ala Thr Thr Thr Ala Ala Thr Ala Ala
    210                 215                 220

Gly Thr Thr Gly Ala Ala Cys Gly Thr Thr Ala Thr Thr Cys Thr Thr
225                 230                 235                 240

Thr Cys Cys Thr Ala Thr Gly Cys Ala Ala Thr Gly Cys Gly Thr Gly
                245                 250                 255

Thr Ala Thr Cys Gly Gly Ala Gly Gly Cys Gly Ala Gly Ala Gly Cys
            260                 265                 270

Ala Ala Gly Thr Cys Ala Thr Ala Gly Gly Thr Gly Gly Cys Thr Gly
        275                 280                 285

Cys Gly Cys Ala Cys Ala Ala Thr Ala Ala Thr Gly Ala Gly Thr
    290                 295                 300

Cys Thr Cys Ala Gly Cys Thr Gly Ala Gly Gly Cys Cys Gly Thr
305                 310                 315                 320

Cys Cys Gly Cys Gly Gly Thr Gly Thr Gly Thr Gly Ala Gly
                325                 330                 335

Thr Gly Gly Thr Cys Ala Thr Cys Cys Thr Cys Thr Cys Cys Cys
            340                 345                 350

Gly Gly Cys Cys Thr Ala Thr Cys Gly Cys Thr Cys Ala Cys Ala Thr
```

```
                355                 360                 365
Cys Gly Cys Cys Thr Cys Thr Cys Ala Ala Thr Gly Thr Gly Gly
        370                 375                 380
Thr Gly Gly Thr Gly Thr Gly Gly Gly Cys Cys Thr Gly Ala Thr Ala Thr
385                 390                 395                 400
Gly Ala Cys Cys Thr Cys Ala Ala Thr Cys Cys Gly Ala Cys Cys
                405                 410                 415
Cys Ala Thr Ala Thr Thr Ala Ala Ala Cys Cys Ala Gly Thr
        420                 425                 430
Ala Ala Ala Gly Cys Ala Thr Thr Cys Ala Cys Cys Ala Cys Gly
        435                 440                 445
Ala Ala Cys Gly Ala Gly Gly Gly Cys Thr Cys Thr Thr Thr Thr
        450                 455                 460
Gly Thr Gly Thr Gly Thr Gly Thr Thr Thr Thr Gly Ala Gly Thr Ala
465                 470                 475                 480
Thr Gly Ala Thr Thr Thr Ala Cys Ala Cys Cys Thr Cys Thr Thr
                485                 490                 495
Thr Gly Thr Gly Cys Ala Thr Cys Thr Cys Thr Cys Thr Gly Gly Thr
        500                 505                 510
Cys Thr Thr Cys Cys Thr Thr Gly Gly Thr Thr Cys Cys Cys Gly Thr
        515                 520                 525
Ala Gly Thr Thr Thr Gly Gly Gly Cys Ala Thr Cys Ala Thr Cys Ala
        530                 535                 540
Cys Thr Cys Ala Cys Gly Cys Thr Thr Cys Cys Thr Cys Gly Ala
545                 550                 555                 560
Cys Cys Thr Thr Cys Gly Thr Thr Cys Thr Thr Cys Thr Thr Thr
                565                 570                 575
Ala Cys Ala Ala Cys Cys Cys Gly Ala Cys Ala Cys Ala Gly Gly
        580                 585                 590
Thr Cys Ala Gly Ala Gly Thr Thr Gly Gly Ala Gly Thr Ala Ala Thr
        595                 600                 605
Cys Ala Ala Ala Ala Ala Gly Gly Gly Thr Gly Cys Ala Cys
610                 615                 620
Gly Ala Ala Thr Gly Ala Gly Ala Thr Ala Cys Ala Thr Thr Ala Gly
625                 630                 635                 640
Ala Thr Thr Thr Thr Gly Ala Cys Ala Gly Ala Thr Ala Thr Cys Cys
                645                 650                 655
Thr Thr Thr Thr Ala Cys Thr Gly Gly Ala Gly Ala Gly Gly Gly Thr
        660                 665                 670
Thr Cys Ala Ala Gly Gly Gly Ala Thr Cys Ala Ala Ala Thr Gly Ala
        675                 680                 685
Ala Cys Ala Gly Cys Gly Gly Gly Cys Gly Thr Gly Gly Cys Ala
        690                 695                 700
Ala Thr Cys Thr Ala Gly Gly Ala Gly Gly Ala Thr Cys Gly
705                 710                 715                 720
Gly Ala Gly Gly Thr Thr Gly Gly Cys Ala Gly Cys Gly Ala Gly Cys
                725                 730                 735
Gly Ala Ala Ala Gly Cys Gly Thr Gly Thr Cys Cys Ala Thr Cys Cys
        740                 745                 750
Thr Thr Thr Thr Gly Gly Cys Thr Gly Thr Cys Ala Cys Ala Cys Cys
        755                 760                 765
Thr Cys Ala Cys Gly Ala Ala Cys Cys Ala Ala Cys Thr Gly Thr Thr
        770                 775                 780
```

```
Ala Gly Cys Ala Gly Gly Cys Cys Ala Gly Cys Ala Cys Gly Ala
785                 790                 795                 800

Thr Gly Ala Cys Ala Thr Ala Cys Gly Ala Gly Ala Ala Thr Cys Thr
            805                 810                 815

Thr Thr Ala Thr Thr Ala Thr Ala Thr Cys Gly Thr Ala Gly Ala Cys
            820                 825                 830

Cys Thr Thr Ala Thr Gly Thr Gly Gly Ala Thr Gly Ala Cys Cys Thr
            835                 840                 845

Thr Thr Gly Gly Thr Gly Cys Thr Gly Thr Gly Thr Gly Thr Cys Thr
    850                 855                 860

Gly Gly Cys Ala Ala Thr Gly Ala Ala Cys Cys Thr Gly Ala Ala Gly
865                 870                 875                 880

Gly Cys Thr Thr Gly Ala Thr Ala Gly Gly Ala Gly Gly Thr Gly
            885                 890                 895

Gly Cys Thr Cys Cys Gly Thr Ala Ala Ala Cys Cys Cys Thr Thr
            900                 905                 910

Thr Gly Thr Cys Cys Thr Thr Thr Cys Cys Ala Cys Gly Cys Thr Gly
    915                 920                 925

Ala Gly Thr Cys Thr Cys Cys Cys Cys Gly Cys Ala Cys Thr Gly
            930                 935                 940

Thr Cys Cys Thr Thr Thr Ala Thr Ala Cys Ala Ala Ala Thr Thr Gly
945                 950                 955                 960

Thr Thr Ala Cys Ala Gly Thr Cys Ala Thr Cys Thr Gly Cys Ala Gly
            965                 970                 975

Gly Cys Gly Gly Thr Thr Thr Thr Cys Thr Thr Thr Gly Gly Cys
            980                 985                 990

Ala Gly Gly Cys Ala Ala Ala Cys
            995                 1000

<210> SEQ ID NO 104
<211> LENGTH: 163
<212> TYPE: DNA
<213> ORGANISM: Nannochloropsis gaditana
<220> FEATURE:
<221> NAME/KEY: misc_feature
<223> OTHER INFORMATION: T9 terminator sequence

<400> SEQUENCE: 104
gagtcaaggg ggaaggtgca tagtgtgcaa caacagcatt aacgtcaaag aaaactgcac      60
gttcaagccc gcgtgaacct gccggtcttc tgatcgccta catatagcag atactagttg     120
tacttttttt tccaagggga acattcatgt atcaatttga aat                       163
```